US011401313B2

(12) United States Patent
Silva Manzano et al.

(10) Patent No.: US 11,401,313 B2
(45) Date of Patent: Aug. 2, 2022

(54) DE NOVO DESIGN OF POTENT AND SELECTIVE INTERLEUKIN MIMETICS

(71) Applicants: UNIVERSITY OF WASHINGTON, Seattle, WA (US); THE BOARD OF TRUSTEES OF THE LELAND STANFORD JUNIOR UNIVERSITY, Stanford, CA (US)

(72) Inventors: Daniel Adriano Silva Manzano, Seattle, WA (US); Shawn Yu, Seattle, WA (US); Umut Ulge, Seattle, WA (US); David Baker, Seattle, WA (US); Kenan Christopher Garcia, Stanford, CA (US); Jamie Spangler, Stanford, CA (US); Carl Walkey, Seattle, WA (US)

(73) Assignees: University of Washington, Seattle, WA (US); The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 16/909,210

(22) Filed: Jun. 23, 2020

(65) Prior Publication Data

US 2020/0347109 A1 Nov. 5, 2020

Related U.S. Application Data

(60) Division of application No. 16/572,038, filed on Sep. 16, 2019, now Pat. No. 10,703,791, which is a continuation of application No. PCT/US2019/038703, filed on Jun. 24, 2019.

(60) Provisional application No. 62/768,733, filed on Nov. 16, 2018, provisional application No. 62/689,769, filed on Jun. 25, 2018.

(51) Int. Cl.

| | |
|---|---|
| ***C07K 14/55*** | (2006.01) |
| ***C07K 14/54*** | (2006.01) |
| ***A61K 47/62*** | (2017.01) |
| ***A61K 47/60*** | (2017.01) |
| ***A61K 38/00*** | (2006.01) |

(52) U.S. Cl.

CPC .............. *C07K 14/55* (2013.01); *A61K 47/60* (2017.08); *A61K 47/62* (2017.08); *C07K 14/5406* (2013.01); *C07K 14/5437* (2013.01); *C07K 14/5443* (2013.01); *A61K 38/00* (2013.01); *C07B 2200/13* (2013.01); *C07K 2319/30* (2013.01); *C07K 2319/33* (2013.01); *C07K 2319/74* (2013.01)

(58) Field of Classification Search

None

See application file for complete search history.

(56) References Cited

U.S. PATENT DOCUMENTS

| | | | |
|---|---|---|---|
| 5,229,109 | A | 7/1993 | Grimm et al. |
| 7,101,965 | B2 | 9/2006 | Theze et al. |
| 7,105,653 | B2 | 9/2006 | Shanafelt et al. |
| 9,844,582 | B2 | 12/2017 | Wittrup et al. |
| 2017/0015722 | A1 | 1/2017 | Garcia et al. |

FOREIGN PATENT DOCUMENTS

| | | | | |
|---|---|---|---|---|
| CN | 111040981 A * | 4/2020 | | |
| WO | WO 02/012337 | 2/2002 | | |
| WO | WO 02/101629 | 12/2002 | | |
| WO | WO-2020106708 A1 * | 5/2020 | ............. | C07K 14/55 |
| WO | WO 21/081193 | 4/2021 | | |
| WO | WO 21/133476 | 7/2021 | | |
| WO | WO 21/188374 | 9/2021 | | |

OTHER PUBLICATIONS

Machine translation of CN 111040981A, generated Sep. 16, 2021 on Google patents (Year: 2021).*

Smyth et al., "Cytokines in cancer immunity and immunotherapy" Immunol. Rev. 202, 275-293 (2004).

Sockolosky et al., "Selective targeting of engineered T cells using orthogonal IL-2 cytokine-receptor complexes", Science 359, 1037-1042 (2018).

Spangler et al., "Insights into cytokine-receptor interactions from cytokine engineering. Annu. Rev.", Immunol. 33, 139-167 (2015).

Stumpp et al., "DARPins: A new generation of protein therapeutics", Drug Discov. Today 13, 695-701 (2008).

Tagaya et al., "IL-15: a pleiotropic cytokine with diverse receptor/signaling pathways whose expression is controlled at multiple levels", Immunity 4, 329-336 (1996).

Taverna et al., "Why are proteins marginally stable?" Proteins 46, 105-109 (2002).

Terwilliger et al., "Iterative model building, structure refnement and density modifcation with the PHENIX AutoBuild wizard" Acta Crystallogr. D 64, 61-69 (2008).

Thanos et al., "Hot-spot mimicry of a cytokine receptor by a small molecule", Proc. Natl. Acad. Sci. U. S. A. 103, 15422-15427 (2006).

Tzeng et al., "Antigen specificity can be irrelevant to immunocytokine efficacy and biodistribution", PNSA 112, 3320-3325 (2015).

Vazquez-Lombardi et al., "Potent antitumour activity of interleukin-2-Fc fusion proteins requires Fc-mediated depletion of regulatory T-cells", Nat. Commun. 8, 15373 (2017).

Vyas et al., "Clinical manufacturing of recombinant human interleukin 15. I. Production cell line development and protein expression in *E. coli* with stop codon optimization", Biotechnol. Prog. 28, 497-507 (2012).

Waldmann, "The Shared and Contrasting Roles of IL2 and IL15 in the Life and Death of Normal and Neoplastic Lymphocytes: Implications for Cancer Therapy", Cancer Immunol. Res. 3, 219-227 (2015).

(Continued)

*Primary Examiner* — Christina Bradley

(74) *Attorney, Agent, or Firm* — McDonnell Boehnen Hulbert & Berghoff LLP

(57) ABSTRACT

De novo designed polypeptides that bind to IL-2 receptor β $\gamma_c$ heterodimer (IL-2Rβ $\gamma_c$), IL-4 receptor α $\gamma_c$ heterodimer (IL-4Rα $\gamma_c$), or IL-13 receptor α subunit (IL-13Rα) are disclosed, as are methods for using and designing the polypeptides.

28 Claims, 80 Drawing Sheets

Specification includes a Sequence Listing.

(56) References Cited

OTHER PUBLICATIONS

Wang et al., "Structure of the quaternary complex of interleukin-2 with its alpha, beta, and gammac receptors", Science 310, 1159-1163 (2005).
Wieckowski et al., "Therapeutic efficacy of the F8-IL2 immunocytokine in a metastatic mouse model of lung adenocarcinoma", Lung Cancer vol. 88 Issue: 1, p. 9-15 (2015).
Winn et al., "Overview of the CCP4 suite and current developments" Acta Crystallogr. D 67, 235-242 (2011).
Yodoi et al., "TCGF (IL 2)-receptor inducing factor(s). I. Regulation of IL 2 receptor on a natural killer-like cell line (YT cells)", J. Immunol. 134, 1623-1630 (1985).
Zhu et al., "Synergistic innate and adaptive immune response to combination immunotherapy with anti-tumor antigen antibodies and extended serum half-life IL-2", Cancer Cell 27, 489-501 (2015).
Prümmer et al., "Treatment-induced antibodies to interleukin-2", Biotherapy 10, 15-24 (1997).
Stockman et al., "Pure Red-Cell Aplasia and Epoetin Therapy", Yearbook of Pediatrics 2006, pp. 54-55 (2006).
Domingues et al. "Rational design of a GCN4-derived mimetic of interleukin-4," Nature Structural Biology, vol. 6, No. 7, Jul. 1999, pp. 652-656 (Year: 1999).
Abraham et al., "GROMACS: High performance molecular simulations through multi-level parallelism from laptops to supercomputers", SoftwareX 1-2, 19-25 (2015).
Adams et al., "PHENIX: a comprehensive Python-based system for macromolecular structure solution" Acta Crystallogr. D 66, 213-221 (2010).
Akdis et al., "Interleukins, from 1 to 37, and interferon-γ: receptors, functions, and roles in diseases", J Allergy Clin. Immunol. 127, 701-21.e1-70 (2011).
Antonelli et al., "Neutralizing antibodies to interferon-alpha: relative frequency in patients treated with different interferon preparations", J. Infect. Dis. 163, 882-885 (1991).
Ardolino et al., "Cytokine treatment in cancer immunotherapy", Oncotarget vol. 6, (2015).
Arenas-Ramirez et al., "Improved cancer immunotherapy by a CD25-mimobody conferring selectivity to human interleukin-2", Sci Transl Med, vol. 8 Issue: 367 (Nov. 2016).
Basser et al., "Development of pancytopenia with neutralizing antibodies to thrombopoietin after multicycle chemotherapy supported by megakaryocyte growth and development factor", Blood 99, 2599-2602 (2002).
Behnel et al., Cython: the best of both worlds Comput. Sci. Eng. 13, 31-39 (2011).
Benatuil et al., "An improved yeast transformation method for the generation of very large human antibody libraries", Protein Eng. Des. Sel. 23, 155-159 (2010).
Berendsen et al., "Molecular dynamics with coupling to an external bath", J. Chem. Phys. 81, 3684-3690 (1984).
Berger et al., "Computationally designed high specifcity inhibitors delineate the roles of BCL2 family proteins in cancer", eLife 5, e20352 (2016).
Blattman et al., "Therapeutic use of IL-2 to enhance antiviral T-cell responses in vivo", Nat. Med. 9, 540-547 (2003).
Bouchaud et al., "The Exon-3-Encoded Domain of IL-15Rα Contributes to IL-15 High-Affinity Binding and Is Crucial for the IL-15 Antagonistic Effect of Soluble IL-15Rα", J. Mol. Biol. 382, 1-12 (2008).
Boyken et al., "De novo design of protein homo-oligomers with modular hydrogen-bond network-mediated specificity", with Supplementary Information, Science, 352(6286):680-87 (May 2016).
Boyman et al., "The role of interleukin-2 during homeostasis and activation of the immune system", Nat. Rev. Immunol. 12, 180-190 (2012).
Bruhn et al., "Crystal structure of the Marburg virus VP35 oligomerization domain", J. Virol. 3, e01085-16 (2017).
Cancer Immunotherapy Market (Therapy Type—Monoclonal Antibodies, Immune Checkpoint Inhibitors (PD-1/PD-L1 and CTLA-4), Immune System Modulators, and Cancer Vaccines; Therapeutic Areas—Lung Cancer, Colorectal Cancer, Breast Cancer, Prostate Cancer, Mel. Transparency Market Research https://www.transparencymarketresearch.com/cancer-immunotherapy-market.html (published Dec. 2016) 4 pages.
Cancer Immunotherapy Market Analysis By Product (Monoclonal Antibodies, Immunomodulators, Oncolytic Viral Therapies, Cancer Vaccines), By Cancer Type, And Segment Forecasts, 2018-2025. Grand View Research, https://vww.grandviewresearch.com/industry-analysis/cancer-immunotherapy-market (published Feb. 2019) 7 pages.
Cancer Immunotherapy Market by Technology (Monoclonal Antibodies, Cytokines & Immunomodulators, and Others), by Application (Lung Cancer, Breast Cancer, Colorectal Cancer, Melanoma, Prostate Cancer, Head & Neck Cancer, and Others) by End User (Hospitals). Allied Market Research https://www.alliedmarketresearch.com/cancer-immunotherapy-market (published May 2017) 4 pages.
Cancer Immunotherapy Market by Type (Monoclonal Antibodies, Cancer Vaccines, Check Point Inhibitors & Immunomodulators), Application (Lung, Breast, Colorectal, Melanoma, Prostate, Head & Neck), End User (Hospital and Clinics)—Global Forecast to 2021. Markets and Markets https://www.marketsandmarkets.com/Market-Reports/cancer-immunotherapy-market-197577894.html (published September 2016) 7 pages.
CAO, "Regulatory T cells and immune tolerance to tumors", Immunol. Res. 46, 79-93 (2009).
Carmenate et al., "Human IL-2 mutein with higher antitumor efficacy than wild type IL-2" J. Immunol. 190, 6230-6238 (2013).
Chang et al., "A general method for facilitating heterodimeric pairing between two proteins: application to expression of alpha and beta T-cell receptor extracellular segments", Proc. Natl Acad. Sci. USA 91, 11408-11412 (1994).
Charych et al., "Modeling the receptor pharmacology, pharmacokinetics, and pharmacodynamics of NKTR-214, a kinetically-controlled interleukin-2 (IL2) receptor agonist for cancer immunotherapy", PLoS One 12, e0179431 (2017).
Charych et al., "NKTR-214, an Engineered Cytokine with Biased IL2 Receptor Binding, Increased Tumor Exposure, and Marked Efficacy in Mouse Tumor Models", Clin. Cancer Res 22, 680-690 (2016).
Chaudhury et al., "PyRosetta: a script-based interface for implementing molecular modeling algorithms using Rosetta", Bioinformatics 26, 689-691 (2010).
Chen et al., "Combination therapy of an IL-15 superagonist complex, ALT-803, and a tumor targeting monoclonal antibody promotes direct antitumor activity and protective vaccinal efect in a syngenic mouse melanoma model", J. Immunother. Cancer 3, 347 (2015).
Chevalier et al., "Massively parallel de novo protein design for targeted therapeutics", with Supplementary Information, Nature 550(7674):74-79 (Sep. 2017).
Correia et al., "Proof of principle for epitope-focused vaccine design", Nature 507, 201-206 (2014).
Crooks et al., "WebLogo: a sequence logo generator", Genome Res. 14, 1188-1190 (2004).
D'Arcy et al., "Microseed matrix screening for optimization in protein crystallization: what have we learned?" Acta Crystallogr. F 70, 1117-1126 (2014).
De Groot et al., "Immunogenicity of protein therapeutics", Trends Immunol. 28, 482-490 (2007).
Domingues et al., "Rational Design of a GCN4-Derived Mimetic of Interleukin-4", Nature Structural Biology, 6(7):652-56 (Jul. 1999).
Dougan et al., "Immune Therapy for Cancer", Annu. Rev. Immunol. 27, 83-117 (2009).
Dougan et al., "Targeting Cytokine Therapy to the Pancreatic Tumor Microenvironment Using PD-L1-Specific VHHs", Cancer Immunol Res 6, 389-401 (2018).
Eckardt et al., "Pure red-cell aplasia due to anti-erythropoietin antibodies", Nephrol. Dial. Transplant 18, 865-869 (2003).
Eckenberg et al., "IL-2R[beta] Agonist P1-30 Acts in Synergy with IL-2, IL-4, IL-9, and IL-15: Biological and Molecular Effects", The Journal of Immunology, 165(8): 4312-18 (Oct. 2000).

(56) References Cited

OTHER PUBLICATIONS

Emsley et al., "Features and development of Coot. Acta Crystallogr", D 66, 486-501 (2010).
Essmann et al., "A smooth particle mesh Ewald method", J. Chem. Phys. 103, 8577-8593 (1995).
Evans, "How good are my data and what is the resolution?", Acta Crystallogr. D 69, 1204-1214 (2013).
Evans, "Scaling and assessment of data quality", Acta Crystallogr. D 62, 72-82 (2006).
Fehniger et al., "Interleukin 15: biology and relevance to human disease", Blood 97, 14-32 (2001).
Fineberg et al., "Immunological responses to exogenous insulin", Endocr. Rev. 28, 625-652 (2007).
Fleishman et al., "Computational design of proteins targeting the conserved stem region of infuenza hemagglutinin", Science 332, 816-821 (2011).
Fleishman et al., "RosettaScripts: a scripting language interface to the Rosetta macromolecular modeling suite", PLoS One 6, e20161 (2011).
Foit et al., "Optimizing Protein Stability In Vivo", Mol. Cell 36, 861-871 (2009).
Fontenot et al., "A function for interleukin 2 in Foxp3-expressing regulatory T cells", Nat. Immunol. 6, 1142-1151 (2005).
Frokjaer, et al., "Protein drug stability: a formulation challenge" Nat. Rev. Drug Discov. 4, 298 (2005).
Giri et al., "Identification and cloning of a novel IL-15 binding protein that is structurally related to the alpha chain of the IL-2 receptor", EMBO J. 14, 3654-63 (1995).
Goldenzweig et al., "Principles of Protein Stability and Their Application in Computational Design", Annu. Rev. Biochem. (2018). doi:10.1146/annurev-biochem-062917-012102.
Goodson, et al., "Site-directed pegylation of recombinant interleukin-2 at its glycosylation site", Biotechnology 8, 343-346 (1990).
He et al., "NMR structures of two designed proteins with high sequence identity but different fold and function", Proc. Natl. Acad. Sci U. S. A. 105, 14412-14417 (2008).
Hondowicz et al., "lnterleukin-2-dependent allergen-specifc tissue-resident memory cells drive asthma", Immunity 44, 155-166 (2016).
Hunter, "Matplotlib: a 2D graphics environment" Comput. Sci. Eng. 9, 90-95 (2007).
Jacobs et al., "Design of structurally distinct proteins using strategies inspired by evolution" Science 352, 687-690 (2016).
Jiang, et al., "S. Role of IL-2 in cancer immunotherapy", OncoImmunology 5, (2016).
Kabsch, "XDS", Acta Crystallogr D 66, 125-132 (2010).
Kang, et al., Tumor-targeted delivery of IL-2 by NKG2D leads to accumulation of antigen-specific CD8+ T cells in the tumor loci and enhanced anti-tumor effects. PLoS One 7, (2012).
Kim et al., "The sequences of small proteins are not extensively optimized for rapid folding by natural selection" Proceedings of the National Academy of Sciences 95, 4982-4986 (1998).
Knipper et al., Interleukin-4 Receptor α Signaling in Myeloid Cells Controls Collagen Fibril Assembly in Skin Repair, Immunity 43, 803-816 (2015).
Krieg, et al,., "Improved IL-2 immunotherapy by selective stimulation of IL-2 receptors on lymphocytes and endothelial cells", Proc. Natl. Acad. Sci. 107, 11906-11911 (2010).
Kureshi et al., "Reprogramming immune proteins as therapeutics using molecular engineering", Current Opinion in Chemical Engineering, 19:27-34 (Dec. 2017).
Kuziel et al., "Unexpected effects of the IL-2 receptor alpha subunit on high affinity IL-2 receptor assembly and function detected with a mutant IL-2 analog", J. Immunol. 150, 3357-3365 (1993).
Laporte et al., "De novo design of an IL-4 antagonist and its structure at 1.9 A" PNAS, 182(6):1889-94 (Jan. 2005).
Leaver-Fay et al., "Chapter nineteen—Rosetta3: An Object-oriented Software Suite for the Simulation and Design of Macromolecules" in "Protein Engineering", Academic Press, Amsterdam, NL, vol. 487:545-74 (2010).
Levin et al., "Exploiting a natural conformational switch to engineer an interleukin-2 'superkine'", Nature, vol. 19 Issue: 7395, p. 529-533 (2012).
Liao, et al., "W. J. Interleukin-2 at the Crossroads of Effector Responses, Tolerance, and Immunotherapy", Immunity 38, 13-25 (2013).
Lin et al., "The role of shared receptor motifs and common Stat proteins in the generation of cytokine pleiotropy and redundancy by IL-2, IL-4, IL-7, IL-13, and IL-15", Immunity 2, 331-339 (1995).
Lindorf-Larsen et al., "Improved side-chain torsion potentials for the Amber f99SB protein force feld" Proteins 78, 1950-1958(2010).
Liu et al., "Inclusion of Strep-Tag II in design of antigen receptors for T-cell immunotherapy", Nat. Biotechnol. 34, 430-434 (2016).
Lotze et al., "In vivo administration of purified human interleukin 2. II. Half life, immunologic effects, and expansion of peripheral lymphoid cells in vivo with recombinant IL 2", J. Immunol. 135, 2865-2875 (1985).
Ma et al., "The pleiotropic functions of interleukin 15: not so interleukin 2-like after all", J. Exp. Med. 191, 753-756 (2000).
Marcos et al., "Principles for designing proteins with cavities formed by curved β sheets", Science 355(6321):201-06 (2017).
Marshall et al., "Rational design and engineering of therapeutic proteins" Drug Discov. Today 8, 212-221 (2003).
McCoy et al., "Phaser crystallographic software" J Appl. Crystallogr. 40, 658-674 (2007).
Minami et al., "MICAN: a protein structure alignment algorithm that can handle multiple-chains, inverse alignments, Cα only models, alternative alignments, and non-sequential alignments", BMC Bioinformatics 14, 24 (2013).
Mitra et al., "Interleukin-2 Activity Can Be Fine Tuned with Engineered Receptor Signaling Clamps" Immunity. 42 (5):826-38 (May 2015).
Moraga et al. Synthekines are surrogate cytokine and growth factor agonists that compel signaling through non-natural receptor dimers. Elife 6, (2017).
Morin et al., "Collaboration gets the most out of software", eLife 2, e01456 (2013).
Mott et al., "The solution structure of the F42A mutant of human interleukin 2", J. Mol. Biol. 247, 979-994 (1995).
Oliphant, "Python for scientifc computing", Comput. Sci. Eng. 9, 10-20 (2007).
Ozaki et al., "Cytokine and cytokine receptor pleiotropy and redundancy", J. Biol. Chem. 277, 29355-29358 (2002).
Pall et al., "A fexible algorithm for calculating pair interactions on SIMD architectures", Comput. Phys. Commun. 184, 2641-2650 (2013).
Parrinello et al., "Polymorphic transitions in single crystals: A new molecular dynamics method", J. Appl. Phys. 52, 7182-7190 (1981).
Perez et al., "IPython: a system for interactive scienlifc computing", Comput. Sci. Eng. 9, 21-29 (2007).
Peyvandi et al., "A Randomized Trial of Factor VIII and Neutralizing Antibodies in Hemophilia A" N. Engl. J. Med. 374(21):2054-64 (May 2016).
Procko et al., "A computationally designed inhibitor of an Epstein-Barr viral Bcl-2 protein induces apoptosis in infected cells", Cell 157, 1644-1656 (2014).
Ring et al., "Mechanistic and structural insight into the functional dichotomy between IL-2 and IL-15", Nat. Immunol. 13, 1187-1195 (2012).
Roberts et al., "J. M. Chemistry for peptide and protein PEGylation", Adv. Drug Deliv. Rev. 64, 116-127 (2012).
Robinson et al., "The potential and promise of IL-15 in immuno-oncogenic therapies", Immunol. Lett. 190, 159-168 (2017).
Ruiz-Gomez et al., "Rational Structure-Based Rescaffolding Approach to De Novo Design of Interleukin 10 (IL-10) Receptor-1 Mimetics", PLOS ONE, 11(4):e0154046 (Apr. 2016).
Sakaguchi, "Naturally arising Foxp3-expressing CD25+CD4+ regulatory T cells in immunological tolerance to self and non-self" Nat. Immunol. (2005). doi:10.1038/ni1178.
Salmon-Her et al., "Implication of interleukin-4 in wound healing", Lab. Invest. 80, 1337-1343 (2000).

(56) References Cited

OTHER PUBLICATIONS

Sarkar et al., "Rational cytokine design for increased lifetime and enhanced potency using pH-activated 'histidine switching'". Nat. Biotechnol. 20, 908-913 (2002).
Siegel et al., "lnterleukin-2 toxicity", J. Clin. Oncol. 9, 694-704 (1991).
Silva et al., "De novo design of potent and selective mimics of IL-2 and IL-15", with Supplementary Information, Nature, 565(7738): 186-91 (Jan. 2019).
Silva et al., "Motif-Driven Design of Protein-Protein Interfaces", Methods Mol. Biol. 1414, 285-304 (2016).
Silva et al., "Structures and disulfide cross-linking of de novo designed therapeutic mini-proteins", FEBS J. (2018). doi:10.1111/febs.14394.
Sim et al., "IL2 Variant Circumvents ICOS+ Regulatory T-cell Expansion and Promotes NK Cell Activation" Cancer Immunology Research, vol. 4, Issue 11, p. 983-994 (Nov. 2016; Epub Oct. 3, 2016).
Smart et al., "Exploiting structure similarity in refnement: automated NCS and target-structure restraints in BUSTER", Acta Crystallogr. D 68, 368-380 (2012).

* cited by examiner

Neo-2/15 ternary crystal (with mIL-2βγ$_c$)

Melanoma (in vitro) proliferation of stimulated T-cells

FIG. 11E

| Position | 2 | 4 | 6 | 8 | 11 | 14 | 32 | 41 | 43 | 44 | 57 | 69 | 77 | 81 |
|---|---|---|---|---|---|---|---|---|---|---|---|---|---|---|
| Codon(s) used | RAS | RAS | SAS | YWC | YWC | YWC | GAW CGT | AWC | TWC ACC | GRA | GMC CTG | AAG GGT | GTT TCT | KTA TAT |
| Combinatorial mutations | D E N | D E N | E D H | H F Y | F Y L | H F Y | E D | N | Y F | E | A D | K | V | L Y |
| Original aa | K | K | Q | L | H | L | R | I | T | G | L | G | S | V |

FIG. 13E

| Position | 8 | 14 | 16 | 28 | 29 | 39 | 41 | 42 | 43 | 52 | 76 | 89 | 93 | 98 |
|---|---|---|---|---|---|---|---|---|---|---|---|---|---|---|
| Codon(s) used | YWC | YWC | MTS<br>GCG | CMG | AAC<br>CCC | THT | KYT | RRA | BTT | TWC<br>ATG | ACT<br>GAT | GAW<br>CGT | MTC | AWC |
| Combinatorial mutations | Y<br>F<br>H | Y<br>F<br>H | M<br>L<br>I | P | N | F<br>Y | A<br>S<br>F | K<br>R<br>G | F<br>L | F<br>Y | D | E<br>D | I | N |
| Original aa | L | L | A | Q | N | S | V | E | V | M | T | R | L | I |

IL-10; Neo-2/15

IL-10; Neo-2/15-PEG

IL-15; Neo-2/15-PEG

┌─ 300

310 Determine a structure for a plurality of residues of a protein using a computing device, where the structure of the plurality of residues provides a particular receptor binding interface;

↓

320 Determine a plurality of designed residues using a mimetic design protocol provided by the computing device, where the plurality of designed residues provide the particular receptor binding interface, and where the plurality of designed residues differ from the plurality of residues

↓

330 Determine one or more connecting helix structures that connect the plurality of designed residues using the computing device

↓

340 Determine a first protein backbone for the protein by assembling the one or more connecting helix structures and the plurality of designed residues over a plurality of combinations using the computing device

↓

350 Design a second protein backbone for the protein for flexibility and low energy structures based on the first protein backbone using the computing device

↓

360 Generate an output related to at least the second protein backbone

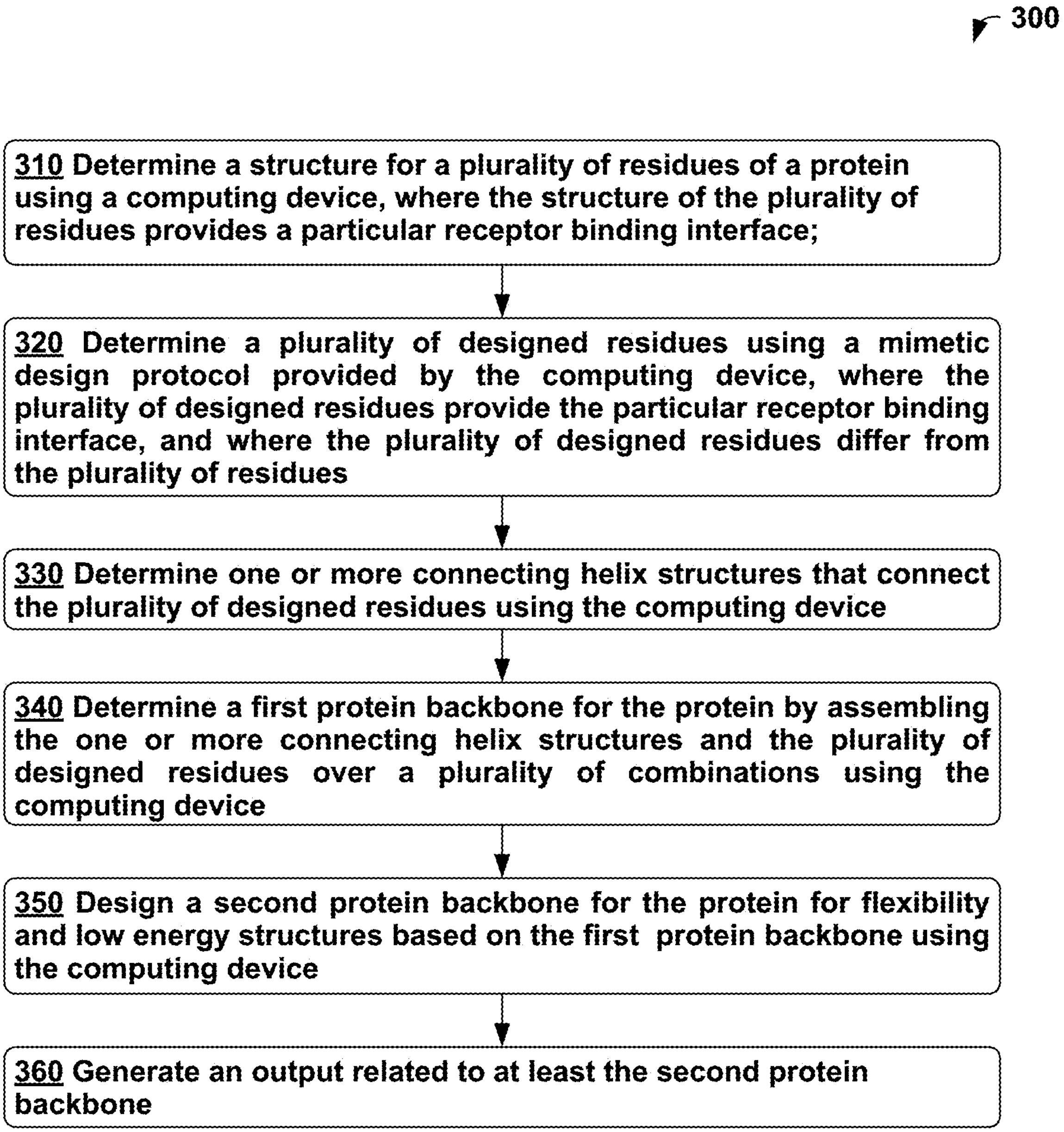

FIG. 24

SEQUENCE LISTING

<160> NUMBER OF SEQ ID NOS: 262

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Glu His Ala Leu Tyr Asp Ala Leu
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

Tyr Ala Phe Asn Phe Glu Leu Ile
1 5

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Ile Thr Ile Leu Gln Ser Trp Ile Phe
1 5

<210> SEQ ID NO 4
<211> LENGTH: 22
<212> TYPE: PRT
<213> ORGANISM: Artificial Sequence
<220> FEATURE:
<223> OTHER INFORMATION: Synthetic

<400> SEQUENCE: 4

Pro Lys Lys Lys Ile Gln Leu His Ala Glu His Ala Leu Tyr Asp Ala
1 5 10 15

Leu Met Ile Leu Asn Ile
20

<210> SEQ ID NO 5
<211> LENGTH: 22
<212> TYPE: PRT
<213> ORGANISM: Artificial Sequence
<220> FEATURE:
<223> OTHER INFORMATION: Synthetic

<400> SEQUENCE: 5

Leu Glu Asp Tyr Ala Phe Asn Phe Glu Leu Ile Leu Glu Glu Ile Ala
1 5 10 15

Arg Leu Phe Glu Ser Gly
20

<210> SEQ ID NO 6
<211> LENGTH: 21
<212> TYPE: PRT
<213> ORGANISM: Artificial Sequence
<220> FEATURE:
<223> OTHER INFORMATION: Synthetic

<400> SEQUENCE: 6

Glu Asp Glu Gln Glu Glu Met Ala Asn Ala Ile Ile Thr Ile Leu Gln
1 5 10 15

Ser Trp Ile Phe Ser
20

<210> SEQ ID NO 7
<211> LENGTH: 19
<212> TYPE: PRT
<213> ORGANISM: Artificial Sequence
<220> FEATURE:
<223> OTHER INFORMATION: Synthetic

<400> SEQUENCE: 7

Lys Asp Glu Ala Glu Lys Ala Lys Arg Met Lys Glu Trp Met Lys Arg
1 5 10 15

-continued

Ile Lys Thr

<210> SEQ ID NO 8
<211> LENGTH: 22
<212> TYPE: PRT
<213> ORGANISM: Artificial Sequence
<220> FEATURE:
<223> OTHER INFORMATION: Synthetic

<400> SEQUENCE: 8

Pro Lys Lys Lys Ile Gln Ile Met Ala Glu Glu Ala Leu Lys Asp Ala
1 5 10 15

Leu Ser Ile Leu Asn Ile
20

<210> SEQ ID NO 9
<211> LENGTH: 22
<212> TYPE: PRT
<213> ORGANISM: Artificial Sequence
<220> FEATURE:
<223> OTHER INFORMATION: Synthetic

<400> SEQUENCE: 9

Leu Glu Arg Phe Ala Lys Arg Phe Glu Arg Asn Leu Trp Gly Ile Ala
1 5 10 15

Arg Leu Phe Glu Ser Gly
20

<210> SEQ ID NO 10
<211> LENGTH: 21
<212> TYPE: PRT
<213> ORGANISM: Artificial Sequence
<220> FEATURE:
<223> OTHER INFORMATION: Synthetic

<400> SEQUENCE: 10

Glu Asp Glu Gln Glu Glu Met Ala Asn Ala Ile Ile Thr Ile Leu Gln
1 5 10 15

Ser Trp Phe Phe Ser
20

<210> SEQ ID NO 11
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally occurring amino acid or is optionally absent

<400> SEQUENCE: 11

Ser Thr Lys Lys Trp Gln Leu Gln Ala Glu His Ala Leu Leu Asp Trp
1 5 10 15

```
Gln Met Ala Leu Asn Lys Xaa Xaa Xaa Xaa Xaa Glu Asn Leu Asn Arg
            20                  25                  30

Ala Ile Thr Ala Ala Gln Ser Trp Ile Ser Xaa Xaa Xaa Xaa Xaa Leu
        35                  40                  45

Asp Lys Ala Glu Asp Ile Arg Arg Asn Ser Asp Gln Ala Arg Arg Glu
    50                  55                  60

Ala Glu Lys Xaa Xaa Xaa Xaa Xaa Arg Asp Leu Ile Ser Asn Ala Gln
65                  70                  75                  80

Val Ile Leu Leu Glu Ala Arg
                85
```

<210> SEQ ID NO 12
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 12

```
Ser Thr Lys Lys Trp Gln Leu Gln Ala Glu His Ala Leu Leu Asp Trp
1               5                   10                  15

Gln Met Ala Leu Asn Lys Xaa Xaa Xaa Xaa Xaa Glu Asn Leu Asn Arg
            20                  25                  30

Ala Ile Thr Ala Ala Gln Ser Cys Ile Ser Xaa Xaa Xaa Xaa Xaa Leu
        35                  40                  45

Asp Lys Ala Glu Asp Ile Arg Arg Asn Ser Asp Gln Ala Arg Arg Glu
    50                  55                  60

Ala Glu Lys Xaa Xaa Xaa Xaa Xaa Arg Asp Leu Ile Ser Asn Ala Gln
65                  70                  75                  80

Val Ile Leu Leu Glu Ala Arg
                85
```

<210> SEQ ID NO 13
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally occurring amino acid or is optionally absent

<400> SEQUENCE: 13

Ser Thr Lys Lys Trp Gln Leu Gln Ala Glu His Ala Leu Leu Asp Trp
1 5 10 15

Gln Met Ala Leu Asn Lys Xaa Xaa Xaa Xaa Xaa Glu Asn Leu Asn Arg
20 25 30

Ala Ile Thr Ala Ala Gln Ser Trp Ile Ser Xaa Xaa Xaa Xaa Xaa Cys
35 40 45

Asp Lys Ala Glu Asp Ile Arg Arg Asn Ser Asp Gln Ala Arg Arg Glu
50 55 60

Ala Glu Lys Xaa Xaa Xaa Xaa Xaa Arg Asp Leu Ile Ser Asn Ala Gln
65 70 75 80

Val Ile Leu Leu Glu Ala Cys
85

<210> SEQ ID NO 14
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
occurring amino acid or is optionally absent

<400> SEQUENCE: 14

Ser Thr Lys Lys Leu Gln Leu Gln Ala Glu His Phe Leu Leu Asp Val
1 5 10 15

Gln Met Ile Leu Asn Glu Xaa Xaa Xaa Xaa Xaa Glu Glu Leu Asn Arg
20 25 30

Ala Ile Thr Asp Ala Gln Ser Trp Ile Ser Xaa Xaa Xaa Xaa Xaa Leu
35 40 45

Asp Arg Ala Glu Glu Leu Ala Arg Asn Leu Glu Lys Val Arg Asp Glu
50 55 60

Ala Leu Lys Xaa Xaa Xaa Xaa Xaa Arg Asp Leu Val Ser Asn Ala Lys
65 70 75 80

Val Ile Ala Leu Glu Leu Lys
85

<210> SEQ ID NO 15
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 15

```
Ser Thr Lys Lys Leu Gln Leu Gln Ala Glu His Phe Leu Leu Asp Val
1               5                   10                  15

Gln Met Ile Leu Asn Glu Xaa Xaa Xaa Xaa Xaa Glu Glu Leu Asn Arg
            20                  25                  30

Cys Ile Thr Asp Ala Gln Ser Trp Ile Ser Xaa Xaa Xaa Xaa Xaa Leu
        35                  40                  45

Asp Arg Ala Glu Glu Cys Ala Arg Asn Leu Glu Lys Val Arg Asp Glu
    50                  55                  60

Ala Leu Lys Xaa Xaa Xaa Xaa Xaa Arg Asp Leu Val Ser Asn Ala Lys
65                  70                  75                  80

Val Ile Ala Leu Glu Leu Lys
                85
```

<210> SEQ ID NO 16
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 16

```
Ser Thr Lys Lys Leu Gln Leu Gln Ala Glu His Phe Leu Leu Asp Val
1               5                   10                  15

Gln Met Ile Leu Asn Glu Xaa Xaa Xaa Xaa Xaa Glu Glu Leu Asn Arg
            20                  25                  30

Ala Ile Thr Asp Ala Gln Ser Cys Ile Ser Xaa Xaa Xaa Xaa Xaa Leu
        35                  40                  45

Asp Arg Ala Glu Glu Leu Ala Arg Asn Leu Glu Lys Val Arg Asp Glu
    50                  55                  60

Ala Leu Lys Xaa Xaa Xaa Xaa Xaa Arg Asp Leu Val Ser Asn Ala Lys
65                  70                  75                  80

Val Ile Ala Leu Glu Leu Lys
                85
```

<210> SEQ ID NO 17
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 17

```
Ser Thr Lys Lys Leu Gln Leu Gln Ala Glu His Phe Leu Leu Asp Val
1               5                   10                  15

Gln Met Ile Leu Asn Glu Xaa Xaa Xaa Xaa Xaa Glu Glu Leu Asn Arg
            20                  25                  30

Ala Ile Thr Asp Ala Gln Ser Trp Ile Ser Xaa Xaa Xaa Xaa Xaa Leu
        35                  40                  45

Asp Arg Ala Glu Glu Leu Cys Arg Asn Leu Glu Lys Val Arg Asp Glu
    50                  55                  60

Ala Leu Lys Xaa Xaa Xaa Xaa Xaa Arg Asp Leu Val Ser Asn Ala Cys
65                  70                  75                  80

Val Ile Ala Leu Glu Leu Lys
                85
```

<210> SEQ ID NO 18
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 18

```
Ser Thr Lys Lys Leu Gln Leu Gln Ala Glu His Ala Leu Leu Asp Ala
1               5                   10                  15

Gln Met Met Leu Asn Arg Xaa Xaa Xaa Xaa Xaa Glu Lys Leu Asn Arg
            20                  25                  30

Ile Ile Thr Thr Met Gln Ser Trp Ile Ser Xaa Xaa Xaa Xaa Xaa Leu
        35                  40                  45

Asp Gly Ala Lys Glu Leu Ala Lys Glu Val Glu Glu Leu Arg Gln Glu
    50                  55                  60

Ala Glu Lys Xaa Xaa Xaa Xaa Xaa Arg Asp Leu Ala Ser Asn Leu Lys
65                  70                  75                  80

Val Ile Leu Leu Glu Leu Ala
                85
```

<210> SEQ ID NO 19
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
occurring amino acid or is optionally absent

<400> SEQUENCE: 19

```
Ser Thr Lys Lys Leu Gln Leu Gln Ala Glu His Ala Leu Leu Asp Ala
1               5                   10                  15

Gln Met Met Leu Asn Arg Xaa Xaa Xaa Xaa Xaa Glu Lys Leu Asn Arg
            20                  25                  30

Ile Ile Thr Thr Met Gln Ser Cys Ile Ser Xaa Xaa Xaa Xaa Xaa Leu
        35                  40                  45

Asp Gly Ala Lys Glu Leu Ala Lys Glu Val Glu Glu Leu Arg Gln Glu
    50                  55                  60

Ala Glu Lys Xaa Xaa Xaa Xaa Xaa Arg Asp Leu Ala Ser Asn Leu Lys
65                  70                  75                  80

Val Ile Leu Leu Glu Leu Ala
                85
```

<210> SEQ ID NO 20
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
occurring amino acid or is optionally absent

<400> SEQUENCE: 20

```
Ser Thr Lys Lys Ile Gln Leu Gln Leu Glu His Ala Leu Leu Asp Val
1               5                   10                  15

Gln Met Ala Leu Asn Arg Xaa Xaa Xaa Xaa Xaa Glu Ser Leu Asn Arg
            20                  25                  30

Met Ile Thr Trp Leu Gln Ser Trp Ile Ser Xaa Xaa Xaa Xaa Xaa Leu
        35                  40                  45

Asp Asn Ala Gln Glu Met Ala Lys Glu Ala Glu Lys Ile Arg Lys Glu
    50                  55                  60
```

```
Met Glu Lys Xaa Xaa Xaa Xaa Xaa Arg Asp Leu Ile Ser Asn Ile Ile
65                  70                  75                  80

Val Ile Leu Leu Glu Leu Ser
                85


<210> SEQ ID NO 21
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 21

Ser Thr Lys Lys Ile Gln Leu Gln Leu Glu His Ala Leu Leu Asp Val
1               5                   10                  15

Gln Met Ala Leu Asn Arg Xaa Xaa Xaa Xaa Xaa Glu Ser Leu Asn Arg
            20                  25                  30

Met Ile Thr Trp Leu Gln Ser Cys Ile Ser Xaa Xaa Xaa Xaa Xaa Leu
        35                  40                  45

Asp Asn Ala Gln Glu Met Ala Lys Glu Ala Glu Lys Ile Arg Lys Glu
    50                  55                  60

Met Glu Lys Xaa Xaa Xaa Xaa Xaa Arg Asp Leu Ile Ser Asn Ile Ile
65                  70                  75                  80

Val Ile Leu Leu Glu Leu Ser
                85


<210> SEQ ID NO 22
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 22

Ser Thr Lys Lys Ile Gln Leu Gln Leu Glu His Ala Leu Leu Asp Val
1               5                   10                  15

Gln Met Ala Leu Asn Arg Xaa Xaa Xaa Xaa Xaa Glu Ser Leu Asn Arg
```

```
            20                  25                  30

Met Ile Thr Trp Leu Gln Ser Trp Ile Ser Xaa Xaa Xaa Xaa Xaa Leu
        35                  40                  45

Asp Asn Ala Gln Glu Met Cys Lys Glu Ala Glu Lys Ile Arg Lys Glu
    50                  55                  60

Met Glu Lys Xaa Xaa Xaa Xaa Xaa Arg Asp Leu Ile Ser Asn Ile Cys
65                  70                  75                  80

Val Ile Leu Leu Glu Leu Ser
                85
```

<210> SEQ ID NO 23
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally occurring amino acid or is optionally absent

<400> SEQUENCE: 23

```
Ser Thr Lys Lys Thr Gln Leu Leu Ala Glu His Ala Leu Leu Asp Ala
1               5                   10                  15

Phe Met Met Leu Asn Val Xaa Xaa Xaa Xaa Xaa Glu Lys Leu Asn Arg
            20                  25                  30

Ile Ile Thr Thr Met Gln Ser Trp Ile Tyr Xaa Xaa Xaa Xaa Xaa Ala
        35                  40                  45

Asp Gly Ala Lys Glu Leu Ala Lys Glu Val Glu Glu Leu Glu Gln Glu
    50                  55                  60

Tyr Glu Lys Xaa Xaa Xaa Xaa Xaa Glu Asp Asp Ala Ser Asn Leu Lys
65                  70                  75                  80

Val Ile Leu Leu Glu Leu Ala
                85
```

<210> SEQ ID NO 24
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally occurring amino acid or is optionally absent

<400> SEQUENCE: 24

Ser Thr Lys Lys Thr Gln Leu Leu Ala Glu His Ala Leu Leu Asp Ala
1 5 10 15

His Met Met Leu Asn Met Xaa Xaa Xaa Xaa Xaa Glu Lys Leu Asn Arg
20 25 30

Ile Ile Thr Thr Met Gln Ser Trp Ile His Xaa Xaa Xaa Xaa Xaa Gly
35 40 45

Asp Gly Ala Gln Glu Leu Ala Lys Glu Val Glu Glu Leu Glu Gln Glu
50 55 60

Tyr Glu Lys Xaa Xaa Xaa Xaa Xaa Glu Asp Glu Ala Ser Asn Leu Lys
65 70 75 80

Val Ile Leu Leu Glu Leu Ala
85

<210> SEQ ID NO 25
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(37)
<223> OTHER INFORMATION: Xaa, when present, can be any naturally occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally occurring amino acid or is optionally absentt

<400> SEQUENCE: 25

Ser Thr Lys Lys Thr Gln Leu Leu Ala Glu His Ala Leu Leu Asp Ala
1 5 10 15

Phe Met Met Leu Asn Met Xaa Xaa Xaa Xaa Xaa Glu Lys Leu Asn Arg
20 25 30

Ile Ile Thr Thr Met Gln Ser Trp Ile Phe Xaa Xaa Xaa Xaa Xaa Gly
35 40 45

Asp Gly Ala Lys Glu Leu Ala Lys Glu Val Glu Glu Leu Glu Gln Glu
50 55 60

Phe Glu Lys Xaa Xaa Xaa Xaa Xaa Glu Asp Glu Ala Ser Asn Leu Lys
65 70 75 80

Val Ile Leu Leu Glu Leu Ala
85

<210> SEQ ID NO 26
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally occurring amino acid or is optionally absent
<220> FEATURE:
<221> NAME/KEY: MISC_FEATURE
<222> LOCATION: (43)..(47)

<223> OTHER INFORMATION: Xaa, when present, can be any naturally occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally occurring amino acid or is optionally absent

<400> SEQUENCE: 26

```
Ser Thr Lys Lys Thr Gln Leu Leu Ala Glu His Ala Leu Leu Asp Ala
1               5                   10                  15

Leu Met Met Leu Asn Met Xaa Xaa Xaa Xaa Xaa Glu Lys Leu Asn Arg
            20                  25                  30

Ile Ile Thr Thr Met Gln Ser Trp Ile Phe Xaa Xaa Xaa Xaa Xaa Gly
        35                  40                  45

Asp Gly Ala Gln Glu Leu Ala Lys Glu Val Glu Glu Leu Glu Gln Glu
    50                  55                  60

Leu Glu Lys Xaa Xaa Xaa Xaa Xaa Glu Asp Tyr Ala Ser Asn Leu Lys
65                  70                  75                  80

Val Ile Leu Leu Glu Leu Ala
                85
```

<210> SEQ ID NO 27
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally occurring amino acid or is optionally absent

<400> SEQUENCE: 27

```
Ser Thr Lys Lys Thr Gln Leu Leu Ala Glu His Ala Leu Leu Asp Ala
1               5                   10                  15

His Met Met Leu Asn Val Xaa Xaa Xaa Xaa Xaa Glu Lys Leu Asn Arg
            20                  25                  30

Ile Ile Thr Thr Met Gln Ser Trp Ile Tyr Xaa Xaa Xaa Xaa Xaa Arg
        35                  40                  45

Asp Gly Ala Gln Glu Leu Ala Lys Glu Val Glu Glu Leu Glu Gln Glu
    50                  55                  60

Leu Glu Lys Xaa Xaa Xaa Xaa Xaa Asp Asp Asp Ala Ser Asn Leu Lys
65                  70                  75                  80

Val Ile Leu Leu Glu Leu Ala
                85
```

<210> SEQ ID NO 28
<211> LENGTH: 87
<212> TYPE: PRT
<213> ORGANISM: Artificial Sequence
<220> FEATURE:
<223> OTHER INFORMATION: Synthetic
<220> FEATURE:

```
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 28

Ser Thr Lys Lys Thr Gln Leu Leu Ala Glu His Ala Leu Leu Asp Ala
1               5                   10                  15

Leu Met Met Leu Asn Leu Xaa Xaa Xaa Xaa Xaa Glu Lys Leu Asn Arg
            20                  25                  30

Ile Ile Thr Thr Met Gln Ser Trp Ile Phe Xaa Xaa Xaa Xaa Xaa Gly
        35                  40                  45

Asp Gly Ala Gln Glu Leu Ala Lys Glu Val Glu Glu Leu Glu Gln Glu
    50                  55                  60

His Glu Lys Xaa Xaa Xaa Xaa Xaa Glu Asp Tyr Ala Ser Asn Leu Lys
65                  70                  75                  80

Val Ile Leu Leu Glu Leu Ala
                85


<210> SEQ ID NO 29
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 29

Ser Thr Lys Lys Thr Gln Leu Leu Ala Glu His Ala Leu Leu Asp Ala
1               5                   10                  15

Tyr Met Met Leu Asn Met Xaa Xaa Xaa Xaa Xaa Glu Lys Leu Asn Arg
            20                  25                  30

Ile Ile Thr Thr Met Gln Ser Trp Ile Leu Xaa Xaa Xaa Xaa Xaa Ser
        35                  40                  45

Asp Gly Ala Gln Glu Leu Ala Lys Glu Val Glu Glu Leu Glu Gln Glu
    50                  55                  60

Leu Glu Lys Xaa Xaa Xaa Xaa Xaa Asp Asp Asp Ala Ser Asn Leu Lys
65                  70                  75                  80

Val Ile Leu Leu Glu Leu Ala
                85
```

```
<210> SEQ ID NO 30
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 30

Ser Thr Lys Lys Thr His Leu Leu Ala Glu His Ala Leu Leu Asp Ala
1               5                   10                  15

Tyr Met Met Leu Asn Val Xaa Xaa Xaa Xaa Xaa Glu Lys Leu Asn Arg
            20                  25                  30

Ile Ile Thr Thr Met Gln Ser Trp Ile Phe Xaa Xaa Xaa Xaa Xaa Gly
        35                  40                  45

Asp Gly Ala Lys Glu Leu Ala Lys Glu Val Glu Glu Leu Glu Gln Glu
    50                  55                  60

Phe Glu Lys Xaa Xaa Xaa Xaa Xaa Asp Asp Asp Ala Ser Asn Leu Lys
65                  70                  75                  80

Val Ile Leu Leu Glu Leu Ala
                85


<210> SEQ ID NO 31
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 31

Ser Thr Lys Lys Thr Gln Leu Leu Ala Glu His Ala Leu Leu Asp Ala
1               5                   10                  15

Tyr Met Met Leu Asn Leu Xaa Xaa Xaa Xaa Xaa Glu Lys Leu Asn Arg
            20                  25                  30

Ile Ile Thr Thr Met Gln Ser Trp Ile Phe Xaa Xaa Xaa Xaa Xaa Ala
        35                  40                  45

Asp Gly Ala Gln Glu Leu Ala Ile Glu Val Glu Glu Leu Glu Gln Glu
    50                  55                  60
```

Tyr Glu Lys Xaa Xaa Xaa Xaa Xaa Asp Asp Tyr Ala Ser Asn Leu Lys
65 70 75 80

Val Ile Leu Leu Glu Leu Ala
85

<210> SEQ ID NO 32
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(27)
<223> OTHER INFORMATION: Xaa, when present, can be any naturally occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally occurring amino acid or is optionally absent

<400> SEQUENCE: 32

Ser Thr Lys Lys Thr Gln Leu Met Ala Glu His Ala Leu Leu Asp Ala
1 5 10 15

Phe Met Met Leu Asn Xaa Xaa Xaa Xaa Xaa Xaa Glu Lys Leu Asn Arg
20 25 30

Ile Ile Thr Thr Met Gln Ser Trp Ile Phe Xaa Xaa Xaa Xaa Xaa Gly
35 40 45

Asp Asp Ala Gln Glu Leu Ala Lys Glu Val Glu Glu Leu Glu Gln Glu
50 55 60

Leu Glu Lys Xaa Xaa Xaa Xaa Xaa Asp Asp Asp Ala Ser Asn Leu Lys
65 70 75 80

Val Ile Leu Leu Glu Leu Ala
85

<210> SEQ ID NO 33
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(27)
<223> OTHER INFORMATION: Xaa, when present, can be any naturally occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally occurring amino acid or is optionally absent

<400> SEQUENCE: 33

Ser Thr Lys Lys Thr Gln Leu Leu Ile Glu His Ala Leu Leu Asp Ala
1 5 10 15

Leu Asp Met Ser Arg Xaa Xaa Xaa Xaa Xaa Xaa Glu Lys Leu Ser Arg
20 25 30

```
Ile Ile Thr Thr Met Gln Ser Trp Ile Phe Xaa Xaa Xaa Xaa Xaa Gly
        35                  40                  45

Asp Gly Ala Gln Gln Leu Ala Lys Glu Val Glu Glu Leu Glu Gln Glu
    50                  55                  60

His Glu Lys Xaa Xaa Xaa Xaa Xaa Glu Asp Glu Ala Ser Asn Leu Lys
65                  70                  75                  80

Val Ile Leu Leu Glu Leu Ala
                85


<210> SEQ ID NO 34
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 34

Ser Thr Lys Lys Thr Gln Leu Leu Leu Glu His Ala Leu Leu Asp Ala
1               5                   10                  15

Leu His Met Arg Arg Xaa Xaa Xaa Xaa Xaa Xaa Glu Lys Leu Ser Arg
            20                  25                  30

Ile Ile Thr Thr Met Gln Ser Trp Ile Phe Xaa Xaa Xaa Xaa Xaa Gly
        35                  40                  45

Asp Gly Ala Gln Glu Leu Ala Lys Glu Val Glu Glu Leu Glu Gln Glu
    50                  55                  60

His Glu Lys Arg Gly Arg Asp Val Glu Asp Asp Ala Ser Asn Leu Lys
65                  70                  75                  80

Val Ile Leu Leu Glu Leu Ala
                85


<210> SEQ ID NO 35
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent
```

<400> SEQUENCE: 35

```
Ser Thr Lys Lys Thr Gln Leu Leu Ile Glu His Ala Leu Leu Asp Ala
1               5                   10                  15

Leu Asn Met Arg Lys Xaa Xaa Xaa Xaa Xaa Xaa Glu Lys Leu Ser Arg
            20                  25                  30

Ile Ile Thr Asp Met Gln Ser Trp Ile Phe Xaa Xaa Xaa Xaa Xaa Gly
        35                  40                  45

Asp Gly Ala Gln Gln Leu Ala Lys Glu Val Glu Glu Leu Glu Gln Glu
    50                  55                  60

His Glu Lys Xaa Xaa Xaa Xaa Xaa Glu Asp Tyr Ala Ser Asn Leu Lys
65                  70                  75                  80

Val Ile Leu Leu Glu Leu Ala
                85
```

<210> SEQ ID NO 36
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(27)
<223> OTHER INFORMATION: Xaa, when present, can be any naturally occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally occurring amino acid or is optionally absent

<400> SEQUENCE: 36

```
Ser Thr Lys Lys Thr Gln Leu Leu Leu Glu His Ala Leu Leu Asp Ala
1               5                   10                  15

Leu His Met Ser Arg Xaa Xaa Xaa Xaa Xaa Xaa Glu Lys Leu Asn Arg
            20                  25                  30

Ile Ile Thr Asp Met Gln Ser Trp Ile Phe Xaa Xaa Xaa Xaa Xaa Gly
        35                  40                  45

Asp Gly Ala Gln Asp Leu Ala Lys Glu Val Glu Glu Leu Glu Gln Glu
    50                  55                  60

His Glu Lys Xaa Xaa Xaa Xaa Xaa Glu Asp Tyr Ala Ser Asn Leu Lys
65                  70                  75                  80

Val Ile Leu Leu Glu Leu Ala
                85
```

<210> SEQ ID NO 37
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(27)
<223> OTHER INFORMATION: Xaa, when present, can be any naturally occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
occurring amino acid or is optionally absent

<400> SEQUENCE: 37

```
Ser Thr Lys Lys Thr Gln Leu Leu Ile Glu His Ala Leu Leu Asp Ala
1               5                   10                  15

Leu His Met Ser Arg Xaa Xaa Xaa Xaa Xaa Xaa Glu Lys Leu Ser Arg
            20                  25                  30

Ile Ile Thr Thr Met Gln Ser Trp Ile Phe Xaa Xaa Xaa Xaa Xaa Gly
        35                  40                  45

Asp Gly Ala Gln His Leu Ala Lys Glu Val Glu Glu Leu Glu Gln Glu
    50                  55                  60

His Glu Lys Xaa Xaa Xaa Xaa Xaa Glu Asp Glu Ala Ser Asn Leu Lys
65                  70                  75                  80

Val Ile Leu Leu Glu Leu Ala
                85
```

<210> SEQ ID NO 38
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(27)
<223> OTHER INFORMATION: Xaa, when present, can be any naturally
occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
occurring amino acid or is optionally absent

<400> SEQUENCE: 38

```
Ser Thr Lys Lys Thr Gln Leu Leu Ile Glu His Ala Leu Leu Asp Ala
1               5                   10                  15

Leu His Met Lys Arg Xaa Xaa Xaa Xaa Xaa Xaa Glu Lys Leu Asn Arg
            20                  25                  30

Ile Ile Thr Asn Met Gln Ser Trp Ile Phe Xaa Xaa Xaa Xaa Xaa Gly
        35                  40                  45

Asp Gly Ala Gln Asp Leu Ala Lys Glu Val Glu Glu Leu Glu Gln Glu
    50                  55                  60

His Glu Lys Xaa Xaa Xaa Xaa Xaa Glu Asp Tyr Ala Ser Asn Leu Lys
65                  70                  75                  80

Val Ile Leu Leu Glu Leu Ala
                85
```

<210> SEQ ID NO 39
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally occurring amino acid or is optionally absent

<400> SEQUENCE: 39

```
Ser Thr Glu Lys Thr Gln Leu Ala Ala Glu His Ala Leu Arg Asp Ala
1               5                   10                  15

Leu Met Leu Lys His Leu Xaa Xaa Xaa Xaa Xaa Glu Lys Leu Ala Arg
            20                  25                  30

Ile Ile Thr Thr Met Gln Ser Trp Gln Phe Xaa Xaa Xaa Xaa Xaa Gly
        35                  40                  45

Asp Gly Ala Gln Glu Leu Ala Lys Glu Val Glu Glu Leu Gln Gln Glu
    50                  55                  60

His Glu Val Xaa Xaa Xaa Xaa Xaa Glu Asp Tyr Ala Ser Asn Leu Lys
65                  70                  75                  80

Val Ile Leu Leu His Leu Ala
                85
```

<210> SEQ ID NO 40
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally occurring amino acid or is optionally absent

<400> SEQUENCE: 40

```
Ser Thr Lys Asn Thr Gln Leu Ala Ala Glu Asp Ala Leu Leu Asp Ala
1               5                   10                  15

Leu Met Leu Arg Asn Leu Xaa Xaa Xaa Xaa Xaa Glu Lys Leu Ala Arg
            20                  25                  30

Ile Ile Thr Thr Met Gln Ser Trp Gln Phe Xaa Xaa Xaa Xaa Xaa Gly
        35                  40                  45

Asp Gly Ala Gln Glu Leu Ala Lys Glu Val Glu Glu Leu Gln Gln Glu
    50                  55                  60

His Glu Glu Xaa Xaa Xaa Xaa Xaa Glu Asp Tyr Ala Ser Asn Leu Lys
65                  70                  75                  80

Val Ile Leu Leu Gln Leu Ala
                85
```

<210> SEQ ID NO 41

```
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(47)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(72)
<223> OTHER INFORMATION: Xaa, when present, can be any naturally
      occurring amino acid or is optionally absent

<400> SEQUENCE: 41

Ser Thr Glu Lys Thr Gln His Ala Ala Glu Asp Ala Leu Arg Asp Ala
1               5                   10                  15

Leu Met Leu Arg Asn Leu Xaa Xaa Xaa Xaa Xaa Glu Lys Leu Ala Arg
            20                  25                  30

Ile Ile Thr Thr Met Gln Ser Trp Gln Phe Xaa Xaa Xaa Xaa Xaa Gly
        35                  40                  45

Asp Gly Ala Gln Glu Leu Ala Lys Glu Val Glu Glu Leu Gln Gln Glu
    50                  55                  60

His Glu Val Xaa Xaa Xaa Xaa Xaa Glu Asp Tyr Ala Ser Asn Leu Lys
65                  70                  75                  80

Val Ile Leu Leu Gln Leu Ala
                85


<210> SEQ ID NO 42
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(30)
<223> OTHER INFORMATION: Xaa, when present, can be any naturally
      occurring amino acid or is optionally absent
<220> FEATURE:
<221> NAME/KEY: MISC_FEATURE
<222> LOCATION: (45)..(49)
<223> OTHER INFORMATION: Xaa, when present, can be any naturally
      occurring amino acid or is optionally absent
<220> FEATURE:
<221> NAME/KEY: MISC_FEATURE
<222> LOCATION: (69)..(72)
<223> OTHER INFORMATION: Xaa, when present, can be any naturally
      occurring amino acid or is optionally absent

<400> SEQUENCE: 42

Thr Gln Lys Lys Gln Gln Leu Leu Ala Glu His Ala Leu Leu Asp Ala
1               5                   10                  15

Leu Met Ile Leu Asn Met Xaa Xaa Xaa Xaa Xaa Xaa Xaa Xaa Asn Arg
            20                  25                  30

Met Ile Thr Ile Ala Gln Ser Trp Ile Phe Thr Gly Xaa Xaa Xaa Xaa
        35                  40                  45

Xaa Glu Ala Lys Glu Met Ile Lys Met Ala Glu Gln Ala Glu Glu Glu
    50                  55                  60

Ala Arg Arg Glu Xaa Xaa Xaa Xaa Glu Asp Tyr Val Ser Asn Leu Lys
```

```
65                  70                  75                  80

Val Ile Leu Lys Glu Ile Ala
                85


<210> SEQ ID NO 43
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 43

Thr Thr Lys Lys Tyr Gln Leu Leu Val Glu His Ala Leu Leu Asp Ala
1               5                   10                  15

Leu Met Met Leu Asn Leu Xaa Xaa Xaa Xaa Xaa Xaa Lys Met Asn Arg
            20                  25                  30

Ile Ile Thr Thr Met Gln Ser Trp Ile Phe Xaa Xaa Xaa Xaa Xaa Xaa
        35                  40                  45

Asp Gln Ala Glu Glu Leu Ala Lys Leu Val Glu Glu Leu Arg Glu Glu
    50                  55                  60

Phe Arg Lys Xaa Xaa Xaa Xaa Xaa Xaa Asp Tyr Ala Ser Asn Leu Lys
65                  70                  75                  80

Val Ile Leu Lys Glu Leu Ser
                85


<210> SEQ ID NO 44
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 44

Thr Thr Lys Lys Ile Gln Leu Leu Val Glu His Ala Leu Leu Asp Ala
1               5                   10                  15

Leu Met Ile Leu Asn Leu Xaa Xaa Xaa Xaa Xaa Xaa Lys Leu Asn Arg
            20                  25                  30
```

```
Ile Ile Thr Thr Leu Gln Ser Trp Ile Phe Xaa Xaa Xaa Xaa Xaa Xaa
        35                  40                  45

Asp Arg Ala Arg Glu Leu Ala Lys Leu Leu Glu Glu Ile Arg Glu Glu
    50                  55                  60

Met Arg Lys Xaa Xaa Xaa Xaa Xaa Xaa Asp Tyr Val Ser Asn Met Ile
65                  70                  75                  80

Val Ile Ile Arg Glu Leu Ala
                85
```

```
<210> SEQ ID NO 45
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 45

Thr Lys Lys Lys Ile Gln Leu Leu Ala Glu His Val Leu Leu Asp Leu
1               5                   10                  15

Leu Met Met Leu Asn Leu Xaa Xaa Xaa Xaa Xaa Xaa Lys Met Asn Arg
            20                  25                  30

Leu Ile Thr Ile Val Gln Ser Trp Ile Phe Xaa Xaa Xaa Xaa Xaa Xaa
        35                  40                  45

Asp Gln Ala Glu Glu Met Ala Lys Trp Val Glu Glu Leu Arg Glu Glu
    50                  55                  60

Phe Arg Lys Xaa Xaa Xaa Xaa Xaa Xaa Asp Tyr Ala Ser Asn Val Lys
65                  70                  75                  80

Val Ile Leu Lys Glu Leu Ser
                85
```

```
<210> SEQ ID NO 46
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 46
```

Thr Lys Lys Lys Tyr Gln Leu Leu Ile Glu His Leu Leu Leu Asp Ala
1 5 10 15

Leu Met Val Leu Asn Met Xaa Xaa Xaa Xaa Xaa Xaa Lys Leu Asn Arg
20 25 30

Ile Ile Thr Ile Leu Gln Ser Trp Ile Phe Xaa Xaa Xaa Xaa Xaa Xaa
35 40 45

Asp Leu Ala Glu Glu Met Glu Lys Leu Met Gln Glu Ile Glu Glu Glu
50 55 60

Leu Arg Arg Xaa Xaa Xaa Xaa Xaa Xaa Asp Tyr Met Ser Asn Met Arg
65 70 75 80

Val Ile Ile Lys Glu Leu Ser
85

<210> SEQ ID NO 47
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally occurring amino acid or is optionally absent

<400> SEQUENCE: 47

Thr Lys Lys Lys Leu Gln Leu Leu Val Glu His Leu Leu Leu Asp Met
1 5 10 15

Leu Met Ile Leu Asn Met Xaa Xaa Xaa Xaa Xaa Xaa Lys Leu Asn Arg
20 25 30

Leu Ile Thr Glu Leu Gln Ser Trp Ile Phe Xaa Xaa Xaa Xaa Xaa Xaa
35 40 45

Asp Lys Ala Glu Glu Met Trp Lys Ile Met Glu Glu Ile Glu Lys Glu
50 55 60

Leu Arg Glu Xaa Xaa Xaa Xaa Xaa Xaa Asp Tyr Met Ser Asn Ala Lys
65 70 75 80

Val Ile Ile Lys Glu Leu Ser
85

<210> SEQ ID NO 48
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally occurring amino acid or is optionally absent

<400> SEQUENCE: 48

```
Thr Ser Lys Lys Gln Gln Leu Leu Ala Glu His Ala Leu Leu Asp Ala
1               5                   10                  15

Leu Met Ile Leu Asn Ile Xaa Xaa Xaa Xaa Xaa Xaa Ala Val Asn Arg
            20                  25                  30

Ala Ile Thr Trp Leu Gln Ser Trp Ile Phe Xaa Xaa Xaa Xaa Xaa Xaa
        35                  40                  45

Asp Gln Ala Glu Glu Met Arg Lys Leu Ala Glu Gln Ile Arg Glu Glu
    50                  55                  60

Met Arg Lys Xaa Xaa Xaa Xaa Xaa Xaa Asp Tyr Val Ser Asn Leu Glu
65                  70                  75                  80

Val Ile Ala Lys Glu Leu Ser
                85
```

<210> SEQ ID NO 49
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally occurring amino acid or is optionally absent

<400> SEQUENCE: 49

```
Thr Lys Lys Lys Tyr Gln Leu Leu Ile Glu His Leu Leu Leu Asp Leu
1               5                   10                  15

Leu Met Val Leu Asn Met Xaa Xaa Xaa Xaa Xaa Xaa Lys Ile Asn Arg
            20                  25                  30

Leu Ile Thr Trp Leu Gln Ser Trp Ile Phe Xaa Xaa Xaa Xaa Xaa Xaa
        35                  40                  45

Asp Leu Ala Glu Glu Met Tyr Lys Ile Leu Glu Glu Leu Arg Glu Glu
    50                  55                  60

Met Arg Glu Xaa Xaa Xaa Xaa Xaa Xaa Asp Tyr Met Ser Asn Met Arg
65                  70                  75                  80

Val Ile Val Lys Glu Leu Ser
                85
```

<210> SEQ ID NO 50
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)

<223> OTHER INFORMATION: Xaa, when present, can be any naturally occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally occurring amino acid or is optionally absent

<400> SEQUENCE: 50

```
Thr Lys Lys Lys Trp Gln Leu Leu Ile Glu His Leu Leu Leu Asp Leu
1               5                   10                  15

Leu Met Ile Leu Asn Leu Xaa Xaa Xaa Xaa Xaa Xaa Lys Leu Asn Arg
            20                  25                  30

Leu Ile Thr Trp Leu Gln Ser Trp Ile Phe Xaa Xaa Xaa Xaa Xaa Xaa
        35                  40                  45

Asp Leu Ala Glu Glu Met Lys Lys Met Met Asp Glu Ile Glu Asp Glu
    50                  55                  60

Leu Arg Glu Xaa Xaa Xaa Xaa Xaa Xaa Asp Tyr Met Ser Asn Ala Lys
65                  70                  75                  80

Val Ile Ile Lys Glu Leu Ser
                85
```

<210> SEQ ID NO 51
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally occurring amino acid or is optionally absent

<400> SEQUENCE: 51

```
Thr Lys Lys Lys Ile Gln Leu Leu Val Glu His Ala Leu Leu Asp Ala
1               5                   10                  15

Leu Met Ile Leu Asn Leu Xaa Xaa Xaa Xaa Xaa Xaa Lys Leu Asn Arg
            20                  25                  30

Ile Ile Thr Thr Met Gln Ser Trp Ile Phe Xaa Xaa Xaa Xaa Xaa Xaa
        35                  40                  45

Asp Gln Ala Glu Glu Leu Ser Lys Leu Val Glu Glu Ile Arg Glu Glu
    50                  55                  60

Met Arg Lys Xaa Xaa Xaa Xaa Xaa Xaa Asp Tyr Val Ser Asn Leu Lys
65                  70                  75                  80

Val Ile Leu Asp Glu Leu Ser
                85
```

<210> SEQ ID NO 52
<211> LENGTH: 87

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (24)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 52

Thr Glu Lys Lys Leu Gln Leu Leu Val Glu His Ala Leu Leu Asp Ala
1               5                   10                  15

Leu Met Ile Leu Asn Leu Trp Xaa Xaa Xaa Xaa Xaa Lys Leu Asn Arg
            20                  25                  30

Ile Ile Thr Thr Met Gln Ser Trp Ile Phe Xaa Xaa Xaa Xaa Xaa Xaa
        35                  40                  45

Asp Lys Ala Glu Glu Leu Ala Lys Leu Val Glu Glu Leu Arg Glu Glu
    50                  55                  60

Ala Arg Glu Xaa Xaa Xaa Xaa Xaa Xaa Asp Tyr Val Ser Asn Leu Lys
65                  70                  75                  80

Val Ile Leu Lys Glu Leu Ser
                85


<210> SEQ ID NO 53
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 53

Thr Lys Lys Lys Tyr Gln Leu Leu Met Glu His Leu Leu Leu Asp Leu
1               5                   10                  15

Leu Met Val Leu Asn Met Xaa Xaa Xaa Xaa Xaa Xaa Lys Leu Asn Arg
            20                  25                  30

Leu Ile Thr Ile Ile Gln Ser Trp Ile Phe Xaa Xaa Xaa Xaa Xaa Xaa
        35                  40                  45

Asp Lys Ala Glu Glu Met Ala Lys Met Leu Lys Glu Ile Glu Asp Glu
    50                  55                  60

Leu Arg Glu Xaa Xaa Xaa Xaa Xaa Xaa Asp Tyr Met Ser Asn Met Ile
65                  70                  75                  80
```

```
Val Ile Met Lys Glu Leu Ser
                85


<210> SEQ ID NO 54
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 54

Thr Thr Lys Lys Ile Gln Leu Leu Val Glu His Ala Leu Leu Asp Ala
1               5                   10                  15

Leu Met Leu Leu Asn Leu Xaa Xaa Xaa Xaa Xaa Xaa Lys Met Asn Arg
            20                  25                  30

Ile Ile Thr Thr Met Gln Ser Trp Ile Phe Xaa Xaa Xaa Xaa Xaa Xaa
        35                  40                  45

Asp Gln Ala Gln Glu Leu Ala Lys Leu Val Glu Glu Leu Arg Glu Glu
    50                  55                  60

Phe Arg Lys Xaa Xaa Xaa Xaa Xaa Xaa Asp Tyr Val Ser Asn Leu Lys
65                  70                  75                  80

Val Ile Leu Glu Glu Leu Ser
                85


<210> SEQ ID NO 55
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 55

Thr Lys Lys Lys Ile Gln Leu Leu Val Glu His Ala Leu Leu Asp Ala
1               5                   10                  15

Leu Met Met Leu Asn Leu Xaa Xaa Xaa Xaa Xaa Xaa Lys Leu Asn Arg
            20                  25                  30

Ile Ile Thr Thr Met Gln Ser Trp Ile Phe Xaa Xaa Xaa Xaa Xaa Xaa
```

```
        35                  40                  45

Asp Gln Ala Glu Glu Leu Ala Lys Leu Val Arg Glu Leu Arg Glu Glu
    50                  55                  60

Phe Arg Lys Xaa Xaa Xaa Xaa Xaa Xaa Asp Tyr Ala Ser Asn Leu Glu
65                  70                  75                  80

Val Ile Leu Arg Glu Leu Ser
                85
```

<210> SEQ ID NO 56
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally occurring amino acid or is optionally absent

<400> SEQUENCE: 56

```
Thr Lys Lys Lys Ile Gln Leu Leu Val Glu His Ala Leu Leu Asp Ala
1               5                   10                  15

Leu Met Ile Leu Asn Leu Xaa Xaa Xaa Xaa Xaa Xaa Lys Leu Asn Arg
            20                  25                  30

Ile Ile Thr Thr Met Gln Ser Trp Ile Phe Xaa Xaa Xaa Xaa Xaa Xaa
        35                  40                  45

Asp Arg Ala Arg Glu Leu Ala Lys Leu Val Glu Glu Ile Arg Asp Glu
    50                  55                  60

Met Glu Lys Xaa Xaa Xaa Xaa Xaa Xaa Asp Tyr Val Ser Asn Leu Lys
65                  70                  75                  80

Val Ile Leu Glu Glu Leu Ala
                85
```

<210> SEQ ID NO 57
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally occurring amino acid or is optionally absent

<400> SEQUENCE: 57

```
Thr Lys Lys Lys Tyr Gln Leu Leu Ile Glu His Val Leu Leu Asp Leu
1               5                   10                  15

Leu Met Leu Leu Asn Leu Xaa Xaa Xaa Xaa Xaa Xaa Lys Met Asn Arg
            20                  25                  30

Leu Ile Thr Ile Leu Gln Ser Trp Ile Phe Xaa Xaa Xaa Xaa Xaa Xaa
        35                  40                  45

Asp Lys Ala Glu Glu Met Ala Lys Leu Leu Lys Glu Leu Arg Glu Glu
    50                  55                  60

Phe Arg Glu Xaa Xaa Xaa Xaa Xaa Xaa Asp Tyr Ile Ser Asn Ala Ile
65                  70                  75                  80

Val Ile Leu Lys Glu Leu Ser
                85
```

<210> SEQ ID NO 58
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally occurring amino acid or is optionally absent

<400> SEQUENCE: 58

```
Thr Lys Lys Lys Ile Gln Leu Leu Val Glu His Ala Leu Leu Asp Ala
1               5                   10                  15

Leu Met Met Leu Asn Leu Xaa Xaa Xaa Xaa Xaa Xaa Lys Leu Asn Arg
            20                  25                  30

Ile Ile Thr Thr Met Gln Ser Trp Ile Phe Xaa Xaa Xaa Xaa Xaa Xaa
        35                  40                  45

Asp Arg Ala Glu Glu Leu Ala Lys Leu Val Glu Glu Leu Arg Glu Glu
    50                  55                  60

Phe Arg Lys Xaa Xaa Xaa Xaa Xaa Xaa Asp Tyr Ala Ser Asn Leu Lys
65                  70                  75                  80

Val Ile Leu Lys Glu Leu Ser
                85
```

<210> SEQ ID NO 59
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally occurring amino acid or is optionally absent
<220> FEATURE:

```
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 59

Thr Lys Lys Lys Ile Gln Leu Leu Val Glu His Ala Leu Leu Asp Ala
1               5                   10                  15

Leu Met Met Leu Asn Leu Xaa Xaa Xaa Xaa Xaa Xaa Lys Leu Asn Arg
            20                  25                  30

Ile Ile Thr Thr Met Gln Ser Trp Ile Phe Xaa Xaa Xaa Xaa Xaa Xaa
        35                  40                  45

Asp Gln Ala Arg Glu Leu Ala Lys Leu Val Glu Glu Leu Arg Glu Glu
    50                  55                  60

Phe Arg Lys Xaa Xaa Xaa Xaa Xaa Xaa Asp Tyr Ala Ser Asn Leu Lys
65                  70                  75                  80

Val Ile Leu Glu Glu Leu Ala
                85


<210> SEQ ID NO 60
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: vnt
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 60

Thr Lys Lys Lys Leu Gln Leu Leu Val Glu His Ala Leu Leu Asp Ala
1               5                   10                  15

Leu Met Leu Leu Asn Leu Xaa Xaa Xaa Xaa Xaa Xaa Lys Leu Asn Arg
            20                  25                  30

Ile Ile Thr Thr Met Gln Ser Trp Ile Phe Xaa Xaa Xaa Xaa Xaa Xaa
        35                  40                  45

Asp Gln Ala Glu Glu Leu Ala Lys Leu Val Glu Glu Ile Arg Glu Glu
    50                  55                  60

Leu Arg Lys Xaa Xaa Xaa Xaa Xaa Xaa Asp Tyr Val Ser Asn Leu Lys
65                  70                  75                  80

Val Ile Leu Lys Glu Leu Ser
                85


<210> SEQ ID NO 61
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
```

<220> FEATURE:
<221> NAME/KEY: MISC_FEATURE
<222> LOCATION: (43)..(48)
<223> OTHER INFORMATION: Xaa, when present, can be any naturally
occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
occurring amino acid or is optionally absent

<400> SEQUENCE: 61

```
Thr Thr Lys Lys Tyr Gln Leu Leu Val Glu His Ala Leu Leu Asp Ala
1               5                   10                  15

Leu Met Ile Leu Asn Leu Xaa Xaa Xaa Xaa Xaa Xaa Lys Leu Asn Arg
            20                  25                  30

Ile Ile Thr Thr Met Gln Ser Trp Ile Phe Xaa Xaa Xaa Xaa Xaa Xaa
        35                  40                  45

Asp Gln Ala Glu Glu Leu Ala Lys Leu Val Arg Glu Ile Arg Glu Glu
    50                  55                  60

Met Arg Lys Xaa Xaa Xaa Xaa Xaa Xaa Asp Tyr Val Ser Asn Leu Glu
65                  70                  75                  80

Val Ile Leu Arg Glu Leu Ser
                85
```

<210> SEQ ID NO 62
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
occurring amino acid or is optionally absent

<400> SEQUENCE: 62

```
Thr Lys Lys Lys Ile Gln Leu Leu Val Glu His Ala Leu Leu Asp Ala
1               5                   10                  15

Leu Met Ile Leu Asn Leu Xaa Xaa Xaa Xaa Xaa Xaa Lys Leu Asn Arg
            20                  25                  30

Ile Ile Thr Thr Met Gln Ser Trp Ile Phe Xaa Xaa Xaa Xaa Xaa Xaa
        35                  40                  45

Asp Arg Ala Glu Glu Leu Ala Lys Leu Val Arg Glu Ile Arg Glu Glu
    50                  55                  60

Met Arg Lys Xaa Xaa Xaa Xaa Xaa Xaa Asp Tyr Val Ser Asn Leu Glu
65                  70                  75                  80

Val Ile Leu Arg Glu Leu Ser
                85
```

<210> SEQ ID NO 63
<211> LENGTH: 87
<212> TYPE: PRT
<213> ORGANISM: Artificial Sequence

```
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 63

Thr Lys Lys Lys Tyr Gln Leu Leu Ile Glu His Leu Leu Leu Asp Leu
1               5                   10                  15

Leu Met Ile Leu Asn Leu Xaa Xaa Xaa Xaa Xaa Xaa Lys Leu Asn Arg
            20                  25                  30

Leu Ile Thr Trp Leu Gln Ser Trp Ile Phe Arg Xaa Xaa Xaa Xaa Xaa
        35                  40                  45

Asp Lys Ala Glu Glu Trp Ala Lys Ile Leu Lys Glu Ile Arg Glu Glu
    50                  55                  60

Leu Arg Glu Xaa Xaa Xaa Xaa Xaa Xaa Asp Tyr Met Ser Asn Ala Ile
65                  70                  75                  80

Val Ile Met Lys Glu Leu Ser
                85


<210> SEQ ID NO 64
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 64

Thr Asp Lys Lys Leu Gln Leu Leu Val Glu His Leu Leu Leu Asp Leu
1               5                   10                  15

Leu Met Met Leu Asn Leu Xaa Xaa Xaa Xaa Xaa Xaa Lys Met Asn Arg
            20                  25                  30

Leu Ile Thr Ile Ala Gln Ser Trp Ile Phe Thr Xaa Xaa Xaa Xaa Xaa
        35                  40                  45

Asp Leu Ala Arg Glu Met Ile Lys Leu Leu Glu Glu Thr Glu Asp Glu
    50                  55                  60

Asn Arg Lys Xaa Xaa Xaa Xaa Xaa Xaa Asp Tyr Val Ser Asn Ala Arg
65                  70                  75                  80

Val Ile Ala Lys Glu Leu Glu
```

```
                85


<210> SEQ ID NO 65
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 65

Thr Lys Lys Lys Ile Gln Leu Leu Val Glu His Ala Leu Leu Asp Ala
1               5                   10                  15

Leu Met Leu Leu Asn Leu Xaa Xaa Xaa Xaa Xaa Xaa Lys Met Asn Arg
            20                  25                  30

Ile Ile Thr Thr Met Gln Ser Trp Ile Phe Xaa Xaa Xaa Xaa Xaa Xaa
        35                  40                  45

Asp Gln Ala Glu Glu Leu Ala Lys Leu Val Glu Glu Leu Lys Glu Glu
    50                  55                  60

Phe Lys Lys Xaa Xaa Xaa Xaa Xaa Xaa Asp Tyr Val Ser Asn Leu Lys
65                  70                  75                  80

Val Ile Leu Lys Glu Leu Ser
                85


<210> SEQ ID NO 66
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 66

Thr Lys Lys Lys Tyr Gln Leu Leu Ile Glu His Ala Leu Leu Asp Ala
1               5                   10                  15

Leu Met Ile Leu Asn Leu Xaa Xaa Xaa Xaa Xaa Xaa Lys Leu Asn Arg
            20                  25                  30

Ile Ile Thr Thr Met Gln Ser Trp Ile Phe Thr Xaa Xaa Xaa Xaa Xaa
        35                  40                  45
```

-continued

```
Asp Lys Ala Glu Glu Leu Glu Lys Leu Ala Lys Glu Ile Glu Asp Glu
    50                  55                  60

Ala Arg Glu Xaa Xaa Xaa Xaa Xaa Xaa Asp Tyr Met Ser Asn Leu Arg
65                  70                  75                  80

Val Ile Leu Lys Glu Leu Ser
                85


<210> SEQ ID NO 67
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 67

Thr Lys Lys Lys Ala Gln Leu Leu Ala Glu His Ala Leu Leu Asp Ala
1               5                   10                  15

Leu Met Leu Leu Asn Leu Xaa Xaa Xaa Xaa Xaa Xaa Arg Leu Asn Arg
            20                  25                  30

Ile Ile Thr Trp Leu Gln Ser Ile Ile Phe Thr Xaa Xaa Xaa Xaa Xaa
        35                  40                  45

Asp Met Val Lys Glu Ala Val Lys Leu Ala Asp Glu Ile Glu Asp Glu
    50                  55                  60

Met Arg Lys Xaa Xaa Xaa Xaa Xaa Xaa Asp Tyr Val Ser Asn Leu Arg
65                  70                  75                  80

Val Ile Leu Gln Glu Leu Ala
                85


<210> SEQ ID NO 68
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 68

Thr Gln Lys Lys Asn Gln Leu Leu Ala Glu His Leu Leu Leu Asp Ala
1               5                   10                  15
```

```
Leu Met Val Leu Asn Gln Xaa Xaa Xaa Xaa Xaa Xaa Val Ala Asn Arg
            20                  25                  30

Ile Ile Thr Trp Ala Gln Ser Trp Ile Phe Glu Xaa Xaa Xaa Xaa Xaa
        35                  40                  45

Asn Lys Ala Glu Glu Ala Lys Lys Leu Ala Lys Lys Leu Glu Glu Glu
    50                  55                  60

Met Arg Lys Xaa Xaa Xaa Xaa Xaa Xaa Asp Tyr Ile Ser Asn Met Lys
65                  70                  75                  80

Val Ile Ala Glu Glu Met Ser
                85
```

<210> SEQ ID NO 69
<211> LENGTH: 107
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (21)..(29)
<223> OTHER INFORMATION: Xaa, when present, can be any naturally occurring amino acid or is optionally absent
<220> FEATURE:
<221> NAME/KEY: MISC_FEATURE
<222> LOCATION: (46)..(50)
<223> OTHER INFORMATION: Xaa, when present, can be any naturally occurring amino acid or is optionally absent
<220> FEATURE:
<221> NAME/KEY: MISC_FEATURE
<222> LOCATION: (77)..(80)
<223> OTHER INFORMATION: Xaa, when present, can be any naturally occurring amino acid or is optionally absent

<400> SEQUENCE: 69

```
Glu Asp Tyr Tyr Ser Asn Leu Lys Val Ile Leu Glu Glu Leu Ala Arg
1               5                   10                  15

Glu Met Glu Arg Xaa Xaa Xaa Xaa Xaa Xaa Xaa Xaa Xaa Trp Arg Gln
            20                  25                  30

Trp Lys Lys Ile Val Glu Arg Ile Arg Gln Ile Arg Ser Xaa Xaa Xaa
        35                  40                  45

Xaa Xaa Asn Glu Ala Lys Glu Leu Leu Asn Arg Leu Ile Thr Tyr Ile
    50                  55                  60

Gln Ser Gln Ile Phe Glu Ile Ser Glu Arg Ile Arg Xaa Xaa Xaa Xaa
65                  70                  75                  80

Glu Lys Lys Glu Glu Ser Trp Lys Lys Trp Gln Leu Leu Leu Glu His
                85                  90                  95

Ala Leu Leu Asp Val Leu Met Leu Leu Asn Asp
            100                 105
```

<210> SEQ ID NO 70
<211> LENGTH: 107
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally occurring amino acid or is optionally absent
<220> FEATURE:
<221> NAME/KEY: MISC_FEATURE
<222> LOCATION: (55)..(56)
<223> OTHER INFORMATION: Xaa, when present, can be any naturally occurring amino acid or is optionally absent
<220> FEATURE:
<221> NAME/KEY: MISC_FEATURE
<222> LOCATION: (79)..(82)
<223> OTHER INFORMATION: Xaa, when present, can be any naturally
occurring amino acid or is optionally absent

<400> SEQUENCE: 70

Pro Glu Lys Lys Arg Gln Leu Leu Leu Glu His Ile Leu Leu Asp Ala
1               5                   10                  15

Leu Met Leu Leu Asn Leu Xaa Xaa Xaa Xaa Xaa Xaa Asn Thr Glu Ser
            20                  25                  30

Lys Phe Glu Asp Tyr Ile Ser Asn Ala Glu Val Ile Ala Glu Glu Leu
        35                  40                  45

Ala Lys Leu Met Glu Ser Xaa Xaa Leu Ser Asp Glu Ala Glu Lys Phe
    50                  55                  60

Lys Lys Ile Lys Gln Trp Leu Arg Glu Val Trp Arg Ile Trp Xaa Xaa
65                  70                  75                  80

Xaa Xaa Trp Ser Thr Leu Glu Asp Lys Ala Arg Glu Leu Leu Asn Arg
                85                  90                  95

Ile Ile Thr Thr Ile Gln Ser Gln Ile Phe Tyr
            100                 105

<210> SEQ ID NO 71
<211> LENGTH: 104
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (25)..(31)
<223> OTHER INFORMATION: Xaa, when present, can be any naturally
occurring amino acid or is optionally absent
<220> FEATURE:
<221> NAME/KEY: MISC_FEATURE
<222> LOCATION: (55)..(57)
<223> OTHER INFORMATION: Xaa, when present, can be any naturally
occurring amino acid or is optionally absent
<220> FEATURE:
<221> NAME/KEY: MISC_FEATURE
<222> LOCATION: (80)..(83)
<223> OTHER INFORMATION: Xaa, when present, can be any naturally
occurring amino acid or is optionally absent

<400> SEQUENCE: 71

Pro Glu Lys Lys Arg Gln Leu Leu Leu Glu His Ile Leu Leu Asp Leu
1               5                   10                  15

Leu Met Ile Leu Asn Met Ile Glu Xaa Xaa Xaa Xaa Xaa Xaa Xaa Ser
            20                  25                  30

Glu Met Glu Asp Tyr Trp Ser Asn Val Arg Val Ile Leu Arg Glu Leu
        35                  40                  45

Ala Arg Leu Met Glu Glu Xaa Xaa Xaa Lys Glu Leu Ser Glu Leu Met
    50                  55                  60

Glu Arg Met Arg Lys Ile Val Glu Lys Ile Arg Gln Ile Val Thr Xaa
65                  70                  75                  80

Xaa Xaa Xaa Leu Asp Thr Ala Arg Glu Trp Leu Asn Arg Leu Ile Thr
                85                  90                  95

Trp Ile Gln Ser Leu Ile Phe Arg
            100

<210> SEQ ID NO 72
<211> LENGTH: 104
<212> TYPE: PRT

<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally occurring amino acid or is optionally absent
<220> FEATURE:
<221> NAME/KEY: MISC_FEATURE
<222> LOCATION: (55)..(57)
<223> OTHER INFORMATION: Xaa, when present, can be any naturally occurring amino acid or is optionally absent
<220> FEATURE:
<221> NAME/KEY: MISC_FEATURE
<222> LOCATION: (80)..(83)
<223> OTHER INFORMATION: Xaa, when present, can be any naturally occurring amino acid or is optionally absent

<400> SEQUENCE: 72

```
Pro Glu Lys Lys Arg Gln Leu Leu Leu Glu His Ile Leu Leu Asp Leu
1               5                   10                  15

Leu Met Ile Leu Asn Met Xaa Xaa Xaa Xaa Xaa Xaa Asn Thr Glu Ser
            20                  25                  30

Glu Met Glu Asp Tyr Trp Ser Asn Val Arg Val Ile Leu Arg Glu Leu
        35                  40                  45

Ala Arg Leu Met Glu Glu Xaa Xaa Xaa Lys Glu Leu Ser Glu Leu Met
    50                  55                  60

Glu Arg Met Arg Lys Ile Val Glu Lys Ile Arg Gln Ile Val Thr Xaa
65                  70                  75                  80

Xaa Xaa Xaa Leu Asp Thr Ala Arg Glu Trp Leu Asn Arg Leu Ile Thr
                85                  90                  95

Trp Ile Gln Ser Leu Ile Phe Arg
            100
```

<210> SEQ ID NO 73
<211> LENGTH: 96
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(27)
<223> OTHER INFORMATION: Xaa, when present, can be any naturally occurring amino acid or is optionally absent
<220> FEATURE:
<221> NAME/KEY: MISC_FEATURE
<222> LOCATION: (47)..(50)
<223> OTHER INFORMATION: Xaa, when present, can be any naturally occurring amino acid or is optionally absent
<220> FEATURE:
<221> NAME/KEY: MISC_FEATURE
<222> LOCATION: (72)..(75)
<223> OTHER INFORMATION: Xaa, when present, can be any naturally occurring amino acid or is optionally absent

<400> SEQUENCE: 73

```
Pro Glu Lys Lys Arg Gln Leu Leu Ala Glu His Leu Leu Leu Asp Val
1               5                   10                  15

Leu Met Met Leu Asn Xaa Xaa Xaa Xaa Xaa Xaa Asp Tyr Ala Ser Asn
            20                  25                  30

Ala Gln Val Ile Ala Asp Glu Phe Arg Glu Leu Ala Arg Glu Xaa Xaa
        35                  40                  45

Xaa Xaa Asp Glu Ala Lys Lys Ala Glu Lys Ile Ile Glu Ala Leu Glu
    50                  55                  60
```

```
Arg Ala Arg Glu Trp Leu Leu Xaa Xaa Xaa Xaa Lys Glu Lys Ala Lys
65                  70                  75                  80

Glu Ala Leu Asn Arg Ala Ile Thr Ile Ala Gln Ser Trp Ile Phe Asn
                85                  90                  95


<210> SEQ ID NO 74
<211> LENGTH: 104
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (55)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (80)..(83)
<223> OTHER INFORMATION: Xaa, when present, can be any naturally
      occurring amino acid or is optionally absent

<400> SEQUENCE: 74

Pro Glu Lys Lys Arg Gln Leu Leu Leu Glu His Leu Leu Leu Asp Leu
1               5                   10                  15

Leu Met Ile Leu Asn Xaa Xaa Xaa Xaa Xaa Xaa Lys Asn Ile Glu Ser
            20                  25                  30

Asp Trp Glu Asp Tyr Met Ser Asn Ile Glu Val Ile Ile Glu Glu Leu
        35                  40                  45

Arg Lys Ile Met Glu Ser Xaa Xaa Xaa Ser Glu Lys Ala Lys Glu Trp
    50                  55                  60

Lys Arg Met Lys Gln Trp Val Arg Arg Ile Leu Glu Ile Val Lys Xaa
65                  70                  75                  80

Xaa Xaa Xaa Leu Glu Glu Ala Lys Glu Trp Leu Asn Arg Leu Ile Thr
                85                  90                  95

Ile Val Gln Ser Glu Ile Phe Glu
            100


<210> SEQ ID NO 75
<211> LENGTH: 104
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (55)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (80)..(83)
<223> OTHER INFORMATION: Xaa, when present, can be any naturally
      occurring amino acid or is optionally absent

<400> SEQUENCE: 75

Trp Glu Lys Lys Arg Gln Leu Leu Leu Glu His Leu Leu Leu Asp Leu
1               5                   10                  15
```

```
Leu Met Ile Leu Asn Xaa Xaa Xaa Xaa Xaa Xaa Gln Asn Thr Glu Ser
            20                  25                  30

Leu Met Glu Asp Tyr Met Ser Asn Ala Lys Val Ile Val Glu Glu Leu
        35                  40                  45

Ala Arg Met Met Arg Ser Xaa Xaa Xaa Glu Asp Lys Ala Arg Glu Trp
    50                  55                  60

Glu Glu Met Lys Lys Arg Ile Glu Glu Ile Arg Gln Ile Ile Gln Xaa
65                  70                  75                  80

Xaa Xaa Xaa Lys Glu Arg Ala Lys Glu Glu Leu Asn Arg Leu Ile Thr
                85                  90                  95

Tyr Val Gln Ser Glu Ile Phe Arg
            100


<210> SEQ ID NO 76
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(27)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 76

Pro Lys Lys Lys Ile Gln Leu Leu Ala Glu His Ala Leu Leu Asp Ala
1               5                   10                  15

Leu Met Ile Leu Asn Xaa Xaa Xaa Xaa Xaa Xaa Gln Asn Ala Glu Glu
            20                  25                  30

Lys Leu Glu Asp Tyr Ala Ser Asn Val Glu Val Ile Leu Glu Glu Ile
        35                  40                  45

Ala Arg Leu Met Glu Ser Gly Xaa Xaa Lys Asp Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Glu Gln Glu Glu Met Ala Asn Arg Ile Ile Thr Leu Leu Gln Ser
                85                  90                  95

Trp Ile Phe Ser
            100


<210> SEQ ID NO 77
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(27)
<223> OTHER INFORMATION: Xaa, when present, can be any naturally
      occurring amino acid or is optionally absent
<220> FEATURE:
<221> NAME/KEY: MISC_FEATURE
```

<222> LOCATION: (54)..(57)
<223> OTHER INFORMATION: Xaa, when present, can be any naturally occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally occurring amino acid or is optionally absent

<400> SEQUENCE: 77

```
Pro Glu Lys Lys Arg Gln Leu Leu Ala Glu His Ala Leu Leu Asp Ala
1               5                   10                  15

Leu Met Ile Leu Asn Xaa Xaa Xaa Xaa Xaa Xaa Gln Asn Ala Glu Glu
            20                  25                  30

Lys Leu Glu Asp Tyr Met Ser Asn Val Glu Val Ile Met Glu Glu Phe
        35                  40                  45

Ala Arg Met Met Arg Xaa Xaa Xaa Xaa Ser Glu Glu Ala Glu Asn Ala
    50                  55                  60

Glu Arg Ile Lys Lys Trp Val Arg Lys Ala Ser Ser Xaa Xaa Xaa Ser
65                  70                  75                  80

Glu Glu Gln Arg Glu Met Met Asn Arg Ala Ile Thr Leu Met Gln Ser
                85                  90                  95

Trp Ile Phe Glu
            100
```

<210> SEQ ID NO 78
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally occurring amino acid or is optionally absent
<220> FEATURE:
<221> NAME/KEY: MISC_FEATURE
<222> LOCATION: (56)..(58)
<223> OTHER INFORMATION: Xaa, when present, can be any naturally occurring amino acid or is optionally absent
<220> FEATURE:
<221> NAME/KEY: MISC_FEATURE
<222> LOCATION: (75)..(78)
<223> OTHER INFORMATION: Xaa, when present, can be any naturally occurring amino acid or is optionally absent

<400> SEQUENCE: 78

```
Pro Glu Lys Lys Arg Gln Leu Leu Ala Glu His Leu Leu Leu Asp Ala
1               5                   10                  15

Leu Met Val Leu Asn Met Xaa Xaa Xaa Xaa Xaa Xaa Asn Thr Glu Glu
            20                  25                  30

Lys Leu Glu Asp Tyr Ile Ser Asn Met Lys Val Ile Ile Lys Glu Met
        35                  40                  45

Ile Glu Leu Met Arg Ser Leu Xaa Xaa Xaa Glu Glu Ala Glu Lys Trp
    50                  55                  60

Lys Glu Ala Leu Lys Ala Val Glu Lys Ile Xaa Xaa Xaa Xaa Asp Ser
65                  70                  75                  80

Glu Thr Ala Arg Glu Leu Ala Asn Arg Ile Ile Thr Leu Ala Gln Ser
                85                  90                  95

Ala Ile Phe Tyr
            100
```

<210> SEQ ID NO 79
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally occurring amino acid or is optionally absent
<220> FEATURE:
<221> NAME/KEY: MISC_FEATURE
<222> LOCATION: (56)..(58)
<223> OTHER INFORMATION: Xaa, when present, can be any naturally occurring amino acid or is optionally absent
<220> FEATURE:
<221> NAME/KEY: MISC_FEATURE
<222> LOCATION: (77)..(78)
<223> OTHER INFORMATION: Xaa, when present, can be any naturally occurring amino acid or is optionally absent

<400> SEQUENCE: 79

Pro Glu Lys Lys Arg Gln Leu Leu Ala Glu His Ala Leu Leu Asp Ala
1 5 10 15

Leu Met Phe Leu Asn Leu Xaa Xaa Xaa Xaa Xaa Xaa Gln Ala Glu Glu
20 25 30

Lys Ile Glu Asp Tyr Ala Ser Asn Leu Arg Val Ile Ala Glu Glu Leu
35 40 45

Ala Arg Leu Phe Glu Asn Leu Xaa Xaa Xaa Asp Glu Ala Gln Lys Ala
50 55 60

Lys Asp Ile Lys Glu Leu Ala Glu Arg Ala Arg Ser Xaa Xaa Ser Ser
65 70 75 80

Glu Lys Arg Lys Glu Ala Met Asn Arg Ala Ile Thr Ile Leu Gln Ser
85 90 95

Met Ile Phe Arg
100

<210> SEQ ID NO 80
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(27)
<223> OTHER INFORMATION: Xaa, when present, can be any naturally occurring amino acid or is optionally absent
<220> FEATURE:
<221> NAME/KEY: MISC_FEATURE
<222> LOCATION: (56)..(58)
<223> OTHER INFORMATION: Xaa, when present, can be any naturally occurring amino acid or is optionally absentt
<220> FEATURE:
<221> NAME/KEY: MISC_FEATURE
<222> LOCATION: (75)..(78)
<223> OTHER INFORMATION: Xaa, when present, can be any naturally occurring amino acid or is optionally absent

<400> SEQUENCE: 80

Pro Glu Lys Lys Arg Gln Leu Leu Ala Glu His Ala Leu Leu Asp Ala
1 5 10 15

Leu Met Ile Leu Asn Ile Xaa Xaa Xaa Xaa Xaa Asp Asn Thr Glu Ser
20 25 30

Lys Leu Glu Asp Tyr Ile Ser Asn Leu Lys Val Ile Leu Glu Glu Ile
35 40 45

-continued

```
Ala Arg Leu Met Glu Ser Leu Xaa Xaa Xaa Asp Glu Ala Glu Lys Ala
    50                  55                  60

Lys Glu Ala Met Arg Leu Ala Asp Lys Ala Xaa Xaa Xaa Xaa Ser Glu
65                  70                  75                  80

Glu Glu Lys Lys Glu Ala Met Asn Arg Val Ile Thr Trp Ala Gln Ser
                85                  90                  95

Trp Ile Phe Asn
            100


<210> SEQ ID NO 81
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(29)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(58)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 81

Pro Glu Lys Lys Arg Gln Leu Leu Ala Glu His Ala Leu Leu Asp Ala
1               5                   10                  15

Leu Met Met Leu Asn Ile Xaa Xaa Xaa Xaa Xaa Xaa Xaa Ala Glu Glu
            20                  25                  30

Lys Leu Glu Asp Tyr Trp Ser Asn Leu Ile Val Ile Leu Arg Glu Ile
        35                  40                  45

Ala Lys Leu Met Glu Ser Leu Xaa Xaa Xaa Asp Glu Ala Glu Lys Ala
    50                  55                  60

Lys Glu Ala Ala Arg Trp Ala Glu Glu Ala Arg Thr Xaa Xaa Xaa Lys
65                  70                  75                  80

Asp Gln Arg Arg Glu Leu Ala Asn Arg Ile Ile Thr Leu Leu Gln Ser
                85                  90                  95

Trp Ile Phe Ser
            100


<210> SEQ ID NO 82
<211> LENGTH: 99
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (55)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (76)..(78)
<223> OTHER INFORMATION: Xaa, when present, can be any naturally
      occurring amino acid or is optionally absent

<400> SEQUENCE: 82

Glu Lys Lys Arg Gln Leu Leu Ala Glu His Leu Leu Leu Asp Ala Leu
```

```
1               5                   10                  15

Met Ile Leu Asn Ile Ile Glu Thr Asn Glu Gln Asn Ala Glu Ser Lys
            20                  25                  30

Leu Glu Asp Tyr Ile Ser Asn Ala Lys Val Ile Leu Asp Glu Phe Arg
        35                  40                  45

Glu Met Ala Arg Asp Leu Xaa Xaa Xaa Asp Glu Ala Lys Lys Ala Glu
    50                  55                  60

Lys Met Lys Arg Trp Leu Glu Lys Met Arg Ser Xaa Xaa Xaa Ser Asp
65                  70                  75                  80

Glu Arg Arg Glu Trp Ala Asn Arg Met Ile Thr Thr Ala Gln Ser Trp
                85                  90                  95

Ile Phe Asn


<210> SEQ ID NO 83
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (44)..(48)
<223> OTHER INFORMATION: Xaa, when present, can be any naturally
      occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally
      occurring amino acid or is optionally absent

<400> SEQUENCE: 83

Thr Asn Lys Lys Ala Gln Leu His Ala Glu Phe Ala Leu His Asp Ala
1               5                   10                  15

Leu Met Leu Leu Asn Leu Xaa Xaa Xaa Xaa Xaa Xaa Arg Leu Asn Arg
            20                  25                  30

Ile Ile Thr Trp Leu Gln Ser Ile Ile Phe Tyr Xaa Xaa Xaa Xaa Xaa
        35                  40                  45

Asp Met Val Lys Glu Ala Val Lys Asp Ala Asp Glu Ile Glu Asp Glu
    50                  55                  60

Met Arg Lys Xaa Xaa Xaa Xaa Xaa Xaa Asp Tyr Val Ser Asn Leu Arg
65                  70                  75                  80

Leu Ile Leu Gln Glu Leu Ala
                85


<210> SEQ ID NO 84
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally
      occurring amino acid or is optionally absent
<220> FEATURE:
<221> NAME/KEY: MISC_FEATURE
<222> LOCATION: (44)..(48)
<223> OTHER INFORMATION: Xaa, when present, can be any naturally
      occurring amino acid or is optionally absent
```

<220> FEATURE:
<221> NAME/KEY: MISC_FEATURE
<222> LOCATION: (68)..(73)
<223> OTHER INFORMATION: Xaa, when present, can be any naturally occurring amino acid or is optionally absent

<400> SEQUENCE: 84

Thr Asn Lys Glu Ala Gln Leu His Ala Glu Phe Ala Leu Tyr Asp Ala
1               5                   10                  15

Leu Met Leu Leu Asn Leu Xaa Xaa Xaa Xaa Xaa Xaa Arg Leu Asn Arg
            20                  25                  30

Ile Ile Thr Trp Leu Gln Ser Ile Ile Phe Tyr Xaa Xaa Xaa Xaa Xaa
        35                  40                  45

Asp Met Val Lys Glu Ala Val Lys Leu Ala Asp Glu Ile Glu Asp Glu
    50                  55                  60

Met Arg Lys Xaa Xaa Xaa Xaa Xaa Xaa Asp Tyr Val Val Asn Leu Arg
65                  70                  75                  80

Leu Ile Leu Gln Glu Leu Ala
                85

<210> SEQ ID NO 85
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)
<223> OTHER INFORMATION: Xaa, when present, can be any naturally occurring amino acid or is optionally absent
<220> FEATURE:
<221> NAME/KEY: MISC_FEATURE
<222> LOCATION: (44)..(48)
<223> OTHER INFORMATION: Xaa, when present, can be any naturally occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally occurring amino acid or is optionally absent

<400> SEQUENCE: 85

Thr Lys Lys Asp Ala Glu Leu Leu Ala Glu Phe Ala Leu Tyr Asp Ala
1               5                   10                  15

Leu Met Leu Leu Asn Leu Xaa Xaa Xaa Xaa Xaa Xaa Arg Leu Asn Glu
            20                  25                  30

Ile Ile Thr Trp Leu Gln Ser Ile Ile Phe Tyr Xaa Xaa Xaa Xaa Xaa
        35                  40                  45

Asp Met Val Lys Glu Ala Val Lys Leu Ala Asp Glu Ile Glu Asp Glu
    50                  55                  60

Met Arg Lys Xaa Xaa Xaa Xaa Xaa Xaa Asp Tyr Val Ser Asn Leu Arg
65                  70                  75                  80

Leu Ile Leu Gln Glu Leu Ala
                85

<210> SEQ ID NO 86
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(28)

<223> OTHER INFORMATION: Xaa, when present, can be any naturally occurring amino acid or is optionally absent
<220> FEATURE:
<221> NAME/KEY: MISC_FEATURE
<222> LOCATION: (43)..(48)
<223> OTHER INFORMATION: Xaa, when present, can be any naturally occurring amino acid or is optionally absent
<220> FEATURE:
<221> NAME/KEY: MISC_FEATURE
<222> LOCATION: (68)..(73)
<223> OTHER INFORMATION: Xaa, when present, can be any naturally occurring amino acid or is optionally absent

<400> SEQUENCE: 86

```
Thr Asn Lys Lys Ala Gln Leu His Ala Glu Phe Ala Leu Tyr Asp Ala
1               5                   10                  15

Leu Met Leu Leu Asn Leu Xaa Xaa Xaa Xaa Xaa Xaa Arg Leu Asn Asp
            20                  25                  30

Ile Ile Thr Trp Leu Gln Ser Ile Ile Phe Xaa Xaa Xaa Xaa Xaa Xaa
        35                  40                  45

Asp Met Val Lys Glu Ala Val Lys Leu Ala Asp Glu Ile Glu Asp Glu
    50                  55                  60

Met Arg Lys Xaa Xaa Xaa Xaa Xaa Xaa Asp Tyr Val Val Asn Leu Arg
65                  70                  75                  80

Tyr Ile Leu Gln Glu Leu Ala
                85
```

<210> SEQ ID NO 87
<211> LENGTH: 107
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (21)..(24)
<223> OTHER INFORMATION: Xaa, when present, can be any naturally occurring amino acid or is optionally absent
<220> FEATURE:
<221> NAME/KEY: MISC_FEATURE
<222> LOCATION: (46)..(50)
<223> OTHER INFORMATION: Xaa, when present, can be any naturally occurring amino acid or is optionally absent
<220> FEATURE:
<221> NAME/KEY: MISC_FEATURE
<222> LOCATION: (77)..(80)
<223> OTHER INFORMATION: Xaa, when present, can be any naturally occurring amino acid or is optionally absent

<400> SEQUENCE: 87

```
Glu Asp Tyr Tyr Ser Asn Leu Lys Leu Ile Leu Glu Glu Leu Ala Arg
1               5                   10                  15

Glu Met Glu Arg Xaa Xaa Xaa Xaa Asp Lys Ala Glu Glu Trp Arg Gln
            20                  25                  30

Trp Lys Lys Ile Val Glu Arg Ile Arg Gln Ile Arg Ser Xaa Xaa Xaa
        35                  40                  45

Xaa Xaa Asn Glu Ala Lys Glu Leu Leu Asn Arg Leu Ile Thr Tyr Ile
    50                  55                  60

Gln Ser Gln Ile Phe Glu Val Leu His Gly Val Gly Xaa Xaa Xaa Xaa
65                  70                  75                  80

Glu Lys Lys Glu Glu Ser Trp Lys Lys Trp Asp Leu Leu Leu Glu His
                85                  90                  95

Ala Leu Leu Asp Val Leu Met Leu Leu Asn Asp
            100                 105
```

<210> SEQ ID NO 88
<211> LENGTH: 107
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (21)..(24)
<223> OTHER INFORMATION: Xaa, when present, can be any naturally occurring amino acid or is optionally absent
<220> FEATURE:
<221> NAME/KEY: MISC_FEATURE
<222> LOCATION: (46)..(50)
<223> OTHER INFORMATION: Xaa, when present, can be any naturally occurring amino acid or is optionally absent
<220> FEATURE:
<221> NAME/KEY: MISC_FEATURE
<222> LOCATION: (77)..(80)
<223> OTHER INFORMATION: Xaa, when present, can be any naturally occurring amino acid or is optionally absent

<400> SEQUENCE: 88

```
Glu Asp Tyr Tyr Ser Asn Leu Lys Val Ile Leu Glu Glu Leu Ala Arg
1               5                   10                  15

Glu Met Glu Arg Xaa Xaa Xaa Xaa Asp Lys Ala Glu Glu Trp Arg Gln
            20                  25                  30

Trp Lys Lys Ile Val Glu Arg Ile Arg Gln Ile Arg Ser Xaa Xaa Xaa
        35                  40                  45

Xaa Xaa Asn Glu Ala Lys Glu Leu Leu Asn Glu Leu Ile Thr Tyr Ile
    50                  55                  60

Gln Ser Gln Ile Phe Glu Val Ile Glu Arg Glu Gly Xaa Xaa Xaa Xaa
65                  70                  75                  80

Glu Lys Lys Glu Glu Ser Trp Lys Lys Trp Glu Leu His Leu Glu His
                85                  90                  95

Ala Leu Leu Asp Val Leu Met Leu Leu Asn Asp
            100                 105
```

<210> SEQ ID NO 89
<211> LENGTH: 107
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (21)..(24)
<223> OTHER INFORMATION: Xaa, when present, can be any naturally occurring amino acid or is optionally absent
<220> FEATURE:
<221> NAME/KEY: MISC_FEATURE
<222> LOCATION: (46)..(50)
<223> OTHER INFORMATION: Xaa, when present, can be any naturally occurring amino acid or is optionally absent
<220> FEATURE:
<221> NAME/KEY: MISC_FEATURE
<222> LOCATION: (77)..(80)
<223> OTHER INFORMATION: Xaa, when present, can be any naturally occurring amino acid or is optionally absent

<400> SEQUENCE: 89

```
Glu Asp Tyr Tyr Ser Asn Leu Lys Leu Ile Leu Glu Glu Leu Ala Arg
1               5                   10                  15

Glu Met Glu Arg Xaa Xaa Xaa Xaa Asp Lys Ala Glu Glu Trp Arg Gln
            20                  25                  30

Trp Lys Lys Ile Val Glu Arg Ile Arg Gln Ile Arg Ser Xaa Xaa Xaa
        35                  40                  45
```

```
Xaa Xaa Asn Glu Ala Lys Glu Leu Leu Asn Arg Leu Ile Thr Tyr Ile
    50                  55                  60

Gln Ser Gln Ile Phe Glu Val Leu Glu Gly Val Gly Xaa Xaa Xaa Xaa
65                  70                  75                  80

Glu Lys Lys Glu Glu Ser Trp Lys Lys Trp Glu Leu His Leu Glu His
                85                  90                  95

Ala Leu Leu Asp Val Leu Met Leu Leu Asn Asp
            100                 105


<210> SEQ ID NO 90
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(32)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 90

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Xaa Xaa Lys Asp Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100


<210> SEQ ID NO 91
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(32)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
```

<223> OTHER INFORMATION: Xaa, when present, can be any naturally occurring amino acid or is optionally absent

<400> SEQUENCE: 91

```
Pro Lys Lys Lys Ile Gln Leu Leu Ala Glu His Ala Leu Phe Asp Leu
1               5                   10                  15

Leu Met Ile Leu Asn Ile Xaa Xaa Xaa Xaa Xaa Xaa Xaa Xaa Xaa Xaa
            20                  25                  30

Lys Leu Glu Asp Tyr Ala Tyr Asn Ala Gly Val Ile Leu Glu Glu Ile
        35                  40                  45

Ala Arg Leu Phe Glu Ser Gly Xaa Xaa Lys Asp Glu Ala Glu Lys Ala
    50                  55                  60

Lys Arg Met Lys Glu Trp Met Lys Arg Ile Lys Asp Xaa Xaa Xaa Glu
65                  70                  75                  80

Asp Glu Gln Glu Glu Met Ala Asn Glu Ile Ile Thr Ile Leu Gln Ser
                85                  90                  95

Trp Asn Phe Ser
            100
```

<210> SEQ ID NO 92
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(32)
<223> OTHER INFORMATION: Xaa, when present, can be any naturally occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally occurring amino acid or is optionally absent

<400> SEQUENCE: 92

```
Pro Lys Lys Lys Ile Gln Ile Thr Ala Glu Glu Ala Leu Lys Asp Ala
1               5                   10                  15

Leu Ser Ile Leu Asn Ile Xaa Xaa Xaa Xaa Xaa Xaa Xaa Xaa Xaa Xaa
            20                  25                  30

Gln Leu Glu Arg Phe Ala Lys Arg Phe Glu Arg Asn Leu Trp Gly Ile
        35                  40                  45

Ala Arg Leu Phe Glu Ser Gly Xaa Xaa Lys Asp Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100
```

<210> SEQ ID NO 93
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(32)
<223> OTHER INFORMATION: Xaa, when present, can be any naturally occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally occurring amino acid or is optionally absent

<400> SEQUENCE: 93

```
Pro Lys Lys Lys Ile Gln Ile Met Ala Glu Glu Ala Leu Lys Asp Ala
1               5                   10                  15

Leu Ser Ile Leu Asn Ile Xaa Xaa Xaa Xaa Xaa Xaa Xaa Xaa Xaa Xaa
            20                  25                  30

Gln Leu Glu Arg Phe Ala Lys Arg Phe Glu Arg Asn Leu Trp Gly Ile
        35                  40                  45

Ala Arg Leu Phe Glu Ser Gly Xaa Xaa Lys Asp Glu Ala Glu Lys Ala
    50                  55                  60

Lys Arg Met Ile Glu Trp Met Lys Arg Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Phe Phe Ser
            100
```

<210> SEQ ID NO 94
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(32)
<223> OTHER INFORMATION: Xaa, when present, can be any naturally occurring amino acid or is optionally absent
<220> FEATURE:
<221> NAME/KEY: MISC_FEATURE
<222> LOCATION: (55)..(56)
<223> OTHER INFORMATION: Xaa, when present, can be any naturally occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally occurring amino acid or is optionally absent

<400> SEQUENCE: 94

```
Pro Lys Lys Lys Ile Gln Leu Tyr Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Glu Leu Glu Asp Tyr Ala Phe Asn Phe Glu Leu Ile Leu Glu Glu Ile
        35                  40                  45

Ala Arg Leu Phe Glu Ser Xaa Xaa Gln Lys Asp Glu Ala Glu Lys Ala
    50                  55                  60

Lys Arg Met Lys Glu Trp Met Lys Arg Ile Lys Thr Xaa Xaa Xaa Glu
65                  70                  75                  80
```

-continued

```
Asp Glu Gln Glu Glu Met Ala Asn Ala Ile Ile Thr Ile Leu Gln Ser
                85                  90                  95

Trp Ile Phe Ser
            100


<210> SEQ ID NO 95
<211> LENGTH: 5
<212> TYPE: PRT
<213> ORGANISM: Artificial Sequence
<220> FEATURE:
<223> OTHER INFORMATION: Synthetic

<400> SEQUENCE: 95

Gly Gly Gly Gly Gly
1               5


<210> SEQ ID NO 96
<211> LENGTH: 5
<212> TYPE: PRT
<213> ORGANISM: Artificial Sequence
<220> FEATURE:
<223> OTHER INFORMATION: Synthetic

<400> SEQUENCE: 96

Gly Ser Gly Gly Gly
1               5


<210> SEQ ID NO 97
<211> LENGTH: 6
<212> TYPE: PRT
<213> ORGANISM: Artificial Sequence
<220> FEATURE:
<223> OTHER INFORMATION: Synthetic

<400> SEQUENCE: 97

Gly Gly Gly Gly Gly Gly
1               5


<210> SEQ ID NO 98
<211> LENGTH: 6
<212> TYPE: PRT
<213> ORGANISM: Artificial Sequence
<220> FEATURE:
<223> OTHER INFORMATION: Synthetic

<400> SEQUENCE: 98

Gly Gly Ser Gly Gly Gly
1               5


<210> SEQ ID NO 99
<211> LENGTH: 16
<212> TYPE: PRT
<213> ORGANISM: Artificial Sequence
<220> FEATURE:
<223> OTHER INFORMATION: Synthetic

<400> SEQUENCE: 99

Gly Gly Ser Gly Gly Ser Gly Gly Gly Ser Gly Gly Ser Gly Ser Gly
1               5                   10                  15


<210> SEQ ID NO 100
<211> LENGTH: 15
<212> TYPE: PRT
<213> ORGANISM: Artificial Sequence
<220> FEATURE:
<223> OTHER INFORMATION: Synthetic
```

<400> SEQUENCE: 100

Gly Ser Gly Gly Ser Gly Gly Gly Ser Gly Gly Ser Gly Ser Gly
1 5 10 15

<210> SEQ ID NO 101
<211> LENGTH: 30
<212> TYPE: PRT
<213> ORGANISM: Artificial Sequence
<220> FEATURE:
<223> OTHER INFORMATION: Synthetic

<400> SEQUENCE: 101

Gly Gly Ser Gly Gly Ser Gly Gly Gly Ser Gly Gly Ser Gly Gly Gly
1 5 10 15

Gly Ser Gly Gly Ser Gly Gly Gly Ser Gly Gly Gly Gly Ser
20 25 30

<210> SEQ ID NO 102
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: X is Q, E, or S

<400> SEQUENCE: 102

Gly Gly Gly Gly Xaa
1 5

<210> SEQ ID NO 103
<211> LENGTH: 87
<212> TYPE: PRT
<213> ORGANISM: Artificial Sequence
<220> FEATURE:
<223> OTHER INFORMATION: Synthetic

<400> SEQUENCE: 103

Ser Thr Lys Lys Trp Gln Leu Gln Ala Glu His Ala Leu Leu Asp Trp
1 5 10 15

Gln Met Ala Leu Asn Lys Ser Pro Glu Pro Asn Glu Asn Leu Asn Arg
20 25 30

Ala Ile Thr Ala Ala Gln Ser Trp Ile Ser Thr Gly Lys Ile Asp Leu
35 40 45

Asp Lys Ala Glu Asp Ile Arg Arg Asn Ser Asp Gln Ala Arg Arg Glu
50 55 60

Ala Glu Lys Arg Gly Ile Asp Val Arg Asp Leu Ile Ser Asn Ala Gln
65 70 75 80

Val Ile Leu Leu Glu Ala Arg
85

<210> SEQ ID NO 104
<211> LENGTH: 87
<212> TYPE: PRT
<213> ORGANISM: Artificial Sequence
<220> FEATURE:
<223> OTHER INFORMATION: Synthetic

<400> SEQUENCE: 104

Ser Thr Lys Lys Trp Gln Leu Gln Ala Glu His Ala Leu Leu Asp Trp
1 5 10 15

-continued

```
Gln Met Ala Leu Asn Lys Ser Pro Glu Pro Asn Glu Asn Leu Asn Arg
            20                  25                  30

Ala Ile Thr Ala Ala Gln Ser Cys Ile Ser Thr Gly Lys Cys Asp Leu
        35                  40                  45

Asp Lys Ala Glu Asp Ile Arg Arg Asn Ser Asp Gln Ala Arg Arg Glu
    50                  55                  60

Ala Glu Lys Arg Gly Ile Asp Val Arg Asp Leu Ile Ser Asn Ala Gln
65                  70                  75                  80

Val Ile Leu Leu Glu Ala Arg
                85


<210> SEQ ID NO 105
<211> LENGTH: 87
<212> TYPE: PRT
<213> ORGANISM: Artificial Sequence
<220> FEATURE:
<223> OTHER INFORMATION: Synthetic

<400> SEQUENCE: 105

Ser Thr Lys Lys Trp Gln Leu Gln Ala Glu His Ala Leu Leu Asp Trp
1               5                   10                  15

Gln Met Ala Leu Asn Lys Ser Pro Glu Pro Asn Glu Asn Leu Asn Arg
            20                  25                  30

Ala Ile Thr Ala Ala Gln Ser Trp Ile Ser Thr Gly Lys Ile Asp Cys
        35                  40                  45

Asp Lys Ala Glu Asp Ile Arg Arg Asn Ser Asp Gln Ala Arg Arg Glu
    50                  55                  60

Ala Glu Lys Arg Gly Ile Asp Val Arg Asp Leu Ile Ser Asn Ala Gln
65                  70                  75                  80

Val Ile Leu Leu Glu Ala Cys
                85


<210> SEQ ID NO 106
<211> LENGTH: 87
<212> TYPE: PRT
<213> ORGANISM: Artificial Sequence
<220> FEATURE:
<223> OTHER INFORMATION: Synthetic

<400> SEQUENCE: 106

Ser Thr Lys Lys Leu Gln Leu Gln Ala Glu His Phe Leu Leu Asp Val
1               5                   10                  15

Gln Met Ile Leu Asn Glu Ser Pro Glu Pro Asn Glu Glu Leu Asn Arg
            20                  25                  30

Ala Ile Thr Asp Ala Gln Ser Trp Ile Ser Thr Gly Lys Ile Asp Leu
        35                  40                  45

Asp Arg Ala Glu Glu Leu Ala Arg Asn Leu Glu Lys Val Arg Asp Glu
    50                  55                  60

Ala Leu Lys Arg Gly Ile Asp Val Arg Asp Leu Val Ser Asn Ala Lys
65                  70                  75                  80

Val Ile Ala Leu Glu Leu Lys
                85


<210> SEQ ID NO 107
<211> LENGTH: 87
<212> TYPE: PRT
<213> ORGANISM: Artificial Sequence
<220> FEATURE:
<223> OTHER INFORMATION: Synthetic
```

<400> SEQUENCE: 107

Ser Thr Lys Lys Leu Gln Leu Gln Ala Glu His Phe Leu Leu Asp Val
1               5                   10                  15

Gln Met Ile Leu Asn Glu Ser Pro Glu Pro Asn Glu Glu Leu Asn Arg
            20                  25                  30

Cys Ile Thr Asp Ala Gln Ser Trp Ile Ser Thr Gly Lys Ile Asp Leu
        35                  40                  45

Asp Arg Ala Glu Glu Cys Ala Arg Asn Leu Glu Lys Val Arg Asp Glu
    50                  55                  60

Ala Leu Lys Arg Gly Ile Asp Val Arg Asp Leu Val Ser Asn Ala Lys
65                  70                  75                  80

Val Ile Ala Leu Glu Leu Lys
                85

<210> SEQ ID NO 108
<211> LENGTH: 87
<212> TYPE: PRT
<213> ORGANISM: Artificial Sequence
<220> FEATURE:
<223> OTHER INFORMATION: Synthetic

<400> SEQUENCE: 108

Ser Thr Lys Lys Leu Gln Leu Gln Ala Glu His Phe Leu Leu Asp Val
1               5                   10                  15

Gln Met Ile Leu Asn Glu Ser Pro Glu Pro Asn Glu Glu Leu Asn Arg
            20                  25                  30

Ala Ile Thr Asp Ala Gln Ser Cys Ile Ser Thr Gly Lys Cys Asp Leu
        35                  40                  45

Asp Arg Ala Glu Glu Leu Ala Arg Asn Leu Glu Lys Val Arg Asp Glu
    50                  55                  60

Ala Leu Lys Arg Gly Ile Asp Val Arg Asp Leu Val Ser Asn Ala Lys
65                  70                  75                  80

Val Ile Ala Leu Glu Leu Lys
                85

<210> SEQ ID NO 109
<211> LENGTH: 87
<212> TYPE: PRT
<213> ORGANISM: Artificial Sequence
<220> FEATURE:
<223> OTHER INFORMATION: Synthetic

<400> SEQUENCE: 109

Ser Thr Lys Lys Leu Gln Leu Gln Ala Glu His Phe Leu Leu Asp Val
1               5                   10                  15

Gln Met Ile Leu Asn Glu Ser Pro Glu Pro Asn Glu Glu Leu Asn Arg
            20                  25                  30

Ala Ile Thr Asp Ala Gln Ser Trp Ile Ser Thr Gly Lys Ile Asp Leu
        35                  40                  45

Asp Arg Ala Glu Glu Leu Cys Arg Asn Leu Glu Lys Val Arg Asp Glu
    50                  55                  60

Ala Leu Lys Arg Gly Ile Asp Val Arg Asp Leu Val Ser Asn Ala Cys
65                  70                  75                  80

Val Ile Ala Leu Glu Leu Lys
                85

<210> SEQ ID NO 110
<211> LENGTH: 87

```
<212> TYPE: PRT
<213> ORGANISM: Artificial Sequence
<220> FEATURE:
<223> OTHER INFORMATION: Synthetic

<400> SEQUENCE: 110

Ser Thr Lys Lys Leu Gln Leu Gln Ala Glu His Ala Leu Leu Asp Ala
1               5                   10                  15

Gln Met Met Leu Asn Arg Ser Pro Glu Pro Asn Glu Lys Leu Asn Arg
            20                  25                  30

Ile Ile Thr Thr Met Gln Ser Trp Ile Ser Thr Gly Lys Ile Asp Leu
        35                  40                  45

Asp Gly Ala Lys Glu Leu Ala Lys Glu Val Glu Glu Leu Arg Gln Glu
    50                  55                  60

Ala Glu Lys Arg Gly Ile Asp Val Arg Asp Leu Ala Ser Asn Leu Lys
65                  70                  75                  80

Val Ile Leu Leu Glu Leu Ala
                85


<210> SEQ ID NO 111
<211> LENGTH: 87
<212> TYPE: PRT
<213> ORGANISM: Artificial Sequence
<220> FEATURE:
<223> OTHER INFORMATION: Synthetic

<400> SEQUENCE: 111

Ser Thr Lys Lys Leu Gln Leu Gln Ala Glu His Ala Leu Leu Asp Ala
1               5                   10                  15

Gln Met Met Leu Asn Arg Ser Pro Glu Pro Asn Glu Lys Leu Asn Arg
            20                  25                  30

Ile Ile Thr Thr Met Gln Ser Cys Ile Ser Thr Gly Lys Cys Asp Leu
        35                  40                  45

Asp Gly Ala Lys Glu Leu Ala Lys Glu Val Glu Glu Leu Arg Gln Glu
    50                  55                  60

Ala Glu Lys Arg Gly Ile Asp Val Arg Asp Leu Ala Ser Asn Leu Lys
65                  70                  75                  80

Val Ile Leu Leu Glu Leu Ala
                85


<210> SEQ ID NO 112
<211> LENGTH: 87
<212> TYPE: PRT
<213> ORGANISM: Artificial Sequence
<220> FEATURE:
<223> OTHER INFORMATION: Synthetic

<400> SEQUENCE: 112

Ser Thr Lys Lys Ile Gln Leu Gln Leu Glu His Ala Leu Leu Asp Val
1               5                   10                  15

Gln Met Ala Leu Asn Arg Ser Pro Glu Pro Asn Glu Ser Leu Asn Arg
            20                  25                  30

Met Ile Thr Trp Leu Gln Ser Trp Ile Ser Thr Gly Lys Ile Asp Leu
        35                  40                  45

Asp Asn Ala Gln Glu Met Ala Lys Glu Ala Glu Lys Ile Arg Lys Glu
    50                  55                  60

Met Glu Lys Arg Gly Ile Asp Val Arg Asp Leu Ile Ser Asn Ile Ile
65                  70                  75                  80

Val Ile Leu Leu Glu Leu Ser
```

85

<210> SEQ ID NO 113
<211> LENGTH: 87
<212> TYPE: PRT
<213> ORGANISM: Artificial Sequence
<220> FEATURE:
<223> OTHER INFORMATION: Synthetic

<400> SEQUENCE: 113

Ser Thr Lys Lys Ile Gln Leu Gln Leu Glu His Ala Leu Leu Asp Val
1               5                   10                  15

Gln Met Ala Leu Asn Arg Ser Pro Glu Pro Asn Glu Ser Leu Asn Arg
            20                  25                  30

Met Ile Thr Trp Leu Gln Ser Cys Ile Ser Thr Gly Lys Cys Asp Leu
        35                  40                  45

Asp Asn Ala Gln Glu Met Ala Lys Glu Ala Glu Lys Ile Arg Lys Glu
    50                  55                  60

Met Glu Lys Arg Gly Ile Asp Val Arg Asp Leu Ile Ser Asn Ile Ile
65                  70                  75                  80

Val Ile Leu Leu Glu Leu Ser
                85

<210> SEQ ID NO 114
<211> LENGTH: 87
<212> TYPE: PRT
<213> ORGANISM: Artificial Sequence
<220> FEATURE:
<223> OTHER INFORMATION: Synthetic

<400> SEQUENCE: 114

Ser Thr Lys Lys Ile Gln Leu Gln Leu Glu His Ala Leu Leu Asp Val
1               5                   10                  15

Gln Met Ala Leu Asn Arg Ser Pro Glu Pro Asn Glu Ser Leu Asn Arg
            20                  25                  30

Met Ile Thr Trp Leu Gln Ser Trp Ile Ser Thr Gly Lys Ile Asp Leu
        35                  40                  45

Asp Asn Ala Gln Glu Met Cys Lys Glu Ala Glu Lys Ile Arg Lys Glu
    50                  55                  60

Met Glu Lys Arg Gly Ile Asp Val Arg Asp Leu Ile Ser Asn Ile Cys
65                  70                  75                  80

Val Ile Leu Leu Glu Leu Ser
                85

<210> SEQ ID NO 115
<211> LENGTH: 87
<212> TYPE: PRT
<213> ORGANISM: Artificial Sequence
<220> FEATURE:
<223> OTHER INFORMATION: Synthetic

<400> SEQUENCE: 115

Ser Thr Lys Lys Thr Gln Leu Leu Ala Glu His Ala Leu Leu Asp Ala
1               5                   10                  15

Phe Met Met Leu Asn Val Val Pro Glu Pro Asn Glu Lys Leu Asn Arg
            20                  25                  30

Ile Ile Thr Thr Met Gln Ser Trp Ile Tyr Thr Gly Lys Ile Asp Ala
        35                  40                  45

Asp Gly Ala Lys Glu Leu Ala Lys Glu Val Glu Glu Leu Glu Gln Glu
    50                  55                  60

Tyr Glu Lys Arg Gly Ile Asp Val Glu Asp Asp Ala Ser Asn Leu Lys
65 70 75 80

Val Ile Leu Leu Glu Leu Ala
85

<210> SEQ ID NO 116
<211> LENGTH: 87
<212> TYPE: PRT
<213> ORGANISM: Artificial Sequence
<220> FEATURE:
<223> OTHER INFORMATION: Synthetic

<400> SEQUENCE: 116

Ser Thr Lys Lys Thr Gln Leu Leu Ala Glu His Ala Leu Leu Asp Ala
1 5 10 15

His Met Met Leu Asn Met Leu Pro Glu Pro Asn Glu Lys Leu Asn Arg
20 25 30

Ile Ile Thr Thr Met Gln Ser Trp Ile His Thr Gly Lys Ile Asp Gly
35 40 45

Asp Gly Ala Gln Glu Leu Ala Lys Glu Val Glu Glu Leu Glu Gln Glu
50 55 60

Tyr Glu Lys Arg Gly Ile Asp Val Glu Asp Glu Ala Ser Asn Leu Lys
65 70 75 80

Val Ile Leu Leu Glu Leu Ala
85

<210> SEQ ID NO 117
<211> LENGTH: 87
<212> TYPE: PRT
<213> ORGANISM: Artificial Sequence
<220> FEATURE:
<223> OTHER INFORMATION: Synthetic

<400> SEQUENCE: 117

Ser Thr Lys Lys Thr Gln Leu Leu Ala Glu His Ala Leu Leu Asp Ala
1 5 10 15

Phe Met Met Leu Asn Met Val Pro Glu Pro Asn Glu Lys Leu Asn Arg
20 25 30

Ile Ile Thr Thr Met Gln Ser Trp Ile Phe Thr Gly Lys Ile Asp Gly
35 40 45

Asp Gly Ala Lys Glu Leu Ala Lys Glu Val Glu Glu Leu Glu Gln Glu
50 55 60

Phe Glu Lys Arg Gly Ile Asp Val Glu Asp Glu Ala Ser Asn Leu Lys
65 70 75 80

Val Ile Leu Leu Glu Leu Ala
85

<210> SEQ ID NO 118
<211> LENGTH: 87
<212> TYPE: PRT
<213> ORGANISM: Artificial Sequence
<220> FEATURE:
<223> OTHER INFORMATION: Synthetic

<400> SEQUENCE: 118

Ser Thr Lys Lys Thr Gln Leu Leu Ala Glu His Ala Leu Leu Asp Ala
1 5 10 15

Leu Met Met Leu Asn Met Val Pro Glu Pro Asn Glu Lys Leu Asn Arg
20 25 30

-continued

```
Ile Ile Thr Thr Met Gln Ser Trp Ile Phe Thr Gly Lys Ile Asp Gly
        35                  40                  45

Asp Gly Ala Gln Glu Leu Ala Lys Glu Val Glu Glu Leu Glu Gln Glu
    50                  55                  60

Leu Glu Lys Arg Gly Ile Asp Val Glu Asp Tyr Ala Ser Asn Leu Lys
65                  70                  75                  80

Val Ile Leu Leu Glu Leu Ala
                85
```

```
<210> SEQ ID NO 119
<211> LENGTH: 87
<212> TYPE: PRT
<213> ORGANISM: Artificial Sequence
<220> FEATURE:
<223> OTHER INFORMATION: Synthetic

<400> SEQUENCE: 119

Ser Thr Lys Lys Thr Gln Leu Leu Ala Glu His Ala Leu Leu Asp Ala
1               5                   10                  15

His Met Met Leu Asn Val Val Pro Glu Pro Asn Glu Lys Leu Asn Arg
            20                  25                  30

Ile Ile Thr Thr Met Gln Ser Trp Ile Tyr Thr Gly Lys Ile Asp Arg
        35                  40                  45

Asp Gly Ala Gln Glu Leu Ala Lys Glu Val Glu Glu Leu Glu Gln Glu
    50                  55                  60

Leu Glu Lys Arg Gly Ile Asp Val Asp Asp Asp Ala Ser Asn Leu Lys
65                  70                  75                  80

Val Ile Leu Leu Glu Leu Ala
                85
```

```
<210> SEQ ID NO 120
<211> LENGTH: 87
<212> TYPE: PRT
<213> ORGANISM: Artificial Sequence
<220> FEATURE:
<223> OTHER INFORMATION: Synthetic

<400> SEQUENCE: 120

Ser Thr Lys Lys Thr Gln Leu Leu Ala Glu His Ala Leu Leu Asp Ala
1               5                   10                  15

Leu Met Met Leu Asn Leu Leu Pro Glu Pro Asn Glu Lys Leu Asn Arg
            20                  25                  30

Ile Ile Thr Thr Met Gln Ser Trp Ile Phe Thr Gly Lys Ile Asp Gly
        35                  40                  45

Asp Gly Ala Gln Glu Leu Ala Lys Glu Val Glu Glu Leu Glu Gln Glu
    50                  55                  60

His Glu Lys Arg Gly Ile Asp Val Glu Asp Tyr Ala Ser Asn Leu Lys
65                  70                  75                  80

Val Ile Leu Leu Glu Leu Ala
                85
```

```
<210> SEQ ID NO 121
<211> LENGTH: 87
<212> TYPE: PRT
<213> ORGANISM: Artificial Sequence
<220> FEATURE:
<223> OTHER INFORMATION: Synthetic

<400> SEQUENCE: 121

Ser Thr Lys Lys Thr Gln Leu Leu Ala Glu His Ala Leu Leu Asp Ala
```

-continued

```
1               5                   10                  15

Tyr Met Met Leu Asn Met Val Pro Glu Pro Asn Glu Lys Leu Asn Arg
            20                  25                  30

Ile Ile Thr Thr Met Gln Ser Trp Ile Leu Thr Gly Lys Ile Asp Ser
        35                  40                  45

Asp Gly Ala Gln Glu Leu Ala Lys Glu Val Glu Glu Leu Glu Gln Glu
    50                  55                  60

Leu Glu Lys Arg Gly Ile Asp Val Asp Asp Asp Ala Ser Asn Leu Lys
65                  70                  75                  80

Val Ile Leu Leu Glu Leu Ala
                85


<210> SEQ ID NO 122
<211> LENGTH: 87
<212> TYPE: PRT
<213> ORGANISM: Artificial Sequence
<220> FEATURE:
<223> OTHER INFORMATION: Synthetic

<400> SEQUENCE: 122

Ser Thr Lys Lys Thr His Leu Leu Ala Glu His Ala Leu Leu Asp Ala
1               5                   10                  15

Tyr Met Met Leu Asn Val Met Pro Glu Pro Asn Glu Lys Leu Asn Arg
            20                  25                  30

Ile Ile Thr Thr Met Gln Ser Trp Ile Phe Thr Gly Lys Ile Asp Gly
        35                  40                  45

Asp Gly Ala Lys Glu Leu Ala Lys Glu Val Glu Glu Leu Glu Gln Glu
    50                  55                  60

Phe Glu Lys Arg Gly Ile Asp Val Asp Asp Asp Ala Ser Asn Leu Lys
65                  70                  75                  80

Val Ile Leu Leu Glu Leu Ala
                85


<210> SEQ ID NO 123
<211> LENGTH: 87
<212> TYPE: PRT
<213> ORGANISM: Artificial Sequence
<220> FEATURE:
<223> OTHER INFORMATION: Synthetic

<400> SEQUENCE: 123

Ser Thr Lys Lys Thr Gln Leu Leu Ala Glu His Ala Leu Leu Asp Ala
1               5                   10                  15

Tyr Met Met Leu Asn Leu Val Pro Glu Pro Asn Glu Lys Leu Asn Arg
            20                  25                  30

Ile Ile Thr Thr Met Gln Ser Trp Ile Phe Thr Gly Lys Ile Asp Ala
        35                  40                  45

Asp Gly Ala Gln Glu Leu Ala Ile Glu Val Glu Glu Leu Glu Gln Glu
    50                  55                  60

Tyr Glu Lys Arg Gly Ile Asp Val Asp Asp Tyr Ala Ser Asn Leu Lys
65                  70                  75                  80

Val Ile Leu Leu Glu Leu Ala
                85


<210> SEQ ID NO 124
<211> LENGTH: 87
<212> TYPE: PRT
<213> ORGANISM: Artificial Sequence
<220> FEATURE:
```

<223> OTHER INFORMATION: Synthetic

<400> SEQUENCE: 124

Ser Thr Lys Lys Thr Gln Leu Met Ala Glu His Ala Leu Leu Asp Ala
1 5 10 15

Phe Met Met Leu Asn Val Leu Pro Glu Pro Asn Glu Lys Leu Asn Arg
20 25 30

Ile Ile Thr Thr Met Gln Ser Trp Ile Phe Thr Gly Lys Ile Asp Gly
35 40 45

Asp Asp Ala Gln Glu Leu Ala Lys Glu Val Glu Glu Leu Glu Gln Glu
50 55 60

Leu Glu Lys Arg Gly Ile Asp Val Asp Asp Asp Ala Ser Asn Leu Lys
65 70 75 80

Val Ile Leu Leu Glu Leu Ala
85

<210> SEQ ID NO 125
<211> LENGTH: 87
<212> TYPE: PRT
<213> ORGANISM: Artificial Sequence
<220> FEATURE:
<223> OTHER INFORMATION: Synthetic

<400> SEQUENCE: 125

Ser Thr Lys Lys Thr Gln Leu Leu Ile Glu His Ala Leu Leu Asp Ala
1 5 10 15

Leu Asp Met Ser Arg Asn Leu Pro Glu Pro Asn Glu Lys Leu Ser Arg
20 25 30

Ile Ile Thr Thr Met Gln Ser Trp Ile Phe Thr Gly Lys Ile Asp Gly
35 40 45

Asp Gly Ala Gln Gln Leu Ala Lys Glu Val Glu Glu Leu Glu Gln Glu
50 55 60

His Glu Lys Arg Gly Glu Asp Val Glu Asp Glu Ala Ser Asn Leu Lys
65 70 75 80

Val Ile Leu Leu Glu Leu Ala
85

<210> SEQ ID NO 126
<211> LENGTH: 87
<212> TYPE: PRT
<213> ORGANISM: Artificial Sequence
<220> FEATURE:
<223> OTHER INFORMATION: Synthetic

<400> SEQUENCE: 126

Ser Thr Lys Lys Thr Gln Leu Leu Leu Glu His Ala Leu Leu Asp Ala
1 5 10 15

Leu His Met Arg Arg Asn Leu Pro Glu Pro Asn Glu Lys Leu Ser Arg
20 25 30

Ile Ile Thr Thr Met Gln Ser Trp Ile Phe Thr Gly Lys Ile Asp Gly
35 40 45

Asp Gly Ala Gln Glu Leu Ala Lys Glu Val Glu Glu Leu Glu Gln Glu
50 55 60

His Glu Lys Arg Gly Arg Asp Val Glu Asp Asp Ala Ser Asn Leu Lys
65 70 75 80

Val Ile Leu Leu Glu Leu Ala
85

<210> SEQ ID NO 127
<211> LENGTH: 87
<212> TYPE: PRT
<213> ORGANISM: Artificial Sequence
<220> FEATURE:
<223> OTHER INFORMATION: Synthetic

<400> SEQUENCE: 127

```
Ser Thr Lys Lys Thr Gln Leu Leu Ile Glu His Ala Leu Leu Asp Ala
1               5                   10                  15

Leu Asn Met Arg Lys Lys Leu Pro Glu Pro Asn Glu Lys Leu Ser Arg
            20                  25                  30

Ile Ile Thr Asp Met Gln Ser Trp Ile Phe Thr Gly Lys Ile Asp Gly
        35                  40                  45

Asp Gly Ala Gln Gln Leu Ala Lys Glu Val Glu Glu Leu Glu Gln Glu
    50                  55                  60

His Glu Lys Arg Gly Gly Asp Val Glu Asp Tyr Ala Ser Asn Leu Lys
65                  70                  75                  80

Val Ile Leu Leu Glu Leu Ala
                85
```

<210> SEQ ID NO 128
<211> LENGTH: 87
<212> TYPE: PRT
<213> ORGANISM: Artificial Sequence
<220> FEATURE:
<223> OTHER INFORMATION: Synthetic

<400> SEQUENCE: 128

```
Ser Thr Lys Lys Thr Gln Leu Leu Leu Glu His Ala Leu Leu Asp Ala
1               5                   10                  15

Leu His Met Ser Arg Glu Leu Pro Glu Pro Asn Glu Lys Leu Asn Arg
            20                  25                  30

Ile Ile Thr Asp Met Gln Ser Trp Ile Phe Thr Gly Lys Ile Asp Gly
        35                  40                  45

Asp Gly Ala Gln Asp Leu Ala Lys Glu Val Glu Glu Leu Glu Gln Glu
    50                  55                  60

His Glu Lys Arg Gly Gly Asp Val Glu Asp Tyr Ala Ser Asn Leu Lys
65                  70                  75                  80

Val Ile Leu Leu Glu Leu Ala
                85
```

<210> SEQ ID NO 129
<211> LENGTH: 87
<212> TYPE: PRT
<213> ORGANISM: Artificial Sequence
<220> FEATURE:
<223> OTHER INFORMATION: Synthetic

<400> SEQUENCE: 129

```
Ser Thr Lys Lys Thr Gln Leu Leu Ile Glu His Ala Leu Leu Asp Ala
1               5                   10                  15

Leu His Met Ser Arg Lys Leu Pro Glu Pro Asn Glu Lys Leu Ser Arg
            20                  25                  30

Ile Ile Thr Thr Met Gln Ser Trp Ile Phe Thr Gly Lys Ile Asp Gly
        35                  40                  45

Asp Gly Ala Gln His Leu Ala Lys Glu Val Glu Glu Leu Glu Gln Glu
    50                  55                  60

His Glu Lys Arg Gly Gly Glu Val Glu Asp Glu Ala Ser Asn Leu Lys
65                  70                  75                  80
```

```
Val Ile Leu Leu Glu Leu Ala
                85


<210> SEQ ID NO 130
<211> LENGTH: 87
<212> TYPE: PRT
<213> ORGANISM: Artificial Sequence
<220> FEATURE:
<223> OTHER INFORMATION: Synthetic

<400> SEQUENCE: 130

Ser Thr Lys Lys Thr Gln Leu Leu Ile Glu His Ala Leu Leu Asp Ala
1               5                   10                  15

Leu His Met Lys Arg Lys Leu Pro Glu Pro Asn Glu Lys Leu Asn Arg
            20                  25                  30

Ile Ile Thr Asn Met Gln Ser Trp Ile Phe Thr Glu Lys Ile Asp Gly
        35                  40                  45

Asp Gly Ala Gln Asp Leu Ala Lys Glu Val Glu Glu Leu Glu Gln Glu
    50                  55                  60

His Glu Lys Arg Gly Gln Asp Val Glu Asp Tyr Ala Ser Asn Leu Lys
65                  70                  75                  80

Val Ile Leu Leu Glu Leu Ala
                85


<210> SEQ ID NO 131
<211> LENGTH: 87
<212> TYPE: PRT
<213> ORGANISM: Artificial Sequence
<220> FEATURE:
<223> OTHER INFORMATION: Synthetic

<400> SEQUENCE: 131

Ser Thr Glu Lys Thr Gln Leu Ala Ala Glu His Ala Leu Arg Asp Ala
1               5                   10                  15

Leu Met Leu Lys His Leu Leu Asn Glu Pro Asn Glu Lys Leu Ala Arg
            20                  25                  30

Ile Ile Thr Thr Met Gln Ser Trp Gln Phe Thr Gly Lys Ile Asp Gly
        35                  40                  45

Asp Gly Ala Gln Glu Leu Ala Lys Glu Val Glu Glu Leu Gln Gln Glu
    50                  55                  60

His Glu Val Arg Gly Ile Asp Val Glu Asp Tyr Ala Ser Asn Leu Lys
65                  70                  75                  80

Val Ile Leu Leu His Leu Ala
                85


<210> SEQ ID NO 132
<211> LENGTH: 87
<212> TYPE: PRT
<213> ORGANISM: Artificial Sequence
<220> FEATURE:
<223> OTHER INFORMATION: Synthetic

<400> SEQUENCE: 132

Ser Thr Lys Asn Thr Gln Leu Ala Ala Glu Asp Ala Leu Leu Asp Ala
1               5                   10                  15

Leu Met Leu Arg Asn Leu Leu Asn Glu Pro Asn Glu Lys Leu Ala Arg
            20                  25                  30

Ile Ile Thr Thr Met Gln Ser Trp Gln Phe Thr Glu Lys Ile Asp Gly
        35                  40                  45
```

```
Asp Gly Ala Gln Glu Leu Ala Lys Glu Val Glu Glu Leu Gln Gln Glu
    50                  55                  60

His Glu Glu Arg Gly Ile Asp Val Glu Asp Tyr Ala Ser Asn Leu Lys
65                  70                  75                  80

Val Ile Leu Leu Gln Leu Ala
                85
```

```
<210> SEQ ID NO 133
<211> LENGTH: 87
<212> TYPE: PRT
<213> ORGANISM: Artificial Sequence
<220> FEATURE:
<223> OTHER INFORMATION: Synthetic

<400> SEQUENCE: 133

Ser Thr Glu Lys Thr Gln His Ala Ala Glu Asp Ala Leu Arg Asp Ala
1               5                   10                  15

Leu Met Leu Arg Asn Leu Leu Asn Glu Pro Asn Glu Lys Leu Ala Arg
            20                  25                  30

Ile Ile Thr Thr Met Gln Ser Trp Gln Phe Thr Glu Lys Ile Asp Gly
        35                  40                  45

Asp Gly Ala Gln Glu Leu Ala Lys Glu Val Glu Glu Leu Gln Gln Glu
    50                  55                  60

His Glu Val Arg Gly Ile Asp Val Glu Asp Tyr Ala Ser Asn Leu Lys
65                  70                  75                  80

Val Ile Leu Leu Gln Leu Ala
                85
```

```
<210> SEQ ID NO 134
<211> LENGTH: 87
<212> TYPE: PRT
<213> ORGANISM: Artificial Sequence
<220> FEATURE:
<223> OTHER INFORMATION: Synthetic

<400> SEQUENCE: 134

Thr Gln Lys Lys Gln Gln Leu Leu Ala Glu His Ala Leu Leu Asp Ala
1               5                   10                  15

Leu Met Ile Leu Asn Met Leu Lys Thr Ser Ser Glu Ala Val Asn Arg
            20                  25                  30

Met Ile Thr Ile Ala Gln Ser Trp Ile Phe Thr Gly Thr Ser Asn Pro
        35                  40                  45

Glu Glu Ala Lys Glu Met Ile Lys Met Ala Glu Gln Ala Glu Glu Glu
    50                  55                  60

Ala Arg Arg Glu Gly Val Asp Thr Glu Asp Tyr Val Ser Asn Leu Lys
65                  70                  75                  80

Val Ile Leu Lys Glu Ile Ala
                85
```

```
<210> SEQ ID NO 135
<211> LENGTH: 87
<212> TYPE: PRT
<213> ORGANISM: Artificial Sequence
<220> FEATURE:
<223> OTHER INFORMATION: Synthetic

<400> SEQUENCE: 135

Thr Thr Lys Lys Tyr Gln Leu Leu Val Glu His Ala Leu Leu Asp Ala
1               5                   10                  15

Leu Met Met Leu Asn Leu Ser Ser Glu Ser Asn Glu Lys Met Asn Arg
```

```
            20                  25                  30

Ile Ile Thr Thr Met Gln Ser Trp Ile Phe Thr Gly Thr Phe Asp Pro
        35                  40                  45

Asp Gln Ala Glu Glu Leu Ala Lys Leu Val Glu Glu Leu Arg Glu Glu
    50                  55                  60

Phe Arg Lys Arg Gly Ile Asp Thr Glu Asp Tyr Ala Ser Asn Leu Lys
65                  70                  75                  80

Val Ile Leu Lys Glu Leu Ser
                85


<210> SEQ ID NO 136
<211> LENGTH: 87
<212> TYPE: PRT
<213> ORGANISM: Artificial Sequence
<220> FEATURE:
<223> OTHER INFORMATION: Synthetic

<400> SEQUENCE: 136

Thr Thr Lys Lys Ile Gln Leu Leu Val Glu His Ala Leu Leu Asp Ala
1               5                   10                  15

Leu Met Ile Leu Asn Leu Ser Ser Glu Ser Asn Glu Lys Leu Asn Arg
            20                  25                  30

Ile Ile Thr Thr Leu Gln Ser Trp Ile Phe Arg Gly Glu Ile Asp Pro
        35                  40                  45

Asp Arg Ala Arg Glu Leu Ala Lys Leu Leu Glu Glu Ile Arg Glu Glu
    50                  55                  60

Met Arg Lys Arg Gly Ile Asp Thr Glu Asp Tyr Val Ser Asn Met Ile
65                  70                  75                  80

Val Ile Ile Arg Glu Leu Ala
                85


<210> SEQ ID NO 137
<211> LENGTH: 87
<212> TYPE: PRT
<213> ORGANISM: Artificial Sequence
<220> FEATURE:
<223> OTHER INFORMATION: Synthetic

<400> SEQUENCE: 137

Thr Lys Lys Lys Ile Gln Leu Leu Ala Glu His Val Leu Leu Asp Leu
1               5                   10                  15

Leu Met Met Leu Asn Leu Ser Ser Glu Ser Asn Glu Lys Met Asn Arg
            20                  25                  30

Leu Ile Thr Ile Val Gln Ser Trp Ile Phe Thr Gly Thr Ile Asp Pro
        35                  40                  45

Asp Gln Ala Glu Glu Met Ala Lys Trp Val Glu Glu Leu Arg Glu Glu
    50                  55                  60

Phe Arg Lys Arg Gly Ile Asp Thr Glu Asp Tyr Ala Ser Asn Val Lys
65                  70                  75                  80

Val Ile Leu Lys Glu Leu Ser
                85


<210> SEQ ID NO 138
<211> LENGTH: 87
<212> TYPE: PRT
<213> ORGANISM: Artificial Sequence
<220> FEATURE:
<223> OTHER INFORMATION: Synthetic

<400> SEQUENCE: 138
```

-continued

Thr Lys Lys Lys Tyr Gln Leu Leu Ile Glu His Leu Leu Leu Asp Ala
1               5                   10                  15

Leu Met Val Leu Asn Met Ser Ser Glu Ser Asn Glu Lys Leu Asn Arg
            20                  25                  30

Ile Ile Thr Ile Leu Gln Ser Trp Ile Phe Thr Gly Thr Trp Asp Pro
        35                  40                  45

Asp Leu Ala Glu Glu Met Glu Lys Leu Met Gln Glu Ile Glu Glu Glu
    50                  55                  60

Leu Arg Arg Arg Gly Ile Asp Thr Glu Asp Tyr Met Ser Asn Met Arg
65                  70                  75                  80

Val Ile Ile Lys Glu Leu Ser
                85

<210> SEQ ID NO 139
<211> LENGTH: 87
<212> TYPE: PRT
<213> ORGANISM: Artificial Sequence
<220> FEATURE:
<223> OTHER INFORMATION: Synthetic

<400> SEQUENCE: 139

Thr Lys Lys Lys Leu Gln Leu Leu Val Glu His Leu Leu Leu Asp Met
1               5                   10                  15

Leu Met Ile Leu Asn Met Ser Ser Glu Ser Asn Glu Lys Leu Asn Arg
            20                  25                  30

Leu Ile Thr Glu Leu Gln Ser Trp Ile Phe Arg Gly Glu Ile Asp Pro
        35                  40                  45

Asp Lys Ala Glu Glu Met Trp Lys Ile Met Glu Glu Ile Glu Lys Glu
    50                  55                  60

Leu Arg Glu Arg Gly Ile Asp Thr Glu Asp Tyr Met Ser Asn Ala Lys
65                  70                  75                  80

Val Ile Ile Lys Glu Leu Ser
                85

<210> SEQ ID NO 140
<211> LENGTH: 87
<212> TYPE: PRT
<213> ORGANISM: Artificial Sequence
<220> FEATURE:
<223> OTHER INFORMATION: Synthetic

<400> SEQUENCE: 140

Thr Ser Lys Lys Gln Gln Leu Leu Ala Glu His Ala Leu Leu Asp Ala
1               5                   10                  15

Leu Met Ile Leu Asn Ile Ser Ser Glu Ser Ser Glu Ala Val Asn Arg
            20                  25                  30

Ala Ile Thr Trp Leu Gln Ser Trp Ile Phe Lys Gly Thr Val Asn Pro
        35                  40                  45

Asp Gln Ala Glu Glu Met Arg Lys Leu Ala Glu Gln Ile Arg Glu Glu
    50                  55                  60

Met Arg Lys Arg Gly Ile Asp Thr Glu Asp Tyr Val Ser Asn Leu Glu
65                  70                  75                  80

Val Ile Ala Lys Glu Leu Ser
                85

<210> SEQ ID NO 141
<211> LENGTH: 87
<212> TYPE: PRT

<213> ORGANISM: Artificial Sequence
<220> FEATURE:
<223> OTHER INFORMATION: Synthetic

<400> SEQUENCE: 141

Thr Lys Lys Lys Tyr Gln Leu Leu Ile Glu His Leu Leu Leu Asp Leu
1 5 10 15

Leu Met Val Leu Asn Met Ser Ser Glu Ser Asn Glu Lys Ile Asn Arg
20 25 30

Leu Ile Thr Trp Leu Gln Ser Trp Ile Phe Thr Gly Thr Tyr Asp Pro
35 40 45

Asp Leu Ala Glu Glu Met Tyr Lys Ile Leu Glu Glu Leu Arg Glu Glu
50 55 60

Met Arg Glu Arg Gly Ile Asp Thr Glu Asp Tyr Met Ser Asn Met Arg
65 70 75 80

Val Ile Val Lys Glu Leu Ser
85

<210> SEQ ID NO 142
<211> LENGTH: 87
<212> TYPE: PRT
<213> ORGANISM: Artificial Sequence
<220> FEATURE:
<223> OTHER INFORMATION: Synthetic

<400> SEQUENCE: 142

Thr Lys Lys Lys Trp Gln Leu Leu Ile Glu His Leu Leu Leu Asp Leu
1 5 10 15

Leu Met Ile Leu Asn Leu Ser Ser Glu Ser Asn Glu Lys Leu Asn Arg
20 25 30

Leu Ile Thr Trp Leu Gln Ser Trp Ile Phe Thr Gly Thr Tyr Asp Pro
35 40 45

Asp Leu Ala Glu Glu Met Lys Lys Met Met Asp Glu Ile Glu Asp Glu
50 55 60

Leu Arg Glu Arg Gly Ile Asp Thr Glu Asp Tyr Met Ser Asn Ala Lys
65 70 75 80

Val Ile Ile Lys Glu Leu Ser
85

<210> SEQ ID NO 143
<211> LENGTH: 87
<212> TYPE: PRT
<213> ORGANISM: Artificial Sequence
<220> FEATURE:
<223> OTHER INFORMATION: Synthetic

<400> SEQUENCE: 143

Thr Lys Lys Lys Ile Gln Leu Leu Val Glu His Ala Leu Leu Asp Ala
1 5 10 15

Leu Met Ile Leu Asn Leu Ser Ser Glu Ser Asn Glu Lys Leu Asn Arg
20 25 30

Ile Ile Thr Thr Met Gln Ser Trp Ile Phe Thr Gly Thr Ile Asp Pro
35 40 45

Asp Gln Ala Glu Glu Leu Ser Lys Leu Val Glu Glu Ile Arg Glu Glu
50 55 60

Met Arg Lys Arg Gly Ile Asp Thr Glu Asp Tyr Val Ser Asn Leu Lys
65 70 75 80

Val Ile Leu Asp Glu Leu Ser
85

<210> SEQ ID NO 144
<211> LENGTH: 87
<212> TYPE: PRT
<213> ORGANISM: Artificial Sequence
<220> FEATURE:
<223> OTHER INFORMATION: Synthetic

<400> SEQUENCE: 144

```
Thr Glu Lys Lys Leu Gln Leu Leu Val Glu His Ala Leu Leu Asp Ala
1               5                   10                  15

Leu Met Ile Leu Asn Leu Trp Ser Glu Ser Asn Glu Lys Leu Asn Arg
            20                  25                  30

Ile Ile Thr Thr Met Gln Ser Trp Ile Phe Thr Gly Arg Ile Asp Pro
        35                  40                  45

Asp Lys Ala Glu Glu Leu Ala Lys Leu Val Glu Glu Leu Arg Glu Glu
    50                  55                  60

Ala Arg Glu Arg Gly Ile Asp Thr Glu Asp Tyr Val Ser Asn Leu Lys
65                  70                  75                  80

Val Ile Leu Lys Glu Leu Ser
                85
```

<210> SEQ ID NO 145
<211> LENGTH: 87
<212> TYPE: PRT
<213> ORGANISM: Artificial Sequence
<220> FEATURE:
<223> OTHER INFORMATION: Synthetic

<400> SEQUENCE: 145

```
Thr Lys Lys Lys Tyr Gln Leu Leu Met Glu His Leu Leu Leu Asp Leu
1               5                   10                  15

Leu Met Val Leu Asn Met Ser Ser Glu Ser Asn Glu Lys Leu Asn Arg
            20                  25                  30

Leu Ile Thr Ile Ile Gln Ser Trp Ile Phe Thr Gly Thr Trp Asp Pro
        35                  40                  45

Asp Lys Ala Glu Glu Met Ala Lys Met Leu Lys Glu Ile Glu Asp Glu
    50                  55                  60

Leu Arg Glu Arg Gly Ile Asp Thr Glu Asp Tyr Met Ser Asn Met Ile
65                  70                  75                  80

Val Ile Met Lys Glu Leu Ser
                85
```

<210> SEQ ID NO 146
<211> LENGTH: 87
<212> TYPE: PRT
<213> ORGANISM: Artificial Sequence
<220> FEATURE:
<223> OTHER INFORMATION: Synthetic

<400> SEQUENCE: 146

```
Thr Thr Lys Lys Ile Gln Leu Leu Val Glu His Ala Leu Leu Asp Ala
1               5                   10                  15

Leu Met Leu Leu Asn Leu Ser Ser Glu Ser Asn Glu Lys Met Asn Arg
            20                  25                  30

Ile Ile Thr Thr Met Gln Ser Trp Ile Phe Glu Gly Arg Ile Asp Pro
        35                  40                  45

Asp Gln Ala Gln Glu Leu Ala Lys Leu Val Glu Glu Leu Arg Glu Glu
    50                  55                  60
```

-continued

```
Phe Arg Lys Arg Gly Ile Asp Thr Glu Asp Tyr Val Ser Asn Leu Lys
65                  70                  75                  80

Val Ile Leu Glu Glu Leu Ser
                85


<210> SEQ ID NO 147
<211> LENGTH: 87
<212> TYPE: PRT
<213> ORGANISM: Artificial Sequence
<220> FEATURE:
<223> OTHER INFORMATION: Synthetic

<400> SEQUENCE: 147

Thr Lys Lys Lys Ile Gln Leu Leu Val Glu His Ala Leu Leu Asp Ala
1               5                   10                  15

Leu Met Met Leu Asn Leu Ser Ser Glu Ser Asn Glu Lys Leu Asn Arg
            20                  25                  30

Ile Ile Thr Thr Met Gln Ser Trp Ile Phe Thr Gly Thr Ile Asp Pro
        35                  40                  45

Asp Gln Ala Glu Glu Leu Ala Lys Leu Val Arg Glu Leu Arg Glu Glu
    50                  55                  60

Phe Arg Lys Arg Gly Ile Asp Thr Glu Asp Tyr Ala Ser Asn Leu Glu
65                  70                  75                  80

Val Ile Leu Arg Glu Leu Ser
                85


<210> SEQ ID NO 148
<211> LENGTH: 87
<212> TYPE: PRT
<213> ORGANISM: Artificial Sequence
<220> FEATURE:
<223> OTHER INFORMATION: Synthetic

<400> SEQUENCE: 148

Thr Lys Lys Lys Ile Gln Leu Leu Val Glu His Ala Leu Leu Asp Ala
1               5                   10                  15

Leu Met Ile Leu Asn Leu Ser Ser Lys Ser Asn Glu Lys Leu Asn Arg
            20                  25                  30

Ile Ile Thr Thr Met Gln Ser Trp Ile Phe Asn Gly Thr Ile Asp Pro
        35                  40                  45

Asp Arg Ala Arg Glu Leu Ala Lys Leu Val Glu Glu Ile Arg Asp Glu
    50                  55                  60

Met Glu Lys Asn Gly Ile Asp Thr Glu Asp Tyr Val Ser Asn Leu Lys
65                  70                  75                  80

Val Ile Leu Glu Glu Leu Ala
                85


<210> SEQ ID NO 149
<211> LENGTH: 87
<212> TYPE: PRT
<213> ORGANISM: Artificial Sequence
<220> FEATURE:
<223> OTHER INFORMATION: Synthetic

<400> SEQUENCE: 149

Thr Lys Lys Lys Tyr Gln Leu Leu Ile Glu His Val Leu Leu Asp Leu
1               5                   10                  15

Leu Met Leu Leu Asn Leu Ser Ser Glu Ser Asn Glu Lys Met Asn Arg
            20                  25                  30

Leu Ile Thr Ile Leu Gln Ser Trp Ile Phe Thr Gly Thr Tyr Asp Pro
```

```
        35                  40                  45

Asp Lys Ala Glu Glu Met Ala Lys Leu Leu Lys Glu Leu Arg Glu Glu
    50                  55                  60

Phe Arg Glu Arg Gly Ile Asp Thr Glu Asp Tyr Ile Ser Asn Ala Ile
65                  70                  75                  80

Val Ile Leu Lys Glu Leu Ser
                85


<210> SEQ ID NO 150
<211> LENGTH: 87
<212> TYPE: PRT
<213> ORGANISM: Artificial Sequence
<220> FEATURE:
<223> OTHER INFORMATION: Synthetic

<400> SEQUENCE: 150

Thr Lys Lys Lys Ile Gln Leu Leu Val Glu His Ala Leu Leu Asp Ala
1               5                   10                  15

Leu Met Met Leu Asn Leu Ser Ser Glu Ser Asn Glu Lys Leu Asn Arg
            20                  25                  30

Ile Ile Thr Thr Met Gln Ser Trp Ile Phe Thr Gly Thr Ile Asp Pro
        35                  40                  45

Asp Arg Ala Glu Glu Leu Ala Lys Leu Val Glu Glu Leu Arg Glu Glu
    50                  55                  60

Phe Arg Lys Arg Gly Ile Asp Thr Glu Asp Tyr Ala Ser Asn Leu Lys
65                  70                  75                  80

Val Ile Leu Lys Glu Leu Ser
                85


<210> SEQ ID NO 151
<211> LENGTH: 87
<212> TYPE: PRT
<213> ORGANISM: Artificial Sequence
<220> FEATURE:
<223> OTHER INFORMATION: Synthetic

<400> SEQUENCE: 151

Thr Lys Lys Lys Ile Gln Leu Leu Val Glu His Ala Leu Leu Asp Ala
1               5                   10                  15

Leu Met Met Leu Asn Leu Ser Ser Glu Ser Asn Glu Lys Leu Asn Arg
            20                  25                  30

Ile Ile Thr Thr Met Gln Ser Trp Ile Phe Asn Gly Thr Ile Asp Pro
        35                  40                  45

Asp Gln Ala Arg Glu Leu Ala Lys Leu Val Glu Glu Leu Arg Glu Glu
    50                  55                  60

Phe Arg Lys Arg Gly Ile Asp Thr Glu Asp Tyr Ala Ser Asn Leu Lys
65                  70                  75                  80

Val Ile Leu Glu Glu Leu Ala
                85


<210> SEQ ID NO 152
<211> LENGTH: 87
<212> TYPE: PRT
<213> ORGANISM: Artificial Sequence
<220> FEATURE:
<223> OTHER INFORMATION: Synthetic

<400> SEQUENCE: 152

Thr Lys Lys Lys Leu Gln Leu Leu Val Glu His Ala Leu Leu Asp Ala
1               5                   10                  15
```

Leu Met Leu Leu Asn Leu Ser Ser Glu Ser Asn Glu Lys Leu Asn Arg
20 25 30

Ile Ile Thr Thr Met Gln Ser Trp Ile Phe Thr Gly Thr Val Asp Pro
35 40 45

Asp Gln Ala Glu Glu Leu Ala Lys Leu Val Glu Glu Ile Arg Glu Glu
50 55 60

Leu Arg Lys Arg Gly Ile Asp Thr Glu Asp Tyr Val Ser Asn Leu Lys
65 70 75 80

Val Ile Leu Lys Glu Leu Ser
85

<210> SEQ ID NO 153
<211> LENGTH: 87
<212> TYPE: PRT
<213> ORGANISM: Artificial Sequence
<220> FEATURE:
<223> OTHER INFORMATION: Synthetic

<400> SEQUENCE: 153

Thr Thr Lys Lys Tyr Gln Leu Leu Val Glu His Ala Leu Leu Asp Ala
1 5 10 15

Leu Met Ile Leu Asn Leu Ser Ser Glu Ser Asn Glu Lys Leu Asn Arg
20 25 30

Ile Ile Thr Thr Met Gln Ser Trp Ile Phe Thr Gly Thr Phe Asp Pro
35 40 45

Asp Gln Ala Glu Glu Leu Ala Lys Leu Val Arg Glu Ile Arg Glu Glu
50 55 60

Met Arg Lys Arg Gly Ile Asp Thr Glu Asp Tyr Val Ser Asn Leu Glu
65 70 75 80

Val Ile Leu Arg Glu Leu Ser
85

<210> SEQ ID NO 154
<211> LENGTH: 87
<212> TYPE: PRT
<213> ORGANISM: Artificial Sequence
<220> FEATURE:
<223> OTHER INFORMATION: Synthetic

<400> SEQUENCE: 154

Thr Lys Lys Lys Ile Gln Leu Leu Val Glu His Ala Leu Leu Asp Ala
1 5 10 15

Leu Met Ile Leu Asn Leu Ser Ser Glu Ser Asn Glu Lys Leu Asn Arg
20 25 30

Ile Ile Thr Thr Met Gln Ser Trp Ile Phe Thr Gly Thr Ile Asp Pro
35 40 45

Asp Arg Ala Glu Glu Leu Ala Lys Leu Val Arg Glu Ile Arg Glu Glu
50 55 60

Met Arg Lys Arg Gly Ile Asp Thr Glu Asp Tyr Val Ser Asn Leu Glu
65 70 75 80

Val Ile Leu Arg Glu Leu Ser
85

<210> SEQ ID NO 155
<211> LENGTH: 87
<212> TYPE: PRT
<213> ORGANISM: Artificial Sequence
<220> FEATURE:
<223> OTHER INFORMATION: Synthetic

<400> SEQUENCE: 155

Thr Lys Lys Lys Tyr Gln Leu Leu Ile Glu His Leu Leu Leu Asp Leu
1 5 10 15

Leu Met Ile Leu Asn Leu Ser Ser Glu Ser Asn Glu Lys Leu Asn Arg
20 25 30

Leu Ile Thr Trp Leu Gln Ser Trp Ile Phe Arg Gly Glu Trp Asp Pro
35 40 45

Asp Lys Ala Glu Glu Trp Ala Lys Ile Leu Lys Glu Ile Arg Glu Glu
50 55 60

Leu Arg Glu Arg Gly Ile Asp Thr Glu Asp Tyr Met Ser Asn Ala Ile
65 70 75 80

Val Ile Met Lys Glu Leu Ser
85

<210> SEQ ID NO 156
<211> LENGTH: 87
<212> TYPE: PRT
<213> ORGANISM: Artificial Sequence
<220> FEATURE:
<223> OTHER INFORMATION: Synthetic

<400> SEQUENCE: 156

Thr Asp Lys Lys Leu Gln Leu Leu Val Glu His Leu Leu Leu Asp Leu
1 5 10 15

Leu Met Met Leu Asn Leu Ser Ser Lys Ser Asn Glu Lys Met Asn Arg
20 25 30

Leu Ile Thr Ile Ala Gln Ser Trp Ile Phe Thr Gly Lys Val Asp Pro
35 40 45

Asp Leu Ala Arg Glu Met Ile Lys Leu Leu Glu Glu Thr Glu Asp Glu
50 55 60

Asn Arg Lys Asn Gly Ile Asp Thr Glu Asp Tyr Val Ser Asn Ala Arg
65 70 75 80

Val Ile Ala Lys Glu Leu Glu
85

<210> SEQ ID NO 157
<211> LENGTH: 87
<212> TYPE: PRT
<213> ORGANISM: Artificial Sequence
<220> FEATURE:
<223> OTHER INFORMATION: Synthetic

<400> SEQUENCE: 157

Thr Lys Lys Lys Ile Gln Leu Leu Val Glu His Ala Leu Leu Asp Ala
1 5 10 15

Leu Met Leu Leu Asn Leu Ser Ser Glu Ser Asn Glu Lys Met Asn Arg
20 25 30

Ile Ile Thr Thr Met Gln Ser Trp Ile Phe Thr Gly Thr Ile Asp Pro
35 40 45

Asp Gln Ala Glu Glu Leu Ala Lys Leu Val Glu Glu Leu Lys Glu Glu
50 55 60

Phe Lys Lys Arg Gly Ile Asp Thr Glu Asp Tyr Val Ser Asn Leu Lys
65 70 75 80

Val Ile Leu Lys Glu Leu Ser
85

<210> SEQ ID NO 158

<211> LENGTH: 87
<212> TYPE: PRT
<213> ORGANISM: Artificial Sequence
<220> FEATURE:
<223> OTHER INFORMATION: Synthetic

<400> SEQUENCE: 158

```
Thr Lys Lys Lys Tyr Gln Leu Leu Ile Glu His Ala Leu Leu Asp Ala
1               5                   10                  15

Leu Met Ile Leu Asn Leu Trp Ser Glu Ser Asn Glu Lys Leu Asn Arg
            20                  25                  30

Ile Ile Thr Thr Met Gln Ser Trp Ile Phe Thr Gly Thr Tyr Asp Pro
        35                  40                  45

Asp Lys Ala Glu Glu Leu Glu Lys Leu Ala Lys Glu Ile Glu Asp Glu
    50                  55                  60

Ala Arg Glu Arg Gly Ile Asp Thr Glu Asp Tyr Met Ser Asn Leu Arg
65                  70                  75                  80

Val Ile Leu Lys Glu Leu Ser
                85
```

<210> SEQ ID NO 159
<211> LENGTH: 87
<212> TYPE: PRT
<213> ORGANISM: Artificial Sequence
<220> FEATURE:
<223> OTHER INFORMATION: Synthetic

<400> SEQUENCE: 159

```
Thr Lys Lys Lys Ala Gln Leu Leu Ala Glu His Ala Leu Leu Asp Ala
1               5                   10                  15

Leu Met Leu Leu Asn Leu Ser Ser Glu Ser Asn Glu Arg Leu Asn Arg
            20                  25                  30

Ile Ile Thr Trp Leu Gln Ser Ile Ile Phe Thr Gly Thr Tyr Asp Pro
        35                  40                  45

Asp Met Val Lys Glu Ala Val Lys Leu Ala Asp Glu Ile Glu Asp Glu
    50                  55                  60

Met Arg Lys Arg Gly Ile Asp Thr Glu Asp Tyr Val Ser Asn Leu Arg
65                  70                  75                  80

Val Ile Leu Gln Glu Leu Ala
                85
```

<210> SEQ ID NO 160
<211> LENGTH: 87
<212> TYPE: PRT
<213> ORGANISM: Artificial Sequence
<220> FEATURE:
<223> OTHER INFORMATION: Synthetic

<400> SEQUENCE: 160

```
Thr Gln Lys Lys Asn Gln Leu Leu Ala Glu His Leu Leu Leu Asp Ala
1               5                   10                  15

Leu Met Val Leu Asn Gln Ser Ser Glu Ser Ser Glu Val Ala Asn Arg
            20                  25                  30

Ile Ile Thr Trp Ala Gln Ser Trp Ile Phe Glu Gly Arg Val Asp Pro
        35                  40                  45

Asn Lys Ala Glu Glu Ala Lys Lys Leu Ala Lys Lys Leu Glu Glu Glu
    50                  55                  60

Met Arg Lys Arg Gly Ile Asp Met Glu Asp Tyr Ile Ser Asn Met Lys
65                  70                  75                  80
```

```
Val Ile Ala Glu Glu Met Ser
                85


<210> SEQ ID NO 161
<211> LENGTH: 107
<212> TYPE: PRT
<213> ORGANISM: Artificial Sequence
<220> FEATURE:
<223> OTHER INFORMATION: Synthetic

<400> SEQUENCE: 161

Glu Asp Tyr Tyr Ser Asn Leu Lys Val Ile Leu Glu Glu Leu Ala Arg
1               5                   10                  15

Glu Met Glu Arg Asn Gly Leu Ser Asp Lys Ala Glu Glu Trp Arg Gln
            20                  25                  30

Trp Lys Lys Ile Val Glu Arg Ile Arg Gln Ile Arg Ser Asn Asn Ser
        35                  40                  45

Asp Leu Asn Glu Ala Lys Glu Leu Leu Asn Arg Leu Ile Thr Tyr Ile
    50                  55                  60

Gln Ser Gln Ile Phe Glu Ile Ser Glu Arg Ile Arg Glu Thr Asp Gln
65                  70                  75                  80

Glu Lys Lys Glu Glu Ser Trp Lys Lys Trp Gln Leu Leu Leu Glu His
                85                  90                  95

Ala Leu Leu Asp Val Leu Met Leu Leu Asn Asp
            100                 105


<210> SEQ ID NO 162
<211> LENGTH: 107
<212> TYPE: PRT
<213> ORGANISM: Artificial Sequence
<220> FEATURE:
<223> OTHER INFORMATION: Synthetic

<400> SEQUENCE: 162

Pro Glu Lys Lys Arg Gln Leu Leu Leu Glu His Ile Leu Leu Asp Ala
1               5                   10                  15

Leu Met Leu Leu Asn Leu Leu Glu Thr Asn Pro Gln Asn Thr Glu Ser
            20                  25                  30

Lys Phe Glu Asp Tyr Ile Ser Asn Ala Glu Val Ile Ala Glu Glu Leu
        35                  40                  45

Ala Lys Leu Met Glu Ser Leu Gly Leu Ser Asp Glu Ala Glu Lys Phe
    50                  55                  60

Lys Lys Ile Lys Gln Trp Leu Arg Glu Val Trp Arg Ile Trp Ser Ser
65                  70                  75                  80

Thr Asn Trp Ser Thr Leu Glu Asp Lys Ala Arg Glu Leu Leu Asn Arg
                85                  90                  95

Ile Ile Thr Thr Ile Gln Ser Gln Ile Phe Tyr
            100                 105


<210> SEQ ID NO 163
<211> LENGTH: 104
<212> TYPE: PRT
<213> ORGANISM: Artificial Sequence
<220> FEATURE:
<223> OTHER INFORMATION: Synthetic

<400> SEQUENCE: 163

Pro Glu Lys Lys Arg Gln Leu Leu Leu Glu His Ile Leu Leu Asp Leu
1               5                   10                  15

Leu Met Ile Leu Asn Met Ile Glu Thr Asn Arg Glu Asn Thr Glu Ser
```

```
            20                  25                  30

Glu Met Glu Asp Tyr Trp Ser Asn Val Arg Val Ile Leu Arg Glu Leu
        35                  40                  45

Ala Arg Leu Met Glu Glu Leu Asn Tyr Lys Glu Leu Ser Glu Leu Met
    50                  55                  60

Glu Arg Met Arg Lys Ile Val Glu Lys Ile Arg Gln Ile Val Thr Asn
65                  70                  75                  80

Asn Ser Ser Leu Asp Thr Ala Arg Glu Trp Leu Asn Arg Leu Ile Thr
                85                  90                  95

Trp Ile Gln Ser Leu Ile Phe Arg
            100


<210> SEQ ID NO 164
<211> LENGTH: 104
<212> TYPE: PRT
<213> ORGANISM: Artificial Sequence
<220> FEATURE:
<223> OTHER INFORMATION: Synthetic

<400> SEQUENCE: 164

Pro Glu Lys Lys Arg Gln Leu Leu Ala Glu His Ala Leu Leu Asp Ala
1               5                   10                  15

Leu Met Leu Leu Asn Ile Ile Glu Thr Asn Ser Lys Asn Thr Glu Ser
            20                  25                  30

Lys Met Glu Asp Tyr Val Ser Asn Leu Glu Val Ile Leu Thr Glu Phe
        35                  40                  45

Lys Lys Leu Ala Glu Lys Leu Asn Phe Ser Glu Glu Ala Glu Arg Ala
    50                  55                  60

Glu Arg Met Lys Arg Trp Ala Arg Lys Ala Tyr Gln Met Met Thr Leu
65                  70                  75                  80

Asp Leu Ser Leu Asp Lys Ala Lys Glu Met Leu Asn Arg Ile Ile Thr
                85                  90                  95

Ile Leu Gln Ser Ile Ile Phe Asn
            100


<210> SEQ ID NO 165
<211> LENGTH: 96
<212> TYPE: PRT
<213> ORGANISM: Artificial Sequence
<220> FEATURE:
<223> OTHER INFORMATION: Synthetic

<400> SEQUENCE: 165

Pro Glu Lys Lys Arg Gln Leu Leu Ala Glu His Leu Leu Leu Asp Val
1               5                   10                  15

Leu Met Met Leu Asn Gly Asn Ala Ser Leu Lys Asp Tyr Ala Ser Asn
            20                  25                  30

Ala Gln Val Ile Ala Asp Glu Phe Arg Glu Leu Ala Arg Glu Leu Gly
        35                  40                  45

Leu Thr Asp Glu Ala Lys Lys Ala Glu Lys Ile Ile Glu Ala Leu Glu
    50                  55                  60

Arg Ala Arg Glu Trp Leu Leu Asn Asn Lys Asp Lys Glu Lys Ala Lys
65                  70                  75                  80

Glu Ala Leu Asn Arg Ala Ile Thr Ile Ala Gln Ser Trp Ile Phe Asn
                85                  90                  95


<210> SEQ ID NO 166
<211> LENGTH: 104
```

```
<212> TYPE: PRT
<213> ORGANISM: Artificial Sequence
<220> FEATURE:
<223> OTHER INFORMATION: Synthetic

<400> SEQUENCE: 166

Pro Glu Lys Lys Arg Gln Leu Leu Leu Glu His Leu Leu Leu Asp Leu
1               5                   10                  15

Leu Met Ile Leu Asn Met Leu Arg Thr Asn Pro Lys Asn Ile Glu Ser
            20                  25                  30

Asp Trp Glu Asp Tyr Met Ser Asn Ile Glu Val Ile Ile Glu Glu Leu
        35                  40                  45

Arg Lys Ile Met Glu Ser Leu Gly Arg Ser Glu Lys Ala Lys Glu Trp
    50                  55                  60

Lys Arg Met Lys Gln Trp Val Arg Arg Ile Leu Glu Ile Val Lys Asn
65                  70                  75                  80

Asn Ser Asp Leu Glu Glu Ala Lys Glu Trp Leu Asn Arg Leu Ile Thr
                85                  90                  95

Ile Val Gln Ser Glu Ile Phe Glu
            100


<210> SEQ ID NO 167
<211> LENGTH: 104
<212> TYPE: PRT
<213> ORGANISM: Artificial Sequence
<220> FEATURE:
<223> OTHER INFORMATION: Synthetic

<400> SEQUENCE: 167

Trp Glu Lys Lys Arg Gln Leu Leu Leu Glu His Leu Leu Leu Asp Leu
1               5                   10                  15

Leu Met Ile Leu Asn Met Trp Arg Thr Asn Pro Gln Asn Thr Glu Ser
            20                  25                  30

Leu Met Glu Asp Tyr Met Ser Asn Ala Lys Val Ile Val Glu Glu Leu
        35                  40                  45

Ala Arg Met Met Arg Ser Gln Gly Leu Glu Asp Lys Ala Arg Glu Trp
    50                  55                  60

Glu Glu Met Lys Lys Arg Ile Glu Glu Ile Arg Gln Ile Ile Gln Asn
65                  70                  75                  80

Asn Ser Ser Lys Glu Arg Ala Lys Glu Glu Leu Asn Arg Leu Ile Thr
                85                  90                  95

Tyr Val Gln Ser Glu Ile Phe Arg
            100


<210> SEQ ID NO 168
<211> LENGTH: 100
<212> TYPE: PRT
<213> ORGANISM: Artificial Sequence
<220> FEATURE:
<223> OTHER INFORMATION: Synthetic

<400> SEQUENCE: 168

Pro Lys Lys Lys Ile Gln Leu Leu Ala Glu His Ala Leu Leu Asp Ala
1               5                   10                  15

Leu Met Ile Leu Asn Ile Val Lys Thr Asn Ser Gln Asn Ala Glu Glu
            20                  25                  30

Lys Leu Glu Asp Tyr Ala Ser Asn Val Glu Val Ile Leu Glu Glu Ile
        35                  40                  45

Ala Arg Leu Met Glu Ser Gly Asp Gln Lys Asp Glu Ala Glu Lys Ala
```

```
    50                  55                  60

Lys Arg Met Lys Glu Trp Met Lys Arg Ile Lys Thr Thr Ala Ser Glu
65                  70                  75                  80

Asp Glu Gln Glu Glu Met Ala Asn Arg Ile Ile Thr Leu Leu Gln Ser
                85                  90                  95

Trp Ile Phe Ser
            100


<210> SEQ ID NO 169
<211> LENGTH: 100
<212> TYPE: PRT
<213> ORGANISM: Artificial Sequence
<220> FEATURE:
<223> OTHER INFORMATION: Synthetic

<400> SEQUENCE: 169

Pro Glu Lys Lys Arg Gln Leu Leu Ala Glu His Ala Leu Leu Asp Ala
1               5                   10                  15

Leu Met Ile Leu Asn Ile Leu Gln Thr Asn Pro Gln Asn Ala Glu Glu
            20                  25                  30

Lys Leu Glu Asp Tyr Met Ser Asn Val Glu Val Ile Met Glu Glu Phe
        35                  40                  45

Ala Arg Met Met Arg Asn Gly Asp Arg Ser Glu Glu Ala Glu Asn Ala
    50                  55                  60

Glu Arg Ile Lys Lys Trp Val Arg Lys Ala Ser Ser Thr Ala Ser Ser
65                  70                  75                  80

Glu Glu Gln Arg Glu Met Met Asn Arg Ala Ile Thr Leu Met Gln Ser
                85                  90                  95

Trp Ile Phe Glu
            100


<210> SEQ ID NO 170
<211> LENGTH: 100
<212> TYPE: PRT
<213> ORGANISM: Artificial Sequence
<220> FEATURE:
<223> OTHER INFORMATION: Synthetic

<400> SEQUENCE: 170

Pro Glu Lys Lys Arg Gln Leu Leu Ala Glu His Leu Leu Leu Asp Ala
1               5                   10                  15

Leu Met Val Leu Asn Met Leu Thr Thr Asn Ser Lys Asn Thr Glu Glu
            20                  25                  30

Lys Leu Glu Asp Tyr Ile Ser Asn Met Lys Val Ile Ile Lys Glu Met
        35                  40                  45

Ile Glu Leu Met Arg Ser Leu Gly Arg Leu Glu Glu Ala Glu Lys Trp
    50                  55                  60

Lys Glu Ala Leu Lys Ala Val Glu Lys Ile Gly Ser Arg Met Asp Ser
65                  70                  75                  80

Glu Thr Ala Arg Glu Leu Ala Asn Arg Ile Ile Thr Leu Ala Gln Ser
                85                  90                  95

Ala Ile Phe Tyr
            100


<210> SEQ ID NO 171
<211> LENGTH: 100
<212> TYPE: PRT
<213> ORGANISM: Artificial Sequence
<220> FEATURE:
```

<223> OTHER INFORMATION: Synthetic

<400> SEQUENCE: 171

Pro Glu Lys Lys Arg Gln Leu Leu Ala Glu His Ala Leu Leu Asp Ala
1               5                   10                  15

Leu Met Phe Leu Asn Leu Val Glu Thr Asn Pro Asp Gln Ala Glu Glu
            20                  25                  30

Lys Ile Glu Asp Tyr Ala Ser Asn Leu Arg Val Ile Ala Glu Glu Leu
        35                  40                  45

Ala Arg Leu Phe Glu Asn Leu Gly Arg Leu Asp Glu Ala Gln Lys Ala
    50                  55                  60

Lys Asp Ile Lys Glu Leu Ala Glu Arg Ala Arg Ser Arg Val Ser Ser
65                  70                  75                  80

Glu Lys Arg Lys Glu Ala Met Asn Arg Ala Ile Thr Ile Leu Gln Ser
                85                  90                  95

Met Ile Phe Arg
            100

<210> SEQ ID NO 172
<211> LENGTH: 100
<212> TYPE: PRT
<213> ORGANISM: Artificial Sequence
<220> FEATURE:
<223> OTHER INFORMATION: Synthetic

<400> SEQUENCE: 172

Pro Glu Lys Lys Arg Gln Leu Leu Ala Glu His Ala Leu Leu Asp Ala
1               5                   10                  15

Leu Met Ile Leu Asn Ile Ile Arg Thr Asn Ser Asp Asn Thr Glu Ser
            20                  25                  30

Lys Leu Glu Asp Tyr Ile Ser Asn Leu Lys Val Ile Leu Glu Glu Ile
        35                  40                  45

Ala Arg Leu Met Glu Ser Leu Gly Leu Ser Asp Glu Ala Glu Lys Ala
    50                  55                  60

Lys Glu Ala Met Arg Leu Ala Asp Lys Ala Gly Ser Thr Ala Ser Glu
65                  70                  75                  80

Glu Glu Lys Lys Glu Ala Met Asn Arg Val Ile Thr Trp Ala Gln Ser
                85                  90                  95

Trp Ile Phe Asn
            100

<210> SEQ ID NO 173
<211> LENGTH: 100
<212> TYPE: PRT
<213> ORGANISM: Artificial Sequence
<220> FEATURE:
<223> OTHER INFORMATION: Synthetic

<400> SEQUENCE: 173

Pro Glu Lys Lys Arg Gln Leu Leu Ala Glu His Ala Leu Leu Asp Ala
1               5                   10                  15

Leu Met Met Leu Asn Ile Leu Arg Thr Asn Pro Asp Asn Ala Glu Glu
            20                  25                  30

Lys Leu Glu Asp Tyr Trp Ser Asn Leu Ile Val Ile Leu Arg Glu Ile
        35                  40                  45

Ala Lys Leu Met Glu Ser Leu Gly Leu Thr Asp Glu Ala Glu Lys Ala
    50                  55                  60

Lys Glu Ala Ala Arg Trp Ala Glu Glu Ala Arg Thr Thr Ala Ser Lys

```
65                  70                  75                  80

Asp Gln Arg Arg Glu Leu Ala Asn Arg Ile Ile Thr Leu Leu Gln Ser
                85                  90                  95

Trp Ile Phe Ser
            100


<210> SEQ ID NO 174
<211> LENGTH: 100
<212> TYPE: PRT
<213> ORGANISM: Artificial Sequence
<220> FEATURE:
<223> OTHER INFORMATION: Synthetic

<400> SEQUENCE: 174

Pro Glu Lys Lys Arg Gln Leu Leu Ala Glu His Leu Leu Leu Asp Ala
1               5                   10                  15

Leu Met Ile Leu Asn Ile Ile Glu Thr Asn Glu Gln Asn Ala Glu Ser
            20                  25                  30

Lys Leu Glu Asp Tyr Ile Ser Asn Ala Lys Val Ile Leu Asp Glu Phe
        35                  40                  45

Arg Glu Met Ala Arg Asp Leu Gly Leu Leu Asp Glu Ala Lys Lys Ala
    50                  55                  60

Glu Lys Met Lys Arg Trp Leu Glu Lys Met Arg Ser Asn Ala Ser Ser
65                  70                  75                  80

Asp Glu Arg Arg Glu Trp Ala Asn Arg Met Ile Thr Thr Ala Gln Ser
                85                  90                  95

Trp Ile Phe Asn
            100


<210> SEQ ID NO 175
<211> LENGTH: 87
<212> TYPE: PRT
<213> ORGANISM: Artificial Sequence
<220> FEATURE:
<223> OTHER INFORMATION: Synthetic

<400> SEQUENCE: 175

Thr Asn Lys Glu Ala Gln Leu His Ala Glu Phe Ala Leu Tyr Asp Ala
1               5                   10                  15

Leu Met Leu Leu Asn Leu Ser Ser Glu Ser Asn Glu Arg Leu Asn Arg
            20                  25                  30

Ile Ile Thr Trp Leu Gln Ser Ile Ile Phe Tyr Glu Thr Tyr Asp Pro
        35                  40                  45

Asp Met Val Lys Glu Ala Val Lys Leu Ala Asp Glu Ile Glu Asp Glu
    50                  55                  60

Met Arg Lys Arg Lys Ile Asp Thr Glu Asp Tyr Val Val Asn Leu Arg
65                  70                  75                  80

Leu Ile Leu Gln Glu Leu Ala
                85


<210> SEQ ID NO 176
<211> LENGTH: 87
<212> TYPE: PRT
<213> ORGANISM: Artificial Sequence
<220> FEATURE:
<223> OTHER INFORMATION: Synthetic

<400> SEQUENCE: 176

Thr Lys Lys Asp Ala Glu Leu Leu Ala Glu Phe Ala Leu Tyr Asp Ala
1               5                   10                  15
```

```
Leu Met Leu Leu Asn Leu Ser Ser Glu Ser Asn Glu Arg Leu Asn Glu
            20                  25                  30

Ile Ile Thr Trp Leu Gln Ser Ile Ile Phe Tyr Gly Thr Tyr Asp Pro
        35                  40                  45

Asp Met Val Lys Glu Ala Val Lys Leu Ala Asp Glu Ile Glu Asp Glu
    50                  55                  60

Met Arg Lys Arg Gly Ile Asp Thr Glu Asp Tyr Val Ser Asn Leu Arg
65                  70                  75                  80

Leu Ile Leu Gln Glu Leu Ala
                85


<210> SEQ ID NO 177
<211> LENGTH: 87
<212> TYPE: PRT
<213> ORGANISM: Artificial Sequence
<220> FEATURE:
<223> OTHER INFORMATION: Synthetic

<400> SEQUENCE: 177

Thr Asn Lys Lys Ala Gln Leu His Ala Glu Phe Ala Leu Tyr Asp Ala
1               5                   10                  15

Leu Met Leu Leu Asn Leu Ser Ser Glu Ser Asn Glu Arg Leu Asn Asp
            20                  25                  30

Ile Ile Thr Trp Leu Gln Ser Ile Ile Phe Thr Gly Thr Tyr Asp Pro
        35                  40                  45

Asp Met Val Lys Glu Ala Val Lys Leu Ala Asp Glu Ile Glu Asp Glu
    50                  55                  60

Met Arg Lys Arg Lys Ile Asp Thr Glu Asp Tyr Val Val Asn Leu Arg
65                  70                  75                  80

Tyr Ile Leu Gln Glu Leu Ala
                85


<210> SEQ ID NO 178
<211> LENGTH: 107
<212> TYPE: PRT
<213> ORGANISM: Artificial Sequence
<220> FEATURE:
<223> OTHER INFORMATION: Synthetic

<400> SEQUENCE: 178

Glu Asp Tyr Tyr Ser Asn Leu Lys Leu Ile Leu Glu Glu Leu Ala Arg
1               5                   10                  15

Glu Met Glu Arg Asn Gly Leu Ser Asp Lys Ala Glu Glu Trp Arg Gln
            20                  25                  30

Trp Lys Lys Ile Val Glu Arg Ile Arg Gln Ile Arg Ser Asn Asn Ser
        35                  40                  45

Asp Leu Asn Glu Ala Lys Glu Leu Leu Asn Arg Leu Ile Thr Tyr Ile
    50                  55                  60

Gln Ser Gln Ile Phe Glu Val Leu His Gly Val Gly Glu Thr Asp Gln
65                  70                  75                  80

Glu Lys Lys Glu Glu Ser Trp Lys Lys Trp Asp Leu Leu Leu Glu His
                85                  90                  95

Ala Leu Leu Asp Val Leu Met Leu Leu Asn Asp
            100                 105


<210> SEQ ID NO 179
<211> LENGTH: 107
<212> TYPE: PRT
```

<213> ORGANISM: Artificial Sequence
<220> FEATURE:
<223> OTHER INFORMATION: Synthetic

<400> SEQUENCE: 179

```
Glu Asp Tyr Tyr Ser Asn Leu Lys Val Ile Leu Glu Glu Leu Ala Arg
1               5                   10                  15

Glu Met Glu Arg Asn Gly Leu Ser Asp Lys Ala Glu Glu Trp Arg Gln
            20                  25                  30

Trp Lys Lys Ile Val Glu Arg Ile Arg Gln Ile Arg Ser Asn Asn Ser
        35                  40                  45

Asp Leu Asn Glu Ala Lys Glu Leu Leu Asn Glu Leu Ile Thr Tyr Ile
    50                  55                  60

Gln Ser Gln Ile Phe Glu Val Ile Glu Arg Glu Gly Glu Thr Asp Gln
65                  70                  75                  80

Glu Lys Lys Glu Glu Ser Trp Lys Lys Trp Glu Leu His Leu Glu His
                85                  90                  95

Ala Leu Leu Asp Val Leu Met Leu Leu Asn Asp
            100                 105
```

<210> SEQ ID NO 180
<211> LENGTH: 107
<212> TYPE: PRT
<213> ORGANISM: Artificial Sequence
<220> FEATURE:
<223> OTHER INFORMATION: Synthetic

<400> SEQUENCE: 180

```
Glu Asp Tyr Tyr Ser Asn Leu Lys Leu Ile Leu Glu Glu Leu Ala Arg
1               5                   10                  15

Glu Met Glu Arg Asn Gly Leu Ser Asp Lys Ala Glu Glu Trp Arg Gln
            20                  25                  30

Trp Lys Lys Ile Val Glu Arg Ile Arg Gln Ile Arg Ser Asn Asn Ser
        35                  40                  45

Asp Leu Asn Glu Ala Lys Glu Leu Leu Asn Arg Leu Ile Thr Tyr Ile
    50                  55                  60

Gln Ser Gln Ile Phe Glu Val Leu Glu Gly Val Gly Glu Thr Asp Gln
65                  70                  75                  80

Glu Lys Lys Glu Glu Ser Trp Lys Lys Trp Glu Leu His Leu Glu His
                85                  90                  95

Ala Leu Leu Asp Val Leu Met Leu Leu Asn Asp
            100                 105
```

<210> SEQ ID NO 181
<211> LENGTH: 100
<212> TYPE: PRT
<213> ORGANISM: Artificial Sequence
<220> FEATURE:
<223> OTHER INFORMATION: Synthetic

<400> SEQUENCE: 181

```
Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Lys Asp Glu Ala Glu Lys Ala
    50                  55                  60
```

Lys Arg Met Lys Glu Trp Met Lys Arg Ile Lys Thr Thr Ala Ser Glu
65 70 75 80

Asp Glu Gln Glu Glu Met Ala Asn Ala Ile Ile Thr Ile Leu Gln Ser
85 90 95

Trp Ile Phe Ser
100

<210> SEQ ID NO 182
<211> LENGTH: 100
<212> TYPE: PRT
<213> ORGANISM: Artificial Sequence
<220> FEATURE:
<223> OTHER INFORMATION: Synthetic

<400> SEQUENCE: 182

Pro Lys Lys Lys Ile Gln Leu Leu Ala Glu His Ala Leu Phe Asp Leu
1 5 10 15

Leu Met Ile Leu Asn Ile Val Lys Thr Asn Ser Gln Asn Ala Glu Glu
20 25 30

Lys Leu Glu Asp Tyr Ala Tyr Asn Ala Gly Val Ile Leu Glu Glu Ile
35 40 45

Ala Arg Leu Phe Glu Ser Gly Asp Gln Lys Asp Glu Ala Glu Lys Ala
50 55 60

Lys Arg Met Lys Glu Trp Met Lys Arg Ile Lys Asp Thr Ala Ser Glu
65 70 75 80

Asp Glu Gln Glu Glu Met Ala Asn Glu Ile Ile Thr Ile Leu Gln Ser
85 90 95

Trp Asn Phe Ser
100

<210> SEQ ID NO 183
<211> LENGTH: 100
<212> TYPE: PRT
<213> ORGANISM: Artificial Sequence
<220> FEATURE:
<223> OTHER INFORMATION: Synthetic

<400> SEQUENCE: 183

Pro Lys Lys Lys Ile Gln Ile Thr Ala Glu Glu Ala Leu Lys Asp Ala
1 5 10 15

Leu Ser Ile Leu Asn Ile Val Lys Thr Asn Ser Pro Pro Ala Glu Glu
20 25 30

Gln Leu Glu Arg Phe Ala Lys Arg Phe Glu Arg Asn Leu Trp Gly Ile
35 40 45

Ala Arg Leu Phe Glu Ser Gly Asp Gln Lys Asp Glu Ala Glu Lys Ala
50 55 60

Lys Arg Met Lys Glu Trp Met Lys Arg Ile Lys Thr Thr Ala Ser Glu
65 70 75 80

Asp Glu Gln Glu Glu Met Ala Asn Ala Ile Ile Thr Ile Leu Gln Ser
85 90 95

Trp Ile Phe Ser
100

<210> SEQ ID NO 184
<211> LENGTH: 100
<212> TYPE: PRT
<213> ORGANISM: Artificial Sequence
<220> FEATURE:
<223> OTHER INFORMATION: Synthetic

<400> SEQUENCE: 184

Pro Lys Lys Lys Ile Gln Ile Met Ala Glu Glu Ala Leu Lys Asp Ala
1 5 10 15

Leu Ser Ile Leu Asn Ile Val Lys Thr Asn Ser Pro Pro Ala Glu Glu
20 25 30

Gln Leu Glu Arg Phe Ala Lys Arg Phe Glu Arg Asn Leu Trp Gly Ile
35 40 45

Ala Arg Leu Phe Glu Ser Gly Asp Gln Lys Asp Glu Ala Glu Lys Ala
50 55 60

Lys Arg Met Ile Glu Trp Met Lys Arg Ile Lys Thr Thr Ala Ser Glu
65 70 75 80

Asp Glu Gln Glu Glu Met Ala Asn Ala Ile Ile Thr Ile Leu Gln Ser
85 90 95

Trp Phe Phe Ser
100

<210> SEQ ID NO 185

<400> SEQUENCE: 185

000

<210> SEQ ID NO 186
<211> LENGTH: 130
<212> TYPE: PRT
<213> ORGANISM: Artificial Sequence
<220> FEATURE:
<223> OTHER INFORMATION: Synthetic

<400> SEQUENCE: 186

Gly Pro Gly Ser His Leu Glu Gln Leu Leu Met Asp Leu Gln Glu Leu
1 5 10 15

Leu Ser Arg Met Glu Asn Tyr Arg Asn Leu Lys Leu Pro Arg Met Leu
20 25 30

Thr Phe Lys Phe Tyr Leu Pro Lys Gln Ala Thr Glu Leu Lys Asp Leu
35 40 45

Gln Cys Leu Glu Asp Glu Leu Gly Pro Leu Arg His Val Leu Asp Leu
50 55 60

Thr Gln Ser Lys Ser Phe Gln Leu Glu Asp Ala Glu Asn Phe Ile Ser
65 70 75 80

Asn Ile Arg Val Thr Val Val Lys Leu Lys Gly Ser Asp Asn Thr Phe
85 90 95

Glu Cys Gln Phe Asp Asp Glu Ser Ala Thr Val Val Asp Phe Leu Arg
100 105 110

Arg Trp Ile Ala Phe Cys Gln Ser Ile Ile Ser Thr Ser Pro Gln Ala
115 120 125

Ala Ala
130

<210> SEQ ID NO 187
<211> LENGTH: 133
<212> TYPE: PRT
<213> ORGANISM: Artificial Sequence
<220> FEATURE:
<223> OTHER INFORMATION: Synthetic

<400> SEQUENCE: 187

Ala Pro Thr Ser Ser Ser Thr Lys Lys Thr Gln Leu Gln Leu Glu His

```
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala His Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Leu Thr Phe Cys Gln Ser Ile
        115                 120                 125

Ile Ser Thr Leu Thr
    130


<210> SEQ ID NO 188
<211> LENGTH: 100
<212> TYPE: PRT
<213> ORGANISM: Artificial Sequence
<220> FEATURE:
<223> OTHER INFORMATION: Synthetic

<400> SEQUENCE: 188

Pro Lys Lys Lys Ile Gln Leu Leu Ala Glu His Ala Leu Leu Asp Ala
1               5                   10                  15

Leu Met Ile Leu Asn Ile Val Lys Thr Asn Ser Gln Asn Ala Glu Glu
            20                  25                  30

Lys Leu Glu Asp Tyr Ala Ser Asn Val Glu Val Ile Leu Glu Glu Ile
        35                  40                  45

Ala Arg Leu Met Glu Ser Gly Asp Gln Lys Asp Glu Ala Glu Lys Ala
    50                  55                  60

Lys Arg Met Lys Glu Trp Met Lys Arg Ile Lys Thr Thr Ala Ser Glu
65                  70                  75                  80

Asp Glu Gln Glu Glu Met Ala Asn Arg Ile Ile Thr Leu Leu Gln Ser
                85                  90                  95

Trp Ile Phe Ser
            100


<210> SEQ ID NO 189
<211> LENGTH: 101
<212> TYPE: PRT
<213> ORGANISM: Artificial Sequence
<220> FEATURE:
<223> OTHER INFORMATION: Synthetic

<400> SEQUENCE: 189

Pro Lys Lys Lys Ile Gln Leu His Ala Glu His Ala Leu Tyr Asp Ala
1               5                   10                  15

Leu Lys Met Ile Leu Asn Ile Val Lys Thr Asn Ser Pro Pro Ala Glu
            20                  25                  30

Glu Lys Leu Glu Asp Tyr Ala Phe Asn Phe Glu Leu Ile Leu Glu Glu
        35                  40                  45

Ile Ala Arg Leu Phe Glu Ser Gly Asp Gln Lys Asp Glu Ala Glu Lys
    50                  55                  60
```

```
Ala Lys Arg Met Lys Glu Trp Met Lys Arg Ile Lys Thr Thr Ala Ser
65                  70                  75                  80

Glu Asp Glu Gln Glu Glu Met Ala Asn Ala Ile Ile Thr Ile Leu Gln
                85                  90                  95

Ser Trp Ile Phe Ser
            100


<210> SEQ ID NO 190
<211> LENGTH: 100
<212> TYPE: PRT
<213> ORGANISM: Artificial Sequence
<220> FEATURE:
<223> OTHER INFORMATION: Synthetic

<400> SEQUENCE: 190

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Cys Leu Phe Glu Ser Gly Asp Gln Lys Asp Glu Ala Glu Lys Ala
    50                  55                  60

Lys Arg Met Lys Glu Trp Met Lys Arg Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100


<210> SEQ ID NO 191
<211> LENGTH: 100
<212> TYPE: PRT
<213> ORGANISM: Artificial Sequence
<220> FEATURE:
<223> OTHER INFORMATION: Synthetic

<400> SEQUENCE: 191

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Cys Ser Gly Asp Gln Lys Asp Glu Ala Glu Lys Ala
    50                  55                  60

Lys Arg Met Lys Glu Trp Met Lys Arg Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100


<210> SEQ ID NO 192
<211> LENGTH: 100
<212> TYPE: PRT
<213> ORGANISM: Artificial Sequence
<220> FEATURE:
<223> OTHER INFORMATION: Synthetic
```

<400> SEQUENCE: 192

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Cys Gln Lys Asp Glu Ala Glu Lys Ala
    50                  55                  60

Lys Arg Met Lys Glu Trp Met Lys Arg Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 193
<211> LENGTH: 100
<212> TYPE: PRT
<213> ORGANISM: Artificial Sequence
<220> FEATURE:
<223> OTHER INFORMATION: Synthetic

<400> SEQUENCE: 193

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Cys Asp Glu Ala Glu Lys Ala
    50                  55                  60

Lys Arg Met Lys Glu Trp Met Lys Arg Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100

<210> SEQ ID NO 194
<211> LENGTH: 100
<212> TYPE: PRT
<213> ORGANISM: Artificial Sequence
<220> FEATURE:
<223> OTHER INFORMATION: Synthetic

<400> SEQUENCE: 194

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Lys Cys Glu Ala Glu Lys Ala
    50                  55                  60

Lys Arg Met Lys Glu Trp Met Lys Arg Ile Lys Thr Thr Ala Ser Glu
65                  70                  75                  80

```
Asp Glu Gln Glu Glu Met Ala Asn Ala Ile Ile Thr Ile Leu Gln Ser
                85                  90                  95

Trp Ile Phe Ser
            100


<210> SEQ ID NO 195
<211> LENGTH: 100
<212> TYPE: PRT
<213> ORGANISM: Artificial Sequence
<220> FEATURE:
<223> OTHER INFORMATION: Synthetic

<400> SEQUENCE: 195

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Lys Asp Glu Ala Cys Lys Ala
    50                  55                  60

Lys Arg Met Lys Glu Trp Met Lys Arg Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100


<210> SEQ ID NO 196
<211> LENGTH: 100
<212> TYPE: PRT
<213> ORGANISM: Artificial Sequence
<220> FEATURE:
<223> OTHER INFORMATION: Synthetic

<400> SEQUENCE: 196

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Lys Asp Glu Ala Glu Lys Ala
    50                  55                  60

Lys Cys Met Lys Glu Trp Met Lys Arg Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100


<210> SEQ ID NO 197
<211> LENGTH: 100
<212> TYPE: PRT
<213> ORGANISM: Artificial Sequence
<220> FEATURE:
<223> OTHER INFORMATION: Synthetic

<400> SEQUENCE: 197

Pro Lys Lys Lys Ile Gln Leu His Ala Glu His Ala Leu Tyr Asp Ala
```

```
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Lys Asp Glu Ala Glu Lys Ala
    50                  55                  60

Lys Arg Met Lys Cys Trp Met Lys Arg Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100


<210> SEQ ID NO 198
<211> LENGTH: 100
<212> TYPE: PRT
<213> ORGANISM: Artificial Sequence
<220> FEATURE:
<223> OTHER INFORMATION: Synthetic

<400> SEQUENCE: 198

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Lys Asp Glu Ala Glu Lys Ala
    50                  55                  60

Lys Arg Met Lys Glu Trp Met Lys Cys Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100


<210> SEQ ID NO 199
<211> LENGTH: 100
<212> TYPE: PRT
<213> ORGANISM: Artificial Sequence
<220> FEATURE:
<223> OTHER INFORMATION: Synthetic

<400> SEQUENCE: 199

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Lys Asp Glu Ala Glu Lys Ala
    50                  55                  60

Lys Arg Met Lys Glu Trp Met Lys Arg Ile Lys Thr Cys Ala Ser Glu
65                  70                  75                  80

Asp Glu Gln Glu Glu Met Ala Asn Ala Ile Ile Thr Ile Leu Gln Ser
                85                  90                  95
```

```
Trp Ile Phe Ser
            100


<210> SEQ ID NO 200
<211> LENGTH: 100
<212> TYPE: PRT
<213> ORGANISM: Artificial Sequence
<220> FEATURE:
<223> OTHER INFORMATION: Synthetic

<400> SEQUENCE: 200

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Lys Asp Glu Ala Glu Lys Ala
    50                  55                  60

Lys Arg Met Lys Glu Trp Met Lys Arg Ile Lys Thr Thr Ala Ser Glu
65                  70                  75                  80

Asp Cys Gln Glu Glu Met Ala Asn Ala Ile Ile Thr Ile Leu Gln Ser
                85                  90                  95

Trp Ile Phe Ser
            100


<210> SEQ ID NO 201
<211> LENGTH: 100
<212> TYPE: PRT
<213> ORGANISM: Artificial Sequence
<220> FEATURE:
<223> OTHER INFORMATION: Synthetic

<400> SEQUENCE: 201

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Lys Asp Glu Ala Glu Lys Ala
    50                  55                  60

Lys Arg Met Lys Glu Trp Met Lys Arg Ile Lys Thr Thr Ala Ser Glu
65                  70                  75                  80

Asp Glu Gln Glu Cys Met Ala Asn Ala Ile Ile Thr Ile Leu Gln Ser
                85                  90                  95

Trp Ile Phe Ser
            100


<210> SEQ ID NO 202
<211> LENGTH: 100
<212> TYPE: PRT
<213> ORGANISM: Artificial Sequence
<220> FEATURE:
<223> OTHER INFORMATION: Synthetic

<400> SEQUENCE: 202

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
```

```
            20                  25                  30

Lys Leu Glu Asp Tyr Ala Phe Asn Phe Glu Leu Ile Leu Glu Glu Ile
        35                  40                  45

Ala Cys Leu Phe Glu Ser Gly Asp Gln Lys Asp Glu Ala Glu Lys Ala
    50                  55                  60

Lys Arg Met Lys Glu Trp Met Lys Cys Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100


<210> SEQ ID NO 203
<211> LENGTH: 100
<212> TYPE: PRT
<213> ORGANISM: Artificial Sequence
<220> FEATURE:
<223> OTHER INFORMATION: Synthetic

<400> SEQUENCE: 203

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Cys Ser Gly Asp Gln Lys Asp Glu Ala Glu Lys Ala
    50                  55                  60

Lys Arg Met Lys Glu Trp Met Lys Cys Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100


<210> SEQ ID NO 204
<211> LENGTH: 100
<212> TYPE: PRT
<213> ORGANISM: Artificial Sequence
<220> FEATURE:
<223> OTHER INFORMATION: Synthetic

<400> SEQUENCE: 204

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Cys Gln Lys Asp Glu Ala Glu Lys Ala
    50                  55                  60

Lys Arg Met Lys Glu Trp Met Lys Cys Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100
```

<210> SEQ ID NO 205
<211> LENGTH: 100
<212> TYPE: PRT
<213> ORGANISM: Artificial Sequence
<220> FEATURE:
<223> OTHER INFORMATION: Synthetic

<400> SEQUENCE: 205

```
Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Cys Asp Glu Ala Glu Lys Ala
    50                  55                  60

Lys Arg Met Lys Glu Trp Met Lys Cys Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100
```

<210> SEQ ID NO 206
<211> LENGTH: 100
<212> TYPE: PRT
<213> ORGANISM: Artificial Sequence
<220> FEATURE:
<223> OTHER INFORMATION: Synthetic

<400> SEQUENCE: 206

```
Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Lys Cys Glu Ala Glu Lys Ala
    50                  55                  60

Lys Arg Met Lys Glu Trp Met Lys Cys Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100
```

<210> SEQ ID NO 207
<211> LENGTH: 100
<212> TYPE: PRT
<213> ORGANISM: Artificial Sequence
<220> FEATURE:
<223> OTHER INFORMATION: Synthetic

<400> SEQUENCE: 207

```
Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
```

```
        35                  40                  45

Ala Arg Leu Phe Glu Ser Gly Asp Gln Lys Asp Glu Ala Cys Lys Ala
    50                  55                  60

Lys Arg Met Lys Glu Trp Met Lys Cys Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100


<210> SEQ ID NO 208
<211> LENGTH: 100
<212> TYPE: PRT
<213> ORGANISM: Artificial Sequence
<220> FEATURE:
<223> OTHER INFORMATION: Synthetic

<400> SEQUENCE: 208

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Lys Asp Glu Ala Glu Lys Ala
    50                  55                  60

Lys Cys Met Lys Glu Trp Met Lys Cys Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100


<210> SEQ ID NO 209
<211> LENGTH: 100
<212> TYPE: PRT
<213> ORGANISM: Artificial Sequence
<220> FEATURE:
<223> OTHER INFORMATION: Synthetic

<400> SEQUENCE: 209

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Cys Leu Phe Glu Ser Gly Asp Gln Lys Asp Glu Ala Glu Lys Ala
    50                  55                  60

Lys Arg Met Lys Glu Trp Met Lys Arg Ile Lys Thr Thr Ala Ser Glu
65                  70                  75                  80

Asp Cys Gln Glu Glu Met Ala Asn Ala Ile Ile Thr Ile Leu Gln Ser
                85                  90                  95

Trp Ile Phe Ser
            100


<210> SEQ ID NO 210
<211> LENGTH: 100
```

<212> TYPE: PRT
<213> ORGANISM: Artificial Sequence
<220> FEATURE:
<223> OTHER INFORMATION: Synthetic

<400> SEQUENCE: 210

```
Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Cys Ser Gly Asp Gln Lys Asp Glu Ala Glu Lys Ala
    50                  55                  60

Lys Arg Met Lys Glu Trp Met Lys Arg Ile Lys Thr Thr Ala Ser Glu
65                  70                  75                  80

Asp Cys Gln Glu Glu Met Ala Asn Ala Ile Ile Thr Ile Leu Gln Ser
                85                  90                  95

Trp Ile Phe Ser
            100
```

<210> SEQ ID NO 211
<211> LENGTH: 100
<212> TYPE: PRT
<213> ORGANISM: Artificial Sequence
<220> FEATURE:
<223> OTHER INFORMATION: Synthetic

<400> SEQUENCE: 211

```
Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Cys Gln Lys Asp Glu Ala Glu Lys Ala
    50                  55                  60

Lys Arg Met Lys Glu Trp Met Lys Arg Ile Lys Thr Thr Ala Ser Glu
65                  70                  75                  80

Asp Cys Gln Glu Glu Met Ala Asn Ala Ile Ile Thr Ile Leu Gln Ser
                85                  90                  95

Trp Ile Phe Ser
            100
```

<210> SEQ ID NO 212
<211> LENGTH: 100
<212> TYPE: PRT
<213> ORGANISM: Artificial Sequence
<220> FEATURE:
<223> OTHER INFORMATION: Synthetic

<400> SEQUENCE: 212

```
Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Cys Asp Glu Ala Glu Lys Ala
```

```
    50                  55                  60

Lys Arg Met Lys Glu Trp Met Lys Arg Ile Lys Thr Thr Ala Ser Glu
65                  70                  75                  80

Asp Cys Gln Glu Glu Met Ala Asn Ala Ile Ile Thr Ile Leu Gln Ser
                85                  90                  95

Trp Ile Phe Ser
            100


<210> SEQ ID NO 213
<211> LENGTH: 100
<212> TYPE: PRT
<213> ORGANISM: Artificial Sequence
<220> FEATURE:
<223> OTHER INFORMATION: Synthetic

<400> SEQUENCE: 213

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Lys Cys Glu Ala Glu Lys Ala
    50                  55                  60

Lys Arg Met Lys Glu Trp Met Lys Arg Ile Lys Thr Thr Ala Ser Glu
65                  70                  75                  80

Asp Cys Gln Glu Glu Met Ala Asn Ala Ile Ile Thr Ile Leu Gln Ser
                85                  90                  95

Trp Ile Phe Ser
            100


<210> SEQ ID NO 214
<211> LENGTH: 100
<212> TYPE: PRT
<213> ORGANISM: Artificial Sequence
<220> FEATURE:
<223> OTHER INFORMATION: Synthetic

<400> SEQUENCE: 214

Pro Lys Lys Lys Ile Gln Leu His Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Lys Leu Glu Asp Tyr Ala Phe Asn Phe Glu Leu Ile Leu Glu Glu Ile
        35                  40                  45

Ala Arg Leu Phe Glu Ser Gly Asp Gln Lys Asp Glu Ala Cys Lys Ala
    50                  55                  60

Lys Arg Met Lys Glu Trp Met Lys Arg Ile Lys Thr Thr Ala Ser Glu
65                  70                  75                  80

Asp Cys Gln Glu Glu Met Ala Asn Ala Ile Ile Thr Ile Leu Gln Ser
                85                  90                  95

Trp Ile Phe Ser
            100


<210> SEQ ID NO 215
<211> LENGTH: 100
<212> TYPE: PRT
<213> ORGANISM: Artificial Sequence
<220> FEATURE:
```

<223> OTHER INFORMATION: Synthetic

<400> SEQUENCE: 215

Pro Lys Lys Lys Ile Gln Leu His Ala Glu His Ala Leu Tyr Asp Ala
1 5 10 15

Leu Met Ile Leu Asn Ile Val Lys Thr Asn Ser Pro Pro Ala Glu Glu
20 25 30

Lys Leu Glu Asp Tyr Ala Phe Asn Phe Glu Leu Ile Leu Glu Glu Ile
35 40 45

Ala Arg Leu Phe Glu Ser Gly Asp Gln Lys Asp Glu Ala Glu Lys Ala
50 55 60

Lys Cys Met Lys Glu Trp Met Lys Arg Ile Lys Thr Thr Ala Ser Glu
65 70 75 80

Asp Cys Gln Glu Glu Met Ala Asn Ala Ile Ile Thr Ile Leu Gln Ser
85 90 95

Trp Ile Phe Ser
100

<210> SEQ ID NO 216
<211> LENGTH: 100
<212> TYPE: PRT
<213> ORGANISM: Artificial Sequence
<220> FEATURE:
<223> OTHER INFORMATION: Synthetic

<400> SEQUENCE: 216

Pro Lys Lys Lys Ile Gln Leu His Ala Glu His Ala Leu Tyr Asp Ala
1 5 10 15

Leu Met Ile Leu Asn Ile Val Lys Thr Asn Ser Pro Pro Ala Glu Glu
20 25 30

Lys Leu Glu Asp Tyr Ala Phe Asn Phe Glu Leu Ile Leu Glu Glu Ile
35 40 45

Ala Arg Leu Phe Glu Ser Gly Asp Gln Lys Asp Glu Ala Glu Lys Ala
50 55 60

Lys Arg Met Lys Cys Trp Met Lys Arg Ile Lys Thr Thr Ala Ser Glu
65 70 75 80

Asp Cys Gln Glu Glu Met Ala Asn Ala Ile Ile Thr Ile Leu Gln Ser
85 90 95

Trp Ile Phe Ser
100

<210> SEQ ID NO 217
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally occurring amino acid or is optionally absent

<400> SEQUENCE: 217

```
Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Cys Leu Phe Glu Ser Gly Xaa Xaa Lys Asp Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100
```

<210> SEQ ID NO 218
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally occurring amino acid or is optionally absent

<400> SEQUENCE: 218

```
Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Cys Ser Gly Xaa Xaa Lys Asp Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100
```

<210> SEQ ID NO 219
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)

```
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 219

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Cys Gln Lys Asp Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100


<210> SEQ ID NO 220
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 220

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Cys Asp Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100


<210> SEQ ID NO 221
```

<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
occurring amino acid or is optionally absent

<400> SEQUENCE: 221

```
Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Cys Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100
```

<210> SEQ ID NO 222
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
occurring amino acid or is optionally absent

<400> SEQUENCE: 222

```
Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Asp Glu Ala Cys Lys Ala
```

```
    50                  55                  60

Lys Arg Met Lys Glu Trp Met Lys Arg Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100


<210> SEQ ID NO 223
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 223

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Asp Glu Ala Glu Lys Ala
    50                  55                  60

Lys Cys Met Lys Glu Trp Met Lys Arg Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100


<210> SEQ ID NO 224
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent
```

<400> SEQUENCE: 224

Pro Lys Lys Lys Ile Gln Leu His Ala Glu His Ala Leu Tyr Asp Ala
1 5 10 15

Leu Met Ile Leu Asn Ile Xaa Xaa Xaa Xaa Xaa Xaa Xaa Xaa Xaa Xaa
20 25 30

Xaa Leu Glu Asp Tyr Ala Phe Asn Phe Glu Leu Ile Leu Glu Glu Ile
35 40 45

Ala Arg Leu Phe Glu Ser Gly Xaa Xaa Lys Asp Glu Ala Glu Lys Ala
50 55 60

Lys Arg Met Lys Cys Trp Met Lys Arg Ile Lys Thr Xaa Xaa Xaa Glu
65 70 75 80

Asp Glu Gln Glu Glu Met Ala Asn Ala Ile Ile Thr Ile Leu Gln Ser
85 90 95

Trp Ile Phe Ser
100

<210> SEQ ID NO 225
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally occurring amino acid or is optionally absent

<400> SEQUENCE: 225

Pro Lys Lys Lys Ile Gln Leu His Ala Glu His Ala Leu Tyr Asp Ala
1 5 10 15

Leu Met Ile Leu Asn Ile Xaa Xaa Xaa Xaa Xaa Xaa Xaa Xaa Xaa Xaa
20 25 30

Xaa Leu Glu Asp Tyr Ala Phe Asn Phe Glu Leu Ile Leu Glu Glu Ile
35 40 45

Ala Arg Leu Phe Glu Ser Gly Xaa Xaa Lys Asp Glu Ala Glu Lys Ala
50 55 60

Lys Arg Met Lys Glu Trp Met Lys Cys Ile Lys Thr Xaa Xaa Xaa Glu
65 70 75 80

Asp Glu Gln Glu Glu Met Ala Asn Ala Ile Ile Thr Ile Leu Gln Ser
85 90 95

Trp Ile Phe Ser
100

<210> SEQ ID NO 226
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally occurring amino acid or is optionally absent

<400> SEQUENCE: 226

```
Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Asp Glu Ala Glu Lys Ala
    50                  55                  60

Lys Arg Met Lys Glu Trp Met Lys Arg Ile Lys Thr Cys Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100
```

<210> SEQ ID NO 227
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally occurring amino acid or is optionally absent

<400> SEQUENCE: 227

```
Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Asp Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Cys Gln Glu Glu Met Ala Asn Ala Ile Ile Thr Ile Leu Gln Ser
                85                  90                  95

Trp Ile Phe Ser
            100
```

<210> SEQ ID NO 228
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally occurring amino acid or is optionally absent

<400> SEQUENCE: 228

```
Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Asp Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Glu Gln Glu Cys Met Ala Asn Ala Ile Ile Thr Ile Leu Gln Ser
                85                  90                  95

Trp Ile Phe Ser
            100
```

<210> SEQ ID NO 229
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally occurring amino acid or is optionally absent

<400> SEQUENCE: 229

```
Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45
```

```
Ala Cys Leu Phe Glu Ser Gly Xaa Xaa Lys Asp Glu Ala Glu Lys Ala
    50                  55                  60

Lys Arg Met Lys Glu Trp Met Lys Cys Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100


<210> SEQ ID NO 230
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 230

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Cys Ser Gly Xaa Xaa Lys Asp Glu Ala Glu Lys Ala
    50                  55                  60

Lys Arg Met Lys Glu Trp Met Lys Cys Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100


<210> SEQ ID NO 231
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 231

Pro Lys Lys Lys Ile Gln Leu His Ala Glu His Ala Leu Tyr Asp Ala
```

```
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Cys Gln Lys Asp Glu Ala Glu Lys Ala
    50                  55                  60

Lys Arg Met Lys Glu Trp Met Lys Cys Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100


<210> SEQ ID NO 232
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 232

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Cys Asp Glu Ala Glu Lys Ala
    50                  55                  60

Lys Arg Met Lys Glu Trp Met Lys Cys Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100


<210> SEQ ID NO 233
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
```

<221> NAME/KEY: MISC_FEATURE
<222> LOCATION: (56)..(57)
<223> OTHER INFORMATION: Xaa, when present, can be any naturally occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally occurring amino acid or is optionally absent

<400> SEQUENCE: 233

```
Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Cys Glu Ala Glu Lys Ala
    50                  55                  60

Lys Arg Met Lys Glu Trp Met Lys Cys Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100
```

<210> SEQ ID NO 234
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally occurring amino acid or is optionally absent

<400> SEQUENCE: 234

```
Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Asp Glu Ala Cys Lys Ala
    50                  55                  60

Lys Arg Met Lys Glu Trp Met Lys Cys Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100
```

<210> SEQ ID NO 235
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally occurring amino acid or is optionally absent

<400> SEQUENCE: 235

```
Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Asp Glu Ala Glu Lys Ala
    50                  55                  60

Lys Cys Met Lys Glu Trp Met Lys Cys Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100
```

<210> SEQ ID NO 236
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally occurring amino acid or is optionally absent

<400> SEQUENCE: 236

```
Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45
```

```
Ala Cys Leu Phe Glu Ser Gly Xaa Xaa Lys Asp Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Cys Gln Glu Glu Met Ala Asn Ala Ile Ile Thr Ile Leu Gln Ser
                85                  90                  95

Trp Ile Phe Ser
            100


<210> SEQ ID NO 237
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 237

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Cys Ser Gly Xaa Xaa Lys Asp Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Cys Gln Glu Glu Met Ala Asn Ala Ile Ile Thr Ile Leu Gln Ser
                85                  90                  95

Trp Ile Phe Ser
            100


<210> SEQ ID NO 238
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 238
```

```
Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Cys Gln Lys Asp Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Cys Gln Glu Glu Met Ala Asn Ala Ile Ile Thr Ile Leu Gln Ser
                85                  90                  95

Trp Ile Phe Ser
            100
```

```
<210> SEQ ID NO 239
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 239

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Cys Asp Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Cys Gln Glu Glu Met Ala Asn Ala Ile Ile Thr Ile Leu Gln Ser
                85                  90                  95

Trp Ile Phe Ser
            100
```

```
<210> SEQ ID NO 240
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
```

```
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 240

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Cys Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Cys Gln Glu Glu Met Ala Asn Ala Ile Ile Thr Ile Leu Gln Ser
                85                  90                  95

Trp Ile Phe Ser
            100


<210> SEQ ID NO 241
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
      occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
      occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
      occurring amino acid or is optionally absent

<400> SEQUENCE: 241

Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Asp Glu Ala Cys Lys Ala
    50                  55                  60

Lys Arg Met Lys Glu Trp Met Lys Arg Ile Lys Thr Xaa Xaa Xaa Glu
65                  70                  75                  80

Asp Cys Gln Glu Glu Met Ala Asn Ala Ile Ile Thr Ile Leu Gln Ser
                85                  90                  95

Trp Ile Phe Ser
            100
```

<210> SEQ ID NO 242
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
occurring amino acid or is optionally absent

<400> SEQUENCE: 242

```
Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Asp Glu Ala Glu Lys Ala
    50                  55                  60

Lys Cys Met Lys Glu Trp Met Lys Arg Ile Lys Thr Xaa Xaa Xaa Glu
65                  70                  75                  80

Asp Cys Gln Glu Glu Met Ala Asn Ala Ile Ile Thr Ile Leu Gln Ser
                85                  90                  95

Trp Ile Phe Ser
            100
```

<210> SEQ ID NO 243
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally
occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally
occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally
occurring amino acid or is optionally absent

<400> SEQUENCE: 243

```
Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
```

```
        35                  40                  45

Ala Arg Leu Phe Glu Ser Gly Xaa Xaa Lys Asp Glu Ala Glu Lys Ala
    50                  55                  60

Lys Arg Met Lys Cys Trp Met Lys Arg Ile Lys Thr Xaa Xaa Xaa Glu
65                  70                  75                  80

Asp Cys Gln Glu Glu Met Ala Asn Ala Ile Ile Thr Ile Leu Gln Ser
                85                  90                  95

Trp Ile Phe Ser
            100


<210> SEQ ID NO 244
<211> LENGTH: 726
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(25)
<223> OTHER INFORMATION: Optional His tag
<220> FEATURE:
<221> NAME/KEY: MISC_FEATURE
<222> LOCATION: (26)..(609)
<223> OTHER INFORMATION: Mouse serum albumin
<220> FEATURE:
<221> NAME/KEY: MISC_FEATURE
<222> LOCATION: (610)..(626)
<223> OTHER INFORMATION: Linker
<220> FEATURE:
<221> NAME/KEY: MISC_FEATURE
<222> LOCATION: (627)..(726)
<223> OTHER INFORMATION: Neo2/15

<400> SEQUENCE: 244

Gly Ser Asp Gly Gly Ser His His His His His His Gly Ser Gly Ser
1               5                   10                  15

Glu Asn Leu Tyr Phe Gln Gly Ser Gly Glu Ala His Lys Ser Glu Ile
            20                  25                  30

Ala His Arg Tyr Asn Asp Leu Gly Glu Gln His Phe Lys Gly Leu Val
        35                  40                  45

Leu Ile Ala Phe Ser Gln Tyr Leu Gln Lys Cys Ser Tyr Asp Glu His
    50                  55                  60

Ala Lys Leu Val Gln Glu Val Thr Asp Phe Ala Lys Thr Cys Val Ala
65                  70                  75                  80

Asp Glu Ser Ala Ala Asn Cys Asp Lys Ser Leu His Thr Leu Phe Gly
                85                  90                  95

Asp Lys Leu Cys Ala Ile Pro Asn Leu Arg Glu Asn Tyr Gly Glu Leu
            100                 105                 110

Ala Asp Cys Cys Thr Lys Gln Glu Pro Glu Arg Asn Glu Cys Phe Leu
        115                 120                 125

Gln His Lys Asp Asp Asn Pro Ser Leu Pro Pro Phe Glu Arg Pro Glu
    130                 135                 140

Ala Glu Ala Met Cys Thr Ser Phe Lys Glu Asn Pro Thr Thr Phe Met
145                 150                 155                 160

Gly His Tyr Leu His Glu Val Ala Arg Arg His Pro Tyr Phe Tyr Ala
                165                 170                 175

Pro Glu Leu Leu Tyr Tyr Ala Glu Gln Tyr Asn Glu Ile Leu Thr Gln
            180                 185                 190

Cys Cys Ala Glu Ala Asp Lys Glu Ser Cys Leu Thr Pro Lys Leu Asp
        195                 200                 205
```

-continued

```
Gly Val Lys Glu Lys Ala Leu Val Ser Ser Val Arg Gln Arg Met Lys
    210                 215                 220

Cys Ser Ser Met Gln Lys Phe Gly Glu Arg Ala Phe Lys Ala Trp Ala
225                 230                 235                 240

Val Ala Arg Leu Ser Gln Thr Phe Pro Asn Ala Asp Phe Ala Glu Ile
                245                 250                 255

Thr Lys Leu Ala Thr Asp Leu Thr Lys Val Asn Lys Glu Cys Cys His
            260                 265                 270

Gly Asp Leu Leu Glu Cys Ala Asp Asp Arg Ala Glu Leu Ala Lys Tyr
        275                 280                 285

Met Cys Glu Asn Gln Ala Thr Ile Ser Ser Lys Leu Gln Thr Cys Cys
    290                 295                 300

Asp Lys Pro Leu Leu Lys Lys Ala His Cys Leu Ser Glu Val Glu His
305                 310                 315                 320

Asp Thr Met Pro Ala Asp Leu Pro Ala Ile Ala Ala Asp Phe Val Glu
                325                 330                 335

Asp Gln Glu Val Cys Lys Asn Tyr Ala Glu Ala Lys Asp Val Phe Leu
            340                 345                 350

Gly Thr Phe Leu Tyr Glu Tyr Ser Arg Arg His Pro Asp Tyr Ser Val
        355                 360                 365

Ser Leu Leu Leu Arg Leu Ala Lys Lys Tyr Glu Ala Thr Leu Glu Lys
    370                 375                 380

Cys Cys Ala Glu Ala Asn Pro Pro Ala Cys Tyr Gly Thr Val Leu Ala
385                 390                 395                 400

Glu Phe Gln Pro Leu Val Glu Glu Pro Lys Asn Leu Val Lys Thr Asn
                405                 410                 415

Cys Asp Leu Tyr Glu Lys Leu Gly Glu Tyr Gly Phe Gln Asn Ala Ile
            420                 425                 430

Leu Val Arg Tyr Thr Gln Lys Ala Pro Gln Val Ser Thr Pro Thr Leu
        435                 440                 445

Val Glu Ala Ala Arg Asn Leu Gly Arg Val Gly Thr Lys Cys Cys Thr
    450                 455                 460

Leu Pro Glu Asp Gln Arg Leu Pro Cys Val Glu Asp Tyr Leu Ser Ala
465                 470                 475                 480

Ile Leu Asn Arg Val Cys Leu Leu His Glu Lys Thr Pro Val Ser Glu
                485                 490                 495

His Val Thr Lys Cys Cys Ser Gly Ser Leu Val Glu Arg Arg Pro Cys
            500                 505                 510

Phe Ser Ala Leu Thr Val Asp Glu Thr Tyr Val Pro Lys Glu Phe Lys
        515                 520                 525

Ala Glu Thr Phe Thr Phe His Ser Asp Ile Cys Thr Leu Pro Glu Lys
    530                 535                 540

Glu Lys Gln Ile Lys Lys Gln Thr Ala Leu Ala Glu Leu Val Lys His
545                 550                 555                 560

Lys Pro Lys Ala Thr Ala Glu Gln Leu Lys Thr Val Met Asp Asp Phe
                565                 570                 575

Ala Gln Phe Leu Asp Thr Cys Cys Lys Ala Ala Asp Lys Asp Thr Cys
            580                 585                 590

Phe Ser Thr Glu Gly Pro Asn Leu Val Thr Arg Cys Lys Asp Ala Leu
        595                 600                 605

Ala Gly Gly Gly Ser Gly Gly Ser Gly Gly Gly Ser Gly Gly Ser Gly
    610                 615                 620

Ser Gly Pro Lys Lys Lys Ile Gln Leu His Ala Glu His Ala Leu Tyr
```

```
625                 630                 635                 640

Asp Ala Leu Met Ile Leu Asn Ile Val Lys Thr Asn Ser Pro Pro Ala
                645                 650                 655

Glu Glu Lys Leu Glu Asp Tyr Ala Phe Asn Phe Glu Leu Ile Leu Glu
            660                 665                 670

Glu Ile Ala Arg Leu Phe Glu Ser Gly Asp Gln Lys Asp Glu Ala Glu
        675                 680                 685

Lys Ala Lys Arg Met Lys Glu Trp Met Lys Arg Ile Lys Thr Thr Ala
    690                 695                 700

Ser Glu Asp Glu Gln Glu Glu Met Ala Asn Ala Ile Ile Thr Ile Leu
705                 710                 715                 720

Gln Ser Trp Ile Phe Ser
                725


<210> SEQ ID NO 245
<211> LENGTH: 87
<212> TYPE: PRT
<213> ORGANISM: Artificial Sequence
<220> FEATURE:
<223> OTHER INFORMATION: Synthetic

<400> SEQUENCE: 245

Thr Asn Lys Lys Ala Gln Leu His Ala Glu Phe Ala Leu His Asp Ala
1               5                   10                  15

Leu Met Leu Leu Asn Leu Ser Ser Glu Ser Asn Glu Arg Leu Asn Arg
            20                  25                  30

Ile Ile Thr Trp Leu Gln Ser Ile Ile Phe Tyr Gly Thr Tyr Asp Pro
        35                  40                  45

Asp Met Val Lys Glu Ala Val Lys Asp Ala Asp Glu Ile Glu Asp Glu
    50                  55                  60

Met Arg Lys Arg Gly Ile Asp Thr Glu Asp Tyr Val Ser Asn Leu Arg
65                  70                  75                  80

Leu Ile Leu Gln Glu Leu Ala
                85


<210> SEQ ID NO 246
<211> LENGTH: 100
<212> TYPE: PRT
<213> ORGANISM: Artificial Sequence
<220> FEATURE:
<223> OTHER INFORMATION: Synthetic

<400> SEQUENCE: 246

Pro Lys Lys Lys Ile Gln Leu Tyr Ala Glu His Ala Leu Tyr Asp Ala
1               5                   10                  15

Leu Met Ile Leu Asn Ile Val Lys Thr Asn Ser Pro Pro Ala Glu Glu
            20                  25                  30

Glu Leu Glu Asp Tyr Ala Phe Asn Phe Glu Leu Ile Leu Glu Glu Ile
        35                  40                  45

Ala Arg Leu Phe Glu Ser Gly Asp Gln Lys Asp Glu Ala Glu Lys Ala
    50                  55                  60

Lys Arg Met Lys Glu Trp Met Lys Arg Ile Lys Thr Thr Ala Ser Glu
65                  70                  75                  80

Asp Glu Gln Glu Glu Met Ala Asn Ala Ile Ile Thr Ile Leu Gln Ser
                85                  90                  95

Trp Ile Phe Ser
            100
```

<210> SEQ ID NO 247
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(33)
<223> OTHER INFORMATION: Xaa, when present, can be any naturally occurring amino acid or is optionally absent
<220> FEATURE:
<221> NAME/KEY: MISC_FEATURE
<222> LOCATION: (56)..(57)
<223> OTHER INFORMATION: Xaa, when present, can be any naturally occurring amino acid or is optionally absent
<220> FEATURE:
<221> NAME/KEY: MISC_FEATURE
<222> LOCATION: (77)..(79)
<223> OTHER INFORMATION: Xaa, when present, can be any naturally occurring amino acid or is optionally absent

<400> SEQUENCE: 247

```
Pro Lys Lys Lys Ile Gln Leu His Ala Glu His Ala Leu Tyr Asp Ala
1               5                   10                  15

Leu Met Ile Leu Asn Ile Xaa Xaa Xaa Xaa Xaa Xaa Xaa Xaa Xaa Xaa
            20                  25                  30

Xaa Leu Glu Asp Tyr Ala Phe Asn Phe Glu Leu Ile Leu Glu Glu Ile
        35                  40                  45

Ala Arg Leu Phe Glu Ser Gly Xaa Xaa Lys Asp Glu Ala Glu Lys Ala
    50                  55                  60

Lys Arg Met Lys Glu Trp Met Lys Arg Ile Lys Thr Xaa Xaa Xaa Glu
65                  70                  75                  80

Asp Glu Gln Glu Glu Met Ala Asn Ala Ile Ile Thr Ile Leu Gln Ser
                85                  90                  95

Trp Ile Phe Ser
            100
```

<210> SEQ ID NO 248
<211> LENGTH: 22
<212> TYPE: PRT
<213> ORGANISM: Artificial Sequence
<220> FEATURE:
<223> OTHER INFORMATION: Synthetic

<400> SEQUENCE: 248

```
Pro Lys Lys Lys Ile Gln Leu His Ala Glu His Ala Leu Tyr Asp Ala
1               5                   10                  15

Leu Met Ile Leu Asn Ile
            20
```

<210> SEQ ID NO 249
<211> LENGTH: 22
<212> TYPE: PRT
<213> ORGANISM: Artificial Sequence
<220> FEATURE:
<223> OTHER INFORMATION: Synthetic

<400> SEQUENCE: 249

```
Ser Thr Lys Lys Thr Gln Leu Gln Leu Glu His Leu Leu Leu Asp Leu
1               5                   10                  15

Gln Met Ile Leu Asn Gly
            20
```

<210> SEQ ID NO 250
<211> LENGTH: 15
<212> TYPE: PRT
<213> ORGANISM: Artificial Sequence
<220> FEATURE:
<223> OTHER INFORMATION: Synthetic

<400> SEQUENCE: 250

Asn Trp Val Asn Val Ile Ser Asp Leu Lys Lys Ile Glu Asp Leu
1 5 10 15

<210> SEQ ID NO 251
<211> LENGTH: 22
<212> TYPE: PRT
<213> ORGANISM: Artificial Sequence
<220> FEATURE:
<223> OTHER INFORMATION: Synthetic

<400> SEQUENCE: 251

Leu Glu Asp Tyr Ala Phe Asn Phe Glu Leu Ile Leu Glu Glu Ile Ala
1 5 10 15

Arg Leu Phe Glu Ser Gly
20

<210> SEQ ID NO 252
<211> LENGTH: 22
<212> TYPE: PRT
<213> ORGANISM: Artificial Sequence
<220> FEATURE:
<223> OTHER INFORMATION: Synthetic

<400> SEQUENCE: 252

Pro Arg Asp Leu Ile Ser Asn Ile Asn Val Ile Val Leu Glu Leu Lys
1 5 10 15

Gly Ser Glu Thr Thr Phe
20

<210> SEQ ID NO 253
<211> LENGTH: 22
<212> TYPE: PRT
<213> ORGANISM: Artificial Sequence
<220> FEATURE:
<223> OTHER INFORMATION: Synthetic

<400> SEQUENCE: 253

Ile His Asp Thr Val Glu Asn Leu Ile Ile Leu Ala Asn Asn Ser Leu
1 5 10 15

Ser Ser Asn Gly Asn Val
20

<210> SEQ ID NO 254
<211> LENGTH: 19
<212> TYPE: PRT
<213> ORGANISM: Artificial Sequence
<220> FEATURE:
<223> OTHER INFORMATION: Synthetic

<400> SEQUENCE: 254

Lys Asp Glu Ala Glu Lys Ala Lys Arg Met Lys Glu Trp Met Lys Arg
1 5 10 15

Ile Lys Thr

<210> SEQ ID NO 255
<211> LENGTH: 19
<212> TYPE: PRT

<213> ORGANISM: Artificial Sequence
<220> FEATURE:
<223> OTHER INFORMATION: Synthetic

<400> SEQUENCE: 255

Ala Thr Glu Leu Lys His Leu Gln Cys Leu Glu Glu Glu Leu Lys Pro
1 5 10 15

Leu Glu Glu

<210> SEQ ID NO 256
<211> LENGTH: 19
<212> TYPE: PRT
<213> ORGANISM: Artificial Sequence
<220> FEATURE:
<223> OTHER INFORMATION: Synthetic

<400> SEQUENCE: 256

Ser Cys Lys Val Thr Ala Met Lys Cys Phe Leu Leu Glu Leu Gln Val
1 5 10 15

Ile Ser Leu

<210> SEQ ID NO 257
<211> LENGTH: 21
<212> TYPE: PRT
<213> ORGANISM: Artificial Sequence
<220> FEATURE:
<223> OTHER INFORMATION: Synthetic

<400> SEQUENCE: 257

Glu Asp Glu Gln Glu Glu Met Ala Asn Ala Ile Ile Thr Ile Leu Gln
1 5 10 15

Ser Trp Ile Phe Ser
20

<210> SEQ ID NO 258
<211> LENGTH: 21
<212> TYPE: PRT
<213> ORGANISM: Artificial Sequence
<220> FEATURE:
<223> OTHER INFORMATION: Synthetic

<400> SEQUENCE: 258

Thr Ala Thr Ile Val Glu Phe Leu Asn Arg Trp Ile Thr Phe Cys Gln
1 5 10 15

Ser Ile Ile Ser Thr
20

<210> SEQ ID NO 259
<211> LENGTH: 21
<212> TYPE: PRT
<213> ORGANISM: Artificial Sequence
<220> FEATURE:
<223> OTHER INFORMATION: Synthetic

<400> SEQUENCE: 259

Glu Lys Asn Ile Lys Glu Phe Leu Gln Ser Phe Val His Ile Val Gln
1 5 10 15

Met Phe Ile Asn Thr
20

<210> SEQ ID NO 260
<211> LENGTH: 4
<212> TYPE: PRT
<213> ORGANISM: Artificial Sequence

```
<220> FEATURE:
<223> OTHER INFORMATION: Synthetic

<400> SEQUENCE: 260

Cys Asn Ser Asn
1


<210> SEQ ID NO 261
<211> LENGTH: 4
<212> TYPE: PRT
<213> ORGANISM: Artificial Sequence
<220> FEATURE:
<223> OTHER INFORMATION: Synthetic

<400> SEQUENCE: 261

Asn Phe Gln Cys
1


<210> SEQ ID NO 262
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: biotin acceptor peptide

<400> SEQUENCE: 262

Leu Asn Asp Ile Phe Glu Ala Gln Lys Ile Glu Trp His Glu
1               5                   10
```

DE NOVO DESIGN OF POTENT AND SELECTIVE INTERLEUKIN MIMETICS

CROSS REFERENCE

This application is a Divisional of U.S. patent application Ser. No. 16/572,038, filed Sep. 16, 2019, which is a Continuation of International Application No. PCT/US2019/038703, filed Jun. 24, 2019, which claims priority to U.S. Provisional Application No. 62/768,733, filed Nov. 16, 2018, and U.S. Provisional Application No. 62/689,769, filed Jun. 25, 2018, the disclosures of which are hereby incorporated by reference in their entirety.

STATEMENT OF GOVERNMENT RIGHTS

This invention was made with Government support under contract AI051321 awarded by the National Institutes of Health. The Government has certain rights in the invention.

BACKGROUND

The considerable potential of central immune cytokine interleukins such as IL-2 and IL-4 for cancer treatment has sparked numerous efforts to improve their therapeutic properties by mutation and/or chemical modification. However, because these approaches are closely tied to native IL-2 or IL-4, they cannot eliminate undesirable properties such as low stability and binding to the IL-2 receptor α subunit (IL-2Rα), to IL-4 receptor α $\gamma_c$ heterodimer (IL-4Rα $\gamma_c$), or to IL-13 receptor α subunit (IL-13Rα).

SUMMARY

In one aspect, a method is provided. A computing device determines a structure for a plurality of residues of a protein where the structure of the plurality of residues provides a particular receptor binding interface. The computing device determines a plurality of designed residues using a mimetic design protocol provided by the computing device, wherein the plurality of designed residues provide the particular receptor binding interface, and wherein the plurality of designed residues differ from the plurality of residues.

The computing device determines one or more connecting helix structures that connect the plurality of designed residues. The computing device determines a first protein backbone for the protein by assembling the one or more connecting helix structures and the plurality of designed residues over a plurality of combinations. The computing device designs a second protein backbone for the protein for flexibility and low energy structures based on the first protein backbone. The computing device generates an output related to at least the second protein backbone.

Also included are non-naturally occurring proteins prepared by the methods described herein. The non-naturally occurring proteins can be cytokines, for example, non-naturally occurring IL-2 or IL-4 (also referred to herein as IL-2, IL-2/15 mimetics or IL-4 mimetics).

In another aspect, a computing device is provided. The computing device includes one or more processors; and data storage that is configured to store at least computer-readable instructions that, when executed by the one or more processors, cause the computing device to perform functions. The functions include: determining a structure for a plurality of residues of a protein that provides a particular receptor binding interface; determining a plurality of designed residues using a mimetic design protocol, wherein the plurality of designed residues provide the particular receptor binding interface, and wherein the plurality of designed residues differ from the plurality of residues; determining one or more connecting helix structures that connect the plurality of designed residues; determining a first protein backbone for the protein by assembling the one or more connecting helix structures and the plurality of designed residues over a plurality of combinations; designing a second protein backbone for the protein for flexibility and low energy structures based on the first protein backbone; and generating an output related to at least the second protein backbone for the protein.

In another aspect, a non-transitory computer-readable medium is provided. The non-transitory computer-readable medium is configured to store at least computer-readable instructions that, when executed by one or more processors of a computing device, cause the computing device to perform functions. The functions include: determining a structure for a plurality of residues of a protein that provides a particular receptor binding interface; determining a plurality of designed residues using a mimetic design protocol, wherein the plurality of designed residues provide the particular receptor binding interface, and wherein the plurality of designed residues differ from the plurality of residues; determining one or more connecting helix structures that connect the plurality of designed residues; determining a first protein backbone for the protein by assembling the one or more connecting helix structures and the plurality of designed residues over a plurality of combinations; designing a second protein backbone for the protein for flexibility and low energy structures based on the first protein backbone; and generating an output related to at least the second protein backbone for the protein.

In another aspect, a device is provided. The device includes: means for determining a structure for a plurality of residues of a protein that provides a particular receptor binding interface; means for determining a plurality of designed residues using a mimetic design protocol, wherein the plurality of designed residues provide the particular receptor binding interface, and wherein the plurality of designed residues differ from the plurality of residues; means for determining one or more connecting helix structures that connect the plurality of designed residues; means for determining a first protein backbone for the protein by assembling the one or more connecting helix structures and the plurality of designed residues over a plurality of combinations; means for designing a second protein backbone for the protein for flexibility and low energy structures based on the first protein backbone; and means for generating an output related to at least the second protein backbone for the protein.

In another aspect, non-naturally occurring polypeptides are provided comprising domains X1, X2, X3, and X4, wherein:

(a) X1 is a peptide comprising the amino acid sequence at least 25%, 27%, 30%, 35%, 40%, 45%,_50%, 55%, 60%, 65%, 70%, 75%, 80%, 85%, 90%, 95%, 98%, or 100% identical to E HAL LYD A L (SEQ ID NO:1);

(b) X2 is a helical-peptide of at least 8 amino acids in length;

(c) X3 is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical to Y AF N FE LL (SEQ ID NO:2);

(d) X4 is a peptide comprising the amino acid sequence at least 25%, 27%, 30%, 40%, 45%, 50%, 55%, 60%, 65%, 70%, 75%, 80%, 85%, 90%, 95%, 98%, or 100% identical to ITILQSWIF (SEQ ID NO:3);

wherein X1, X2, X3, and X4 may be in any order in the polypeptide;

wherein amino acid linkers may be present between any of the domains; and wherein the polypeptide binds to IL-2 receptor $\beta\gamma_c$ heterodimer (IL-2R$\beta\gamma_c$), IL-4 receptor $\alpha\gamma_c$ heterodimer (IL-4R$\alpha\gamma_c$), or IL-13 receptor α subunit (IL-13Rα).

In other aspects are provided pharmaceutical compositions comprising one or more polypeptide disclosed herein and a pharmaceutically acceptable carrier, recombinant nucleic acids encoding a polypeptide disclosed herein, expression vectors comprising the recombinant nucleic acids disclosed herein, and recombinant host cells comprising one or more expression vector disclosed herein. In a further aspect, methods for treating cancer are provided, comprising administering to a subject having cancer one or more polypeptide, recombinant nucleic acid, expression vector comprising the recombinant nucleic acid, and/or recombinant host cells disclosed herein or a pharmaceutical composition thereof in an amount effective to treat the tumor.

DESCRIPTION OF THE DRAWINGS

The following figures are in accordance with example embodiments:

FIG. 1A) The designed mimetics have four helices; three mimetic IL-2 interactions with hIL-2R$\gamma_c$, while the fourth holds the first three in place. Top: in the first generation of designs, each of the core elements of IL-2 (helices H1-H4) were independently idealized using fragment-assembly from a clustered ideal fragment database (size: 4 a.a.); bottom: in the second generation of designs the core elements were instead built using parametric equations that recapitulate the shape of each disembodied helix, allowing changes in the length of each helix by +/−8 a.a.; FIG. 1B) Pairs of helices were reconnected using ideal loop fragments (size: 4 a.a. or 7 a.a., for gen-1 and gen-2 respectively, see Methods), representative examples are shown with newly built elements connecting each pair of helices; FIG. 1C) The helix hairpins generated in FIG. 1B were assembled in all possible combinations to generate fully connected protein backbones; FIG. 1D) The designs and experimentally matured versions were tested for binding by yeast display, and those exhibiting high affinity binding were recombinantly expressed (*E. coli*) and tested for binding using surface plasmon resonance and IL-2 like phospho-STAT5 (pSTAT5) signaling. The results for 3 designs of the first generation and 10 designs from the second generation are shown in the 2D-plot in solid symbols. The open star is Neoleukin-2/15, the arrow originates in its parent (unoptimized) design.

FIG. 2A) From top to bottom: In surface plasmon resonance experiments, neoleukin-2/15 does not bind human or murine IL-2Rα, but binds both human and murine IL-2Rβ with similar affinity ($K_d$— 11.2 nM and 16.1 nM, for human and mice receptor, respectively). Like natural IL-2, neoleukin-2/15 binds poorly to the $\gamma_c$ receptor, and exhibits cooperative binding for both human and murine IL-2R$\beta\gamma_c$ ($K_d$~18.8 nM and 38.4 nM, for the human and mice heterodimeric receptor, while the Kd of native hIL-2 and Super-2 are ~193.6 nM and 300.9 nM, see Table E1). FIG. 2B) top: In-vitro pSTAT5 signaling studies demonstrate that neoleukin-2/15 elicits IL-2-like signaling in human cells ($EC_{50}$), and activates with identical potency ($EC_{50}$~73.0 pM and 49.2 pM on CD25+ and CD25− cells, respectively) human YT-1 NK cells with or without IL-2Rα expression (CD25); bottom: similarly ex vivo experiments in murine CD4+ primary cells demonstrate that neoleukin-2/15 can also elicit potent IL-2 like signaling in murine cells, and is independent of IL-2Rα expression ($EC_{50}$~24 pM and 129 pM on CD25+ and CD25− cells, respectively); FIG. 2C) top: binding experiments (OCTET) show that neoleukin-2/15 can be incubated for 2 hours at 80° C. without any noticeable loss of binding, whereas human and murine IL-2 quickly lose activity; bottom: an ex vivo experiment on cultured murine splenocytes that require IL-2 for survival, demonstrates that neoleukin-2/15 incubated at 95° C. for 1 hour still drives cell survival effectively (~70% relative luminescence, at 10 ng/ml), while mIL2 and Super-2 are virtually inactive (~10% and 0.1%, respectively at 10 ng/ml).

FIG. 3A) Top: structural alignment of neoleukin-2/15 (Neo-2/15) chain A with the design model (r.m.s.d. 1.11 Å for 100° C.α atoms); bottom: detail of interface helices H1, H3 and H4 (numbered according to hIL-2, see FIG. 1). The interface side chains are shown in sticks; FIG. 3B) crystallographic structure of the ternary complex of Neo-2/15 with mIL-2Rβ and $\gamma_c$ (r.m.s.d 1.27 Å for the 93 modeled Cα atoms of Neo-2/15 in the ternary complex); FIG. 3C) structural alignment of monomeric Neo-2/15 (chain A) with Neo-2/15 in the ternary complex (r.m.s.d 1.71 Å for the 93 modeled Cα atoms in the ternary complex). Helix H4 shows an approximately 4.0+ shift of helix H4 in the ternary-complex structure compared to the monomeric crystal structure; FIG. 3D) crystallographic structure of: hIL-2 (cartoon representation). The regions that interact with the IL-2Rβ and $\gamma_c$ are denoted. The loop-rich region from hIL-2 that interacts with IL-2Rα does not exist in the de novo mimetic Neo-2/15. FIG. 3E): crystallographic structure of neoleukin-2/15 from the ternary complex in "b)" (cartoon representation). The regions that interact with the IL-2Rβ and $\gamma_c$ are denoted. The loop-rich region from hIL-2 that interacts with IL-2Rα does not exist in the de novo mimetic Neo-2/15.

FIG. 4A) Dose escalation effect of neoleukin-2/15 (Neo-2/15) in naive mice T cells. Naive C57BL/6 mice were treated daily with neoleukin-2/15 or mIL-2 at the indicated concentrations (n=2-3 per group). After 14 days, spleens were harvested and analyzed by flow cytometry using the indicated markers. The bar plot shows that mIL-2 enhanced CD4+ Treg expansion in a dose dependent fashion, while Neo-2/15 had little or no effect in expansion of Treg cells. Neoleukin-2/15 drove a higher CD8+:Treg ratio compared to mIL-2; FIG. 4B) Effect of Neo-2/15 in mice in an airway inflammation model (20 μg/day/mouse, 7 days). Similar to naive mice, Neo-2/15 does not increase the frequency of antigen-specific CD4+ Foxp3+ $T_{regs}$ in the lymphoid organs, and is comparably effective to mIL-2 in increasing the frequency of lung resident (Thy 1.2-by intravascular labeling) CD8+ T cells; FIG. 4C) Neoleukin-2/15 does not have detectable immunogenicity. C57BL/6 mice were inoculated with $5\times10^5$ B16F10 cells by subcutaneous injection. Starting on day 1, mice were treated daily with neoleukin-2/15 (10 μg) or equimolar mIL-2 by intraperitoneal (i.p.) injection (n=10 for each group). After 14 days, serum (antiserum) was collected and IgG was detected by ELISA in plates coated with fetal bovine serum (FBS 10%, negative control), neoleukin-2/15, mIL-2, hIL-2, or Ovalbumin (OVA) as negative control (the dotted line shows the average of the negative control). Anti-Neo-2/15 polyclonal antibody was used as positive control (black, n=2) and did not cross react with mIL-2 or h-IL2; FIG. 4D) C57BL/6 mice were immunized with 500 µg KO Neo-2/15 in complete Freund's adjuvant and boosted on days 7 and 15 with 500 µg KO Neo-2/15 in incomplete Freund's adjuvant. Reactivity against KO Neo-2/15 and native Neo-2/15, as well as cross-reactivity with mouse IL-2 were determined by incubation of serum (diluted 1:1,000 in PBS) with plate-bound KO Neo-2/15, Neo-2/15 or mouse IL-2 as indicated. Serum binding was detected using an anti-mouse secondary antibody conjugated to HRP followed by incubation with TMB. Data are reported as optical density at 450 nm. Top, naive mouse serum; bottom, immunized mouse serum. FIG. 4E-4G) Therapeutic efficacy of Neoleukin-2/15: FIG. 4E) BALB/C mice were inoculated with CT26 tumors. Starting on day 6, mice were treated daily with i.p. injection of mIL-2 or neoleukin-2/15 (10 µg), or were left untreated (n=5 per group). Tumor growth curves (top, show only data for surviving mice). Survival curves (bottom). Mice were euthanized when weight loss exceeded 10% of initial weight or when tumor size reached 1,300 $mm^3$. FIG. 4F) C57BL/6 mice were inoculated with B16 tumors as in "a)". Starting on day 1, mice were treated daily with i.p. injection of neoleukin-2/15 (10 µg) or equimolar mIL-2 (n=10 per group). Twice-weekly treatment with TA99 was added on day 3. Mice were euthanized when weight loss exceeded 10% of initial weight or when tumor size reached 2,000 $mm^3$. Tumor growth curves (top and bottom left). Survival curve, inset shows average weight change (top right). Quantification of cause of death (bottom right). FIG. 4G) Neo-2/15 elicits a higher CD8+:Treg ratio than mouse IL-2. C57BL/6 mice were inoculated with B16 tumors and treated by daily i.p. injection as indicated. Treatment with TA99 (bottom plot) was started on day 5 and continued twice-weekly. Tumors were harvested from mice when they reached 2,000 $mm^3$ and analyzed by flow cytometry. The CD8:Treg cell ratio was calculated by dividing the percentage $CD45^+$ $CD3^+$ cells that were $CD8^+$ by the percentage that were $CD4^+$ $CD25^+$ $FoxP3^+$.

FIG. 5A) BALB/C mice were inoculated with CT26 tumors. Starting on day-9 and ending on day-14, mice were treated daily with i.p. injection of mIL-2 or neoleukin-2/15 at the specified concentrations, or were left untreated (n=5 per group). Tumor growth curves (top, show only data for surviving mice). Survival curves (bottom). Mice were euthanized when weight loss exceeded 10% of initial weight or when tumor size reached 1,300 $mm^3$. FIG. 5B-5D) The bar-plots compare the T cell populations for BALB/C mice (n=3 per group) that were inoculated with CT26 tumors and treated starting from day-6 with by daily i.p. injection of 10 µg of Neolukin-2/15 or 10 µg mIL-2 or no-treatment (No Tx). On day-14 the percentage of Treg cells ($CD4^+$ $CD45^+$ $FoxP3^+$, top graph) and CD8:Treg cell ratio (($CD45^+$ $CD3^+$ $CD8^+$)/Treg, bottom graph) was assessed in: FIG. 5B) tumors, FIG. 5C) neighboring inguinal lymph node (LN), and FIG. 5D) spleen.

FIG. 6A-6D) Tumor growth curves (bottom) and survival curves (top) for C57BL/6 mice that were inoculated with B16 tumors and treated with low (1 µg/mice/day, a-b) or high doses of neoleukin-2/15 (10 µg/mice/day, c-d). Starting on day 1, mice (n=5 per group) were treated daily with i.p. injection of FIG. 6A): single agent neoleukin-2/15 at 1 µg/mice or equimolar mIL-2 (n=5 per group), or FIG. 6B): the same treatments in combination with a twice-weekly treatment with TA99 (started on day 5). Mice were euthanized when tumor size reached 2,000 $mm^3$. C57BL/6 mice were inoculated with B16 tumors and treated by daily i.p. injection as indicated. FIG. 6C-6D) Similar to "a-b)", but starting on day 4, mice were treated daily with i.p. injection of 10 µg/mouse of neoleukin-2/15, or equimolar mIL-2, either alone FIG. 6C) or in combination with twice-weekly TA99 started on day 4 FIG. 6D). Mice were euthanized when tumor size reached 2,000 $mm^3$. The therapeutic effect of Neoleukin-2/15 is dose dependent (higher doses are better) and is potentiated in the presence of the antibody TA99. The experiments were performed once. In all the growth curves, data are mean±s.e.m. Results were analysed by one-way ANOVA (95% confidence interval), except for survival curves that were assessed using the Mantel-Cox test (95% confidence interval).

FIG. 7A) Neo-2/15 structurally aligned into the structure of IL-4 in complex with IL-4Rα and $\gamma_c$ (from PDB code 3BPL). Fourteen IL-4 residues that contact IL-4Rα and that were grafted into Neo-2/15 are labeled. FIG. 7B) Neoleukin-4 (Neo-4), a new protein with sixteen amino acid mutations compared to Neo-2/15. These mutations are labeled; thirteen of these were derived from the IL-4 residues depicted in panel "a)" that mediate contact with IL-4Rα, and three of them (H8M, K68I and I98F, underlined in the figure) were introduced by directed evolution using random mutagenesis and screening for high binding affinity variants. FIG. 7C) Biolayer interferometry data showing that Neo-4, like IL-4, binds to IL-4Rα alone, has no affinity for $\gamma_c$ alone, but binds to $\gamma_c$ when IL-4Rα is present in solution.

FIG. 8A) Anti-CD3/CD28 stimulated or FIG. 8B) unstimulated human primary CD4 (top) or CD8 (bottom) T cells were cultured in indicated concentrations of human IL2 or neoleukin-2/15. T cell proliferation is measured as fold change over T cells cultured without IL2 supplement. Neo-2/15 is as effective as native IL-2 at inducing proliferation of stimulated CAR-T cells, and more effective than native IL-2 at inducing proliferation of unstimulated CAR-T cells, particularly of unstimulated CD8 CAR-T cells.

The solid horizontal line highlights positions where the Neo-2/15 amino acid has a probability score ≥30% (that is, these amino acids contribute more generally to receptor binding as they are globally enriched in the binding populations across all of the de novo IL-2 mimics tested). The topology of each helix in Neo-2/15 is shown left of each logo. The sequences of the Neo-2/15 helices and those of the corresponding helices (structurally aligned) in human IL-2 and IL-15 are shown below the graphs, highlighting the distinctiveness of the Neo-2/15 helices and binding interfaces.

Figure 10A:
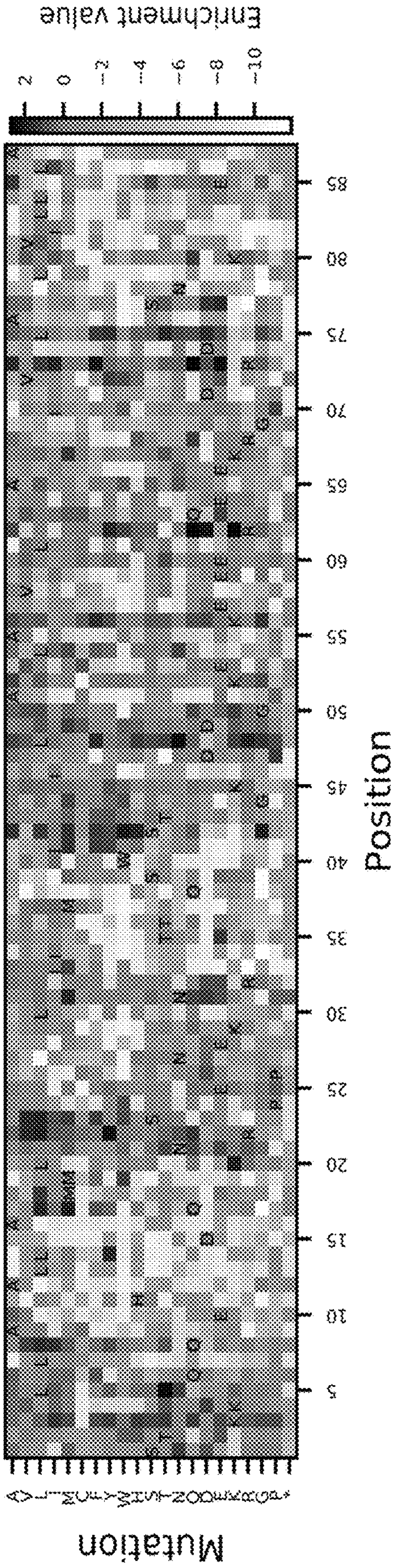
Figure 10B:
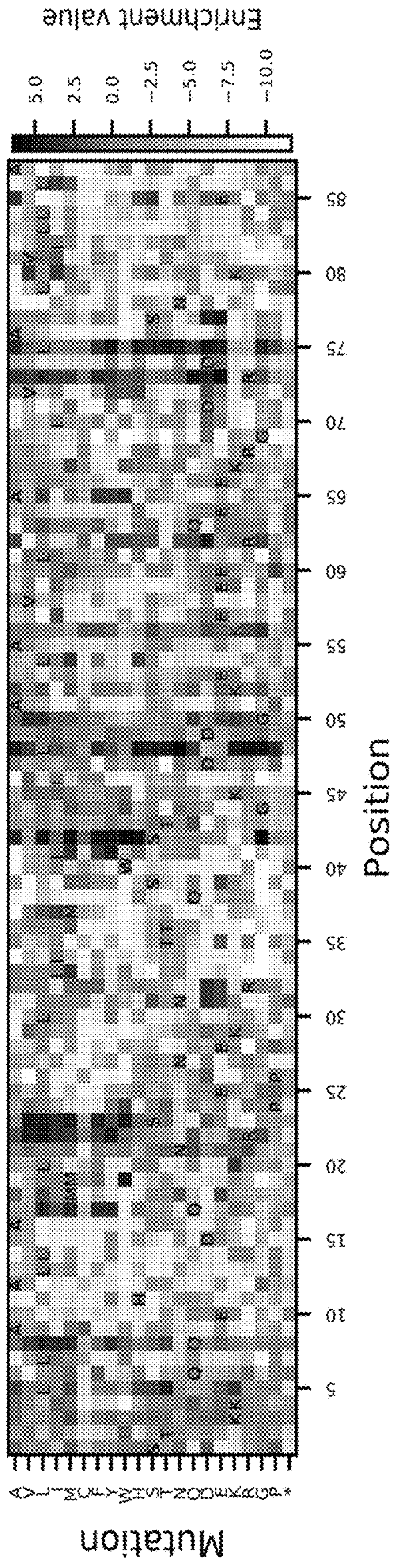
Figure 10C:
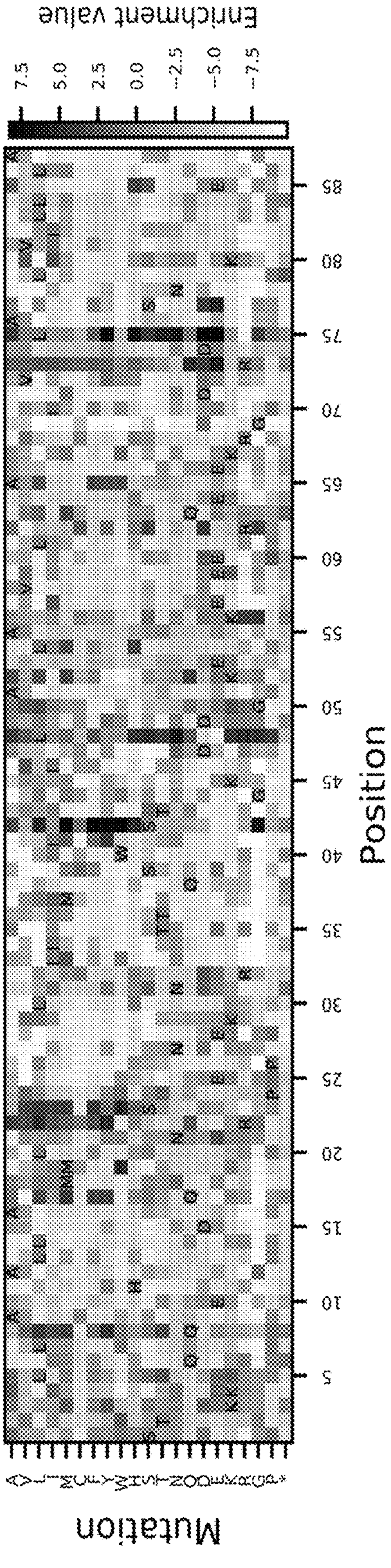
Figure 10D:

FIG. 10A-10D. Experimental optimization of G1_neo2_40. FIG. 10A-10C) Heatmaps for G1_neo2_40 single-site mutagenesis library showing enrichment at specific positions after consecutive rounds of increasing selection with FIG. 10A) 50 nM, FIG. 10B) 2 nM, and FIG. 10C) 0.1 nM IL-2Rβ$\gamma_c$ heterodimer. Based on these enrichment data, a combinatorial library was designed with nucleotide diversity $1.5\times10^6$. FIG. 10D) Amino acid residues available in the initial combinatorial library are depicted indicating residues predicted to be advantageous (shown above the original sequence) and deleterious (shown below the original sequence; in the depiction of the original sequence, black indicates residues that are represented in the combinatorial library and gray, residues not represented in the combinatorial library.

Figure 11A:
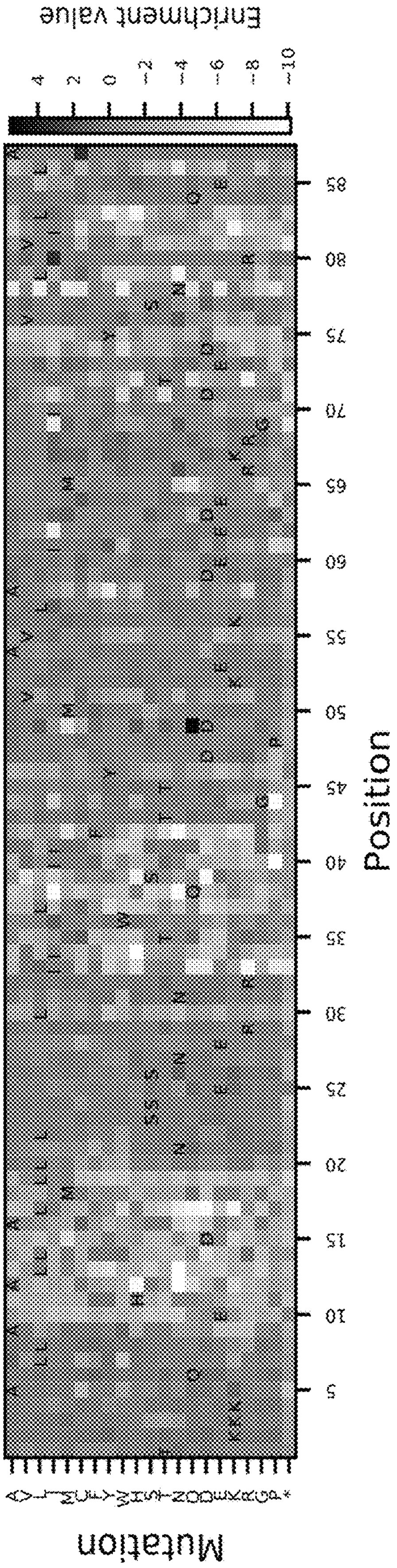
Figure 11B:
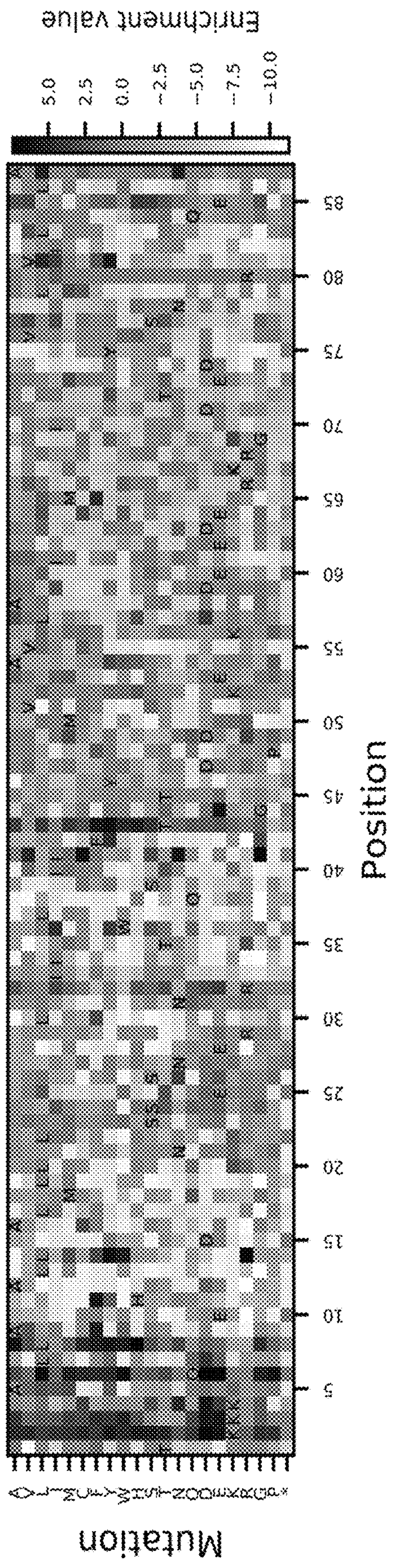
Figure 11C:
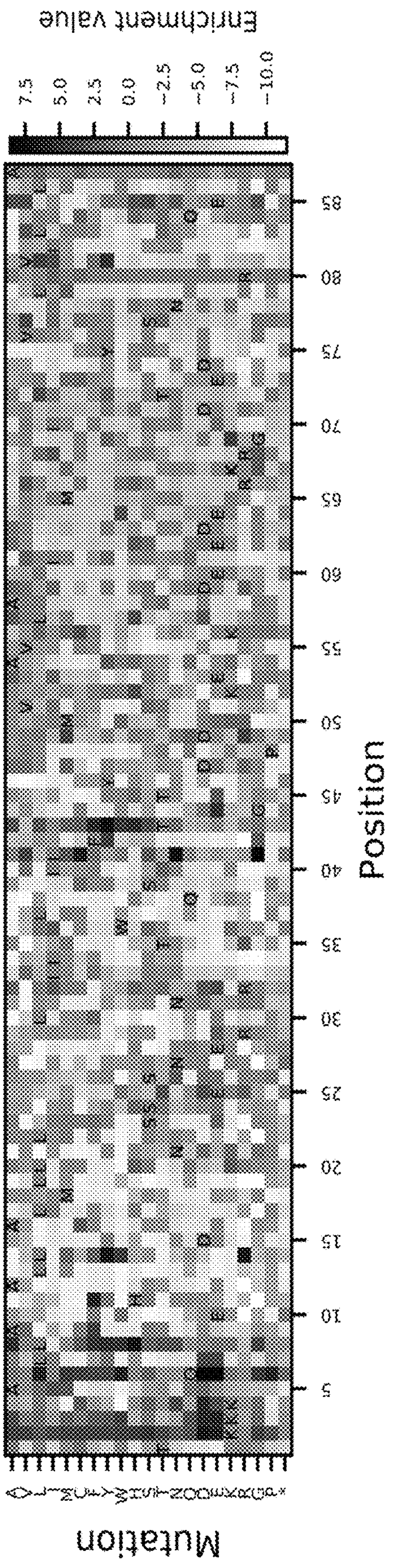
Figure 11D:
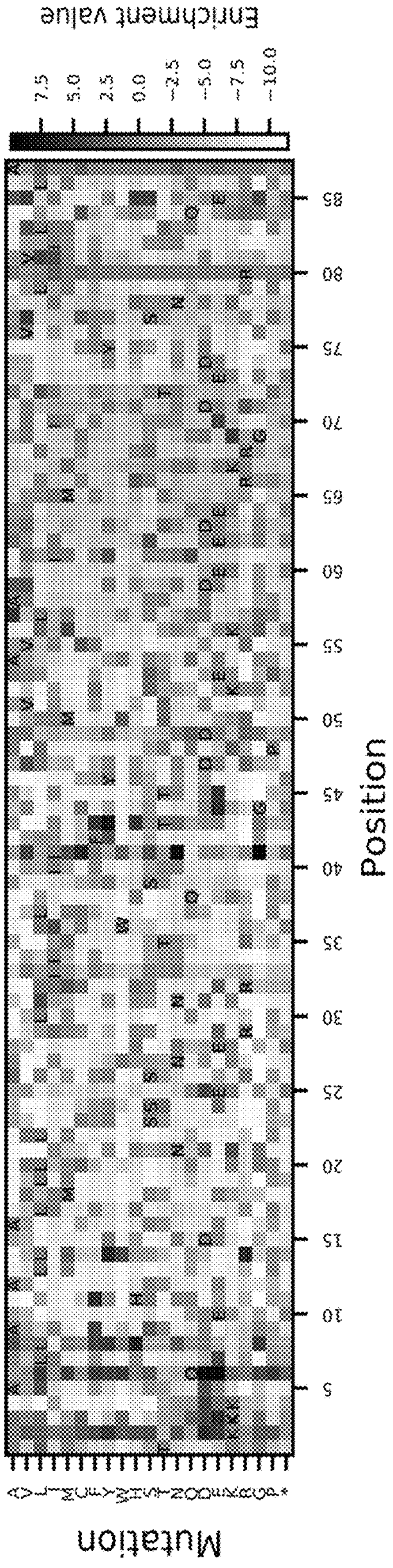

FIG. 11A-11E. Experimental optimization of G2_neo2_40_1F_seg27. Heatmaps for G2_neo2_40_1F_seg27 single-site mutagenesis library showing enrichment at specific positions after consecutive rounds of increasing selection with FIG. 11A) 10 nM, FIG. 11B) 1 nM, FIG. 11C) 0.1 nM, and FIG. 11D) 0.1 nM IL-2Rβ$\gamma_c$ heterodimer. Based on these enrichment data, a combinatorial library was designed with nucleotide diversity $5.3\times10^6$. FIG. 11E) Amino acid residues available in the initial combinatorial library are depicted indicating residues predicted to be advantageous; black indicates residues in the starting sequence represented in the combinatorial library.

Figure 12A:
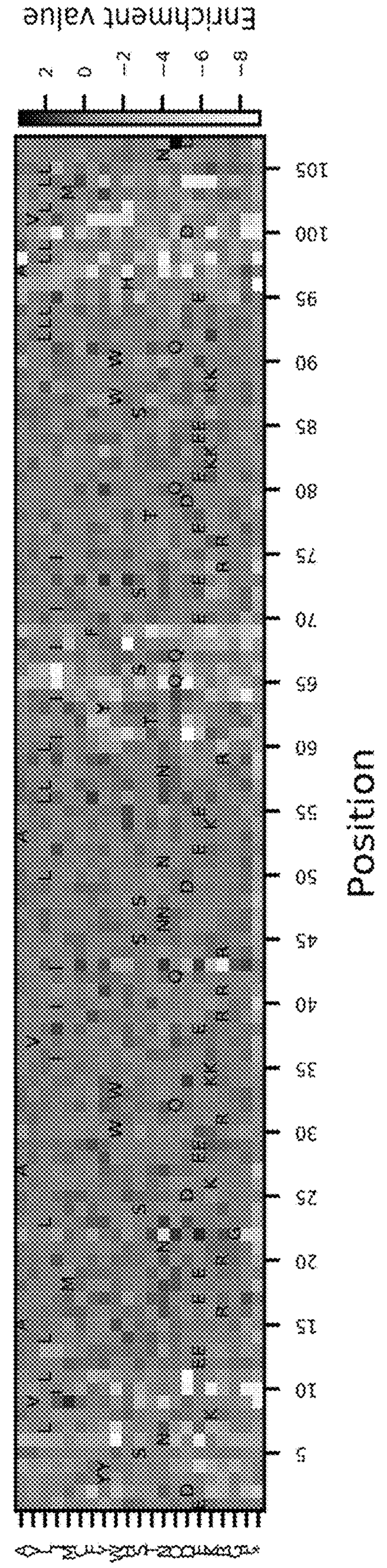
Figure 12B:
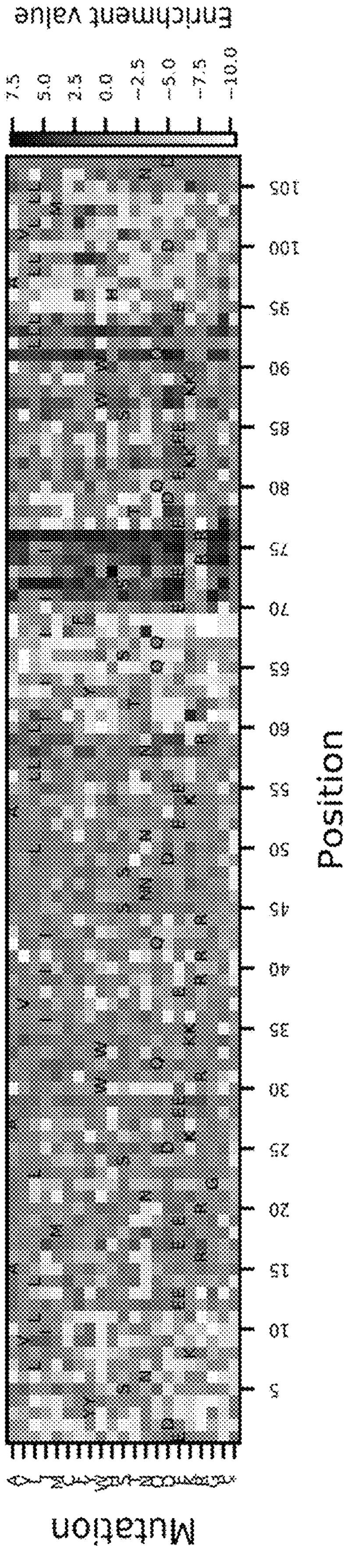
Figure 12C:
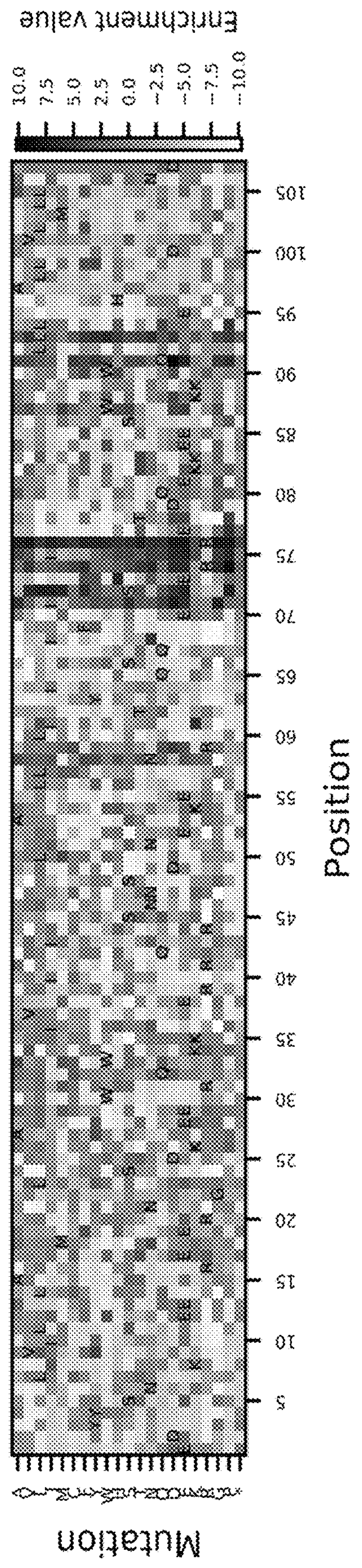
Figure 12D:
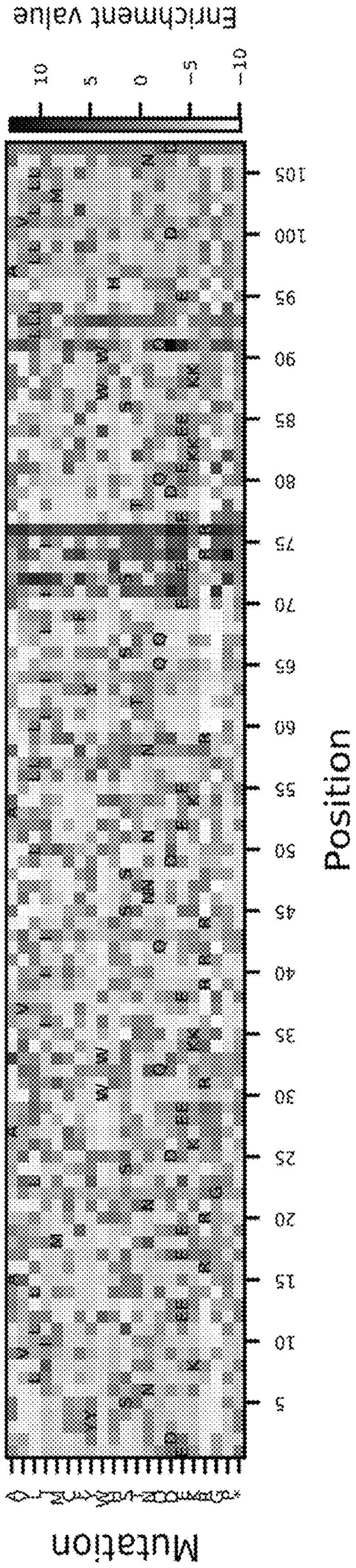
Figure 12E:
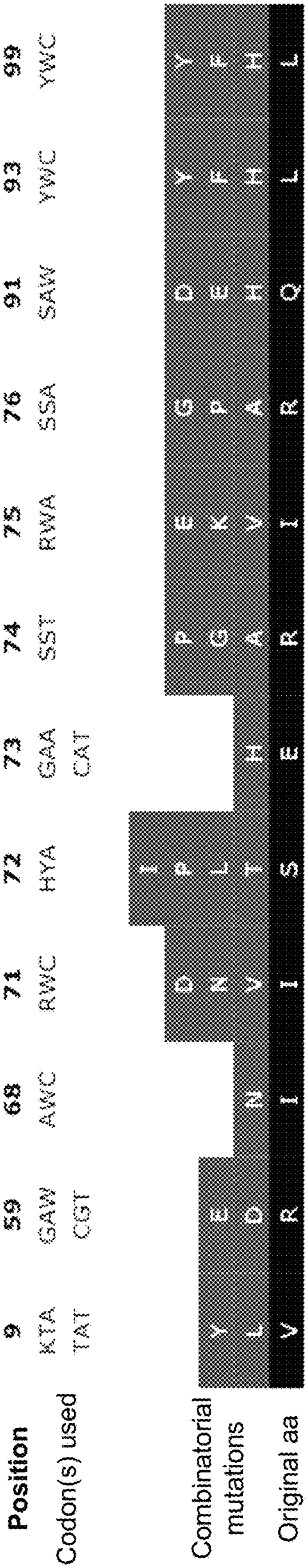

FIG. 12A-12E. Experimental optimization of G2_neo2_40_1F_seg29. Heatmaps for G2_neo2_40_1F_seg29 single-site mutagenesis library showing enrichment at specific positions after consecutive rounds of increasing selection with FIG. 12A) 10 nM, FIG. 12B) 1 nM, FIG. 12C) 0.1 nM, and FIG. 12D) 0.1 nM IL-2Rβ$\gamma_c$ heterodimer. Based on these enrichment data, a combinatorial library was designed with nucleotide diversity $2.9\times10^6$. FIG. 12E) Amino acid residues available in the initial combinatorial library are depicted indicating residues predicted to be advantageous; black indicates residues in the starting sequence represented in the combinatorial library.

Figure 13A:
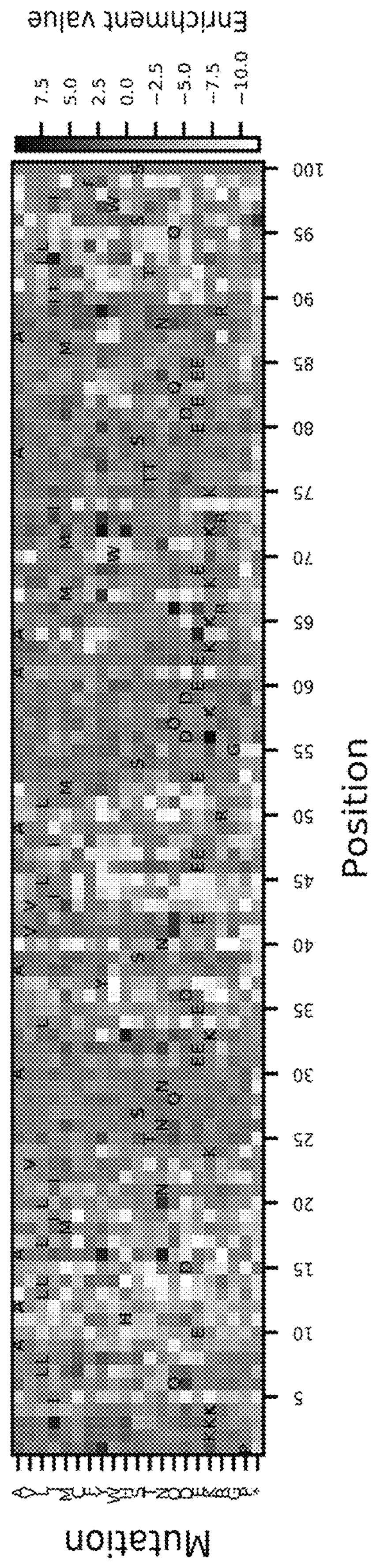
Figure 13B:
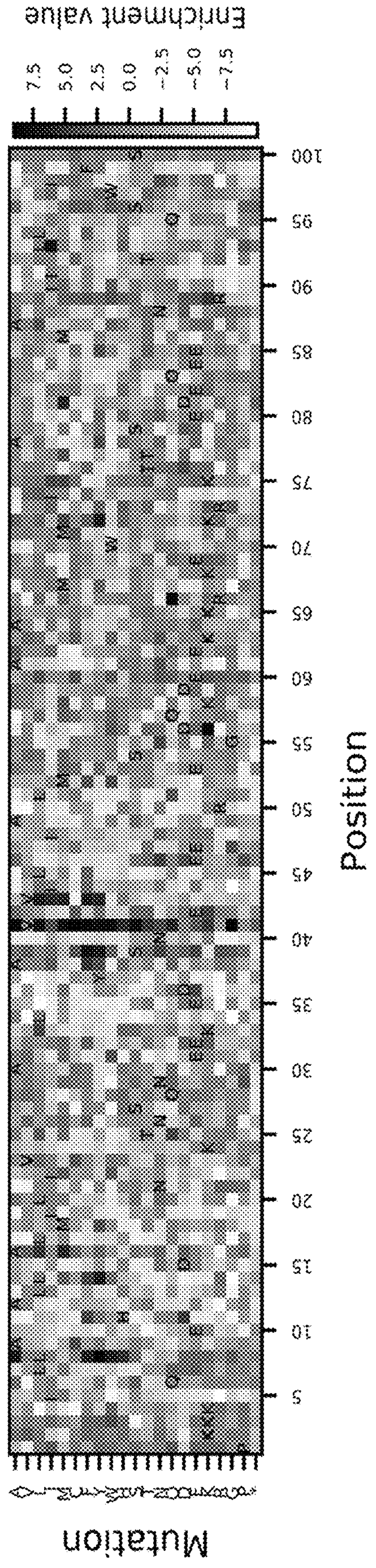
Figure 13C:
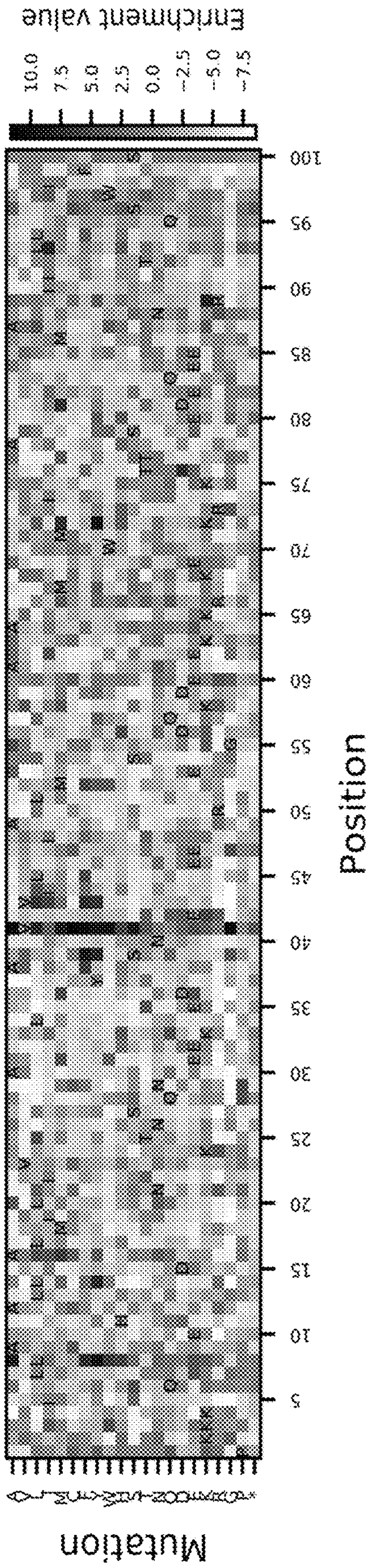
Figure 13D:
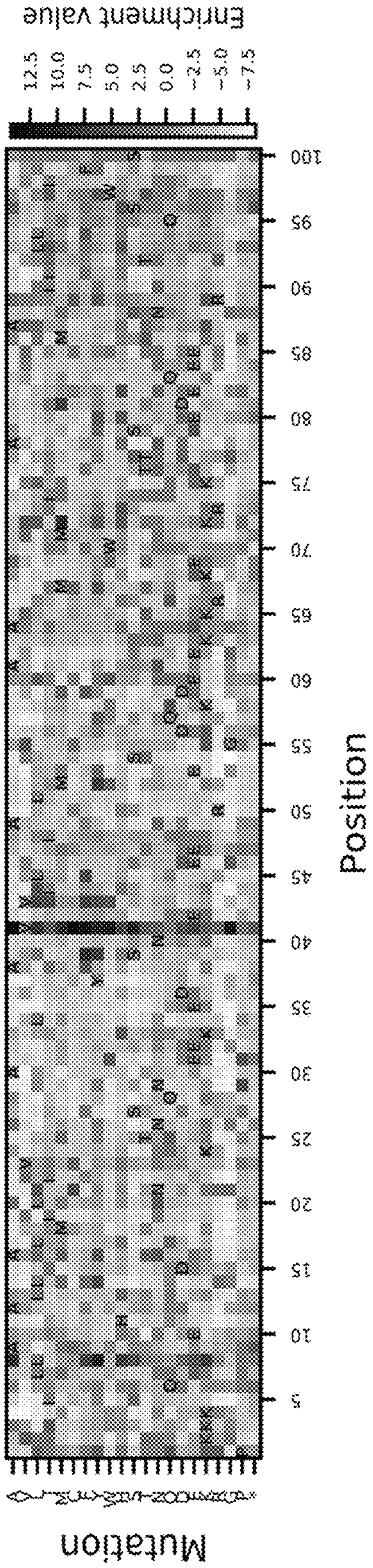

FIG. 13A-13E. Experimental optimization of G2_neo2_40_1F_seg36. Heatmaps for G2_neo2_40_1F_seg36 single-site mutagenesis library showing enrichment at specific positions after consecutive rounds of increasing selection with FIG. 13A) 10 nM, FIG. 13B) 1 nM, FIG. 13C) 0.1 nM, and FIG. 13D) 0.1 nM IL-2Rβ$\gamma_c$ heterodimer. Based on these enrichment data, a combinatorial library was designed with nucleotide diversity $2.7\times10^6$. FIG. 13E) Amino acid residues available in the initial combinatorial library are depicted indicating residues predicted to be advantageous; black indicates residues in the starting sequence represented in the combinatorial library.

Figure 14A:
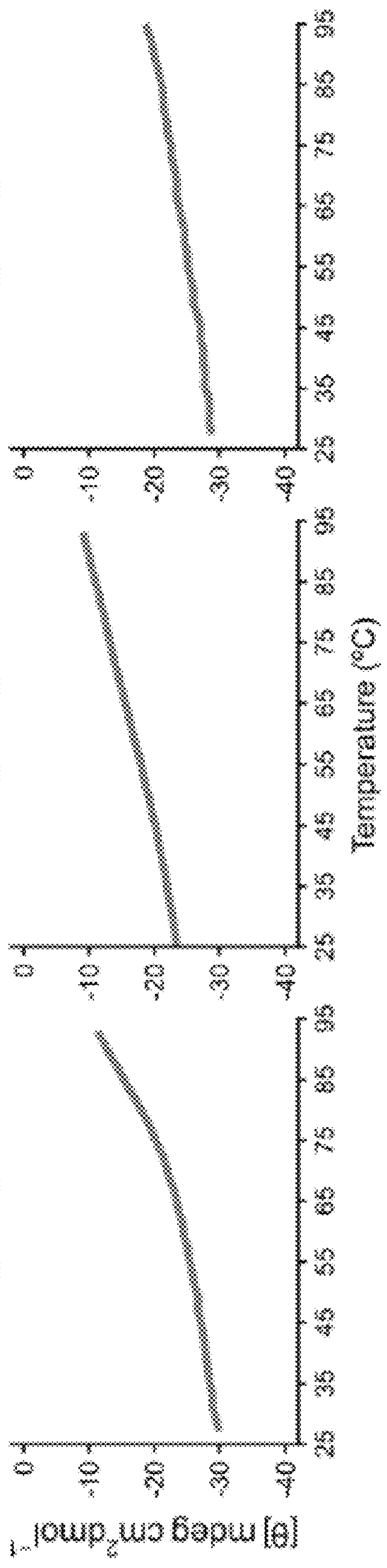
Figure 14B:
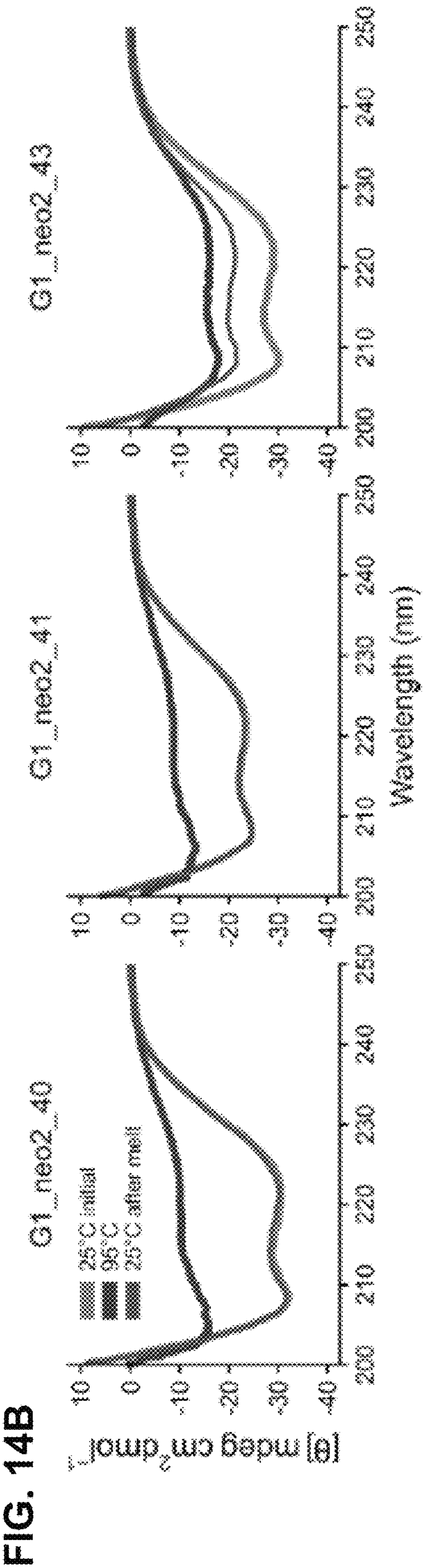

FIG. 14A-14B. Circular Dichroism (CD) thermal denaturation experiments for multiple IL-2/IL-15 de novo designed mimetics, generation-1. FIG. 14A) Thermal denaturation curves and FIG. 14B) wavelength scans.

Figure 15A:
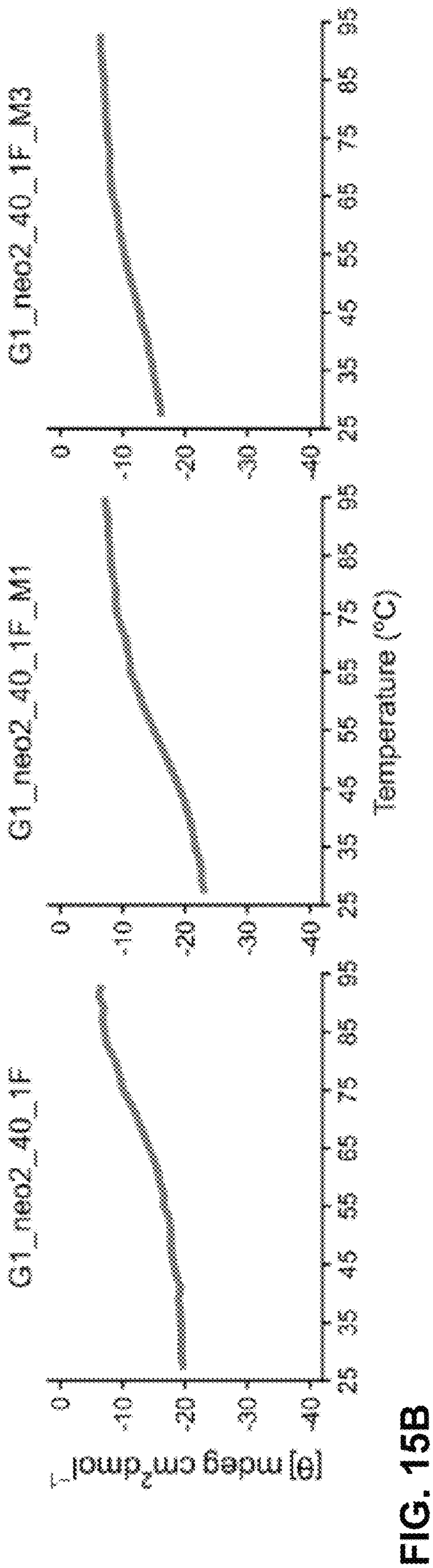
Figure 15B:
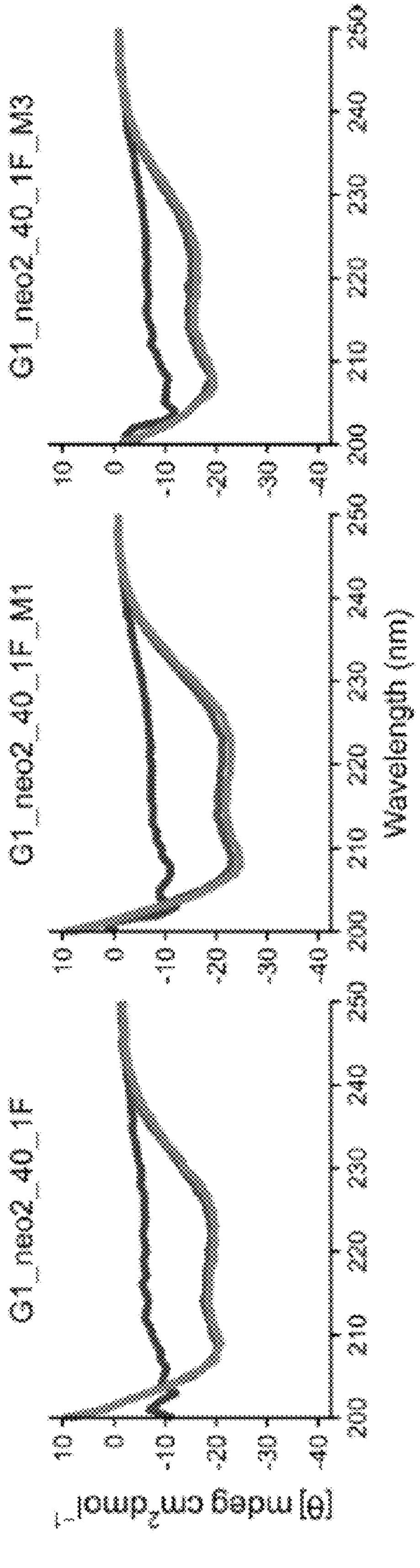

FIG. 15A-15B. Circular Dichroism (CD) thermal denaturation experiments for multiple IL-2/IL-15 de novo designed mimetics, generation-1 experimentally optimized. FIG. 15A) Thermal denaturation curves and FIG. 15B) wavelength scans.

Figure 16A:
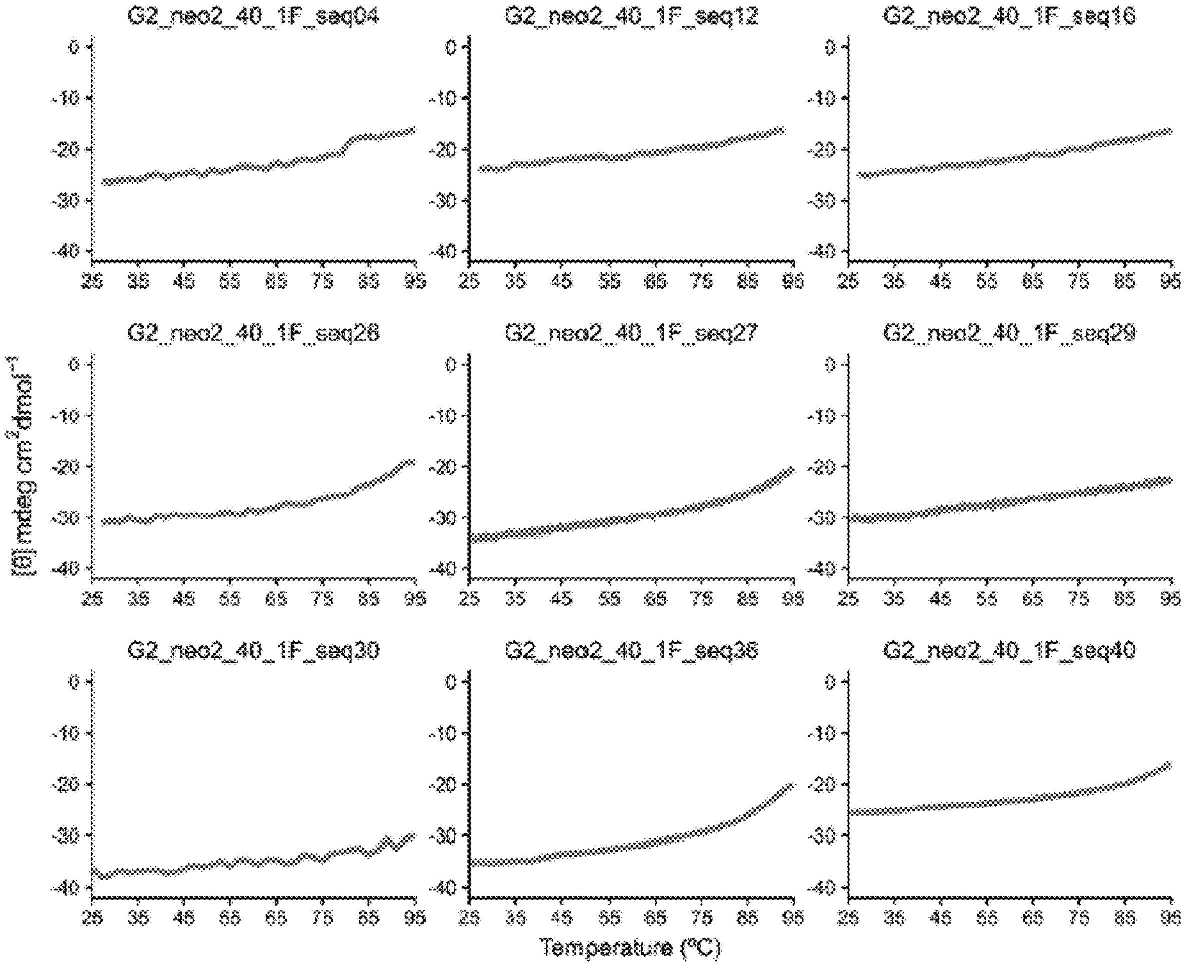
Figure 16B:
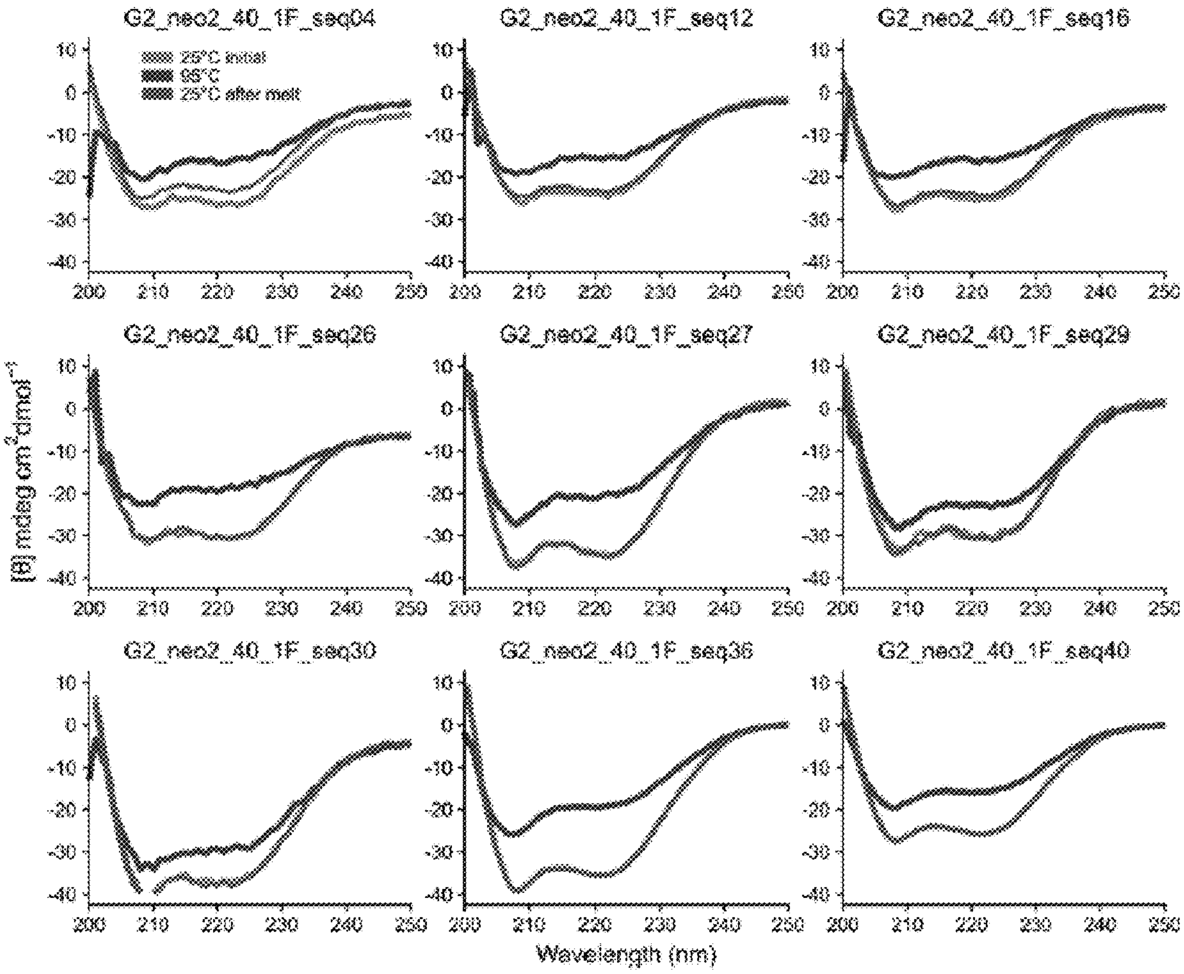
Figure 16C:
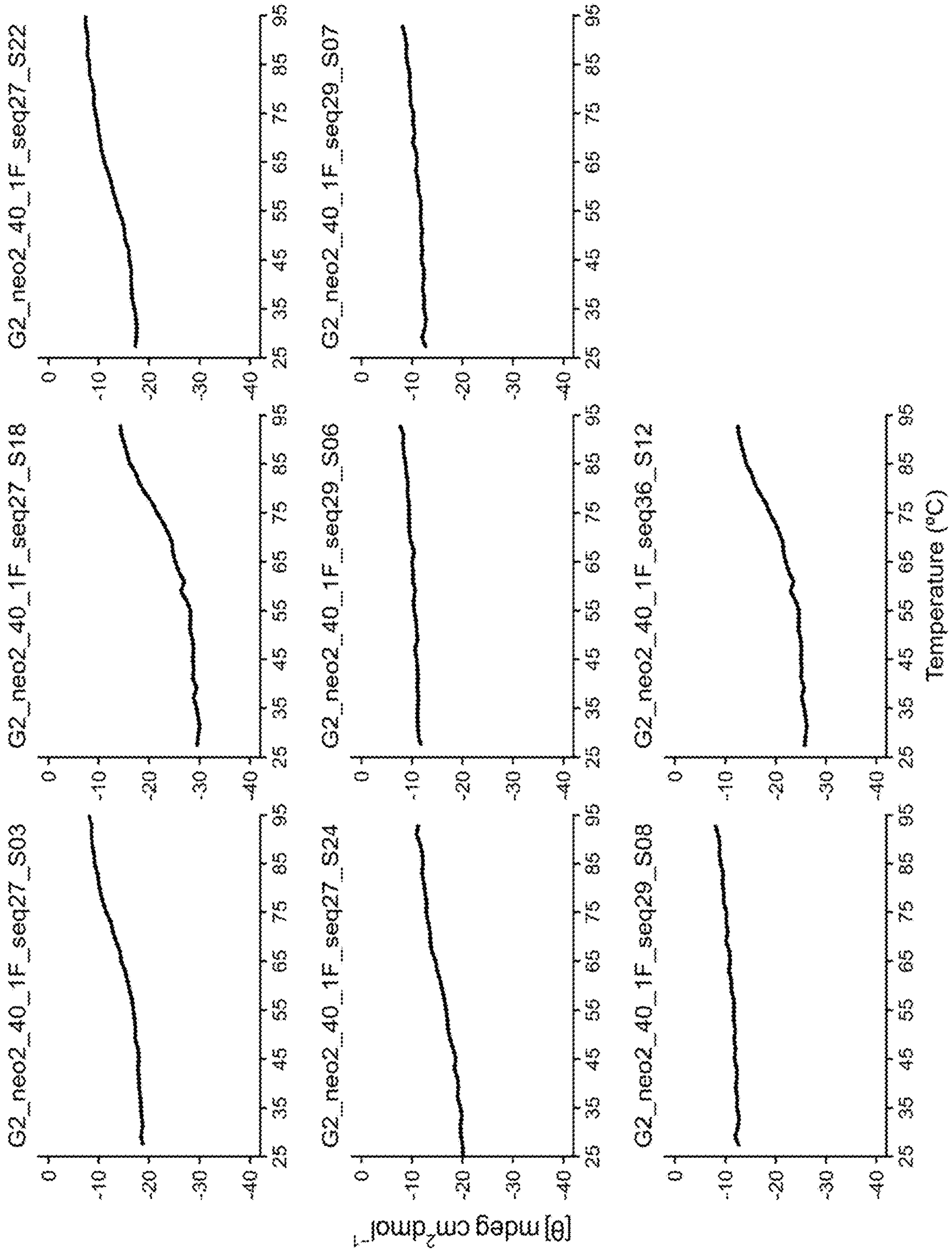
Figure 16D:
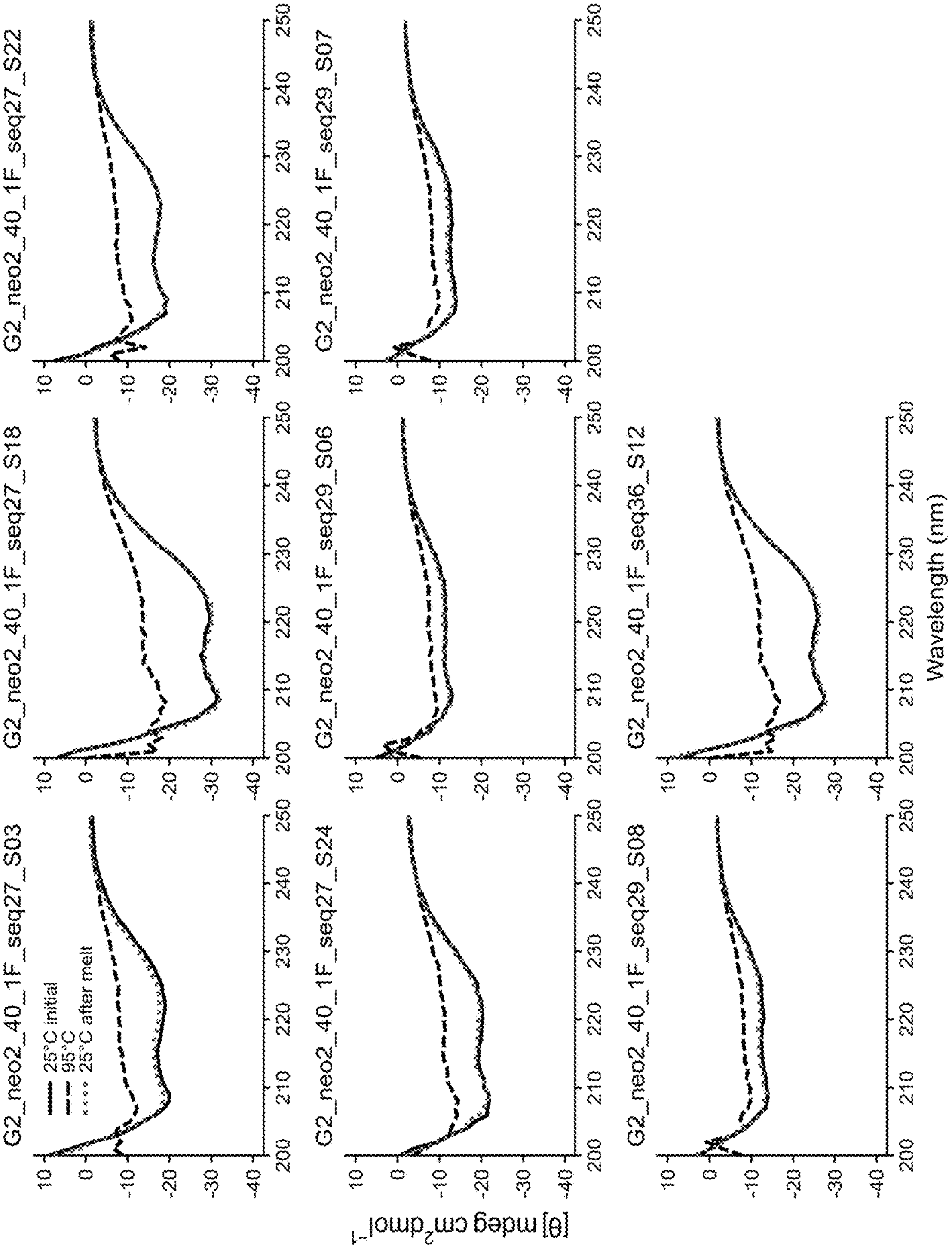

FIG. 16A-16D. Circular dichroism thermal melts for IL-2/IL-15 mimetic designs generation-2. FIG. 16A and FIG. 16C) Thermal denaturation curves and FIG. 16B and FIG. 16D) wavelength scans.

Figure 17A:
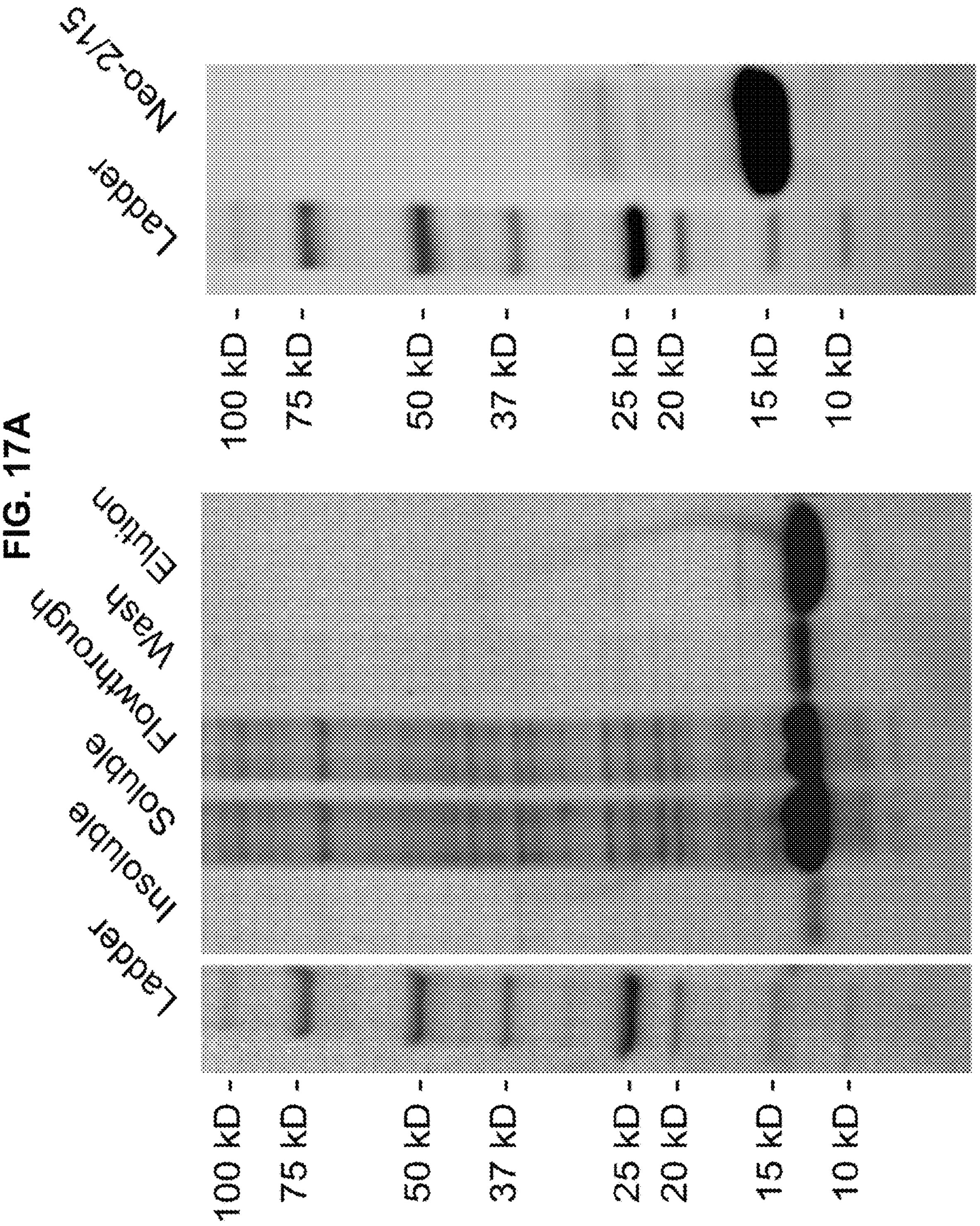
Figure 17B:
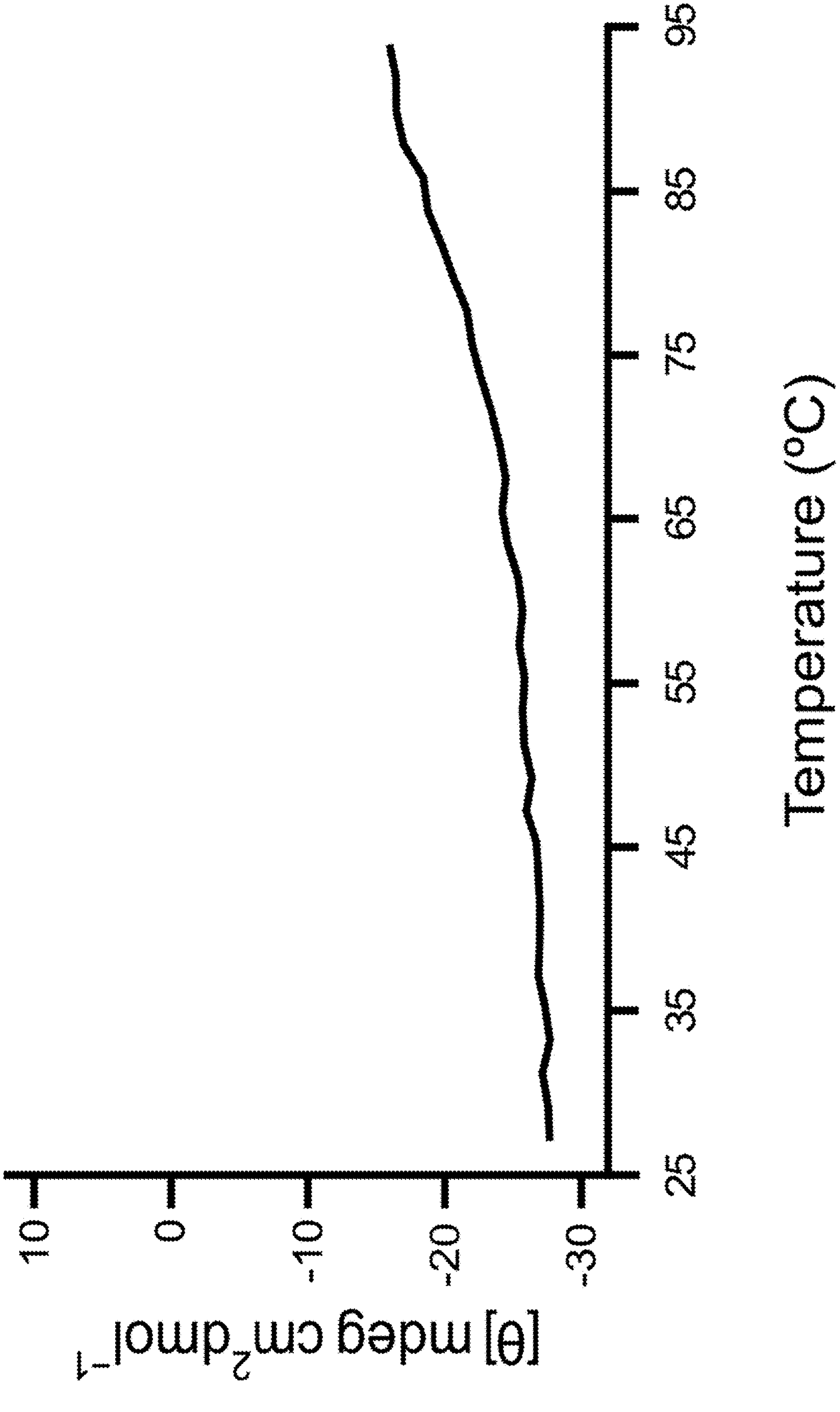
Figure 17C:
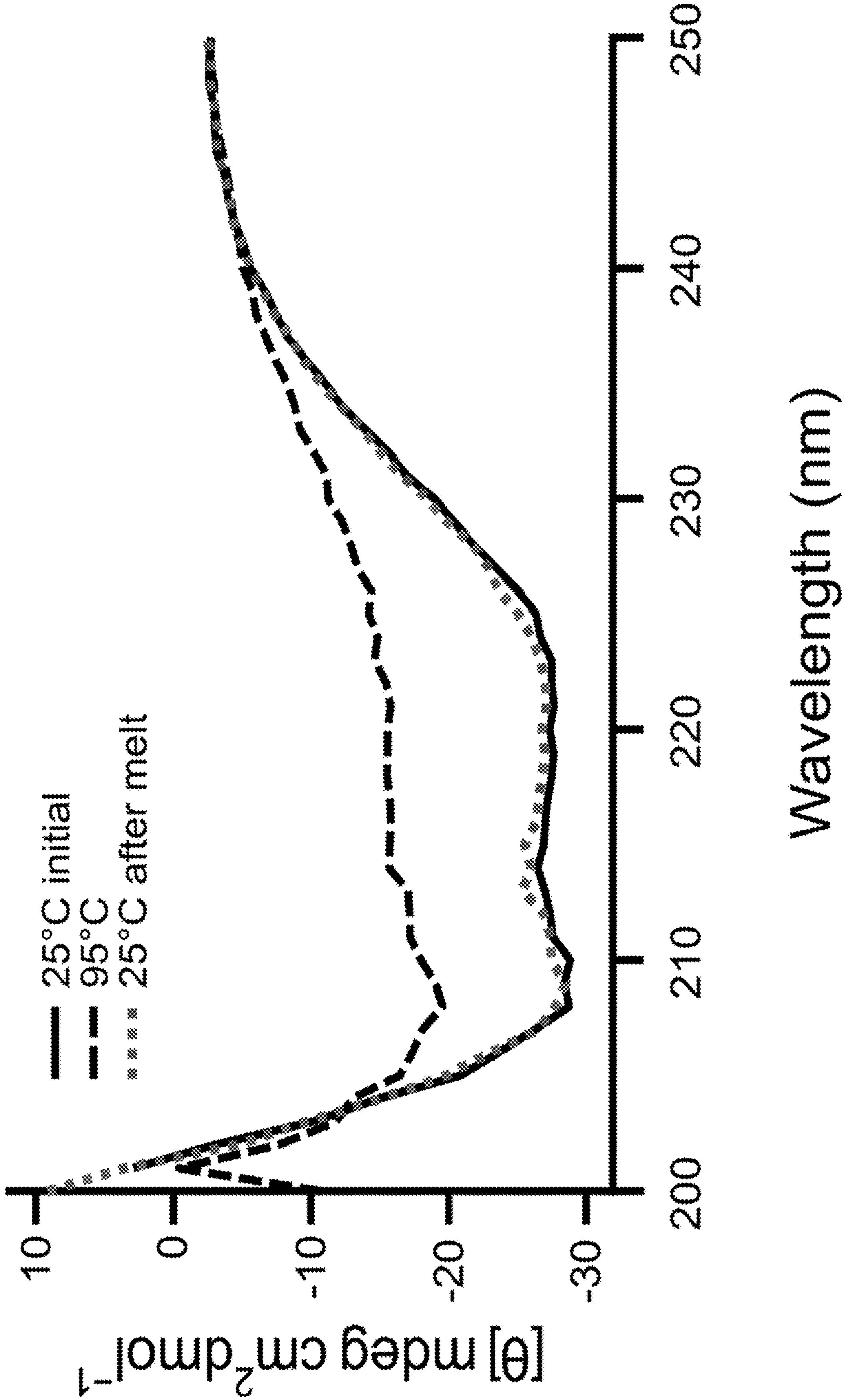

FIG. 17A-17C. Expression, purification, and thermal denaturation characterization of neoleukin-2/15. FIG. 17A) SDS Tris-Tricine gel electrophoresis showing expression and purification over affinity column. FIG. 17B) Circular dichroism at 222 nm during thermal melting from 25° C. to 95° C., showing robust temperature stability. FIG. 17C) Circular dichroism wavelength scans at 25° C., 95° C. and then again 25° C., showing that neoleukin-2/15 does not fully melt at 95° C. and refolds fully after cooling back to 25° C.

Figure 18A:
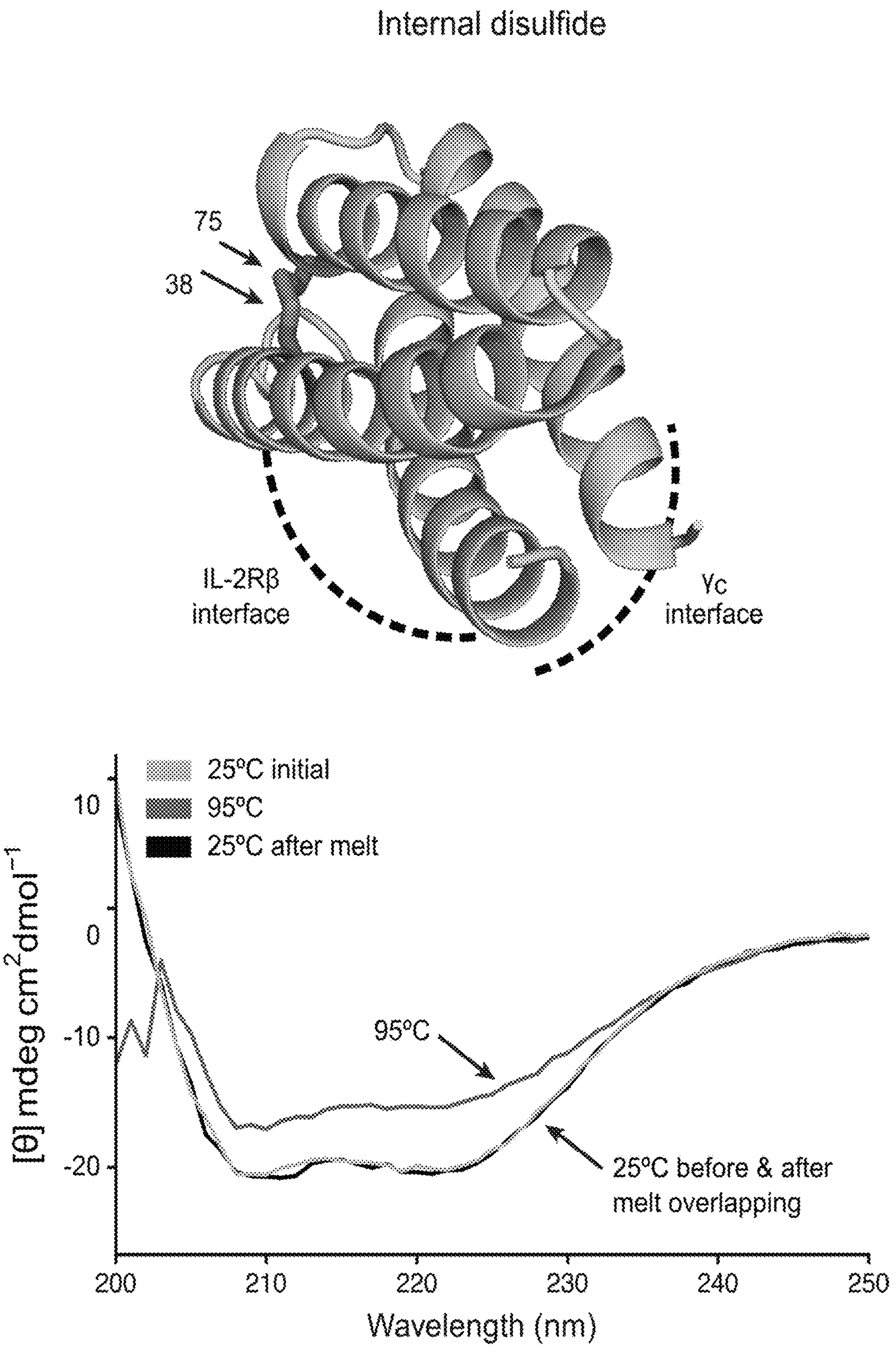
Figure 18B:
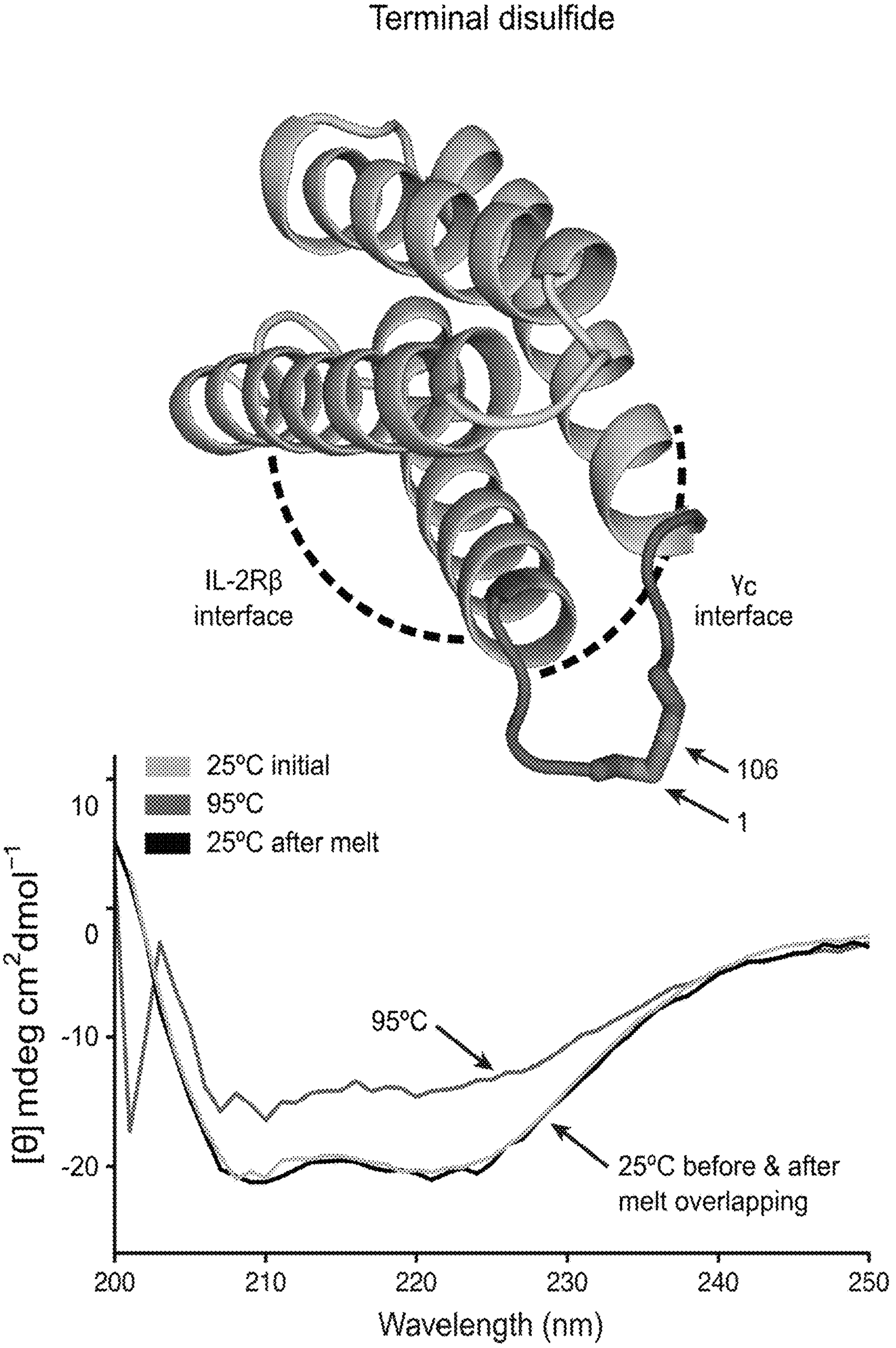
Figure 18C:
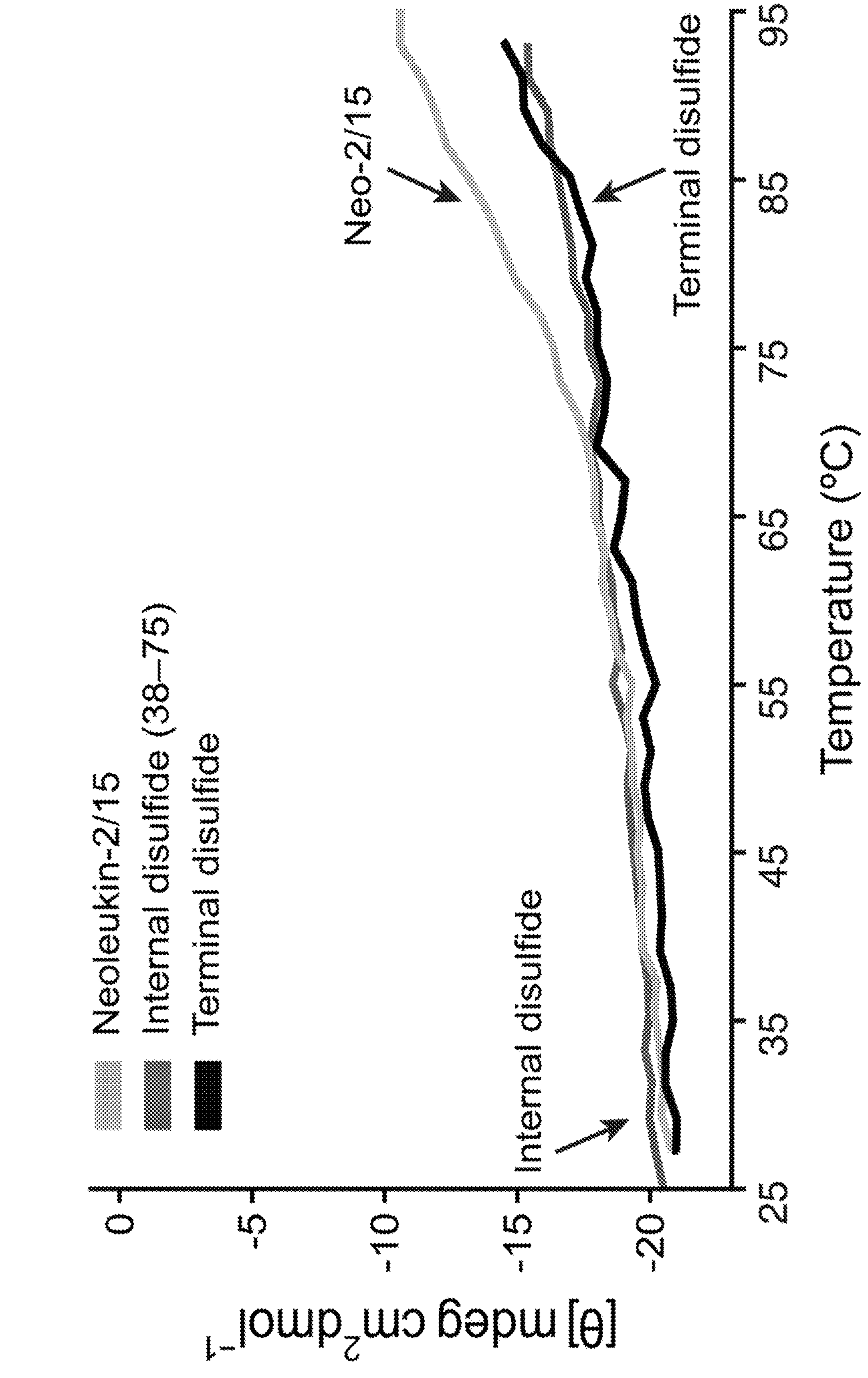
Figure 18D:
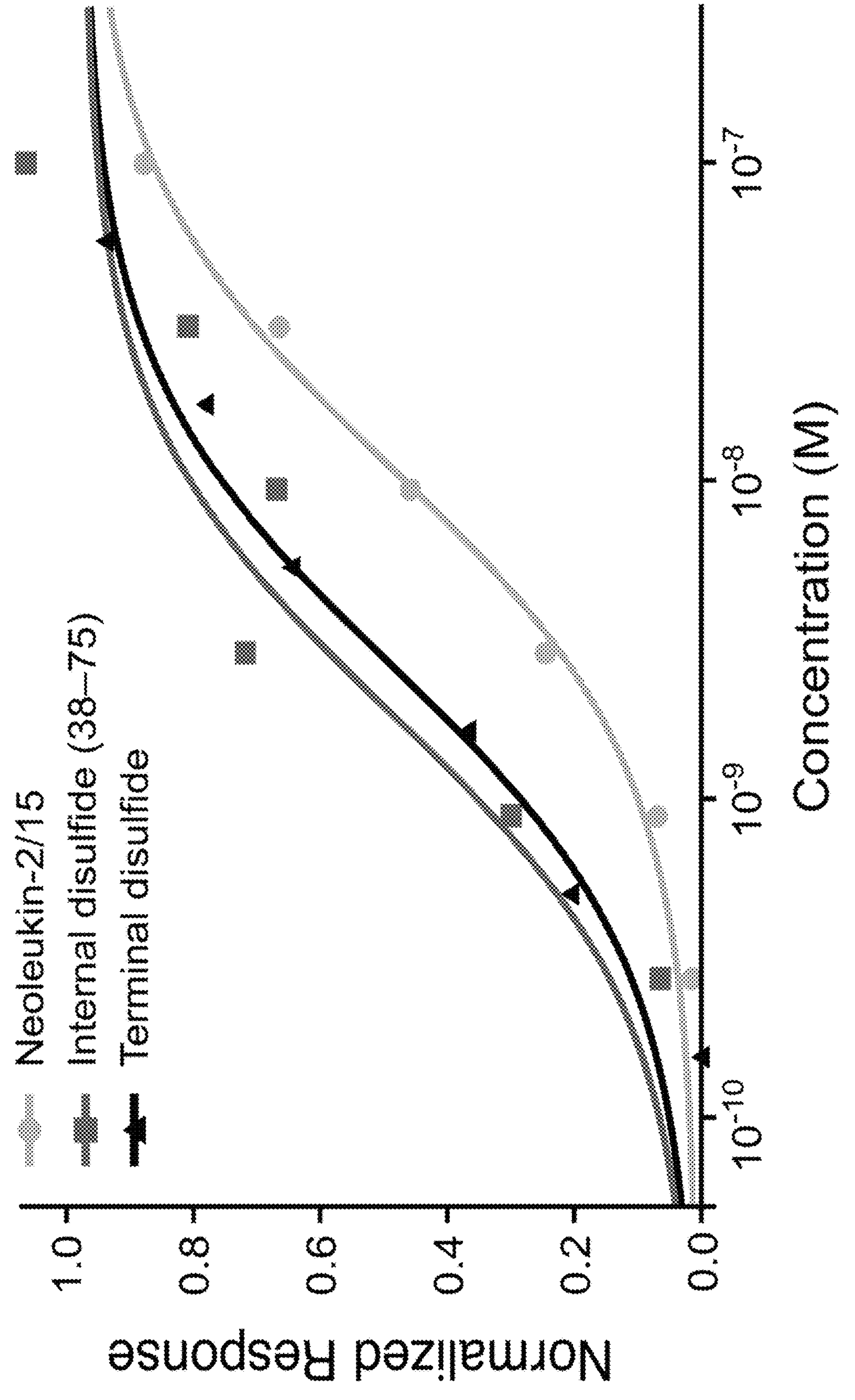

FIG. 18A-18D. Single disulfide stapled variants of neoleukin-2/15 with higher thermal stability. Structural model of disulfide stabilized variants of Neoleukin-2/15 are shown with positions of the mutated residues labeled and the disulfide bond shown. Two strategies were used to generated the disulfide variants: FIG. 18A) internal placement at residues 38 and 75 and terminal linkage; FIG. 18B) for the terminal variant, three residues were added to each terminus in order to limit any distortions to the starting structure that would otherwise be required to form the disulfide bond. CD spectra at 25° C., 95° C. and 25° C. after cooling for the internal and terminal disulfide variants are shown below their structural models. Both variants show very little signal loss at 95° C. and complete refolding upon cooling; FIG. 18C) thermal melts of each variant were performed by monitoring CD signal at 222.0 nm over a range of temperatures. Each of the disulfide variants shows improved stability relative the native; FIG. 18D) binding strength of each variant to IL-2Rβγc was measured by biolayer interferometry. Contrary to disrupting the binding interaction, these data show the introduction of the disulfide bond improves the binding of the mimetics to IL-2Rβγc. Both disulfide-bonded variants exhibit an improvement in binding IL-2Rβγc (Kd~1.3±0.49 and 1.8±0.26 nM, for the internal and external disulfide-staples, respectively, compared to 6.9±0.61 nM for Neo-2/15 under the same experimental conditions), which is consistent with the expected effect of disulfide-induced stabilization of the protein's binding site.

Figure 19A:
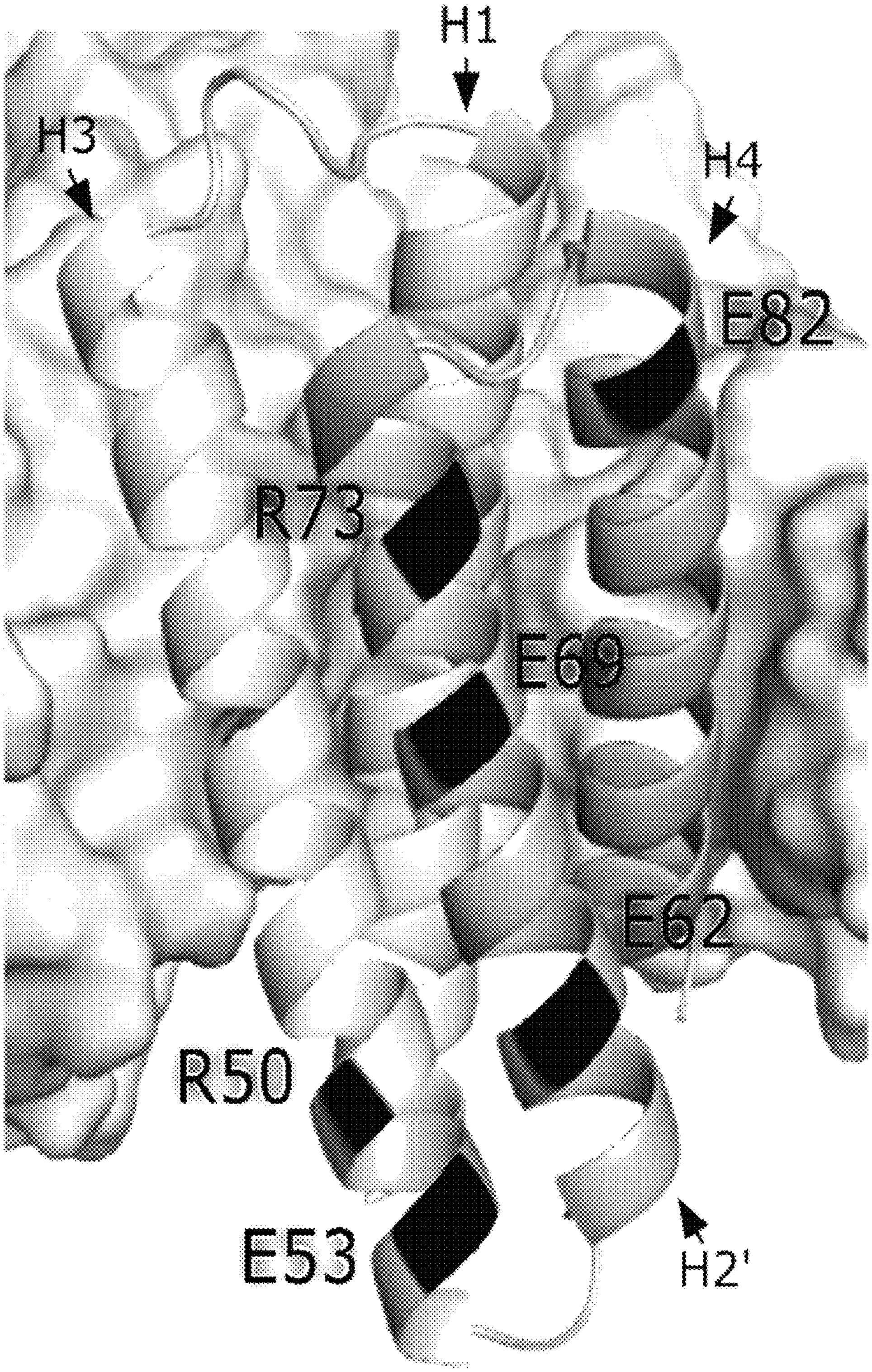
Figure 19B:
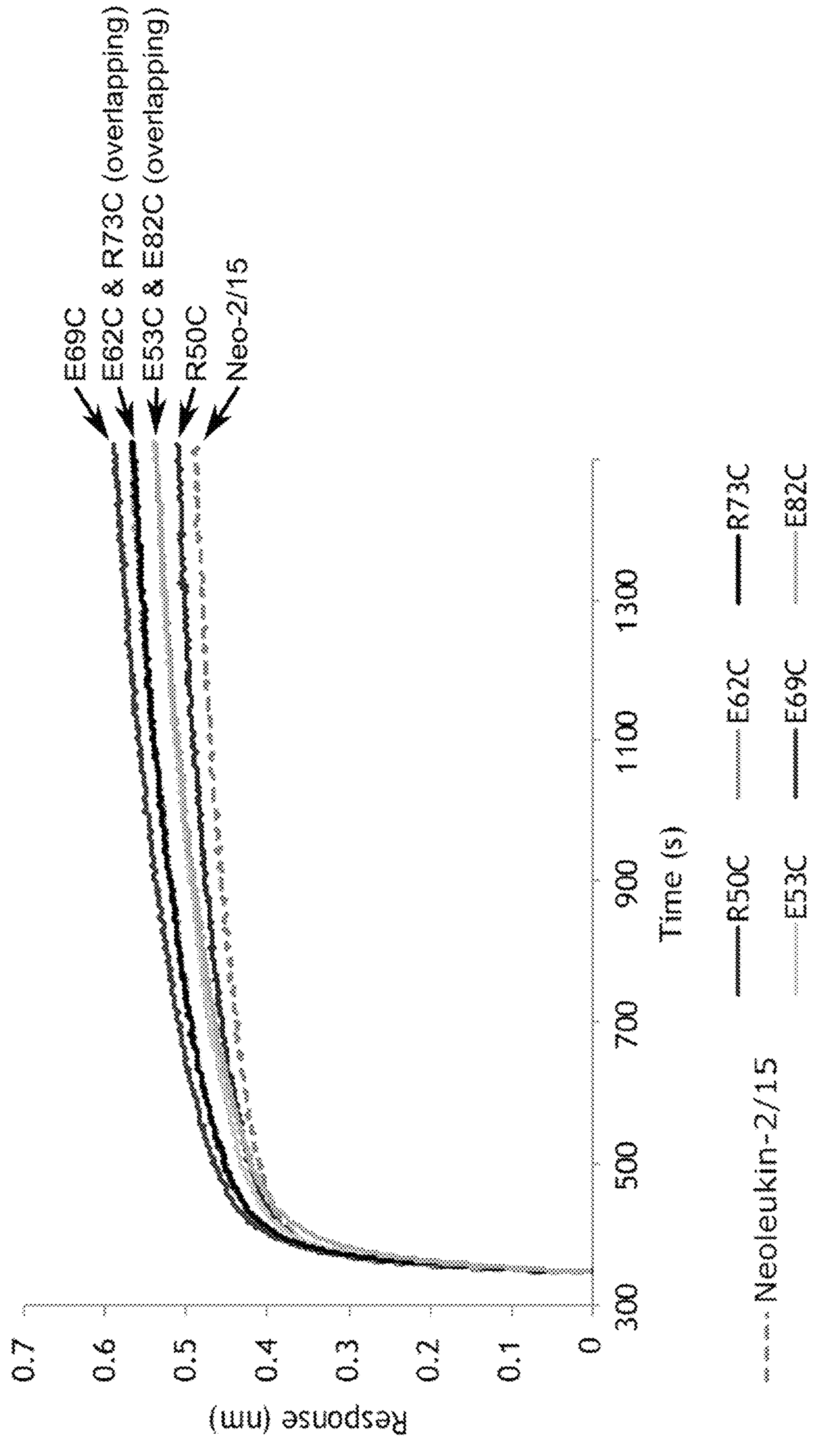

FIG. 19A-19B. Robustness of neoleukin-2/15 to single-point cysteine mutants on non-binding interface positions. FIG. 19A) Schematic showing point mutant positions in neolukin-2/15 that can individually be mutated to cysteine without interfering with expression of the protein or binding to IL-2Rβγc. Positions were chosen to avoid interference with receptor binding. FIG. 19B) Association kinetics of Neolukin-2/15 cysteine mutants with IL-2Rβ$\gamma_c$ measured using biolayer interferometry. All of the variants associate with receptor approximately similarly to Neo-2/15.

Figure 20A:
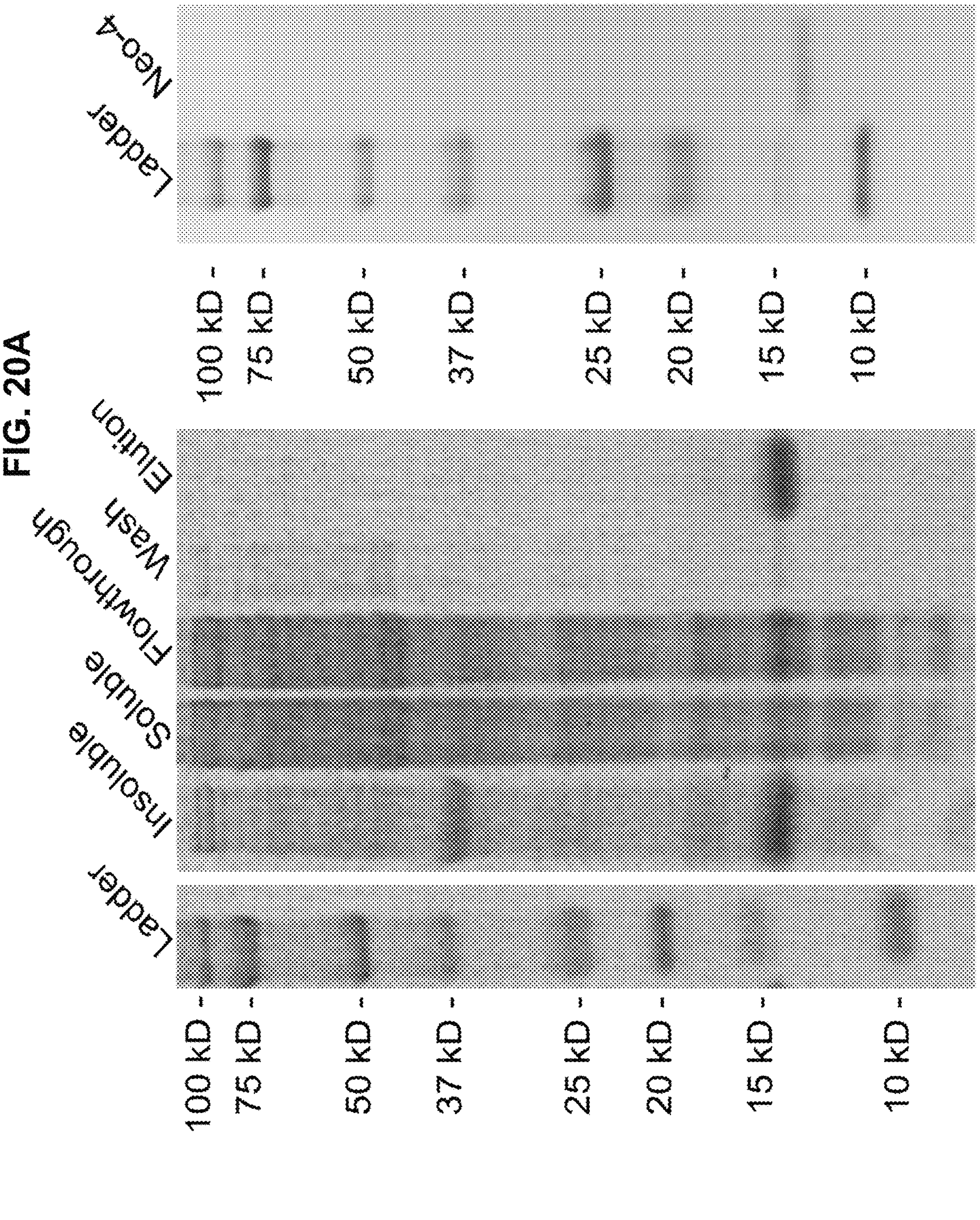
Figure 20B:
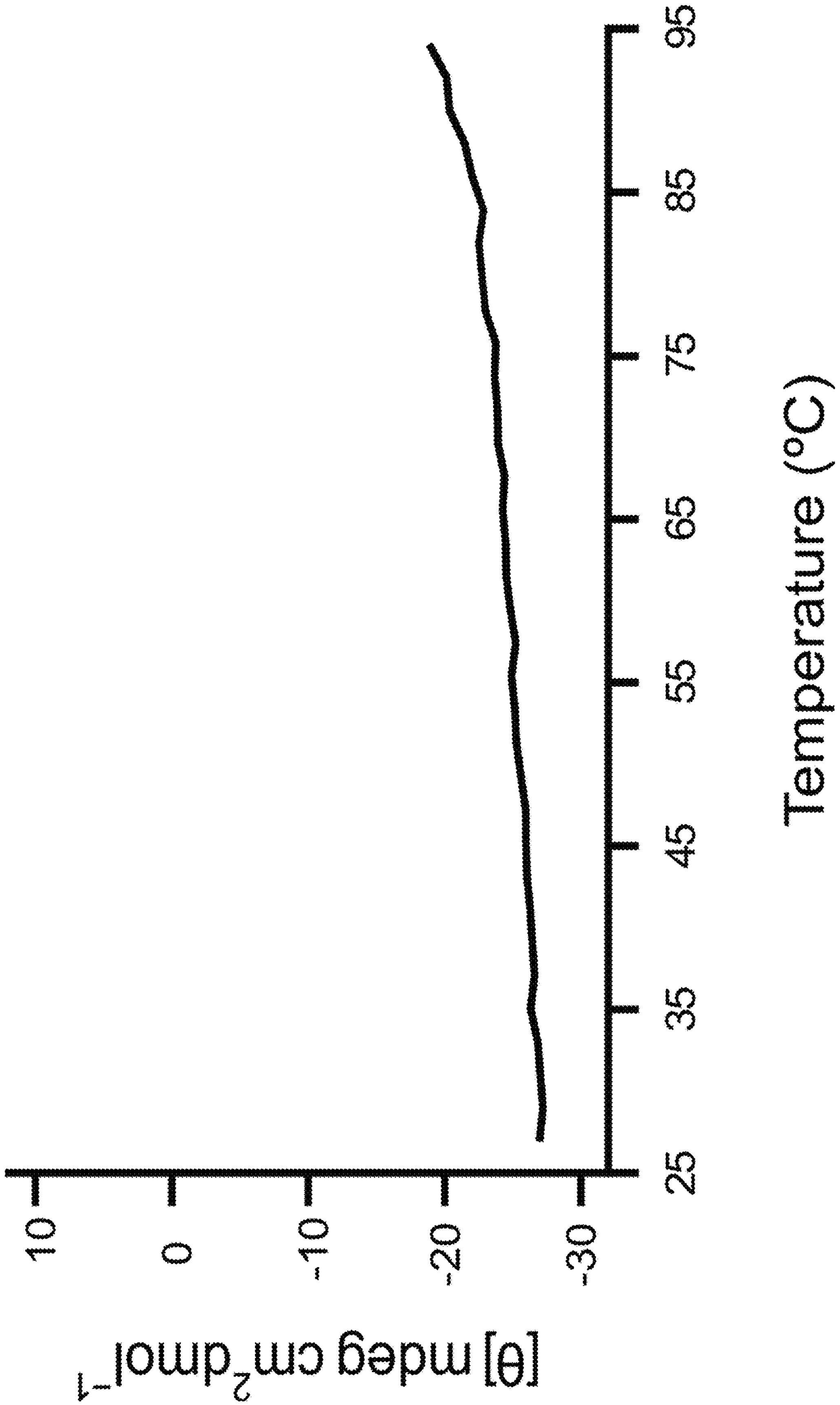
Figure 20C:
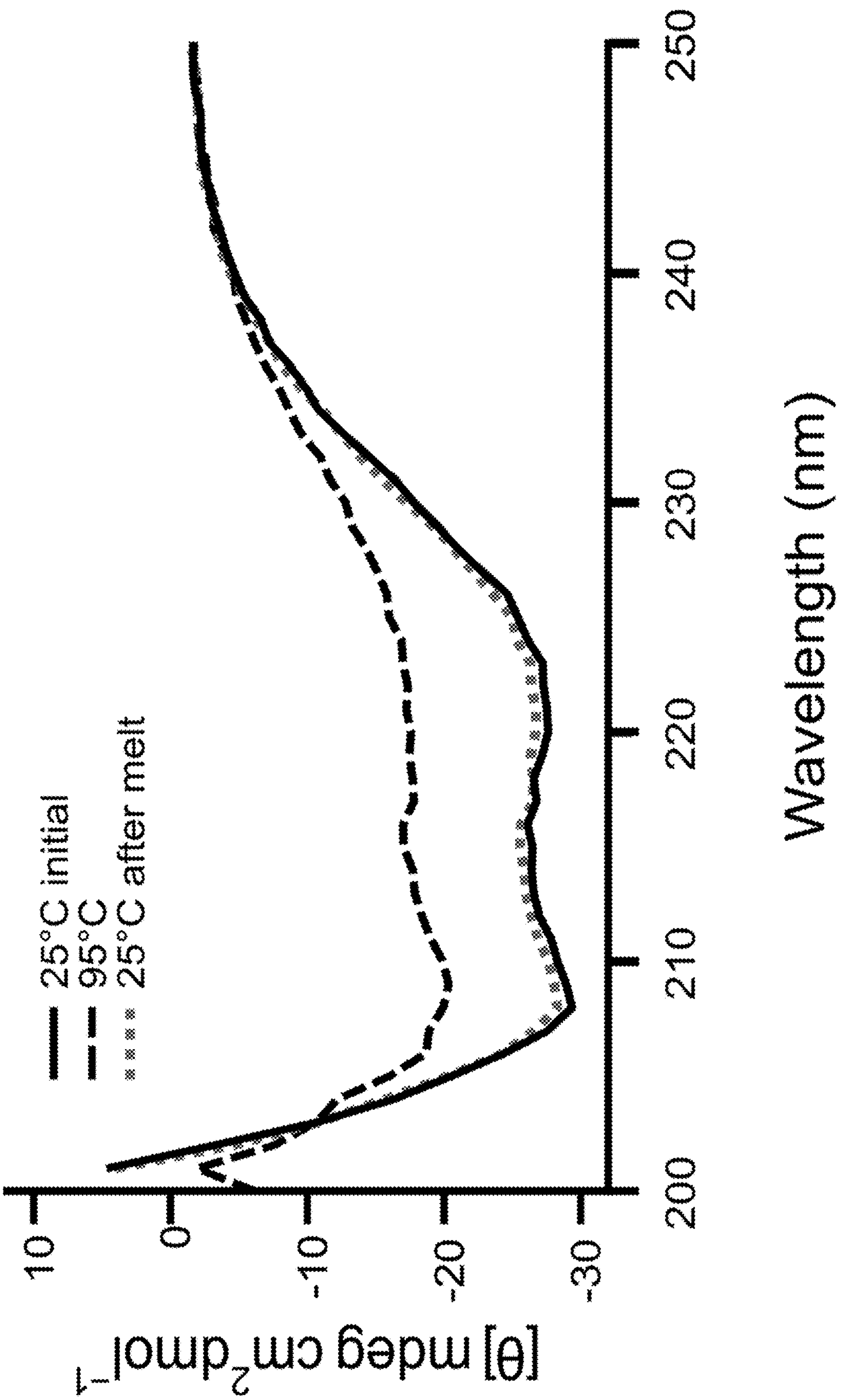
Figure 21A:
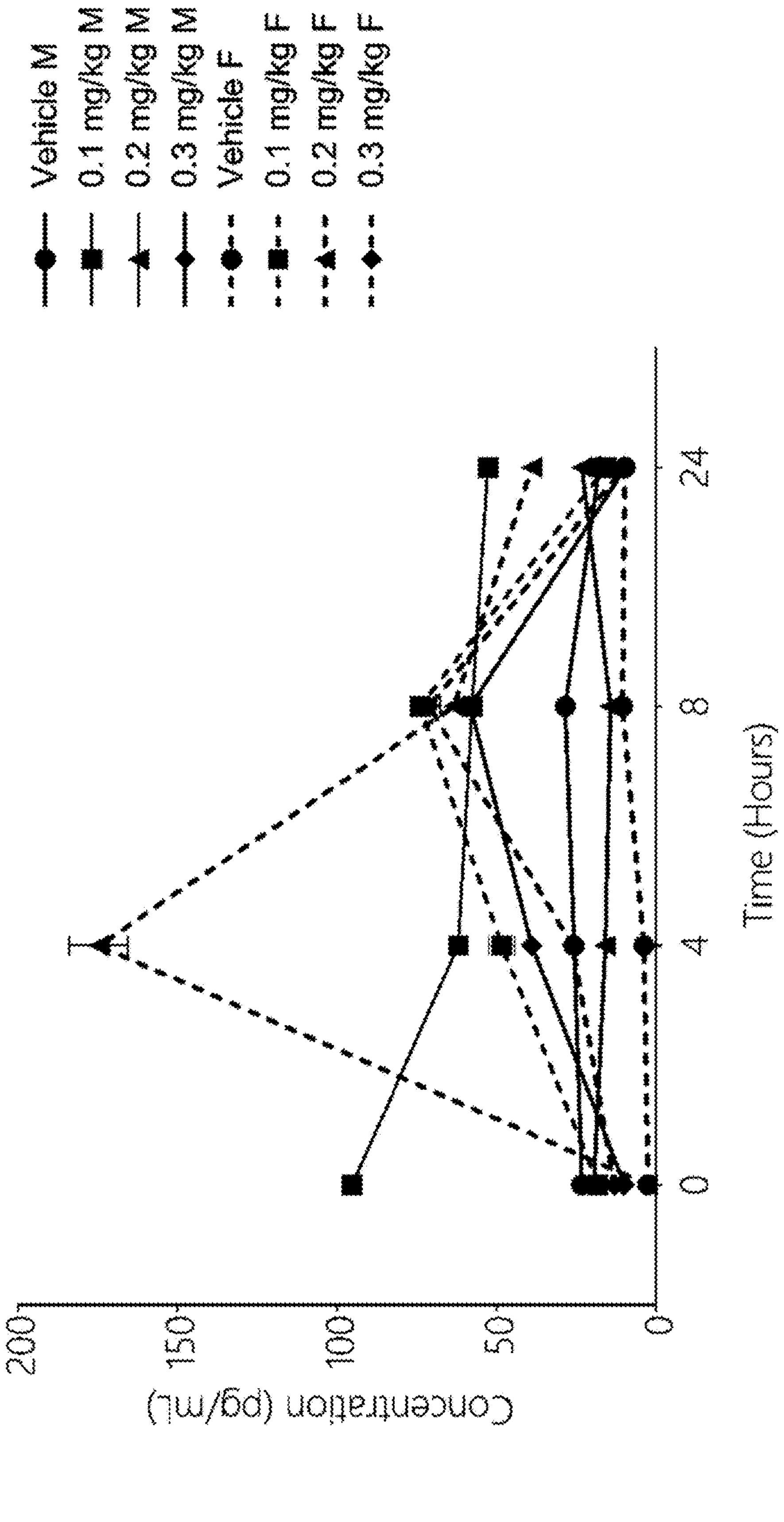
Figure 21B:
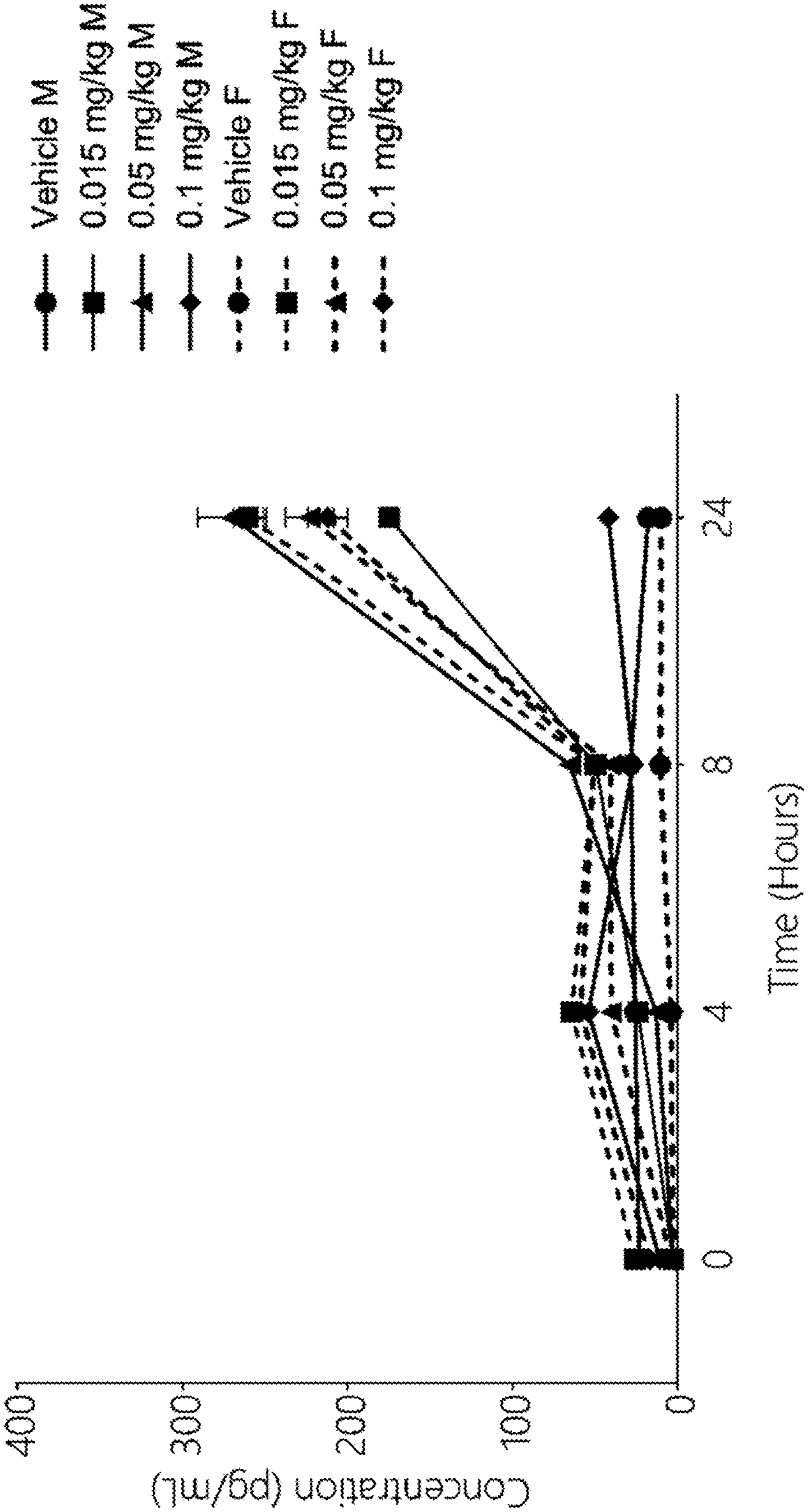
Figure 21C:
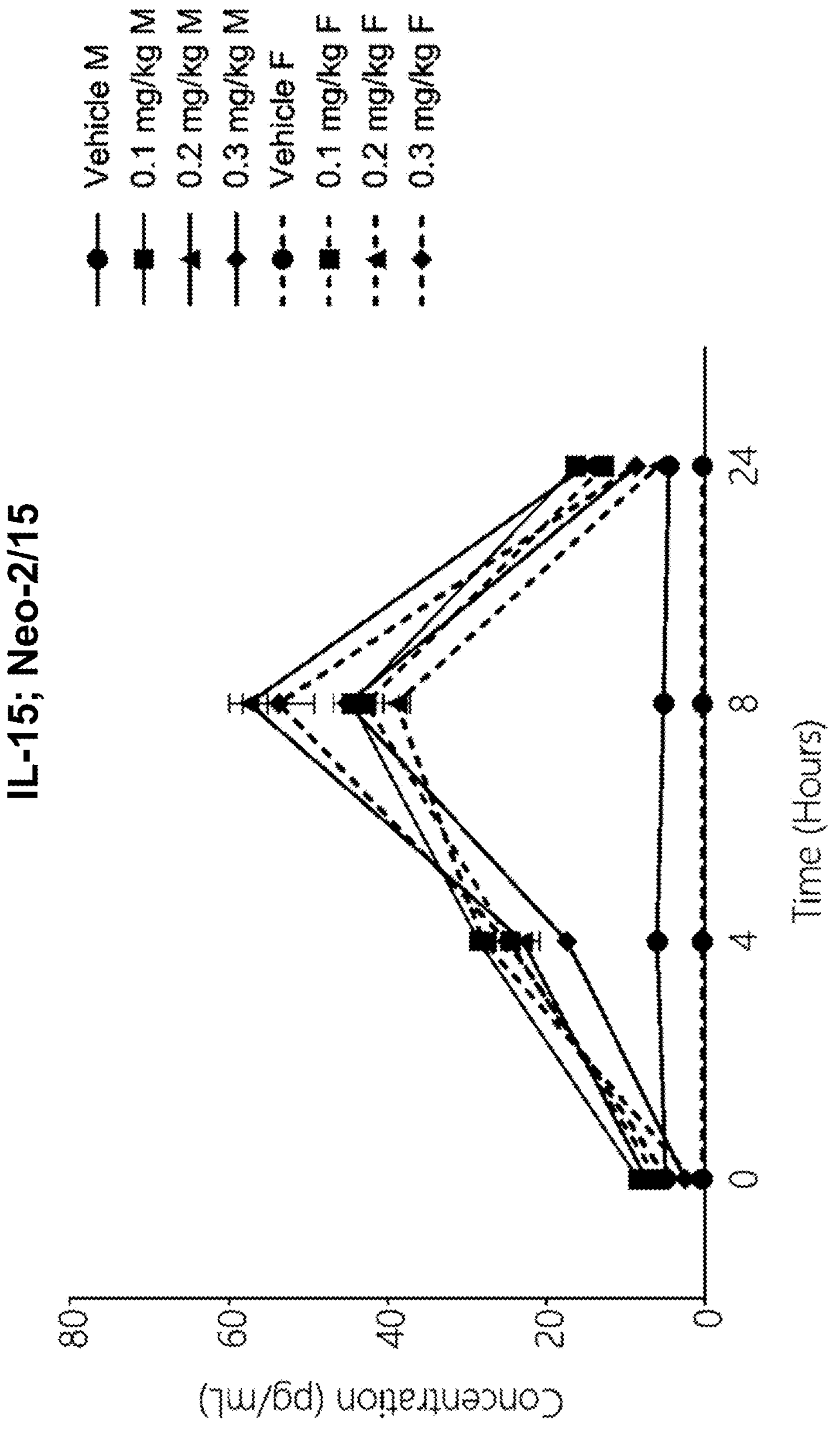
Figure 21D:
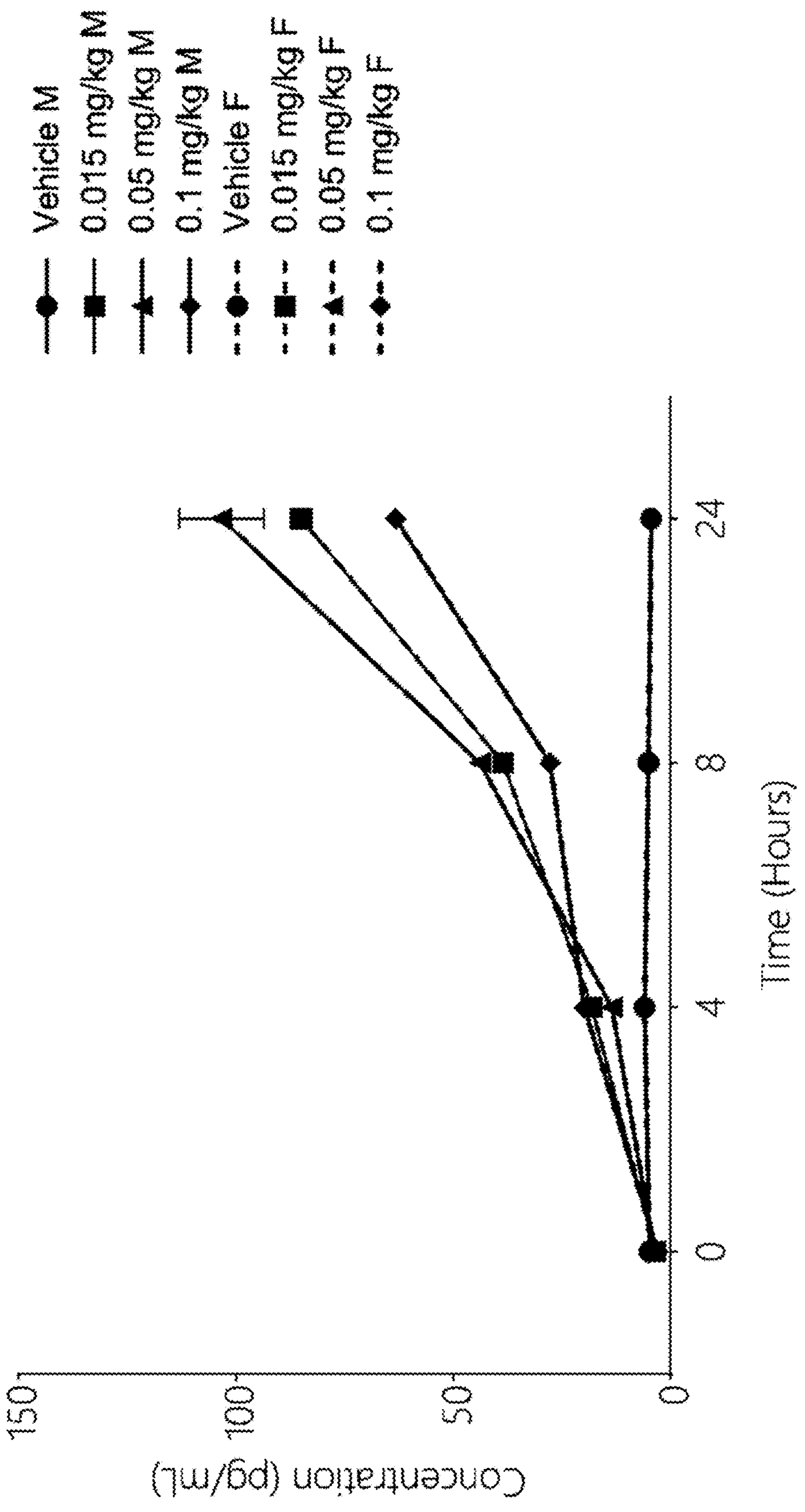

FIG. 20A-20C. Expression, purification, and thermal denaturation characterization of neoleukin-4. FIG. 20A) SDS Tris-Tricine gel electrophoresis showing expression and purification over affinity column. FIG. 20B) Circular dichroism at 222 nm during thermal melting from 25° C. to 95° C., showing robust temperature stability. FIG. 20C) Circular dichroism wavelength scans at 25° C., 95° C. and then again 25° C., showing that neoleukin-4 does not fully melt at 95° C. and refolds fully after cooling back to 25° C.

FIG. 21A-21D. Cytokine levels in non-human primates response to Neo-2/15 or Neo-2/15-PEG. Two non-human primates (NHP) per group, one male and one female per group, were assigned to treatment with either vehicle, Neo-2/15 or Neo-2/15-PEG (comprising Neo-2/15 with a single cysteine mutation of E62C conjugated to PEG40K). Animals were administered either 0 (vehicle), 0.1, 0.2 or 0.3 mg/kg of Neo-2/15, or 0.05, 0.10 or 0.15 mg/kg of Neo-2/15-PEG, by intravenous bolus. Animals treated with Neo-2/15 PEG were administered by intravenous bolus. Cytokine samples were taken 0, 4, 8 and 24 hours post dose. Cytokine serum samples were prepared and frozen at <−70° C. and shipped for analysis where samples were analyzed through a Luminex multiplex immunoassays system. Several cytokines, including IL-10 (FIG. 21A-21B) and IL-15 (FIG. 21C-21D) demonstrated marked differences in the time course of cytokine production, consistent with a more sustained pharmacodynamic effect for the PEGylated molecule.

Figure 22:
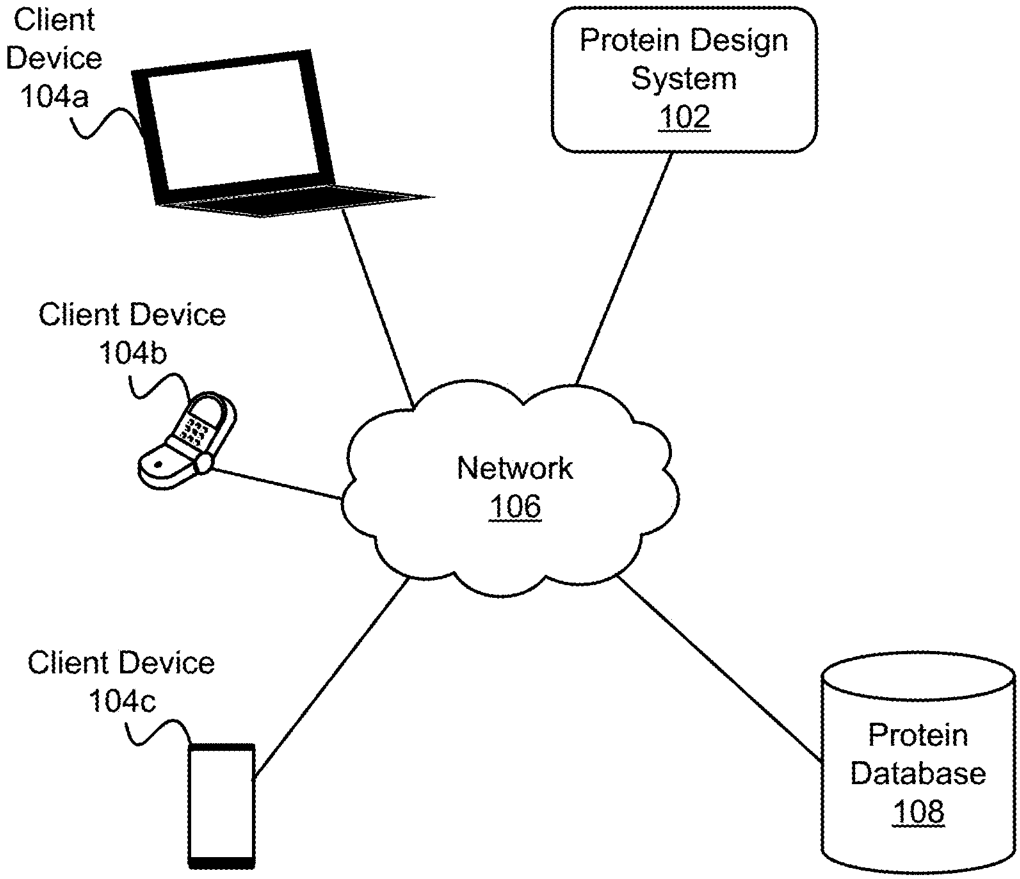

FIG. 22: A block diagram of an example computing network.

Figure 23A:
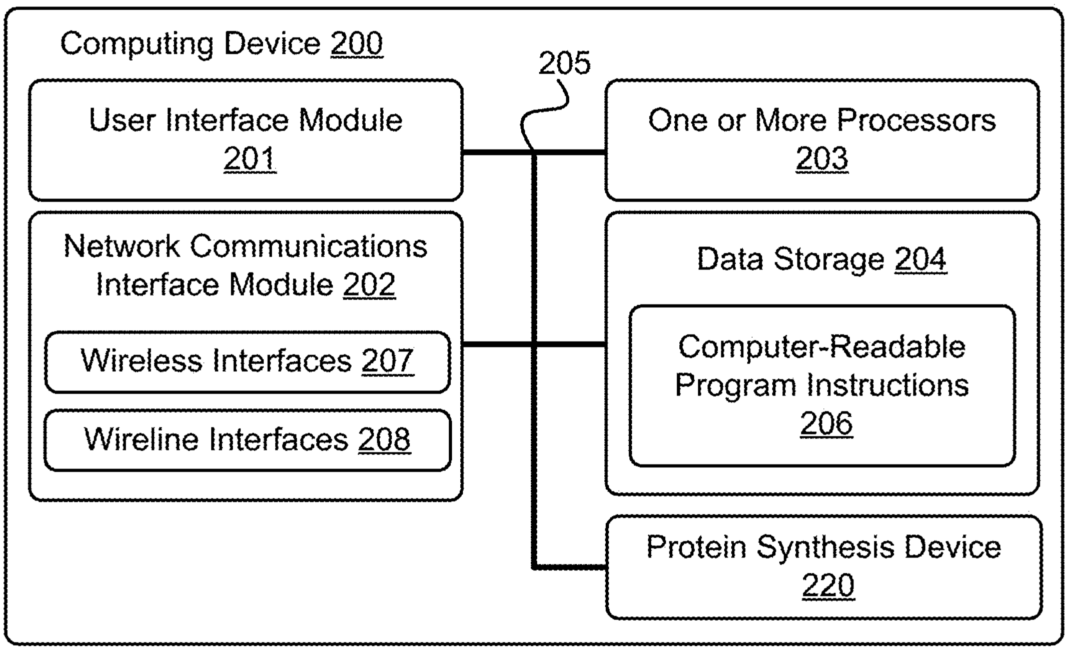

FIG. 23A: A block diagram of an example computing device.

Figure 23B:
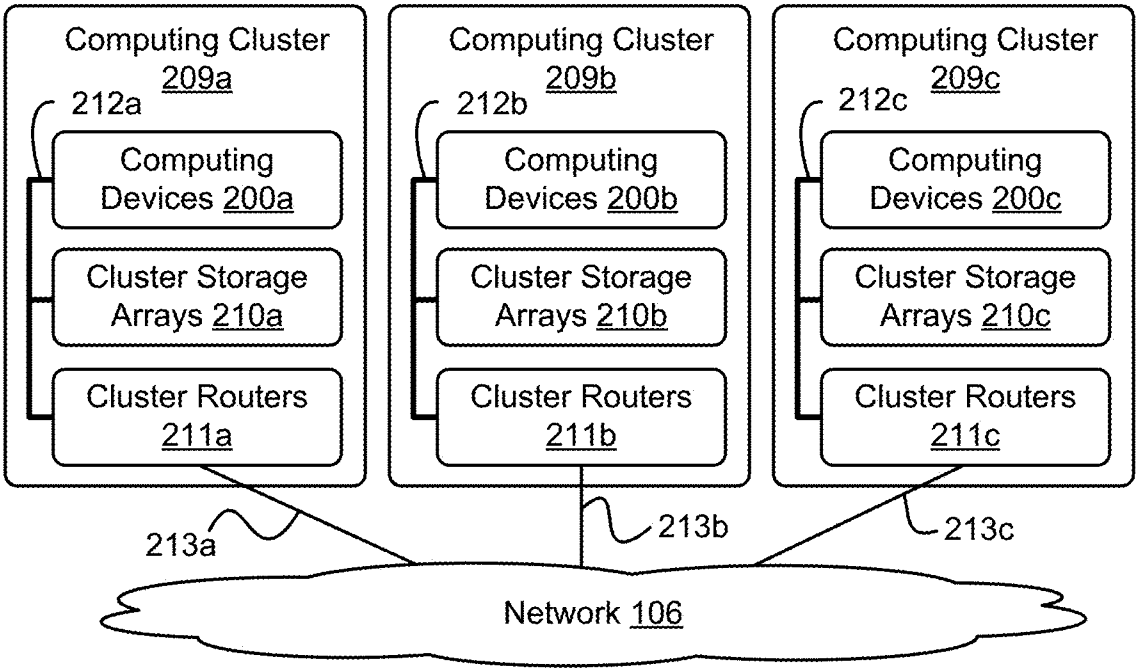

FIG. 23B: A block diagram of an example network of computing devices arranged as a cloud-based server system.

FIG. 24: A flowchart of a method.

DETAILED DESCRIPTION

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural or singular number, respectively. Additionally, the words "herein," "above" and "below" and words of similar import, when used in this application, shall refer to this application as a whole and not to any particular portions of this application.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

All embodiments of any aspect of the invention can be used in combination, unless the context clearly dictates otherwise.

In one aspect, the invention provides non-naturally occurring polypeptides comprising domains X1, X2, X3, and X4, wherein:

(a) X1 is a peptide comprising the amino acid sequence at least 25% identical to EHALYDAL (SEQ ID NO:1);

(b) X2 is a helical-peptide is a of at least 8 amino acids in length;

(c) X3 is a peptide comprising the amino acid sequence at least 25% identical to YAFNFELI (SEQ ID NO:2);

(d) X4 is a peptide comprising the amino acid sequence at least 25% identical to ITILQSWIF (SEQ ID NO:3);

wherein X1, X2, X3, and X4 may be in any order in the polypeptide;

wherein amino acid linkers may be present between any of the domains; and wherein the polypeptide binds to IL-2 receptor $\beta\gamma_c$ heterodimer (IL-2R$\beta\gamma_c$) IL-4 receptor $\alpha\gamma_c$ heterodimer (IL-4R$\alpha\gamma_c$), or IL-13 receptor α subunit (IL-13Rα). In various γ embodiments, the polypeptides bind IL-2R$\beta\gamma_c$ or IL-4R$\alpha\gamma_c$ with a binding affinity of 200 nM or less, 100 nM or less, 50 nM or less or 25 nM or less.

In one aspect, the invention provides non-naturally occurring polypeptides comprising domains X1, X2, X3, and X4, wherein:

(a) X1 is a peptide comprising the amino acid sequence at least 85% identical to EHALYDAL (SEQ ID NO:1);

(b) X2 is a helical-peptide of at least 8 amino acids in length;

(c) X3 is a peptide comprising the amino acid sequence at least 85% identical to YAFNFELI (SEQ ID NO:2);

(d) X4 is a peptide comprising the amino acid sequence at least 85% identical to ITILQSWIF (SEQ ID NO:3);

wherein X1, X2, X3, and X4 may be in any order in the polypeptide;

wherein amino acid linkers may be present between any of the domains; and wherein the polypeptide binds to IL-2 receptor $\beta\gamma_c$ heterodimer (IL-2R$\beta\gamma_c$). In various embodiments, the polypeptides bind IL-2R$\beta\gamma_c$ with a binding affinity of 200 nM or less, 100 nM or less, 50 nM or less or 25 nM or less.

In one aspect, the invention provides non-naturally occurring polypeptides comprising domains X1, X2, X3, and X4, wherein:

(a) X1 is a peptide comprising the amino acid sequence EHALYDAL (SEQ ID NO:1);

(b) X2 is a helical-peptide of at least 8 amino acids in length;

(c) X3 is a peptide comprising the amino acid sequence YAFNFELI (SEQ ID NO:2);

(d) X4 is a peptide comprising the amino acid sequence ITILQSWIF (SEQ ID NO:3);

wherein X1, X2, X3, and X4 may be in any order in the polypeptide;

wherein amino acid linkers may be present between any of the domains; and wherein the polypeptide binds to IL-2 receptor $\beta\gamma_c$ heterodimer (IL-2R$\beta\gamma_c$). In γ various embodiments, the polypeptides bind IL-2R$\beta\gamma_c$ with a binding affinity of 200 nM or less, 100 nM or less, 50 nM or less or 25 nM or less.

As shown in the examples that follow, the polypeptides of the disclosure are (a) mimetics of IL-2 and interleukin-15 (IL-15) that bind to the IL-2 receptor $\beta\gamma_c$ heterodimer (IL-2R$\beta\gamma_c$), but have no binding site for IL-2Rα or IL-15Rα, or (b) mimetics of IL-4 that bind to the IL-4 receptor $\alpha\gamma_c$ heterodimer (IL-4R$\alpha\gamma_c$) or IL-13 receptor α subunit (IL-13Rα) (natural IL-4 and the IL-4 mimetics described herein cross-react with IL-13 receptor, forming an IL-4Rα/IL13Rα heterodimer). The designs are hyper-stable, bind to human and mouse IL-2R$\beta\gamma_c$ or IL-4R$\alpha\gamma_c$ with higher affinity than the natural cytokines, and elicit downstream cell signaling independent of IL-2Rα and IL-15Rα, or independent of IL-13Rα. The polypeptides can be used, for example, to treat cancer.

The term protein mimetic as used herein refers to a protein that imitates certain aspects of the function of another protein. The two proteins typically have different amino acid sequence and/or different structures. Provided herein, among other things, are de novo mimetics of IL-2 and IL-15.

The aspects of the function of IL-2 and IL-15 that these mimetics imitate is the induction of heterodimerization of IL-2Rβ γc, leading to phosphorylation of STAT5. Because IL-2 and IL-15 both signal through heterodimerization of IL-2Rβ γc, these mimetics imitate this biological function of both IL-2 and IL-15. These mimetics may be referred to herein as mimetics of IL-2, of IL-15, or of both IL-2 and IL-15.

Also provided are de novo mimetics of IL-4. These mimetics are capable of imitating certain functions of IL-4. The function of IL-4 that these mimetics imitate is the induction of heterodimerization of IL-4Rα $\gamma_c$ (and/or heterodimerization of IL-4Rα/IL-13Rα).

Native hIL-2 comprises four helices connected by long irregular loops. The N-terminal helix (H1) interacts with both the beta and gamma subunits, the third helix (H3) interacts with the beta subunit, and the C-terminal helix (H4) with the gamma subunit; the alpha subunit interacting surface is formed by the irregular second helix (H2) and two long loops, one connecting H1 to H2 and the other connecting H3 and H4. Idealized proteins were designed and produced in which H1, H3 and H4 are replaced by idealized structural domains, including but not limited to helices and beta strands (referred to as domains X1, X3 and X4, respectively) displaying an IL-2Rβ $\gamma_c$ or IL-4Rα $\gamma_c$ interface inspired by H1, H3 and H4, and in which H2 is replaced with an idealized helix (referred to as domain X2) that offers better packing. As shown in the examples, extensive mutational studies have been carried out, demonstrating that the amino acid sequence of each peptide domain each can be extensively modified without loss of binding to the IL-2 or IL-4 receptor, and that the domains can be placed in any order while retaining binding to the IL-2 or IL-4 receptor. The polypeptides may comprise L amino acids and glycine, D-amino acids and glycine, or combinations thereof.

Thus, X1, X2, X3, and X4 may be in any order in the polypeptide; in non-limiting embodiments, the ordering may be X1-X2-X3-X4; X1-X3-X2-X4; X1-X4-X2-X3; X3-X2-X1-X4; X4-X3-X2-X1; X2-X3-X4-X1; X2-X1-X4-X3; etc.

The domains may be separated by amino acid linkers of any length of amino acid composition. There is no requirement for linkers; in one embodiment there are no linkers present between any of the domains. In other embodiments, an amino acid linker may be present between 1, 2, or all 3 junctions between domains X1, X2, X3, and X4. The linker may be of any length as deemed appropriate for an intended use.

In various embodiments, X1 is a peptide comprising the amino acid sequence at least 25%, 27%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% identical to SEQ ID NO:1. In other embodiments, X3 is a peptide comprising the amino acid sequence at least 25%, 27%, 30%, 35%, 40%, 45%, 50%, 55%, 60%, 65%, 70%, 75%, 80%, 85%, 90%, 91%, 92%, 93%, 94%, 95% m 96%, 97%, 98%, 99%, or 100% identical to SEQ ID NO:2. In further embodiments, X4 is a peptide comprising the amino acid sequence at least 25%, 27%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% identical to SEQ ID NO:3.

In one embodiment, the polypeptides are IL-2/15 mimetics and (i) X1 includes one or both of the following: H at residue 2 and Y at residue 5; and/or (ii) X3 includes 1, 2, 3, 4, or all 5 of the following: Y at residue 1, F at residue 3, N at residue 4, L at residue 7, and I at residue 8. In a further embodiment, (iii) X4 includes I at residue 8.

In another embodiment, the polypeptides are IL-4 mimetics, and (i) X1 includes E at residue 2 and K at residue 5; and (ii) X3 includes F at residue 1, K at residue 3, R at residue 4, R at residue 7, and N at residue 8. In a further embodiment, (iii) X4 includes F at residue 8.

In all of these embodiments, X1, X3, and X4 may be any suitable length, meaning each domain may contain any suitable number of additional amino acids other than the peptides of SEQ ID NOS:1, 2, and 3, respectively. In one embodiment, X1 is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical along its length to the peptide PKKKIQLHAEHALYDALMILNI (SEQ ID NO: 4); X3 is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical along its length the peptide LEDYAFNFELILEEIARLFESG (SEQ ID NO:5); and X4 is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical along its length to the peptide EDEQEEMANAIITILQSWIFS (SEQ ID NO:6).

In one embodiment, X1 is a peptide comprising the amino acid sequence at least 80% identical along its length to the peptide PKKKIQLHAEHALYDALMILNI (SEQ ID NO: 4); X3 is a peptide comprising the amino acid sequence at least 80% identical along its length the peptide LEDYAFNFELILEEIARLFESG (SEQ ID NO:5); and X4 is a peptide comprising the amino acid sequence at least 80% identical along its length to the peptide EDEQEEMANAIITILQSWIFS (SEQ ID NO:6).

In one embodiment, X1 is a peptide comprising the amino acid sequence at least 85% identical along its length to the peptide PKKKIQALHAEHALYDALMILNI (SEQ 4); X3 is a peptide comprising the amino acid sequence at least 85% identical along its length the peptide LEDYAFNFELILEEIARLFESG (SEQ ID NO:5); and X4 is a peptide comprising the amino acid sequence at least 85% identical along its length to the peptide EDEQEEMANAIITILQSWIFS (SEQ ID NO:6).

In one embodiment, X1 is a peptide comprising the acid sequence at least 90% identical along its length to the peptide PKKKIOLHAEHALYDALMILNI (SEQ ID NO: 4); X3 is a peptide comprising the amino acid sequence at least 90% identical along its length the peptide LEDYAFNFELILEEIARLFESG (SEQ ID NO:5); and X4 is a peptide comprising the amino acid sequence at least 90% identical along its length to the peptide EDEQEEMANAIITILQSWIFS (SEQ ID NO:6).

In one embodiment, X1 is a peptide comprising the amino acid sequence at least 95% identical along its length to the peptide PKKKIQLHAEHALYDALMILNI (SEQ ID NO: 4); X3 is a peptide comprising the amino acid sequence at least 95% identical along its length the peptide LEDYAFNFELILEEIARLFESG (SEQ ID NO:5); and X4 is a peptide comprising the amino acid sequence at least 95% identical along its length to the peptide EDEQEEMANAIITILQSWIFS(SEQ ID NO:6).

In one embodiment, X1 is a peptide comprising the amino acid sequence 100% identical along its length to the peptide PKKKIQLHAEHALYDALMILNI (SEQ ID NO: 4); X3 is a peptide comprising the amino acid sequence 100% identical along its length to the peptide LEDYAFN FE LI LEE I ARLFESG (SEQ ID NO:5); and X4 is a peptide comprising the amino acid sequence 100% identical along its length to the peptide EDEQEEMANAI I TIL Q S W IFS(SEQ ID NO:6).

In one embodiment, the polypeptides are IL-2/15 mimetics and (i) X1 includes 1, 2, 3, 4, or all 5 of the following: L at residue 7, H at residue 8, H at residue 11, Y at residue 14; M at residue 18; and/or (ii) X3 includes 1, 2, 3, 4, 5, 6, 7, or all 8 of the following: D at residue 3, Y at residue 4, F at residue 6, N at residue 7, L at residue 10, I at residue 11, Eat residue 13, or E at residue 14. In a further embodiment, (iii) X4 includes I at residue 19.

In one embodiment of IL-2 mimetics, amino acid substitutions relative to the reference peptide domains (i.e.: SEQ ID NOS: 1, 2, 3, 4, 5, or 6) do not occur at AA residues marked in bold font.

In another embodiment, the polypeptides are IL-4/IL-13 mimetics, and

X1 is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical along its length to the peptide PKKKIQIMA EEALKDALSILNI (SEQ ID NO: 8); X3 is a peptide comprising the amino acid sequence at least 37%, 40%, 45%, 50%, 55%, 60%, 65%, 70%, 75%, 80%, 85%, 90%, 95%, 98%, or 100% identical along its length the peptide LERFAKRFERNLWGIARLFESG (SEQ ID NO: 9); and X4 is a peptide comprising the amino acid sequence at least 25%, 27%, 30%, 35%, 40%, 45%, 50%, 55%, 60%, 65%, 70%, 75%, 80%, 85%, 90%, 95%, 98%, or 100% identical along its length to the peptide EDEQEEMANA IITILQSWFFS (SEQ ID NO: 10).

wherein (i) X1 includes I at residue 7, T or M at residue 8, E at residue 11, K at residue 14 and S at residue 18; and (ii) X3 includes R at residue 3, F at residue 4, K at residue 6, R at residue 7, R at residue 10, N at residue 11, W at residue 13, and G at residue 14.

In a further embodiment, (iii) X4 includes F at residue 19.

In one embodiment, amino acid substitutions relative to the reference peptide domains are conservative amino acid substitutions. As used herein, "conservative amino acid substitution" means a given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are known. Polypeptides comprising conservative amino acid substitutions can be tested in any one of the assays described herein to confirm that a desired activity, e.g. antigen-binding activity and specificity of a native or reference polypeptide is retained. Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into H is; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In one embodiment, amino acid residues in X1 relative to SEQ ID NO:4 are selected from the group consisting of:

| | | | | | | | | | | |
|---|---|---|---|---|---|---|---|---|---|---|
| Position 01: | A | F | I | L | M | P | Q | R | S | W |
| Position 02: | A | D | E | G | V | K | | | | |
| Position 03: | D | E | F | W | K | | | | | |
| Position 04: | D | E | K | N | P | R | W | | | |
| Position 05: | D | E | H | I | K | L | M | S | | |
| Position 06: | A | D | E | G | L | P | S | W | Q | |
| Position 07: | D | E | L | Q | Y | I | | | | |
| Position 08: | A | F | H | W | Y | M | T | | | |
| Position 09: | C | F | P | A | | | | | | |
| Position 10: | C | D | E | F | K | P | | | | |
| Position 11: | D | F | H | E | | | | | | |
| Position 12: | A | D | E | P | S | T | V | | | |
| Position 13: | H | I | L | M | P | R | V | W | | |
| Position 14: | F | R | W | Y | K | | | | | |
| Position 15: | D | E | N | Y | | | | | | |
| Position 16: | A | C | L | M | S | | | | | |
| Position 17: | F | I | L | M | P | R | | | | |
| Position 18: | G | M | Q | Y | S | | | | | |
| Position 19: | I | L | M | P | Q | V | | | | |
| Position 20: | A | K | L | M | Q | R | S | | | |
| Position 21: | G | K | N | P | R | S | W | | | |
| Position 22: | D | E | I | K | M | N | W | Y | | |

In one embodiment the polypeptides are IL-4 mimetics, and position 7 is I, position 8 is M or T, position 11 is E, position 14 is K, and position 18 is S.

In another embodiment the polypeptides are IL-2 mimetics, and 1, 2, 3, 4, or 5 of the following are not true: position 7 is I, position 8 is M or T, position 11 is E, position 14 is K, and position 18 is S.

In another embodiment, amino acid residues in X3 relative to SEQ ID NO:5 are selected from the group consisting of:

| | | | | | | | | | | | |
|---|---|---|---|---|---|---|---|---|---|---|---|
| Position 01: | A | L | | | | | | | | | |
| Position 02: | D | E | G | K | M | T | | | | | |
| Position 03: | D | E | N | Y | R | | | | | | |
| Position 04: | C | D | G | T | Y | F | | | | | |
| Position 05: | A | F | H | S | V | W | Y | | | | |
| Position 06: | A | F | I | M | T | V | Y | K | | | |
| Position 07: | D | K | N | S | T | R | | | | | |
| Position 08: | A | C | G | L | M | S | V | F | | | |
| Position 09: | C | H | K | L | R | S | T | V | E | | |
| Position 10: | F | I | L | M | Y | R | | | | | |
| Position 11: | I | L | N | T | Y | | | | | | |
| Position 12: | F | K | L | M | S | V | | | | | |
| Position 13: | A | D | F | G | I | N | P | Q | S | T | E |
| W | | | | | | | | | | | |
| Position 14: | A | E | F | G | H | S | V | | | | |
| Position 15: | C | I | L | M | V | W | | | | | |
| Position 16: | A | D | G | S | T | V | | | | | |
| Position 17: | H | K | L | N | R | | | | | | |
| Position 18: | C | D | G | I | L | Q | R | T | W | | |
| Position 19: | D | F | M | N | W | | | | | | |
| Position 20: | A | C | E | F | G | M | S | Y | | | |
| Position 21: | D | E | G | H | L | M | R | S | T | V | W |
| Position 22: | A | D | G | K | N | S | Y | | | | |

In another embodiment, the polypeptides are IL-4/IL-13 mimetics and position 3 is R, position 4 is F, position 6 is K, position 7 is R, position 10 is R, position 11 is N, position 13 is W, and position 14 is G.

In another embodiment, the polypeptides are IL-2 mimetics and 1, 2, 3, 4, 5, 6, 7, or all 8 of the following are not true: position 3 is R, position 4 is F, position 6 is K, position 7 is R, position 10 is R, position 11 is N, position 13 is W, and position 14 is G.

In any of such embodiments, the polypeptide further allows for a cysteine at position 17 relative to SEQ ID NO:5 in addition to the amino acid residues of H, K, L, N and R. Accordingly, amino acid residues in X3 relative to SEQ ID NO:5 can be selected from the group consisting of:

| | | | | | | | | | | | | |
|---|---|---|---|---|---|---|---|---|---|---|---|---|
| Position 01: | A | L | | | | | | | | | | |
| Position 02: | D | E | G | K | M | T | | | | | | |
| Position 03: | D | E | N | Y | R | | | | | | | |
| Position 04: | C | D | G | T | Y | F | | | | | | |
| Position 05: | A | F | H | S | V | W | Y | | | | | |
| Position 06: | A | F | I | M | T | V | Y | K | | | | |
| Position 07: | D | K | N | S | T | R | | | | | | |
| Position 08: | A | C | G | L | M | S | V | F | | | | |
| Position 09: | C | H | K | L | R | S | T | V | E | | | |
| Position 10: | F | I | L | M | Y | R | | | | | | |
| Position 11: | I | L | N | T | Y | | | | | | | |
| Position 12: | F | K | L | M | S | V | | | | | | |
| Position 13: | A | D | F | G | I | N | P | Q | S | T | E | W |
| Position 14: | A | E | F | G | H | S | V | | | | | |
| Position 15: | C | I | L | M | V | W | | | | | | |
| Position 16: | A | D | G | S | T | V | | | | | | |
| Position 17: | H | K | L | N | R | C | | | | | | |
| Position 18: | C | D | G | I | L | Q | R | T | W | | | |
| Position 19: | D | F | M | N | W | | | | | | | |
| Position 20: | A | C | E | F | G | M | S | Y | | | | |
| Position 21: | D | E | G | H | L | M | R | S | T | V | W | |
| Position 22: | A | D | G | K | N | S | Y | | | | | |

In another embodiment, amino acid residues in X4 relative to SEQ ID NO:6 are selected from the group consisting of:

| | | | | | | | | | | |
|---|---|---|---|---|---|---|---|---|---|---|
| Position 01: | D | E | G | K | V | | | | | |
| Position 02: | D | I | M | S | | | | | | |
| Position 03: | E | G | H | K | | | | | | |
| Position 04: | E | G | I | K | Q | R | S | | | |
| Position 05: | A | D | E | G | H | S | V | | | |
| Position 06: | C | D | E | G | I | M | Q | R | T | V |
| Position 07: | C | E | L | M | P | R | T | | | |
| Position 08: | A | F | L | M | W | | | | | |
| Position 09: | A | G | L | N | Q | R | T | | | |
| Position 10: | A | C | D | E | F | H | I | W | | |
| Position 11: | I | M | N | S | V | W | | | | |
| Position 12: | I | K | L | S | V | | | | | |
| Position 13: | C | L | M | R | S | T | | | | |
| Position 14: | I | L | P | T | Y | | | | | |
| Position 15: | F | G | I | L | M | N | V | | | |
| Position 16: | H | K | Q | R | | | | | | |
| Position 17: | C | F | K | S | W | Y | | | | |
| Position 18: | K | Q | T | W | | | | | | |
| Position 19: | C | G | N | I | | | | | | |
| Position 20: | C | F | G | L | Y | | | | | |
| Position 21: | A | F | G | H | S | Y | | | | |

In another embodiment, the polypeptides are IL-4/IL-13 mimetics and position 19 is I. In another embodiment, the polypeptides are IL-2 mimetics and position 19 is not I.

In any of such embodiments, the polypeptide further allows for a cysteine at position 3 relative to SEQ ID NO:6 in addition to the amino acid residues of E, G, H and K.

Accordingly, amino acid residues in X4 relative to SEQ ID NO:6 can be selected from the group consisting of:

| | | | | | | | | | | |
|---|---|---|---|---|---|---|---|---|---|---|
| Position 01: | D | E | G | K | V | | | | | |
| Position 02: | D | I | M | S | | | | | | |
| Position 03: | E | G | H | K | C | | | | | |
| Position 04: | E | G | I | K | Q | R | S | | | |
| Position 05: | A | D | E | G | H | S | V | | | |
| Position 06: | C | D | E | G | I | M | Q | R | T | V |
| Position 07: | C | E | L | M | P | R | T | | | |
| Position 08: | A | F | L | M | W | | | | | |
| Position 09: | A | G | L | N | Q | R | T | | | |
| Position 10: | A | C | D | E | F | H | I | W | | |
| Position 11: | I | M | N | S | V | W | | | | |
| Position 12: | I | K | L | S | V | | | | | |
| Position 13: | C | L | M | R | S | T | | | | |
| Position 14: | I | L | P | T | Y | | | | | |
| Position 15: | F | G | I | L | M | N | V | | | |
| Position 16: | H | K | Q | R | | | | | | |
| Position 17: | C | F | K | S | W | Y | | | | |
| Position 18: | K | Q | T | W | | | | | | |
| Position 19: | C | G | N | I | | | | | | |
| Position 20: | C | F | G | L | Y | | | | | |
| Position 21: | A | F | G | H | S | Y | | | | |

As noted herein, domain X2 is a structural domain, and thus any amino acid sequence that connects the relevant other domains (depending on domain order) and allows them to fold can be used. The length required will depend on the structure of the protein being made and can be 8 amino acids or longer. In one exemplary and non-limiting embodiment, X2 is a peptide comprising the amino acid sequence at least 20%, 27%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% identical along its length to KDEAEKAKRMKEWMKRIKT (SEQ ID NO:7). In a further embodiment, amino acid residues in X2 relative to SEQ ID NO:7 are selected from the group consisting of:

| | | | | | | | | | | |
|---|---|---|---|---|---|---|---|---|---|---|
| Position 01: | A | H | L | M | R | S | V | K | | |
| Position 02: | A | D | E | Q | R | S | T | V | W | Y |
| Position 03: | C | E | G | K | L | N | Q | R | W | |
| Position 04: | A | F | G | N | S | T | V | Y | | |
| Position 05: | A | E | G | I | M | R | V | | | |
| Position 06: | C | E | K | L | N | R | V | | | |
| Position 07: | A | C | E | I | L | S | T | V | W | |
| Position 08: | H | K | L | M | S | T | W | Y | | |
| Position 09: | A | I | L | M | Q | S | R | | | |
| Position 10: | A | I | M | S | W | Y | | | | |
| Position 11: | C | I | K | L | S | V | | | | |
| Position 12: | C | E | K | L | P | Q | R | T | | |
| Position 13: | A | D | H | N | W | | | | | |
| Position 14: | A | C | G | I | L | S | T | V | M | |
| Position 15: | A | E | G | I | K | L | M | R | V | |
| Position 16: | G | H | L | R | S | T | V | | | |
| Position 17: | A | I | L | V | | | | | | |
| Position 18: | A | C | D | E | G | H | I | K | M | S |
| Position 19: | D | E | G | L | N | V | T | | | |

In another embodiment, the polypeptides are IL-4/IL-13 mimetics and position 11 is I. In another embodiment, the polypeptides are IL-2 mimetics and position 11 is not I.

In any of such embodiments, the polypeptide further allows for a cysteine at positions 5 or 16 relative to SEQ ID NO:7.

Alternatively, in any of such embodiments, the polypeptide further allows for a cysteine at positions 1, 2, 5, 9 or 16 relative to SEQ ID NO:7

Accordingly, amino acid residues in X2 relative to SEQ ID NO:7 can be selected from the group consisting of:

| | | | | | | | | | | |
|---|---|---|---|---|---|---|---|---|---|---|
| Position 01: | A | H | L | M | R | S | V | K | C | |
| Position 02: | A | D | E | Q | R | S | T | V | W | Y C |
| Position 03: | C | E | G | K | L | N | Q | R | W | |
| Position 04: | A | F | G | N | S | T | V | Y | | |
| Position 05: | A | E | G | I | M | R | V | C | | |
| Position 06: | C | E | K | L | N | R | V | | | |
| Position 07: | A | C | E | I | L | S | T | V | W | |
| Position 08: | H | K | L | M | S | T | W | Y | | |
| Position 09: | A | I | L | M | Q | S | R | C | | |
| Position 10: | A | I | M | S | W | Y | | | | |
| Position 11: | C | I | K | L | S | V | | | | |
| Position 12: | C | E | K | L | P | Q | R | T | | |
| Position 13: | A | D | H | N | W | | | | | |
| Position 14: | A | C | G | I | L | S | T | V | M | |
| Position 15: | A | E | G | I | K | L | M | R | V | |
| Position 16: | G | H | L | R | S | T | V | C | | |
| Position 17: | A | I | L | V | | | | | | |
| Position 18: | A | C | D | E | G | H | I | K | M | S |
| Position 19: | D | E | G | L | N | V | T | | | |

In another embodiment, the polypeptide comprises a polypeptide at least at least 25%, 27%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% identical along its length to the amino acid sequence selected from the group consisting of the following polypeptides (i.e.: SEQ ID NOS:11-94, 103-184, 190-243, and 245-247). Underlined residues are linkers and are optional and each residue of the linker, when present, may comprise any amino acid. For each variant below, two SEQ ID NOS are provided: a first SEQ ID NO: that includes the linker positions as optional and variable, and a second SEQ ID NO: that lists the sequence as shown below.

G1_neo2_33
H1->H4->H2'->H3
(SEQ ID NO: 11)
STKKWQLQAEHALLDWQMALNKSPEPNENLNRAITAAQSWISTGKIDLDK
AEDIRRNSDQARREAEKRGIDVRDLISNAQVILLEAR (SEQ ID NO: 103)
STKKWQLQAEHALLDWQMALNKSPEPNENLNRAITAAQSWISTGKIDLDK
AEDIRRNSDQARREAEKRGIDVRDLISNAQVILLEAR G1_neo2_34
H1->H4->H2'->H3
(SEQ ID NO: 12)
STKKWQLQAEHALLDWQMALNKSPEPNENLNRAITAAQSCISTGKCDLDK
AEDIRRNSDQARREAEKRGIDVRDLISNAQVILLEAR (SEQ ID NO: 104)
STKKWQLQAEHALLDWQMALNKSPEPNENLNRAITAAQSCISTGKCDLDK
AEDIRRNSDQARREAEKRGIDVRDLISNAQVILLEAR G1_neo2_35
H1->H4->H2'->H3
(SEQ ID NO: 13)
STKKWQLQAEHALLDWQMALNKSPEPNENLNRAITAAQSWISTGKIDCDK
AEDIRRNSDQARREAEKRGIDVRDLISNAQVILLEAC (SEQ ID NO: 105)
STKKWQLQAEHALLDWQMALNKSPEPNENLNRAITAAQSWISTGKIDCDK
AEDIRRNSDQARREAEKRGIDVRDLISNAQVILLEAC -continued G1_neo2_36
H1->H4->H2'->H3
(SEQ ID NO: 14)
STKKLQLQAEHFLLDVQMILNESPEPNEELNRAITDAQSWISTGKIDLDR
AEELARNLEKVRDEALKRGIDVRDLVSNAKVIALELK (SEQ ID NO: 106)
STKKLQLQAEHFLLDVQMILNESPEPNEELNRAITDAQSWISTGKIDLDR
AEELARNLEKVRDEALKRGIDVRDLVSNAKVIALELK G1_neo2_37
H1->H4->H2'->H3
(SEQ ID NO: 15)
STKKLQLQAEHFLLDVQMILNESPEPNEELNRCITDAQSWISTGKIDLDR
AEECARNLEKVRDEALKRGIDVRDLVSNAKVIALELK (SEQ ID NO: 107)
STKKLQLQAEHFLLDVQMILNESPEPNEELNRCITDAQSWISTGKIDLDR
AEECARNLEKVRDEALKRGIDVRDLVSNAKVIALELK G1_neo2_38
H1->H4->H2'->H3
(SEQ ID NO: 16)
STKKLQLQAEHFLLDVQMILNESPEPNEELNRAITDAQSCISTGKCDLDR
AEELARNLEKVRDEALKRGIDVRDLVSNAKVIALELK (SEQ ID NO: 108)
STKKLQLQAEHFLLDVQMILNESPEPNEELNRAITDAQSCISTGKCDLDR
AEELARNLEKVRDEALKRGIDVRDLVSNAKVIALELK G1_neo2_39
H1->H4->H2'->H3
(SEQ ID NO: 17)
STKKLQLQAEHFLLDVQMILNESPEPNEELNRAITDAQSWISTGKIDLDR
AEELCRNLEKVRDEALKRGIDVRDLVSNACVIALELK (SEQ ID NO: 109)
STKKLQLQAEHFLLDVQMILNESPEPNEELNRAITDAQSWISTGKIDLDR
AEELCRNLEKVRDEALKRGIDVRDLVSNACVIALELK G1_neo2_40
H1->H4->H2'->H3
(SEQ ID NO: 18)
STKKLQLQAEHALLDAQMMLNRSPEPNEKLNRIITTMQSWISTGKIDLDG
AKELAKEVEELRQEAEKRGIDVRDLASNLKVILLELA (SEQ ID NO: 110)
STKKLQLQAEHALLDAQMMLNRSPEPNEKLNRIITTMQSWISTGKIDLDG
AKELAKEVEELRQEAEKRGIDVRDLASNLKVILLELA G1_neo2_41
H1->H4->H2'->H3
(SEQ ID NO: 19)
STKKLQLQAEHALLDAQMMLNRSPEPNEKLNRIITTMQSCISTGKCDLDG
AKELAKEVEELRQEAEKRGIDVRDLASNLKVILLELA (SEQ ID NO: 111)
STKKLQLQAEHALLDAQMMLNRSPEPNEKLNRIITTMQSCISTGKCDLDG
AKELAKEVEELRQEAEKRGIDVRDLASNLKVILLELA G1_neo2_42
H1->H4->H2'->H3
(SEQ ID NO: 20)
STKKIQLQLEHALLDVQMALNRSPEPNESLNRMITWLQSWISTGKIDLDN
AQEMAKEAEKIRKEMEKRGIDVRDLISNIIVILLELS -continued (SEQ ID NO: 112)
STKKIQLQLEHALLDVQMALNRSPEPNESLNRMITWLQSWISTGKIDLDN
AQEMAKEAEKIRKEMEKRGIDVRDLISNIIVILLELS G1_neo2_43
H1->H4->H2'->H3
(SEQ ID NO: 21)
STKKIQLQLEHALLDVQMALNRSPEPNESLNRMITWLQSCISTGKCDLDN
AQEMAKEAEKIRKEMEKRGIDVRDLISNIIVILLELS (SEQ ID NO: 113)
STKKIQLQLEHALLDVQMALNRSPEPNESLNRMITWLQSCISTGKCDLDN
AQEMAKEAEKIRKEMEKRGIDVRDLISNIIVILLELS G1_neo2_44
H1->H4->H2'->H3
(SEQ ID NO: 22)
STKKIQLQLEHALLDVQMALNRSPEPNESLNRMITWLQSWISTGKIDLDN
AQEMCKEAEKIRKEMEKRGIDVRDLISNICVILLELS (SEQ ID NO: 114)
STKKIQLQLEHALLDVQMALNRSPEPNESLNRMITWLQSWISTGKIDLDN
AQEMCKEAEKIRKEMEKRGIDVRDLISNICVILLELS G1_neo2_40_1A
H1->H4->H2'->H3
(SEQ ID NO: 23)
STKKTQLLAEHALLDAFMMLNVVPEPNEKLNRIITTMQSWIYTGKIDADG
AKELAKEVEELEQEYEKRGIDVEDDASNLKVILLELA (SEQ ID NO: 115)
STKKTQLLAEHALLDAFMMLNVVPEPNEKLNRIITTMQSWIYTGKIDADG
AKELAKEVEELEQEYEKRGIDVEDDASNLKVILLELA G1_neo2_40_1B
H1->H4->H2'->H3
(SEQ ID NO: 24)
STKKTQLLAEHALLDAHMMLNMLPEPNEKLNRIITTMQSWIHTGKIDGDG
AQELAKEVEELEQEYEKRGIDVEDEASNLKVILLELA (SEQ ID NO: 116)
STKKTQLLAEHALLDAHMMLNMLPEPNEKLNRIITTMQSWIHTGKIDGDG
AQELAKEVEELEQEYEKRGIDVEDEASNLKVILLELA G1_neo2_40_1C
H1->H4->H2'->H3
(SEQ ID NO: 25)
STKKTQLLAEHALLDAFMMLNMVPEPNEKLNRIITTMQSWIFTGKIDGDG
AKELAKEVEELEQEFEKRGIDVEDEASNLKVILLELA (SEQ ID NO: 117)
STKKTQLLAEHALLDAFMMLNMVPEPNEKLNRIITTMQSWIFTGKIDGDG
AKELAKEVEELEQEFEKRGIDVEDEASNLKVILLELA G1_neo2_40_1D
H1->H4->H2'->H3
(SEQ ID NO: 26)
STKKTQLLAEHALLDALMMLNMVPEPNEKLNRIITTMQSWIFTGKIDGDG
AQELAKEVEELEQELEKRGIDVEDYASNLKVILLELA (SEQ ID NO: 118)
STKKTQLLAEHALLDALMMLNMVPEPNEKLNRIITTMQSWIFTGKIDGDG
AQELAKEVEELEQELEKRGIDVEDYASNLKVILLELA -continued G1_neo2_40_1E
H1->H4->H2'->H3
(SEQ ID NO: 27)
STKKTQLLAEHALLDAHMMLNVVPEPNEKLNRIITTMQSWIYTGKIDRDG
AQELAKEVEELEQELEKRGIDVDDDASNLKVILLELA (SEQ ID NO: 119)
STKKTQLLAEHALLDAHMMLNVVPEPNEKLNRIITTMQSWIYTGKIDRDG
AQELAKEVEELEQELEKRGIDVDDDASNLKVILLELA G1_neo2_40_1F
H1->H4->H2'->H3
(SEQ ID NO: 28)
STKKTQLLAEHALLDALMMLNLLPEPNEKLNRIITTMQSWIFTGKIDGDG
AQELAKEVEELEQEHEKRGIDVEDYASNLKVILLELA (SEQ ID NO: 120)
STKKTQLLAEHALLDALMMLNLLPEPNEKLNRIITTMQSWIFTGKIDGDG
AQELAKEVEELEQEHEKRGIDVEDYASNLKVILLELA G1_neo2_40_1G
H1->H4->H2'->H3
(SEQ ID NO: 29)
STKKTQLLAEHALLDAYMMLNMVPEPNEKLNRIITTMQSWILTGKIDSDG
AQELAKEVEELEQELEKRGIDVDDDASNLKVILLELA (SEQ ID NO: 121)
STKKTQLLAEHALLDAYMMLNMVPEPNEKLNRIITTMQSWILTGKIDSDG
AQELAKEVEELEQELEKRGIDVDDDASNLKVILLELA G1_neo2_40_1H
H1->H4->H2'->H3
(SEQ ID NO: 30)
STKKTHLLAEHALLDAYMMLNVMPEPNEKLNRIITTMQSWIFTGKIDGDG
AKELAKEVEELEQEFEKRGIDVDDDASNLKVILLELA (SEQ ID NO: 122)
STKKTHLLAEHALLDAYMMLNVMPEPNEKLNRIITTMQSWIFTGKIDGDG
AKELAKEVEELEQEFEKRGIDVDDDASNLKVILLELA G1_neo2_40_1I
H1->H4->H2'->H3
(SEQ ID NO: 31)
STKKTQLLAEHALLDAYMMLNLVPEPNEKLNRIITTMQSWIFTGKIDADG
AQELAIEVEELEQEYEKRGIDVDDYASNLKVILLELA (SEQ ID NO: 123)
STKKTQLLAEHALLDAYMMLNLVPEPNEKLNRIITTMQSWIFTGKIDADG
AQELAIEVEELEQEYEKRGIDVDDYASNLKVILLELA G1_neo2_40_1J
H1->H4->H2'->H3
(SEQ ID NO: 32)
STKKTQLMAEHALLDAFMMLNVLPEPNEKLNRIITTMQSWIFTGKIDGDD
AQELAKEVEELEQELEKRGIDVDDDASNLKVILLELA (SEQ ID NO: 124)
STKKTQLMAEHALLDAFMMLNVLPEPNEKLNRIITTMQSWIFTGKIDGDD
AQELAKEVEELEQELEKRGIDVDDDASNLKVILLELA G1_neo2_40_1F_H1
H1->H4->H2'->H3
(SEQ ID NO: 33)
STKKTQLLIEHALLDALDMSRNLPEPNEKLSRIITTMQSWIFTGKIDGDG
AQQLAKEVEELEQEHEKRGEDVEDEASNLKVILLELA -continued (SEQ ID NO: 125)
STKKTQLLIEHALLDALDMSRNLPEPNEKLSRIITTMQSWIFTGKIDGDG

AQQLAKEVEELEQEHEKRGEDVEDEASNLKVILLELA

G1_neo2_40_1F_H2
H1->H4->H2'->H3
(SEQ ID NO: 34)
STKKTQLLLEHALLDALHMRRNLPEPNEKLSRIITTMQSWIFTGKIDGDG

AQELAKEVEELEQEHEKRGRDVEDDASNLKVILLELA (SEQ ID NO: 126)
STKKTQLLLEHALLDALHMRRNLPEPNEKLSRIITTMQSWIFTGKIDGDG

AQELAKEVEELEQEHEKRGRDVEDDASNLKVILLELA

G1_neo2_40_1F_H3
H1->H4->H2'->H3
(SEQ ID NO: 35)
STKKTQLLIEHALLDALNMRKKLPEPNEKLSRIITDMQSWIFTGKIDGDG

AQQLAKEVEELEQEHEKRGGDVEDYASNLKVILLELA (SEQ ID NO: 127)
STKKTQLLIEHALLDALNMRKKLPEPNEKLSRIITDMQSWIFTGKIDGDG

AQQLAKEVEELEQEHEKRGGDVEDYASNLKVILLELA

G1_neo2_40_1F_H4
H1->H4->H2'->H3
(SEQ ID NO: 36)
STKKTQLLLEHALLDALHMSRELPEPNEKLNRIITDMQSWIFTGKIDGDG

AQDLAKEVEELEQEHEKRGGDVEDYASNLKVILLELA (SEQ ID NO: 128)
STKKTQLLLEHALLDALHMSRELPEPNEKLNRIITDMQSWIFTGKIDGDG

AQDLAKEVEELEQEHEKRGGDVEDYASNLKVILLELA

G1_neo2_40_1F_H5
H1->H4->H2'->H3
(SEQ ID NO: 37)
STKKTQLLIEHALLDALHMSRKLPEPNEKLSRIITTMQSWIFTGKIDGDG

AQHLAKEVEELEQEHEKRGGEVEDEASNLKVILLELA (SEQ ID NO: 129)
STKKTQLLIEHALLDALHMSRKLPEPNEKLSRIITTMQSWIFTGKIDGDG

AQHLAKEVEELEQEHEKRGGEVEDEASNLKVILLELA

G1_neo2_40_1F_H6
H1->H4->H2'->H3
(SEQ ID NO: 38)
STKKTQLLIEHALLDALHMKRKLPEPNEKLNRIITNMQSWIFTEKIDGDG

AQDLAKEVEELEQEHEKRGQDVEDYASNLKVILLELA (SEQ ID NO: 130)
STKKTQLLIEHALLDALHMKRKLPEPNEKLNRIITNMQSWIFTEKIDGDG

AQDLAKEVEELEQEHEKRGQDVEDYASNLKVILLELA

G1_neo2_40_1F_M1
H1->H4->H2'->H3
(SEQ ID NO: 39)
STEKTQLAAEHALRDALMLKHLLNEPNEKLARIITTMQSWQFTGKIDGDG

AQELAKEVEELQQEHEVRGIDVEDYASNLKVILLHLA (SEQ ID NO: 131)
STEKTQLAAEHALRDALMLKHLLNEPNEKLARIITTMQSWQFTGKIDGDG

AQELAKEVEELQQEHEVRGIDVEDYASNLKVILLHLA

-continued

G1_neo2_40_1F_M2
H1->H4->H2'->H3
(SEQ ID NO: 40)
STKNTQLAAEDALLDALMLRNLLNEPNEKLARIITTMQSWQFTEKIDGDG

AQELAKEVEELQQEHEERGIDVEDYASNLKVILLQLA (SEQ ID NO: 132)
STKNTQLAAEDALLDALMLRNLLNEPNEKLARIITTMQSWQFTEKIDGDG

AQELAKEVEELQQEHEERGIDVEDYASNLKVILLQLA

G1_neo2_40_1F_M3
H1->H4->H2'->H3
(SEQ ID NO: 41)
STEKTQHAAEDALRDALMLRNLLNEPNEKLARIITTMQSWQFTEKIDGDG

AQELAKEVEELQQEHEVRGIDVEDYASNLKVILLQLA (SEQ ID NO: 133)
STEKTQHAAEDALRDALMLRNLLNEPNEKLARIITTMQSWQFTEKIDGDG

AQELAKEVEELQQEHEVRGIDVEDYASNLKVILLQLA

G2_neo2_40_1F_seq02
H1->H4->H2'->H3
(SEQ ID NO: 42)
TQKKQQLLAEHALLDALMILNMLKTSSEAVNRMITIAQSWIFTGTSNPEE

AKEMIKMAEQAEEEARREGVDTEDYVSNLKVILKEIA (SEQ ID NO: 134)
TQKKQQLLAEHALLDALMILNMLKTSSEAVNRMITIAQSWIFTGTSNPEE

AKEMIKMAEQAEEEARREGVDTEDYVSNLKVILKEIA

G2_neo2_40_1F_seq03
H1->H4->H2'->H3
(SEQ ID NO: 43)
TTKKYQLLVEHALLDALMMLNLSSESNEKMNRIITTMQSWIFTGTFDPDQ

AEELAKLVEELREEFRKRGIDTEDYASNLKVILKELS (SEQ ID NO: 135)
TTKKYQLLVEHALLDALMMLNLSSESNEKMNRIITTMQSWIFTGTFDPDQ

AEELAKLVEELREEFRKRGIDTEDYASNLKVILKELS

G2_neo2_40_1F_seq04
H1->H4->H2'->H3
(SEQ ID NO: 44)
TTKKIQLLVEHALLDALMILNLSSESNEKLNRIITTLQSWIFRGEIDPDR

ARELAKLLEEIREEMRKRGIDTEDYVSNMIVIIRELA (SEQ ID NO: 136)
TTKKIQLLVEHALLDALMILNLSSESNEKLNRIITTLQSWIFRGEIDPDR

ARELAKLLEEIREEMRKRGIDTEDYVSNMIVIIRELA

G2_neo2_40_1F_seq05
H1->H4->H2'->H3
(SEQ ID NO: 45)
TKKKIQLLAEHVLLDLLMMLNLSSESNEKMNRLITIVQSWIFTGTIDPDQ

AEEMAKWVEELREEFRKRGIDTEDYASNVKVILKELS (SEQ ID NO: 137)
TKKKIQLLAEHVLLDLLMMLNLSSESNEKMNRLITIVQSWIFTGTIDPDQ

AEEMAKWVEELREEFRKRGIDTEDYASNVKVILKELS

G2_neo2_40_1F_seq06
H1->H4->H2'->H3
(SEQ ID NO: 46)
TKKKYQLLIEHLLLDALMVLNMSSESNEKLNRIITILQSWIFTGTWDPDL

AEEMEKLMQEIEEELRRRGIDTEDYMSNMRVIIKELS

-continued (SEQ ID NO: 138)
TKKKYQLLIEHLLLDALMVLNMSSESNEKLNRIITILQSWIFTGTWDPDL

AEEMEKLMQEIEEELRRRGIDTEDYMSNMRVIIKELS

G2_neo2_40_1F_seq07
H1->H4->H2'->H3
(SEQ ID NO: 47)
TKKKLQLLVEHLLLDMLMILNMSSESNEKLNRLITELQSWIFRGEIDPDK

AEEMWKIMEEIEKELRERGIDTEDYMSNAKVIIKELS (SEQ ID NO: 139)
TKKKLQLLVEHLLLDMLMILNMSSESNEKLNRLITELQSWIFRGEIDPDK

AEEMWKIMEEIEKELRERGIDTEDYMSNAKVIIKELS

G2_neo2_40_1F_seq08
H1->H4->H2'->H3
(SEQ ID NO: 48)
TSKKQQLLAEHALLDALMILNISSESSEAVNRAITWLQSWIFKGTVNPDQ

AEEMRKLAEQIREEMRKRGIDTEDYVSNLEVIAKELS (SEQ ID NO: 140)
TSKKQQLLAEHALLDALMILNISSESSEAVNRAITWLQSWIFKGTVNPDQ

AEEMRKLAEQIREEMRKRGIDTEDYVSNLEVIAKELS

G2_neo2_40_1F_seq09
H1->H4->H2'->H3
(SEQ ID NO: 49)
TKKKYQLLIEHLLLDLLMVLNMSSESNEKINRLITWLQSWIFTGTYDPDL

AEEMYKILEELREEMRERGIDTEDYMSNMRVIVKELS (SEQ ID NO: 141)
TKKKYQLLIEHLLLDLLMVLNMSSESNEKINRLITWLQSWIFTGTYDPDL

AEEMYKILEELREEMRERGIDTEDYMSNMRVIVKELS

G2_neo2_40_1F_seq10
H1->H4->H2'->H3
(SEQ ID NO: 50)
TKKKWQLLIEHLLLDLLMILNLSSESNEKLNRLITWLQSWIFTGTYDPDL

AEEMKKMMDEIEDELRERGIDTEDYMSNAKVIIKELS (SEQ ID NO: 142)
TKKKWQLLIEHLLLDLLMILNLSSESNEKLNRLITWLQSWIFTGTYDPDL

AEEMKKMMDEIEDELRERGIDTEDYMSNAKVIIKELS

G2_neo2_40_1F_seq11
H1->H4->H2'->H3
(SEQ ID NO: 51)
TKKKIQLLVEHALLDALMILNLSSESNEKLNRIITTMQSWIFTGTIDPDQ

AEELSLVEEIREEMRKRGIDTEDYVSNLKVILDELS (SEQ ID NO: 143)
TKKKIQLLVEHALLDALMILNLSSESNEKLNRIITTMQSWIFTGTIDPDQ

AEELSLVEEIREEMRKRGIDTEDYVSNLKVILDELS

G2_neo2_40_1F_seq12
H1->H4->H2'->H3
(SEQ ID NO: 52)
TEKKLQLLVEHALLDALMILNLWSESNEKLNRIITTMQSWIFTGRIDPDK

AEELAKLVEELREEARERGIDTEDYVSNLKVILKELS (SEQ ID NO: 144)
TEKKLQLLVEHALLDALMILNLWSESNEKLNRIITTMQSWIFTGRIDPDK

AEELAKLVEELREEARERGIDTEDYVSNLKVILKELS

G2_neo2_40_1F_seq13
H1->H4->H2'->H3
(SEQ ID NO: 53)
TKKKYQLLMEHLLLDLLMVLNMSSESNEKLNRLITIIQSWIFTGTWDPDK

AEEMAKMLKEIEDELRERGIDTEDYMSNMIVIMKELS (SEQ ID NO: 145)
TKKKYQLLMEHLLLDLLMVLNMSSESNEKLNRLITIIQSWIFTGTWDPDK

AEEMAKMLKEIEDELRERGIDTEDYMSNMIVIMKELS

G2_neo2_40_1F_seq14
H1->H4->H2'->H3
(SEQ ID NO: 54)
TTKKIQLLVEHALLDALMLLNLSSESNEKMNRIITTMQSWIFEGRIDPDQ

AQEELAKLVEELREEFRKRGIDTEDYVSNLKVILEELS (SEQ ID NO: 146)
TTKKIQLLVEHALLDALMLLNLSSESNEKMNRIITTMQSWIFEGRIDPDQ

AQEELAKLVEELREEFRKRGIDTEDYVSNLKVILEELS

G2_neo2_40_1F_seq15
H1->H4->H2'->H3
(SEQ ID NO: 55)
TKKKIQLLVEHALLDALMMLNLSSESNEKLNRIITTMQSWIFTGTIDPDQ

AEELAKLVRELREEFRKRGIDTEDYASNLEVILRELS (SEQ ID NO: 147)
TKKKIQLLVEHALLDALMMLNLSSESNEKLNRIITTMQSWIFTGTIDPDQ

AEELAKLVRELREEFRKRGIDTEDYASNLEVILRELS

G2_neo2_40_1F_seq16
H1->H4->H2'->H3
(SEQ ID NO: 56)
TKKKIQLLVEHALLDALMILNLSSKSNEKLNRIITTMQSWIFNGTIDPDR

ARELAKLVEEIRDEMEKNGIDTEDYVSNLKVILEELA (SEQ ID NO: 148)
TKKKIQLLVEHALLDALMILNLSSKSNEKLNRIITTMQSWIFNGTIDPDR

ARELAKLVEEIRDEMEKNGIDTEDYVSNLKVILEELA

G2_neo2_40_1F_seq17
H1->H4->H2'->H3
(SEQ ID NO: 57)
TKKKYQLLIEHVLLDLLMLLNLSSESNEKMNRLITILQSWIFTGTYDPDK

AEEMAKLLKELREEFRERGIDTEDYISNAIVILKELS (SEQ ID NO: 149)
TKKKYQLLIEHVLLDLLMLLNLSSESNEKMNRLITILQSWIFTGTYDPDK

AEEMAKLLKELREEFRERGIDTEDYISNAIVILKELS

G2_neo2_40_1F_seq18
H1->H4->H2'->H3
(SEQ ID NO: 58)
TKKKIQLLVEHALLDALMMLNLSSESNEKLNRIITTMQSWIFTGTIDPDR

AEELAKLVEELREEFRKRGIDTEDYASNLKVILKELS (SEQ ID NO: 150)
TKKKIQLLVEHALLDALMMLNLSSESNEKLNRIITTMQSWIFTGTIDPDR

AEELAKLVEELREEFRKRGIDTEDYASNLKVILKELS

G2_neo2_40_1F_seq19
H1->H4->H2'->H3
(SEQ ID NO: 59)
TKKKIQLLVEHALLDALMMLNLSSESNEKLNRIITTMQSWIFNGTIDPDQ

ARELAKLVEELREEFRKRGIDTEDYASNLKVILEELA

-continued (SEQ ID NO: 151)
TKKKIQLLVEHALLDALMMLNLSSESNEKLNRIITTMQSWIFNGTIDPDQ

ARELAKLVEELREEFRKRGIDTEDYASNLKVILEELA

G2_neo2_40_1F_seq20
H1->H4->H2'->H3
(SEQ ID NO: 60)
TKKKLQLLVEHALLDALMLLNLSSESNEKLNRIITTMQSWIFTGTVDPDQ

AEELAKLVEEIREELRKRGIDTEDYVSNLKVILKELS (SEQ ID NO: 152)
TKKKLQLLVEHALLDALMLLNLSSESNEKLNRIITTMQSWIFTGTVDPDQ

AEELAKLVEEIREELRKRGIDTEDYVSNLKVILKELS

G2_neo2_40_1F_seq21
H1->H4->H2'->H3
(SEQ ID NO: 61)
TTKKYQLLVEHALLDALMILNLSSESNEKLNRIITTMQSWIFTGTFDPDQ

AEELAKLVREIREEMRKRGIDTEDYVSNLEVILRELS (SEQ ID NO: 153)
TTKKYQLLVEHALLDALMILNLSSESNEKLNRIITTMQSWIFTGTFDPDQ

AEELAKLVREIREEMRKRGIDTEDYVSNLEVILRELS

G2_neo2_40_1F_seq22
H1->H4->H2'->H3
(SEQ ID NO: 62)
TKKKIQLLVEHALLDALMILNLSSESNEKLNRIITTMQSWIFTGTIDPDR

AEELAKLVREIREEMRKRGIDTEDYVSNLEVILRELS (SEQ ID NO: 154)
TKKKIQLLVEHALLDALMILNLSSESNEKLNRIITTMQSWIFTGTIDPDR

AEELAKLVREIREEMRKRGIDTEDYVSNLEVILRELS

G2_neo2_40_1F_seq23
H1->H4->H2'->H3
(SEQ ID NO: 63)
TKKKYQLLIEHLLLDLLMILNLSSESNEKLNRLITWLQSWIFRGEWDPDK

AEEWAKILKEIREELRERGIDTEDYMSNAIVIMKELS (SEQ ID NO: 155)
TKKKYQLLIEHLLLDLLMILNLSSESNEKLNRLITWLQSWIFRGEWDPDK

AEEWAKILKEIREELRERGIDTEDYMSNAIVIMKELS

G2_neo2_40_1F_seq24
H1->H4->H2'->H3
(SEQ ID NO: 64)
TDKKLQLLVEHLLLDLLMMLNLSSKSNEKMNRLITIAQSWIFTGKVDPDL

AREMIKLLEETEDENRKNGIDTEDYVSNARVIAKELE (SEQ ID NO: 156)
TDKKLQLLVEHLLLDLLMMLNLSSKSNEKMNRLITIAQSWIFTGKVDPDL

AREMIKLLEETEDENRKNGIDTEDYVSNARVIAKELE

G2_neo2_40_1F_seq25
H1->H4->H2'->H3
(SEQ ID NO: 65)
TKKKIQLLVEHALLDALMLLNLSSESNEKMNRIITTMQSWIFTGTIDPDQ

AEELAKLVEELKEEFKKRGIDTEDYVSNLKVILKELS (SEQ ID NO: 157)
TKKKIQLLVEHALLDALMLLNLSSESNEKMNRIITTMQSWIFTGTIDPDQ

AEELAKLVEELKEEFKKRGIDTEDYVSNLKVILKELS

G2_neo2_40_1F_seq26
H1->H4->H2'->H3
(SEQ ID NO: 66)
TKKKYQLLIEHALLDALMILNLWSESNEKLNRIITTMQSWIFTGTYDPDK

AEELEKLAKEIEDEARERGIDTEDYMSNLRVILKELS (SEQ ID NO: 158)
TKKKYQLLIEHALLDALMILNLWSESNEKLNRIITTMQSWIFTGTYDPDK

AEELEKLAKEIEDEARERGIDTEDYMSNLRVILKELS

G2_neo2_40_1F_seq27
H1->H4->H2'->H3
(SEQ ID NO: 67)
TKKKAQLLAEHALLDALMLLNLSSESNERLNRIITWLQSIIFTGTYDPDM

VKEAVKLADEIEDEMRKRGIDTEDYVSNLRVILQELA (SEQ ID NO: 159)
TKKKAQLLAEHALLDALMLLNLSSESNERLNRIITWLQSIIFTGTYDPDM

VKEAVKLADEIEDEMRKRGIDTEDYVSNLRVILQELA

G2_neo2_40_1F_seq28
H1->H4->H2'->H3
(SEQ ID NO: 68)
TQKKNQLLAEHLLLDALMVLNQSSESSEVANRIITWAQSWIFEGRVDPNK

AEEAKKLAKKLEEEMRKRGIDMEDYISNMKVIAEEMS (SEQ ID NO: 160)
TQKKNQLLAEHLLLDALMVLNQSSESSEVANRIITWAQSWIFEGRVDPNK

AEEAKKLAKKLEEEMRKRGIDMEDYISNMKVIAEEMS

G2_neo2_40_1F_seq29
H3->H2'->H4->H1
(SEQ ID NO: 69)
EDYYSNLKVILEELAREMERNGLSDKAEEWRQWKKIVERIRQIRSNNSDL

NEAKELLNRLITYIQSQIFEISERIRETDQEKKEESWKKWQLLLEHALLD

VLMLLND (SEQ ID NO: 161)
EDYYSNLKVILEELAREMERNGLSDKAEEWRQWKKIVERIRQIRSNNSDL

NEAKELLNRLITYIQSQIFEISERIRETDQEKKEESWKKWQLLLEHALLD

VLMLLND

G2_neo2_40_1F_seq30
H1->H3->H2'->H4
(SEQ ID NO: 70)
PEKKRQLLLEHILLDALMLLNLXXXXXXNTESKFEDYISNAEVIAEELAK

LMESXXLSDEAEKFKKIKQWLREVWRIWXXXXWSTLEDKARELLNRIITT

IQSQIFY (SEQ ID NO: 162)
PEKKRQLLLEHILLDALMLLNLLETNPQNTESKFEDYISNAEVIAEELAK

LMESLGLSDEAEKFKKIKQWLREVWRIWSSTNWSTLEDKARELLNRIITT

IQSQIFY

G2_neo2_40_1F_seq31
H1->H3->H2'->H4
(SEQ ID NO: 71)
PEKKRQLLLEHILLDLLMILNMXXXXXXNTESEMEDYWSNVRVILRELAR

LMEEXXXKELSELMERMRKIVEKIRQIVTXXXXLDTAREWLNRLITWIQS

LIFR

-continued (SEQ ID NO: 163)
PEKKRQLLLEHILLDLLMILNMIETNRENTESEMEDYWSNVRVILRELAR
LMEELNYKELSELMERMRKIVEKIRQIVTNNSSLDTAREWLNRLITWIQS
LIFR G2_neo2_40_1F_seq32
H1->H3->H2'->H4
(SEQ ID NO: 72)
PEKKRQLLAEHALLDALMLLNIIETNSKNTESKMEDYVSNLEVILTEFKK
LAEKLNFSEEAERAERMKRWARKAYQMMTLDLSLDKAKEMLNRIITILQS
IIFN (SEQ ID NO: 164)
PEKKRQLLAEHALLDALMLLNIIETNSKNTESKMEDYVSNLEVILTEFKK
LAEKLNFSEEAERAERMKRWARKAYQMMTLDLSLDKAKEMLNRIITILQS
IIFN G2_neo2_40_1F_seq33
H1->H3->H2'->H4
(SEQ ID NO: 73)
PEKKRQLLAEHLLLDVLMMLNGNASLKDYASNAQVIADEFRELARELGLT
DEAKKAEKIIEALERAREWLLNNKDKEKAKEALNRAITIAQSWIFN (SEQ ID NO: 165)
PEKKRQLLAEHLLLDVLMMLNGNASLKDYASNAQVIADEFRELARELGLT
DEAKKAEKIIEALERAREWLLNNKDKEKAKEALNRAITIAQSWIFN G2_neo2_40_1F_seq34
H1->H3->H2'->H4
(SEQ ID NO: 74)
PEKKRQLLLEHLLLDLLMILNMLRTNPKNIESDWEDYMSNIEVIIEELRK
IMESLGRSEKAKEWKRMKQWVRRILEIVKNNSDLEEAKEWLNRLITIVQS
EIFE (SEQ ID NO: 166)
PEKKRQLLLEHLLLDLLMILNMLRTNPKNIESDWEDYMSNIEVIIEELRK
IMESLGRSEKAKEWKRMKQWVRRILEIVKNNSDLEEAKEWLNRLITIVQS
EIFE G2_neo2_40_1F_seq35
H1->H3->H2'->H4
(SEQ ID NO: 75)
WEKKRQLLLEHLLLDLLMILNMWRTNPQNTESLMEDYMSNAKVIVEELAR
MMRSQGLEDKAREWEEMKKRIEEIRQIIQNNSSKERAKEELNRLITYVQS
EIFR (SEQ ID NO: 167)
WEKKRQLLLEHLLLDLLMILNMWRTNPQNTESLMEDYMSNAKVIVEELAR
MMRSQGLEDKAREWEEMKKRIEEIRQIIQNNSSKERAKEELNRLITYVQS
EIFR G2_neo2_401F_seq36
H1->H3->H2'->H4
(SEQ ID NO: 76)
PKKKIQLLAEHALLDALMILNIVKTNSQNAEEKLEDYASNVEVILEEIAR
LMESGDQKDEAEKAKRMKEWMKRIKTTASEDEQEEMANRIITLLQSWIFS (SEQ ID NO: 168)
PKKKIQLLAEHALLDALMILNIVKTNSQNAEEKLEDYASNVEVILEEIAR
LMESGDQKDEAEKAKRMKEWMKRIKTTASEDEQEEMANRIITLLQSWIFS -continued G2_neo2_40_1F_seq37
H1->H3->H2'->H4
(SEQ ID NO: 77)
PEKKRQLLAEHALLDALMILNXXXXXXQNAEEKLEDYMSNVEVIMEEFAR
MMRXXXXSEEAENAERIKKWVRKASSXXXSEEQREMMNRAITLMQSWIFE (SEQ ID NO: 169)
PEKKRQLLAEHALLDALMILNILQTNPQNAEEKLEDYMSNVEVIMEEFAR
MMRNGDRSEEAENAERIKKWVRKASSTASSEEQREMMNRAITLMQSWIFE G2_neo2_40_1F_seq38
H1->H3->H2'->H4
(SEQ ID NO: 78)
PEKKRQLLAEHLLLDALMVLNMXXXXXXNTEEKLEDYISNMKVIIKEMIE
LMRSLXXXEEAEKWKEALKAVEKIXXXXDSETARELANRIITLAQSAIFY (SEQ ID NO: 170)
PEKKRQLLAEHLLLDALMVLNMLTTNSKNTEEKLEDYISNMKVIIKEMIE
LMRSLGRLEEAEKWKEALKAVEKIGSRMDSETARELANRIITLAQSAIFY G2_neo2_40_1F_seq39
H1->H3->H2'->H4
(SEQ ID NO: 79)
PEKKRQLLAEHALLDALMFLNLXXXXXXQAEEKIEDYASNLRVIAEELAR
LFENLXXXDEAQKAKDIKELAERARSXXSSEKRKEAMNRAITILQSMIFR (SEQ ID NO: 171)
PEKKRQLLAEHALLDALMFLNLVETNPDQAEEKIEDYASNLRVIAEELAR
LFENLGRLDEAQKAKDIKELAERARSRVSSEKRKEAMNRAITILQSMIFR G2_neo2_40_1F_seq40
H1->H3->E2'->H4
(SEQ ID NO: 80)
PEKKRQLLAEHALLDALMILNIIRTNSDNTESKLEDYISNLKVILEEIAR
LMESLGLSDEAEKAKEAMRLADKAGSTASEEEKKEAMNRVITWAQSWIFN (SEQ ID NO 172)
PEKKRQLLAEHALLDALMILNIIRTNSDNTESKLEDYISNLKVILEEIAR
LMESLGLSDEAEKAKEAMRLADKAGSTASEEEKKEAMNRVITWAQSWIFN G2_neo2_40_1F_seq41
H1->H3->H2'->H4
(SEQ ID NO: 81)
PEKKRQLLAEHALLDALMMLNILRTNPDNAEEKLEDYWSNLIVILREIAK
LMESLGLTDEAEKAKEAARWAEEARTTASKDQRRELANRIITLLQSWIFS (SEQ ID NO: 173)
PEKKRQLLAEHALLDALMMLNILRTNPDNAEEKLEDYWSNLIVILREIAK
LMESLGLTDEAEKAKEAARWAEEARTTASKDQRRELANRIITLLQSWIFS G2_neo2_40_1F_seq42
H1->H3->H2'->H4
(SEQ ID NO: 82)
PEKKRQLLAEHLLLDALMILNIIETNEQNAESKLEDYISNAKVILDEFRE
MARDLGLLDEAKKAEKMKRWLEKMRSNASSDERREWANRMITTAQSWIFN (SEQ ID NO: 174)
PEKKRQLLAEHLLLDALMILNIIETNEQNAESKLEDYISNAKVILDEFRE
MARDLGLLDEAKKAEKMKRWLEKMRSNASSDERREWANRMITTAQSWIFN G2_neo2_40_1F_seq27_S3
H1->H4->H2'->H3
(SEQ ID NO: 83)
TNKKAQLHAEFALHDALMLLNLSSESNERLNRIITWLQSIIFYGTYDPDM
VKEAVKDADEIEDEMRKRGIDTEDYVSNLRLILQELA -continued (SEQ ID NO: 245)
TNKKAQLHAEFALHDALMLLNLSSESNERLNRIITWLQSIIFYGTYDPDM

VKEAVKDADEIEDEMRKRGIDTEDYVSNLRLILQELA

G2_neo2_40_1F_seq27_S18
H1->H4->H2'->H3
(SEQ ID NO: 84)
TNKEAQLHAEFALYDALMLLNLSSESNERLNRIITWLQSIIFYETYDPDM

VKEAVKLADEIEDEMRKRKIDTEDYVVNLRLILQELA (SEQ ID NO: 175)
TNKEAQLHAEFALYDALMLLNLSSESNERLNRIITWLQSIIFYETYDPDM

VKEAVKLADEIEDEMRKRKIDTEDYVVNLRLILQELA

G2_neo2_40_1F_seq27_S22
H1->H4->H2'->H3
(SEQ ID NO: 85)
TKKDAELLAEFALYDALMLLNLSSESNERLNEIITWLQSIIFYGTYDPDM

VKEAVKLADEIEDEMRKRGIDTEDYVSNLRLILQELA (SEQ ID NO: 176)
TKKDAELLAEFALYDALMLLNLSSESNERLNEIITWLQSIIFYGTYDPDM

VKEAVKLADEIEDEMRKRGIDTEDYVSNLRLILQELA

G2_neo2_40_1F_seq27_S24
H1->H4->H2'->H3
(SEQ ID NO: 86)
TNKKAQLHAEFALYDALMLLNLSSESNERLNDIITWLQSIIFTGTYDPDM

VKEAVKLADEIEDEMRKRKIDTEDYVVNLRYILQELA (SEQ ID NO: 177)
TNKKAQLHAEFALYDALMLLNLSSESNERLNDIITWLQSIIFTGTYDPDM

VKEAVKLADEIEDEMRKRKIDTEDYVVNLRYILQELA

G2_neo2_40_1F_seq29_S6
H3->H2'->H4->H1
(SEQ ID NO: 87)
EDYYSNLKLILEELAREMERNGLSDKAEEWRQWKKIVERIRQIRSNNSDL

NEAKELLNRLITYIQSQIFEVLHGVGETDQEKKEESWKKWDLLLEHALLD

VLMLLND (SEQ ID NO: 178)
EDYYSNLKLILEELAREMERNGLSDKAEEWRQWKKIVERIRQIRSNNSDL

NEAKELLNRLITYIQSQIFEVLHGVGETDQEKKEESWKKWDLLLEHALLD

VLMLLND

G2_neo2_40_1F_seq29_S7
H3->H2'->H4->H1
(SEQ ID NO: 88)
EDYYSNLKVILEELAREMERNGLSDKAEEWRQWKKIVERIRQIRSNNSDL

NEAKELLNELITYIQSQIFEVIEREGETDQEKKEESWKKWELHLEHALLD

VLMLLND (SEQ ID NO: 179)
EDYYSNLKVILEELAREMERNGLSDKAEEWRQWKKIVERIRQIRSNNSDL

NEAKELLNELITYIQSQIFEVIEREGETDQEKKEESWKKWELHLEHALLD

VLMLLND

-continued

G2_neo2_40_1F_seq29_S8
H3->H2'->H4->H1
(SEQ ID NO: 89)
EDYYSNLKLILEELAREMERNGLSDKAEEWRQWKKIVERIRQIRSNNSDL

NEAKELLNRLITYIQSQIFEVLEGVGETDQEKKEESWKKWELHLEHALLD

VLMLLND (SEQ ID NO: 180)
EDYYSNLKLILEELAREMERNGLSDKAEEWRQWKKIVERIRQIRSNNSDL

NEAKELLNRLITYIQSQIFEVLEGVGETDQEKKEESWKKWELHLEHALLD

VLMLLND

Neoleukin-2/15 (i.e. G2_neo2_40_1F_seq36_S11)
H1->H3->H2'->H4
(SEQ ID NO: 90)
PKKKIQLHAEHALYDALMILNIVKTNSPPAEEKLEDYAFNFELILEEIAR

LFESGDQKDEAEKAKRMKEWMKRIKTTASEDEQEEMANAIITILQSWIFS (SEQ ID NO: 181)
PKKKIQLHAEHALYDALMILNIVKTNSPPAEEKLEDYAFNFELILEEIAR

LFESGDQKDEAEKAKRMKEWMKRIKTTASEDEQEEMANAIITILQSWIFS

G2_neo2_40_1F_seq36_S12
H1->H3->H2'->H4
(SEQ ID NO: 91)
PKKKIQLLAEHALFDLLMILNIVKTNSQNAEEKLEDYAYNAGVILEEIAR

LFESGDQKDEAEKAKRMKEWMKRIKDTASEDEQEEMANEIITILQSWNFS (SEQ ID NO: 182)
PKKKIQLLAEHALFDLLMILNIVKTNSQNAEEKLEDYAYNAGVILEEIAR

LFESGDQKDEAEKAKRMKEWMKRIKDTASEDEQEEMANEIITILQSWNFS

Neoleukin-2/15-H8Y-K33E
H1->H3->H2'->H4
(SEQ ID NO: 94)
PKKKIQLYAEHALYDALMILNIVKTNSPPAEEELEDYAFNFELILEEIAR

LFESGDQKDEAEKAKRMKEWMKRIKTTASEDEQEEMANAIITILQSWIFS (SEQ ID NO: 246)
PKKKIQLYAEHALYDALMILNIVKTNSPPAEEELEDYAFNFELILEEIAR

LFESGDQKDEAEKAKRMKEWMKRIKTTASEDEQEEMANAIITILQSWIFS

Neoleukin-2/15(K32 is considered to be a residue of the optional linker in this depicted sequence)
H1->H3->H2'->H4
(SEQ ID NO: 247)
PKKKIQLHAEHALYDALMILNIVKTNSPPAEEKLEDYAFNFELILEEIAR

LFESGDQKDEAEKAKRMKEWMKRIKTTASEDEQEEMANAIITILQSWIFS

IL4_G2_neo2_40_1F_seq36_S11
(SEQ ID NO: 92)
PKKKIQITAEEALKDALSILNIVKTNSPPAEEQLERFAKRFERNLWGIAR

LFESGDQKDEAEKAKRMKEWMKRIKTTASEDEQEEMANAIITILQSWIFS (SEQ ID NO: 183)
PKKKIQITAEEALKDALSILNIVKTNSPPAEEQLERFAKRFERNLWGIAR

LFESGDQKDEAEKAKRMKEWMKRIKTTASEDEQEEMANAIITILQSWIFS

Neoleukin-4 (i.e. IL4_G2_neo2_40_1F_seq36_S11_MIF)
(SEQ ID NO: 93)
PKKKIQIMAEEALKDALSILNIVKTNSPPAEEQLERFAKRFERNLWGIAR

LFESGDQKDEAEKAKRMIEWMKRIKTTASEDEQEEMANAIITILQSWFFS

-continued (SEQ ID NO: 184)

PKKKIQIMAEEALKDALSILNIVKTNSPPAEEQLERFAKRFERNLWGIAR

LFESGDQKDEAEKAKRMIEWMKRIKTTASEDEQEEMANAIITILQSWFFS

For each variant below, two SEQ ID NOs are provided: a first SEQ ID NO: that lists the sequence as shown below, and a second SEQ ID NO: that includes the linker positions as optional and variable.

>Neoleukin-2/15_R50C (SEQ ID NO: 190)

PKKKIQLHAEHALYDALMILNIVKTNSPPAEEKLEDYAFNFELILEEIACL

FESGDQKDEAEKAKRMKEWMKRIKTTASEDEQEEMANAIITILQSWIFS*

>Neoleukin-2/15_R50C (SEQ ID NO: 217)

PKKKIQLHAEHALYDALMILNIXXXXXXXXXXXLEDYAFNFELILEEIACL

FESGXXKDEAEKAKRMKEWMKRIKTXXXEDEQEEMANAIITILQSWIFS*

>Neoleukin-2/15_E53C (SEQ ID NO: 191)

PKKKIQLHAEHALYDALMILNIVKTNSPPAEEKLEDYAFNFELILEEIARL

FCSGDQKDEAEKAKRMKEWMKRIKTTASEDEQEEMANAIITILQSWIFS*

>Neoleukin-2/15_E53C (SEQ ID NO: 218)

PKKKIQLHAEHALYDALMILNIXXXXXXXXXXXLEDYAFNFELILEEIARL

FCSGXXKDEAEKAKRMKEWMKRIKTXXXEDEQEEMANAIITILQSWIFS*

>Neoleukin-2/15_D56C (SEQ ID NO: 192)

PKKKIQLHAEHALYDALMILNIVKTNSPPAEEKLEDYAFNFELILEEIARL

FESGCQKDEAEKAKRMKEWMKRIKTTASEDEQEEMANAIITILQSWIFS*

>Neoleukin-2/15_D56C (SEQ ID NO: 219)

PKKKIQLHAEHALYDALMILNIXXXXXXXXXXXLEDYAFNFELILEEIARL

FESGCQKDEAEKAKRMKEWMKRIKTXXXEDEQEEMANAIITILQSWIFS*

>Neoleukin-2/15_K58C (SEQ ID NO: 193)

PKKKIQLHAEHALYDALMILNIVKTNSPPAEEKLEDYAFNFELILEEIARL

FESGDQCDEAEKAKRMKEWMKRIKTTASEDEQEEMANAIITILQSWIFS*

>Neoleukin-2/15_K58C (SEQ ID NO: 220)

PKKKIQLHAEHALYDALMILNIXXXXXXXXXXXLEDYAFNFELILEEIARL

FESGXXCDEAEKAKRMKEWMKRIKTXXXEDEQEEMANAIITILQSWIFS*

>Neoleukin-2/15_D59C (SEQ ID NO: 194)

PKKKIQLHAEHALYDALMILNIVKTNSPPAEEKLEDYAFNFELILEEIARL

FESGDQKCEAEKAKRMKEWMKRIKTTASEDEQEEMANAIITILQSWIFS*

>Neoleukin-2/15_D59C (SEQ ID NO: 221)

PKKKIQLHAEHALYDALMILNIXXXXXXXXXXXLEDYAFNFELILEEIARL

FESGXXKCEAEKAKRMKEWMKRIKTXXXEDEQEEMANAIITILQSWIFS*

>Neoleukin-2/15_E62C (SEQ ID NO: 195)

PKKKIQLHAEHALYDALMILNIVKTNSPPAEEKLEDYAFNFELILEEIARL

FESGDQKDEACKAKRMKEWMKRIKTTASEDEQEEMANAIITILQSWIFS*

-continued

>Neoleukin-2/15_E62C (SEQ ID NO: 222)

PKKKIQLHAEHALYDALMILNIXXXXXXXXXXXLEDYAFNFELILEEIARL

FESGXXKDEACKAKRMKEWMKRIKTXXXEDEQEEMANAIITILQSWIFS*

>Neoleukin-2/15_R66C (SEQ ID NO: 196)

PKKKIQLHAEHALYDALMILNIVKTNSPPAEEKLEDYAFNFELILEEIARL

FESGDQKDEAEKAKCMKEWMKRIKTTASEDEQEEMANAIITILQSWIFS*

>Neoleukin-2/15_R66C (SEQ ID NO: 223)

PKKKIQLHAEHALYDALMILNIXXXXXXXXXXXLEDYAFNFELILEEIARL

FESGXXKDEAEKAKCMKEWMKRIKTXXXEDEQEEMANAIITILQSWIFS*

>Neoleukin-2/15_E69C (SEQ ID NO: 197)

PKKKIQLHAEHALYDALMILNIVKTNSPPAEEKLEDYAFNFELILEEIARL

FESGDQKDEAEKAKRMKCWMKRIKTTASEDEQEEMANAIITILQSWIFS*

>Neoleukin-2/15_E69C (SEQ ID NO: 224)

PKKKIQLHAEHALYDALMILNIXXXXXXXXXXXLEDYAFNFELILEEIARL

FESGXXKDEAEKAKRMKCWMKRIKTXXXEDEQEEMANAIITILQSWIFS*

>Neoleukin-2/15_R73C (SEQ ID NO: 198)

PKKKIQLHAEHALYDALMILNIVKTNSPPAEEKLEDYAFNFELILEEIARL

FESGDQKDEAEKAKRMKEWMKCIKTTASEDEQEEMANAIITILQSWIFS*

>Neoleukin-2/15_R73C (SEQ ID NO: 225)

PKKKIQLHAEHALYDALMILNIXXXXXXXXXXXLEDYAFNFELILEEIARL

FESGXXKDEAEKAKRMKEWMKCIKTXXXEDEQEEMANAIITILQSWIFS*

>Neoleukin-2/15_T77C (SEQ ID NO: 199)

PKKKIQLHAEHALYDALMILNIVKTNSPPAEEKLEDYAFNFELILEEIARL

FESGDQKDEAEKAKRMKEWMKRIKTCASEDEQEEMANAIITILQSWIFS*

>Neoleukin-2/15_T77C (SEQ ID NO: 226)

PKKKIQLHAEHALYDALMILNIXXXXXXXXXXXLEDYAFNFELILEEIARL

FESGXXKDEAEKAKRMKEWMKRIKTCASEDEQEEMANAIITILQSWIFS*

>Neoleukin-2/15_E82C (SEQ ID NO: 200)

PKKKIQLHAEHALYDALMILNIVKTNSPPAEEKLEDYAFNFELILEEIARL

FESGDQKDEAEKAKRMKEWMKRIKTTASEDCQEEMANAIITILQSWIFS*

>Neoleukin-2/15_E82C (SEQ ID NO: 227)

PKKKIQLHAEHALYDALMILNIXXXXXXXXXXXLEDYAFNFELILEEIARL

FESGXXKDEAEKAKRMKEWMKRIKTXXXEDCQEEMANAIITILQSWIFS*

>Neoleukin-2/15_E85C (SEQ ID NO: 201)

PKKKIQLHAEHALYDALMILNIVKTNSPPAEEKLEDYAFNFELILEEIARL

FESGDQKDEAEKAKRMKEWMKRIKTTASEDEQECMANAIITILQSWIFS*

>Neoleukin-2/15_E85C (SEQ ID NO: 228)

PKKKIQLHAEHALYDALMILNIXXXXXXXXXXXLEDYAFNFELILEEIARL

FESGXXKDEAEKAKRMKEWMKRIKTXXXEDEQECMANAIITILQSWIFS*

-continued

>Neoleukin-2/15_R50C_R73C (SEQ ID NO: 202)

PKKKIQLHAEHALYDALMILNIVKTNSPPAEEKLEDYAFNFELILEEIACL
FESGDQKDEAEKAKRMKEWMKCIKTTASEDEQEEMANAIITILQSWIFS*

>Neoleukin-2/15_R50C_R73C (SEQ ID NO: 229)

PKKKIQLHAEHALYDALMILNIXXXXXXXXXXXLEDYAFNFELILEEIACL
FESGXXKDEAEKAKRMKEWMKCIKTXXXEDEQEEMANAIITILQSWIFS*

>Neoleukin-2/15_E53C_R73C (SEQ ID NO: 203)

PKKKIQLHAEHALYDALMILNIVKTNSPPAEEKLEDYAFNFELILEEIARL
FCSGDQKDEAEKAKRMKEWMKCIKTTASEDEQEEMANAIITILQSWIFS*

>Neoleukin-2/15_E53C_R73C (SEQ ID NO: 230)

PKKKIQLHAEHALYDALMILNIXXXXXXXXXXXLEDYAFNFELILEEIARL
FCSGXXKDEAEKAKRMKEWMKCIKTXXXEDEQEEMANAIITILQSWIFS*

>Neoleukin-2/15_D56C_R73C (SEQ ID NO: 204)

PKKKIQLHAEHALYDALMILNIVKTNSPPAEEKLEDYAFNFELILEEIARL
FESGCQKDEAEKAKRMKEWMKCIKTTASEDEQEEMANAIITILQSWIFS*

>Neoleukin-2/15_D56C_R73C (SEQ ID NO: 231)

PKKKIQLHAEHALYDALMILNIXXXXXXXXXXXLEDYAFNFELILEEIARL
FESGCQKDEAEKAKRMKEWMKCIKTXXXEDEQEEMANAIITILQSWIFS*

>Neoleukin-2/15_K58C_R73C (SEQ ID NO: 205)

PKKKIQLHAEHALYDALMILNIVKTNSPPAEEKLEDYAFNFELILEEIARL
FESGDQCDEAEKAKRMKEWMKCIKTTASEDEQEEMANAIITILQSWIFS*

>Neoleukin-2/15_K58C_R73C (SEQ ID NO: 232)

PKKKIQLHAEHALYDALMILNIXXXXXXXXXXXLEDYAFNFELILEEIARL
FESGXXCDEAEKAKRMKEWMKCIKTXXXEDEQEEMANAIITILQSWIFS*

>Neoleukin-2/15_D59C_R73C (SEQ ID NO: 206)

PKKKIQLHAEHALYDALMILNIVKTNSPPAEEKLEDYAFNFELILEEIARL
FESGDQKCEAEKAKRMKEWMKCIKTTASEDEQEEMANAIITILQSWIFS*

>Neoleukin-2/15_D59C_R73C (SEQ ID NO: 233)

PKKKIQLHAEHALYDALMILNIXXXXXXXXXXXLEDYAFNFELILEEIARL
FESGXXKCEAEKAKRMKEWMKCIKTXXXEDEQEEMANAIITILQSWIFS*

>Neoleukin-2/15_E62C_R73C (SEQ ID NO: 207)

PKKKIQLHAEHALYDALMILNIVKTNSPPAEEKLEDYAFNFELILEEIARL
FESGDQKDEACKAKRMKEWMKCIKTTASEDEQEEMANAIITILQSWIFS*

>Neoleukin-2/15_E62C_R73C (SEQ ID NO: 234)

PKKKIQLHAEHALYDALMILNIXXXXXXXXXXXLEDYAFNFELILEEIARL
FESGXXKDEACKAKRMKEWMKCIKTXXXEDEQEEMANAIITILQSWIFS*

>Neoleukin-2/15_R66C_R73C (SEQ ID NO: 208)

PKKKIQLHAEHALYDALMILNIVKTNSPPAEEKLEDYAFNFELILEEIARL
FESGDQKDEAEKAKCMKEWMKCIKTTASEDEQEEMANAIITILQSWIFS*

>Neoleukin-2/15_R66C_R73C (SEQ ID NO: 235)

PKKKIQLHAEHALYDALMILNIXXXXXXXXXXXLEDYAFNFELILEEIARL
FESGXXKDEAEKAKCMKEWMKCIKTXXXEDEQEEMANAIITILQSWIFS*

>Neoleukin-2/15_R50C_E82C (SEQ ID NO: 209)

PKKKIQLHAEHALYDALMILNIVKTNSPPAEEKLEDYAFNFELILEEIACL
FESGDQKDEAEKAKRMKEWMKRIKTTASEDCQEEMANAIITILQSWIFS*

>Neoleukin-2/15_R50C_E82C (SEQ ID NO: 236)

PKKKIQLHAEHALYDALMILNIXXXXXXXXXXXLEDYAFNFELILEEIACL
FESGXXKDEAEKAKRMKEWMKRIKTXXXEDCQEEMANAIITILQSWIFS*

>Neoleukin-2/15_E53C_E82C (SEQ ID NO: 210)

PKKKIQLHAEHALYDALMILNIVKTNSPPAEEKLEDYAFNFELILEEIARL
FCSGDQKDEAEKAKRMKEWMKRIKTTASEDCQEEMANAIITILQSWIFS*

>Neoleukin-2/15_E53C_E82C (SEQ ID NO: 237)

PKKKIQLHAEHALYDALMILNIXXXXXXXXXXXLEDYAFNFELILEEIARL
FCSGXXKDEAEKAKRMKEWMKRIKTXXXEDCQEEMANAIITILQSWIFS*

>Neoleukin-2/15_D56C_E82C (SEQ ID NO: 211)

PKKKIQLHAEHALYDALMILNIVKTNSPPAEEKLEDYAFNFELILEEIARL
FESGCQKDEAEKAKRMKEWMKRIKTTASEDCQEEMANAIITILQSWIFS*

>Neoleukin-2/15_D56C_E82C (SEQ ID NO: 238)

PKKKIQLHAEHALYDALMILNIXXXXXXXXXXXLEDYAFNFELILEEIARL
FESGCQKDEAEKAKRMKEWMKRIKTXXXEDCQEEMANAIITILQSWIFS*

>Neoleukin-2/15_K58C_E82C (SEQ ID NO: 212)

PKKKIQLHAEHALYDALMILNIVKTNSPPAEEKLEDYAFNFELILEEIARL
FESGDQCDEAEKAKRMKEWMKRIKTTASEDCQEEMANAIITILQSWIFS*

>Neoleukin-2/15_K58C_E82C (SEQ ID NO: 239)

PKKKIQLHAEHALYDALMILNIXXXXXXXXXXXLEDYAFNFELILEEIARL
FESGXXCDEAEKAKRMKEWMKRIKTXXXEDCQEEMANAIITILQSWIFS*

>Neoleukin-2/15_D59C_E82C (SEQ ID NO: 213)

PKKKIQLHAEHALYDALMILNIVKTNSPPAEEKLEDYAFNFELILEEIARL
FESGDQKCEAEKAKRMKEWMKRIKTTASEDCQEEMANAIITILQSWIFS*

>Neoleukin-2/15_D59C_E82C (SEQ ID NO: 240)

PKKKIQLHAEHALYDALMILNIXXXXXXXXXXXLEDYAFNFELILEEIARL
FESGXXKCEAEKAKRMKEWMKRIKTXXXEDCQEEMANAIITILQSWIFS*

>Neoleukin-2/15_E62C_E82C (SEQ ID NO: 214)

PKKKIQLHAEHALYDALMILNIVKTNSPPAEEKLEDYAFNFELILEEIARL
FESGDQKDEACKAKRMKEWMKRIKTTASEDCQEEMANAIITILQSWIFS*

>Neoleukin-2/15_E62C_E82C (SEQ ID NO: 241)

PKKKIQLHAEHALYDALMILNIXXXXXXXXXXXLEDYAFNFELILEEIARL
FESGXXKDEACKAKRMKEWMKRIKTXXXEDCQEEMANAIITILQSWIFS*

-continued

```
>Neoleukin-2/15_R66C_E82C
                                              (SEQ ID NO: 215)
PKKKIQLHAEHALYDALMILNIVKTNSPPAEEKLEDYAFNFELILEEIARL

FESGDQKDEAEKAKCMKEWMKRIKTTASEDCQEEMANAIITILQSWIFS*

>Neoleukin-2/15_R66C_E82C
                                              (SEQ ID NO: 242)
PKKKIQLHAEHALYDALMILNIXXXXXXXXXXXLEDYAFNFELILEEIARL

FESGXXKDEAEKAKCMKEWMKRIKTXXXEDCQEEMANAIITILQSWIFS*

>Neoleukin-2/15_E69C_E82C
                                              (SEQ ID NO: 216)
PKKKIQLHAEHALYDALMILNIVKTNSPPAEEKLEDYAFNFELILEEIARL

FESGDQKDEAEKAKRMKCWMKRIKTTASEDCQEEMANAIITILQSWIFS*

>Neoleukin-2/15_E69C_E82C
                                              (SEQ ID NO: 243)
PKKKIQLHAEHALYDALMILNIXXXXXXXXXXXLEDYAFNFELILEEIARL

FESGXXKDEAEKAKRMKCWMKRIKTXXXEDCQEEMANAIITILQSWIFS*
```

In one embodiment, the polypeptide comprises a polypeptide at least at least 25%, 27%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% identical along its length to the amino acid sequence selected from the group consisting of SEQ ID NO:90, 181, and 247.

In another embodiment, the polypeptide comprises a polypeptide identical to the amino acid sequence of SEQ ID NO:90, 181, or 247, wherein the polypeptide (i) does not bind to human or murine IL-2Ralpha, (ii) binds to human IL2RB with an affinity of about 11.2 nM (iii) binds to murine IL2RB with an affinity of about 16.1 nm (iv) binds to human IL-2R$\beta\gamma_c$ with an affinity of about 18.8 nM and (v) binds to murine IL-2R$\beta\gamma_c$ with an affinity of about 3.4 nM.

In any of these embodiments of the full length polypeptides, the polypeptide may be an IL-4/IL-13 mimetic, wherein position 7 is I, position 8 is T or M, position 11 is E, position 14 is K, position 18 is S, position 33 is Q, position 36 is R, position 37 is F, position 39 is K, position 40 is R, position 43 is R, position 44 is N, position 46 is W, and position 47 is G. In a further embodiment, position 68 is I and position 98 is F.

In any of these embodiments of the full length polypeptides, the polypeptide may be an IL-2 mimetic, wherein 1, 2, 3, 4, 5, 6, 7, 8, 9, 10, 11, 12, 13, or all 14 of the following are not true: position 7 is I, position 8 is T or M, position 11 is E, position 14 is K, position 18 is S, position 33 is Q, position 36 is R, position 37 is F, position 39 is K, position 40 is R, position 43 is R, position 44 is N, position 46 is W, and position 47 is G. In a further embodiment, one or both of the following are not true: position 68 is I and position 98 is F.

In one embodiment, the IL-2 mimetic polypeptides of any embodiment or combination of embodiments disclosed herein have a three dimensional structure with structural coordinates having a root mean square deviation of common residue backbone atoms or alpha carbon atoms of less than 2.5 Angstroms, less than 1.5 Angstroms, or less than 1 Angstrom when superimposed on backbone atoms or alpha carbon atoms of the three dimensional structure of native IL-2.

In another embodiment, the IL-2 mimetic polypeptides of any embodiment or combination of embodiments disclosed herein have a three dimensional structure with structural coordinates having a root mean square deviation of common residue backbone atoms or alpha carbon atoms of less than 2.5 Angstroms, less than 1.5 Angstroms, or less than 1 Angstrom when superimposed on backbone atoms or alpha carbon atoms of a three dimensional structure having the structural coordinates of Table E2.

In a further embodiment, the IL-2 mimetic polypeptides of any embodiment or combination of embodiments disclosed herein, when in ternary complex with the mouse IL-2 receptor $\beta\gamma_c$, have a three dimensional structure wherein the structural coordinates of common residue backbone atoms or alpha carbon atoms have a root mean square deviation of less than 2.5 Angstroms, less than 1.5 Angstroms, or less than 1 Angstrom when superimposed on backbone atoms or alpha carbon atoms of the three dimensional structure of native IL-2 when in ternary complex with the mouse IL-2 receptor $\beta\gamma_c$.

In another embodiment, the IL-4 mimetic polypeptides of any embodiment or combination of embodiments disclosed herein have a three dimensional structure with structural coordinates comprising a root mean square deviation of common residue backbone atoms or alpha carbon atoms of less than 2.5 Angstroms less than 1.5 Angstroms, or less than 1 Angstrom when superimposed on backbone atoms or alpha carbon atoms of the three dimensional structure of native IL-4.

In each of these embodiments, the three dimensional structure of the polypeptide may be determined using computational modeling or alternatively, the three dimensional structure of the polypeptide is determined using crystallographically-determined structural data.

In one embodiment of any embodiment or combination of embodiments disclosed herein, X1, X2, X3, and X4 are alpha-helical domains. In another embodiment, the amino acid length of each of X1, X2, X3 and X4 is independently at least about 8, 10, 12, 14, 16, 19, or more amino acids in length. In other embodiments, the amino acid length of each of X1, X2, X3 and X4 is independently no more than 1000, 500, 400, 300, 200, 100, or 50 amino acids in length. In various further embodiments, the amino acid length of each of X1, X2, X3 and X4 is independently between about 8-1000, 8-500, 8-400, 8-300, 8-200, 8-100, 8-50, 10-1000, 10-500, 10-400, 10-300, 10-200, 10-100, 10-50, 12-1000, 12-500, 12-400, 12-300, 12-200, 12-100, 12-50, 14-1000, 14-500, 14-400, 14-300, 14-200, 14-100, 14-50, 16-1000, 16-500, 16-400, 16-300, 16-200, 16-100, 16-50, 19-1000, 19-500, 19-400, 19-300, 19-200, 19-100, or about 19-50 amino acids in length.

In another embodiment, the IL-2 mimetic polypeptides of any embodiment or combination of embodiments disclosed herein, X1 binds to the beta and the gamma subunit of the human IL-2 receptor. In another embodiment of the IL-2 mimetic polypeptides of any embodiment or combination of embodiments disclosed herein, X2 does not bind to the human IL-2 receptor. In another embodiment, of the IL-2 mimetic polypeptides of any embodiment or combination of embodiments disclosed herein, X3 binds to the beta subunit of the human IL-2 receptor. In a further embodiment of the IL-2 mimetic polypeptides of any embodiment or combination of embodiments disclosed herein, X4 binds to the gamma subunit of the human IL-2 receptor. In another embodiment or the IL-2 mimetic polypeptides of any embodiment or combination of embodiments disclosed herein, the polypeptide does not bind to the alpha subunit of the human or murine IL-2 receptor. In one embodiment, binding to the receptors is specific binding as determined by surface plasmon resonance at biologically relevant concentrations. In another embodiment, the IL-2 mimetic polypeptides of any embodiment or combination of embodiments disclosed herein that bind to the IL-2 receptor $\beta\gamma_c$ heterodimer (IL-2R$\beta\gamma_c$) do so with a binding affinity of 200 nm or less, 100 nm or less, 50 nM or less, or 25 nM or less. In a further embodiment of the IL-2 mimetic polypeptides of any embodiment or combination of embodiments disclosed herein, the polypeptide's affinity for the human and mouse IL-2 receptors is about equal to or greater than that of native IL-2.

In one embodiment of the IL-4 mimetic polypeptides of any embodiment or combination of embodiments disclosed herein that bind to the IL-4 receptor $\alpha\gamma_c$heterodimer (IL-4R$\alpha\gamma_c$) do so with a binding affinity of 200 nm or less, 100 nm or less, 50 nM or less, or 25 nM or less. In another embodiment of the IL-4 mimetic polypeptides of any embodiment or combination of embodiments disclosed herein, the polypeptide's affinity for the human and mouse IL-4 receptors is about equal to or greater than that of native IL-4.

In one embodiment of the IL-2 mimetic polypeptides of any embodiment or combination of embodiments disclosed herein, the polypeptide stimulates STAT5 phosphorylation in cells expressing the IL-2 receptor with potency about equal to or greater than native IL-2. In another embodiment of the IL-2 mimetic polypeptides of any embodiment or combination of embodiments disclosed herein, the polypeptide stimulates STAT5 phosphorylation in cells expressing the IL-2 receptor with potency about equal to or greater than native IL-2 in cells expressing IL-2 receptor $\beta\gamma_c$ heterodimer but lacking the IL-2 receptor $\alpha$.

In another embodiment, the IL-2 mimetic polypeptides of any embodiment or combination of embodiments disclosed herein demonstrate thermal stability about equal to or greater than the thermal stability of native IL-2.

In a further embodiment, the polypeptides of any embodiment or combination of embodiments disclosed herein, the polypeptides maintain or recover at least 70%, 80%, or 90% of their folded structure after thermal stability testing, and/or maintain or recover at least 80% of their ellipticity spectrum after thermal stability testing, and/or maintain or recover at least 70% or 80% of their activity after thermal stability testing. In one embodiment, such activity is determined by a STAT5 phosphorylation assay. In another embodiment, thermal stability is measured by circular dichroism (CD) spectroscopy at 222 nM. In a further embodiment, the thermal stability test comprises heating the polypeptide from 25 degrees Celsius to 95 degrees Celsius in a one hour time frame, cooling the polypeptide to 25 degrees Celsius in a 5 minute time frame and monitoring ellipticity at 222 nm.

The polypeptides described herein may be chemically synthesized or recombinantly expressed (when the polypeptide is genetically encodable). The polypeptides may be linked to other compounds, such as stabilization compounds to promote an increased half-life in vivo, including but not limited to albumin, PEGylation (attachment of one or more polyethylene glycol chains), HESylation, PASylation, glycosylation, or may be produced as an Fc-fusion or in deimmunized variants. Such linkage can be covalent or non-covalent. For example, addition of polyethylene glycol ("PEG") containing moieties may comprise attachment of a PEG group linked to maleimide group ("PEG-MAL") to a cysteine residue of the polypeptide. Suitable examples of PEG-MAL are methoxy PEG-MAL 5 kD; methoxy PEG-MAL 20 kD; methoxy (PEG)2-MAL 40 kD; methoxy PEG (MAL)2 5 kD; methoxy PEG(MAL)2 20 kD; methoxy PEG(MAL)2 40 kD; or any combination thereof. See also U.S. Pat. No. 8,148,109. In other embodiments, the PEG may comprise branched chain PEGs and/or multiple PEG chains.

In one embodiment, the stabilization compound, including but not limited to a PEG-containing moiety, is linked at a cysteine residue in the polypeptide. In another embodiment, the cysteine residue is present in the X2 domain. In some embodiments, the cysteine residue is present, for example, in any one of a number of positions in the X2 domain. In some such embodiments, the X2 domain is at least 19 amino acids in length and the cysteine residue is at positions 1, 2, 5, 9 or 16 relative to those 19 amino acids. In a further embodiment, the stabilization compound, including but not limited to a PEG-containing moiety, is linked to the cysteine residue via a maleimide group, including but not limited to linked to a cysteine residue present at amino acid residue 62 relative to SEQ ID NO:90.

In some aspects, the polypeptide is a Neo-2/15 polypeptide and an amino acid of Neo-2/15 is mutated to a cysteine residue for attachment of a stabilization moiety (e.g., PEG-containing moiety) thereto. In some aspects, the polypeptide is a Neo-2/15 polypeptide and the amino acid at positions 50, 53, 62, 69, 73, 82, 56, 58, 59, 66, 77, or 85 or a combination thereof relative to SEQ ID NO:90, 181, or 247 is mutated to a cysteine residue for attachment of a stabilization moiety (e.g., PEG-containing moiety) thereto. Accordingly, in a further embodiment, the polypeptide comprises a polypeptide at least 25%, 27%, 30%, 35%, 40%, 45%, 50%, 55%, 60%, 65%, 70%, 75%, 80%, 85%, 90%, 95%, 98%, or 100% identical to the full length of the amino acid sequence of SEQ ID NO:90, 181, or 247 [Neo-2/15], and wherein one, two, three, four, five, or all six of the following mutations are present:

R50C;
E53C;
E62C;
E69C;
R73C; and/or
E82C.

In a further embodiment, the polypeptide comprises a polypeptide at least 25%, 27%, 30%, 35%, 40%, 45%, 50%, 55%, 60%, 65%, 70%, 75%, 80%, 85%, 90%, 95%, 98%, or 100% identical to the full length of the amino acid sequence of SEQ ID NO:90, 181, or 247, and wherein one, two, three, four, five, six, seven, eight, nine, ten, eleven, or all twelve of the following mutations are present D56C;
K58C;
D59C;
R66C;
T77C;
E85C;
R50C;
E53C;
E62C;
E69C;
R73C; and/or
E82C.

In a further embodiment, the polypeptide comprises a polypeptide at least 25%, 27%, 30%, 35%, 40%, 45%, 50%, 55%, 60%, 65%, 70%, 75%, 80%, 85%, 90%, 95%, 98%, or 100% identical to the full length of the amino acid sequence selected from the group consisting of SEQ ID NOS: 190-243.

In one embodiment, the polypeptide comprises a polypeptide at least at least 25%, 27%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% identical along its length to the amino acid sequence selected from the group consisting of SEQ ID NO:190 and 217. In one aspect, the polypeptide comprises a polypeptide at least at least 25%, 27%, 30%, 35%, 40%, 45%, 50%, 55%, 60%, 65%, 70%, 75%, 80%, 85%, 90%, 91%, 92%, 93%, 94%, 95%, 96%, 97%, 98% 99%, or 100% identical along its length to the amino acid sequence of SEQ ID NO:190.

In one embodiment, the polypeptide comprises a polypeptide at least at least 25%, 27%, 30%, 35%, 40%, 45%, 50%, 55%, 60%, 65%, 70%, 75%, 80%, 85%, 90%, 91%, 92% 93%, 94%, 95%, 96%, 97%, 98%, 99%, or 100% identical along its length to the amino acid sequence selected from the group consisting of SEQ ID NO:191 and 218. In one aspect, the polypeptide comprises a polypeptide at least at least 25%, 27%, 30%, 35%, 40%, 45%, 50%, 55%, 60%, 65%, 70%, 75%, 80%, 85%, 90%, 91%, 92%, 93%, 94%, 95%, 96%, 97%, 98% 99%, or 100% identical along its length to the amino acid sequence of SEQ ID NO:191.

In one embodiment, the polypeptide comprises a polypeptide at least at least 25%, 27%, 30%, 35%, 40%, 45%, 50%, 55%, 60%, 65%, 70%, 75%, 80%, 85%, 90%, 91%, 92% 93%, 94%, 95%, 96%, 97%, 98%, 99%, or 100% identical along its length to the amino acid sequence selected from the group consisting of SEQ ID NO:192 and 219. In one aspect, the polypeptide comprises a polypeptide at least at least 25%, 27%, 30%, 35%, 40%, 45%, 50%, 55%, 60%, 65%, 70%, 75%, 80%, 85%, 90%, 91%, 92%, 93%, 94%, 95%, 96%, 97%, 98% 99%, or 100% identical along its length to the amino acid sequence of SEQ ID NO:192.

In one embodiment, the polypeptide comprises a polypeptide at least at least 25%, 27%, 30%, 35%, 40%, 45%, 50%, 55%, 60%, 65%, 70%, 75%, 80%, 85%, 90%, 91%, 92% 93%, 94%, 95%, 96%, 97%, 98%, 99%, or 100% identical along its length to the amino acid sequence selected from the group consisting of SEQ ID NO:193 and 220. In one aspect, the polypeptide comprises a polypeptide at least at least 25%, 27%, 30%, 35%, 40%, 45%, 50%, 55%, 60%, 65%, 70%, 75%, 80%, 85%, 90%, 91%, 92%, 93%, 94%, 95%, 96%, 97%, 98% 99%, or 100% identical along its length to the amino acid sequence of SEQ ID NO:193.

In one embodiment, the polypeptide comprises a polypeptide at least at least 25%, 27%, 30%, 35%, 40%, 45%, 50%, 55%, 60%, 65%, 70%, 75%, 80%, 85%, 90%, 91%, 92% 93%, 94%, 95%, 96%, 97%, 98%, 99%, or 100% identical along its length to the amino acid sequence selected from the group consisting of SEQ ID NO:194 and 221. In one aspect, the polypeptide comprises a polypeptide at least at least 25%, 27%, 30%, 35%, 40%, 45%, 50%, 55%, 60%, 65%, 70%, 75%, 80%, 85%, 90%, 91%, 92%, 93%, 94%, 95%, 96%, 97%, 98% 99%, or 100% identical along its length to the amino acid sequence of SEQ ID NO:194.

In one embodiment, the polypeptide comprises a polypeptide at least at least 25%, 27%, 30%, 35%, 40%, 45%, 50%, 55%, 60%, 65%, 70%, 75%, 80%, 85%, 90%, 91%, 92% 93%, 94%, 95%, 96%, 97%, 98%, 99%, or 100% identical along its length to the amino acid sequence selected from the group consisting of SEQ ID NO:195 and 222. In one aspect, the polypeptide comprises a polypeptide at least at least 25%, 27%, 30%, 35%, 40%, 45%, 50%, 55%, 60%, 65%, 70%, 75%, 80%, 85%, 90%, 91%, 92%, 93%, 94%, 95%, 96%, 97%, 98% 99%, or 100% identical along its length to the amino acid sequence of SEQ ID NO:195.

In one embodiment, the polypeptide comprises a polypeptide at least at least 25%, 27%, 30%, 35%, 40%, 45%, 50%, 55%, 60%, 65%, 70%, 75%, 80%, 85%, 90%, 91%, 92% 93%, 94%, 95%, 96%, 97%, 98%, 99%, or 100% identical along its length to the amino acid sequence selected from the group consisting of SEQ ID NO:196 and 223. In one aspect, the polypeptide comprises a polypeptide at least at least 25%, 27%, 30%, 35%, 40%, 45%, 50%, 55%, 60%, 65%, 70%, 75%, 80%, 85%, 90%, 91%, 92%, 93%, 94%, 95%, 96%, 97%, 98% 99%, or 100% identical along its length to the amino acid sequence of SEQ ID NO:196.

In one embodiment, the polypeptide comprises a polypeptide at least at least 25%, 27%, 30%, 35%, 40%, 45%, 50%, 55%, 60%, 65%, 70%, 75%, 80%, 85%, 90%, 91%, 92% 93%, 94%, 95%, 96%, 97%, 98%, 99%, or 100% identical along its length to the amino acid sequence selected from the group consisting of SEQ ID NO:197 and 224. In one aspect, the polypeptide comprises a polypeptide at least at least 25%, 27%, 30%, 35%, 40%, 45%, 50%, 55%, 60%, 65%, 70%, 75%, 80%, 85%, 90%, 91%, 92%, 93%, 94%, 95%, 96%, 97%, 98% 99%, or 100% identical along its length to the amino acid sequence of SEQ ID NO:197.

In one embodiment, the polypeptide comprises a polypeptide at least at least 25%, 27%, 30%, 35%, 40%, 45%, 50%, 55%, 60%, 65%, 70%, 75%, 80%, 85%, 90%, 91%, 92% 93%, 94%, 95%, 96%, 97%, 98%, 99%, or 100% identical along its length to the amino acid sequence selected from the group consisting of SEQ ID NO:198 and 225. In one aspect, the polypeptide comprises a polypeptide at least at least 25%, 27%, 30%, 35%, 40%, 45%, 50%, 55%, 60%, 65%, 70%, 75%, 80%, 85%, 90%, 91%, 92%, 93%, 94%, 95%, 96%, 97%, 98% 99%, or 100% identical along its length to the amino acid sequence of SEQ ID NO:198.

In one embodiment, the polypeptide comprises a polypeptide at least at least 25%, 27%, 30%, 35%, 40%, 45%, 50%, 55%, 60%, 65%, 70%, 75%, 80%, 85%, 90%, 91%, 92% 93%, 94%, 95%, 96%, 97%, 98%, 99%, or 100% identical along its length to the amino acid sequence selected from the group consisting of SEQ ID NO:199 and 226. In one aspect, the polypeptide comprises a polypeptide at least at least 25%, 27%, 30%, 35%, 40%, 45%, 50%, 55%, 60%, 65%, 70%, 75%, 80%, 85%, 90%, 91%, 92%, 93%, 94%, 95%, 96%, 97%, 98% 99%, or 100% identical along its length to the amino acid sequence of SEQ ID NO:199.

In one embodiment, the polypeptide comprises a polypeptide at least at least 25%, 27%, 30%, 35%, 40%, 45%, 50%, 55%, 60%, 65%, 70%, 75%, 80%, 85%, 90%, 91%, 92% 93%, 94%, 95%, 96%, 97%, 98%, 99%, or 100% identical along its length to the amino acid sequence selected from the group consisting of SEQ ID NO:200 and 227. In one aspect, the polypeptide comprises a polypeptide at least at least 25%, 27%, 30%, 35%, 40%, 45%, 50%, 55%, 60%, 65%, 70%, 75%, 80%, 85%, 90%, 91%, 92%, 93%, 94%, 95%, 96%, 97%, 98% 99%, or 100% identical along its length to the amino acid sequence of SEQ ID NO:200.

In one embodiment, the polypeptide comprises a polypeptide at least at least 25%, 27%, 30%, 35%, 40%, 45%, 50%, 55%, 60%, 65%, 70%, 75%, 80%, 85%, 90%, 91%, 92% 93%, 94%, 95%, 96%, 97%, 98%, 99%, or 100% identical along its length to the amino acid sequence selected from the group consisting of SEQ ID NO:201 and 228. In one aspect, the polypeptide comprises a polypeptide at least at least 25%, 27%, 30%, 35%, 40%, 45%, 50%, 55%, 60%, 65%, 70%, 75%, 80%, 85%, 90%, 91%, 92%, 93%, 94%, 95%, 96%, 97%, 98% 99%, or 100% identical along its length to the amino acid sequence of SEQ ID NO:201.

In another embodiment, the polypeptide comprises a polypeptide at least 25%, 27%, 30%, 35%, 40%, 45%, 50%, 55%, 60%, 65%, 70%, 75%, 80%, 85%, 90%, 95%, 98%, or 100% identical to the full length of the amino acid sequence selected from the group consisting of SEQ ID NO:195, 207, 214, 222, 234, and 241; or wherein the polypeptide comprises a polypeptide at least 25%, 27%, 30%, 35%, 40%, 45%, 50%, 55%, 60%, 65%, 70%, 75%, 80%, 85%, 90%, 95%, 98%, or 100% identical to the full length of the amino acid sequence selected from the group consisting of SEQ ID NO:195, 207, and 214.

In a further embodiment, the polypeptide further comprises a targeting domain. In this embodiment, the polypeptide can be directed to a target of interest. The targeting domain may be covalently or non-covalently bound to the polypeptide. In embodiments where the targeting domain is non-covalently bound to the polypeptide, any suitable means for such non-covalent binding may be used, including but not limited to streptavidin-biotin linkers.

In another embodiment, the targeting domain, when present, is a translational fusion with the polypeptide. In this embodiment, the polypeptide and the targeting domain may directly abut each other in the translational fusion or may be linked by a polypeptide linker suitable for an intended purpose. Exemplary such linkers include, but are not limited, to those disclosed in WO2016178905, WO2018153865 (in particular, at page 13), and WO 2018170179 (in particular, at paragraphs [0316]-[0317]). In other embodiments, suitable linkers include, but are not limited to peptide linkers, such as GGGGG (SEQ ID NO: 95), GSGGG (SEQ ID NO: 96), GGGGGG (SEQ ID NO: 97), GGSGGG (SEQ ID NO: 98), GGSGGSGGGSGGSGSG (SEQ ID NO: 99), GSGGSGGGSGGSGSG (SEQ ID NO: 100), GGSGGSGGGSGGSGGGGSGGSGGGSGGGGS (SEQ ID NO: 101), and $[GGGGX]_n$ (SEQ ID NO: 102), where X is Q, E or S and n is 2-5.

The targeting domains are polypeptide domains or small molecules that bind to a target of interest. In one non-limiting embodiment, the targeting domain binds to a cell surface protein; in this embodiment, the cell may be any cell type of interest that includes a surface protein that can be bound by a suitable targeting domain. In one embodiment, the cell surface proteins are present on the surface of cells selected from the group consisting of tumor cells, tumor vascular component cells, tumor microenvironment cells (e.g. fibroblasts, infiltrating immune cells, or stromal elements), other cancer cells and immune cells (including but not limited to CD8+ T cells, T-regulatory cells, dendritic cells, NK cells, or macrophages). When the cell surface protein is on the surface of a tumor cell, vascular component cell, or tumor microenvironment cell (e.g. fibroblasts, infiltrating immune cells, or stromal elements), any suitable tumor cell, vascular component cell, or tumor microenvironment cell surface marker may be targeted, including but not limited to EGFR, EGFRvIII, Her2, HER3, EpCAM, MSLN, 1UC16, PSMA, TROP2, ROR1, RON, PD L1, CD47, CTLA-4, CD5, CDI9, CD20, CD25, CD37, CD30, CD33, CD40, CD45, CAMPATH-1, BCMA, CS-1, PD-L1, B7-H3, B7-DC, HLD-DR, carcinoembryonic antigen (CEA), TAG-72, MUC1, folate-binding protein, A33, G250, prostate-specific membrane antigen (PSMA), ferritin, GD2, GD3, GM2, $Le^y$, CA-125, CA19-9, epidermal growth factor, p185HER2, IL-2 receptor, EGFRvIII (de2-7 EGFR)_fibroblast activation protein, tenascin, a metalloproteinase, endosialin, vascular endothelial growth factor, avB3, WT1, LMP2, HPV E6, HPV E7, Her-2/neu, MAGE A3, p53 nonmutant, NY-ESO-1, MelanA/MART1, Ras mutant, gp100, p53 mutant, PR1, her-abl, tyronsinase, survivin, PSA, hTERT, a Sarcoma translocation breakpoint protein, EphA2, PAP, ML-IAP, AFP, ERG, NA17, PAX3, ALK, androgen receptor, cyclin B 1, polysialic acid, MYCN, RhoC, TRP-2, fucosyl GM1, mesothelin (MSLN), PSCA, MAGE Al, sLe(animal), CYP1B1, PLAN/1, GM3, BORIS, Tn, GloboH, ETV6-AML, NY-BR-1, RGS5, SART3, STn Carbonic anhydrase IX, PAX5, OY-TESL Sperm protein 17, LCK, HMWMAA, AKAP-4, SSX2, XAGE 1, Legumain, Tie 3, VEGFR2, MAD-CT-1, PDGFR-B, MAD-CT-2, ROR2, TRAIL, MUC16, MAGE A4, MAGE C2, GAGE, EGFR, CMET, HER3_MUC15, CA6, NAP12B, TROP2, CLDN6, CLDN16, CLDN18.2, CLorf186, RON, LY6E, FRA, DLL3, PTK7, STRA6, TMPRSS3, TMPRSS4, TMEM238, UPK1B, VTCN1, LIV1, ROR1, and Fos-related. antigen 1.

In other embodiments, when the cell surface protein is on the surface of a tumor cell, vascular component cell, or tumor microenvironment cell (e.g. fibroblasts, infiltrating immune cells, or stromal elements), any suitable tumor cell, vascular component cell, or tumor microenvironment cell surface marker may be targeted, including but not limited to targets in the following list:

(1) BMPR1B (bone morphogenetic protein receptor-type IB, Genbank accession no. NM. sub.--001203);

(2) E16 (LAT1, SLC7A5, Genbank accession no. NM.sub.--003486);

(3) STEAP1 (six transmembrane epithelial antigen of prostate, Genbank accession no. NM.sub.--012449);

(4) 0772P (CA125, MUC16, Genbank accession no. AF361486);

(5) MPF (MPF, MSLN, SMR, megakaryocyte potentiating factor, mesothelin, Genbank accession no. NM.sub.--005823);

(6) Napi3b (NAPI-3B, NPTIIb, SLC34A2, solute carrier family 34 (sodium phosphate), member 2, type II sodium-dependent phosphate transporter 3b, Genbank accession no. NM.sub.--006424);

(7) Sema 5b (FLJ10372, KIAA1445, Mm. 42015, SEMASB, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878);

(8) PSCA hlg (2700050C12Rik, C530008O16Rik, RIKEN cDNA 2700050C12, RIKEN cDNA 2700050C12 gene, Genbank accession no. AY358628);

(9) ETBR (Endothelin type B receptor, Genbank accession no. AY275463);

(10) MSG783 (RNF124, hypothetical protein FLJ20315, Genbank accession no. NM.sub.--017763);

(11) STEAP2 (HGNC.sub.--8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138);

(12) TrpM4 (BR22450, FLJ20041, TRPM4, TRPM4B, transient receptor potential cation channel, subfamily M, member 4, Genbank accession no. NM.sub.--017636);

(13) CRIPTO (CR, CR1, CRGF, CRIPTO, TDGF1, teratocarcinoma-derived growth factor, Genbank accession no. NP.sub.--003203 or NM.sub.--003212);

(14) CD21 (CR2 (Complement receptor 2) or C3DR(C3d/Epstein Barr virus receptor) or Hs. 73792, Genbank accession no. M26004);

(15) CD79b (IGb (immunoglobulin-associated beta), B29, Genbank accession no. NM.sub.--000626);

(16) FcRH2 (IFGP4, IRTA4, SPAP1A (SH2 domain containing phosphatase anchor protein 1a), SPAP1B, SPAP1C, Genbank accession no. NM_--030764);

(17) HER2 (Genbank accession no. M11730);

(18) NCA (Genbank accession no. M18728);

(19) MDP (Genbank accession no. BC017023);
(20) IL20R.alpha. (Genbank accession no. AF184971);
(21) Brevican (Genbank accession no. AF229053);
(22) Ephb2R (Genbank accession no. NM_--004442);
(23) ASLG659 (Genbank accession no. AX092328);
(24) PSCA (Genbank accession no. AJ297436);
(25) GEDA (Genbank accession no. AY260763);
(26) BAFF-R (Genbank accession no. NP_--443177.1);
(27) CD22 (Genbank accession no. NP-001762.1);
(28) CD79a (CD79A, CD79.alpha., immunoglobulin-associated alpha, a B cell-specific protein that covalently interacts with Ig beta (CD79B) and forms a complex on the surface with Ig M molecules, transduces a signal involved in B-cell differentiation, Genbank accession No. NP_--001774.1);
(29) CXCRS (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia, Genbank accession No. NP_--001707.1);
(30) HLA-DOB (Beta subunit of MHC class II molecule (Ia antigen) that binds peptides and presents them to CD4+ T lymphocytes, Genbank accession No. NP_--002111.1);
(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability, Genbank accession No. NP_--002552.2);
(32) CD72 (B-cell differentiation antigen CD72, Lyb-2, Genbank accession No. NP_--001773.1);
(33) LY64 (Lymphocyte antigen 64 (RP 105), type I membrane protein of the leucine rich repeat (LRR) family, regulates B-cell activation and apoptosis, loss of function is associated with increased disease activity in patients with systemic lupus erythematosis, Genbank accession No. NP_--005573.1);
(34) FCRH1 (Fc receptor-like protein 1, a putative receptor for the immunoglobulin Fc domain that contains C2 type Ig-like and ITAM domains, may have a role in B-lymphocyte differentiation, Genbank accession No. NP_--443170.1); or
(35) IRTA2 (Immunoglobulin superfamily receptor translocation associated 2, a putative immunoreceptor with possible roles in B cell development and lymphomagenesis; deregulation of the gene by translocation occurs in some B cell malignancies, Genbank accession No. NP_--112571.1).

In another embodiment, the targeting domain binds to immune cell surface markers. In this embodiment, the target may be cell surface proteins on any suitable immune cell, including but not limited to CD8+ T cells, T-regulatory cells, dendritic cells, NK cells or macrophages. The targeting domain may target any suitable immune cell surface marker (whether an endogenous or an engineered immune cell, including but not limited to engineered CAR-T cells), including but not limited to CD3, CD4, CD8, CD7.9, CD20, CD21, CD25, CD37, CD30, CD33, CD40, CD68, CD123, CD254, PD-1, B7-H3, and CTLA-4. In another embodiment, the targeting domain binds to PD-1, PDL-1, CTLA-4, TROP2, B7-H3, CD33, CD22, carbonic anhydrase IX, CD123, Nectin-4, tissue factor antigen, CD154, B7-H3, B7-H4, FAP (fibroblast activation protein) or MUC16, and/or wherein the targeting domain binds to PD-1, PDL-1, CTLA-4, TROP2, B7-H3, CD33, CD22, carbonic anhydrase IX, CD123, Nectin-4, tissue factor antigen, CD154, B7-H3, B7-H4, FAP (fibroblast activation protein) or MUC16.

In all these embodiments, the targeting domains can be any suitable polypeptides that bind to targets of interest and can be incorporated into the polypeptide of the disclosure. In non-limiting embodiments, the targeting domain may include but is not limited to an scFv, a F(ab), a F(ab')$_2$, a B cell receptor (BCR), a DARPin, an affibody, a monobody, a nanobody, diabody, an antibody (including a monospecific or bispecific antibody); a cell-targeting oligopeptide including but not limited to RGD integrin-binding peptides, de novo designed binders, aptamers, a bicycle peptide, conotoxins, small molecules such as folic acid, and a virus that binds to the cell surface.

In another embodiment, the polypeptides include at least one disulfide bond (i.e.: 1, 2, 3, 4, or more disulfide bonds). Any suitable disulfide bonds may be used, such as disulfide bonds linking two different helices. In one embodiment, the disulfide bonds include a disulfide bond linking helix 1 (X1) and helix 4 (X4). The disulfide bond may, for example, improve the thermal stability of the polypeptide as compared to a substantially similar polypeptide with no disulfide bond linking two domains together.

The polypeptides and peptide domains of the invention may include additional residues at the N-terminus, C-terminus, or both that are not present in the polypeptides or peptide domains of the disclosure; these additional residues are not included in determining the percent identity of the polypeptides or peptide domains of the disclosure relative to the reference polypeptide. Such residues may be any residues suitable for an intended use, including but not limited to detection tags (i.e.: fluorescent proteins, antibody epitope tags, etc.), adaptors, ligands suitable for purposes of purification (His tags, etc.), other peptide domains that add functionality to the polypeptides, etc. Residues suitable for attachment of such groups may include cysteine, lysine or p-acetylphenylalanine residues or can be tags, such as amino acid tags suitable for reaction with transglutaminases as disclosed in U.S. Pat. Nos. 9,676,871 and 9,777,070.

In a further aspect, the present invention provides nucleic acids, including isolated nucleic acids, encoding a polypeptide of the present invention that can be genetically encoded. The isolated nucleic acid sequence may comprise RNA or DNA. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the invention.

In another aspect, the present invention provides recombinant expression vectors comprising the isolated nucleic acid of any aspect of the invention operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors include but are not limited to, plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The expression vector must be replicable in the host organisms either as an episome or by integration into host chromosomal DNA. In various embodiments, the expression vector may comprise a plasmid, viral-based vector (including but not limited to a retroviral vector or oncolytic virus), or any other suitable expression vector. In some embodiments, the expression vector can be administered in the methods of the disclosure to express the polypeptides in vivo for therapeutic benefit. In non-limiting embodiments, the expression vectors can be used to transfect or transduce cell therapeutic targets (including but not limited to CAR-T cells or tumor cells) to effect the therapeutic methods disclosed herein.

In a further aspect, the present disclosure provides host cells that comprise the recombinant expression vectors disclosed herein, wherein the host cells can be either prokaryotic or eukaryotic. The cells can be transiently or stably engineered to incorporate the expression vector of the invention, using techniques including but not limited to bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press); *Culture of Animal Cells: A Manual of Basic Technique,* $2^{nd}$ Ed. (R. I. Freshney. 1987. Liss, Inc. New York, N.Y.)). A method of producing a polypeptide according to the invention is an additional part of the invention. The method comprises the steps of (a) culturing a host according to this aspect of the invention under conditions conducive to the expression of the polypeptide, and (b) optionally, recovering the expressed polypeptide. The expressed polypeptide can be recovered from the cell free extract, but preferably they are recovered from the culture medium.

In a further aspect, the present disclosure provides antibodies that selectively bind to the polypeptides of the disclosure. The antibodies can be polyclonal, monoclonal antibodies, humanized antibodies, and fragments thereof, and can be made using techniques known to those of skill in the art. As used herein, "selectively bind" means preferential binding of the antibody to the polypeptide of the disclosure, as opposed to one or more other biological molecules, structures, cells, tissues, etc., as is well understood by those of skill in the art.

In another aspect, the present disclosure provides pharmaceutical compositions, comprising one or more polypeptides, nucleic acids, expression vectors, and/or host cells of the disclosure and a pharmaceutically acceptable carrier. The pharmaceutical compositions of the disclosure can be used, for example, in the methods of the disclosure described below. The pharmaceutical composition may comprise in addition to the polypeptide of the disclosure (a) a lyoprotectant; (b) a surfactant; (c) a bulking agent; (d) a tonicity adjusting agent; (e) a stabilizer; (f) a preservative and/or (g) a buffer.

In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The polypeptides, nucleic acids, expression vectors, and/or host cells may be the sole active agent in the pharmaceutical composition, or the composition may further comprise one or more other active agents suitable for an intended use.

In a further aspect, the present disclosure provides methods for treating and/or limiting cancer, comprising administering to a subject in need thereof a therapeutically effective amount of one or more polypeptides, nucleic acids, expression vectors, and/or host cells of the disclosure, salts thereof, conjugates thereof, or pharmaceutical compositions thereof, to treat and/or limit the cancer. When the method comprises treating cancer, the one or more polypeptides, nucleic acids, expression vectors, and/or host cells are administered to a subject that has already been diagnosed as having cancer. As used herein, "treat" or "treating" means accomplishing one or more of the following: (a) reducing the size or volume of tumors and/or metastases in the subject; (b) limiting any increase in the size or volume of tumors and/or metastases in the subject; (c) increasing survival; (d) reducing the severity of symptoms associated with cancer; (e) limiting or preventing development of symptoms associated with cancer; and (f) inhibiting worsening of symptoms associated with cancer.

When the method comprises limiting development of cancer, the one or more polypeptides, nucleic acids, expression vectors, and/or host cells are administered prophylactically to a subject that is not known to have cancer, but may be at risk of cancer. As used herein, "limiting" means to limit development of cancer in subjects at risk of cancer, including but not limited to subjects with a family history of cancer, subjects genetically predisposed to cancer, subjects that are symptomatic for cancer, etc.

The methods can be used to treat or limit development of any suitable cancer, including but not limited to colon cancer, melanoma, renal cell cancer, head and neck squamous cell cancer, gastric cancer, urothelial carcinoma, Hodgkin lymphoma, non-small cell lung cancer, small cell lung cancer, hepatocellular carcinoma, pancreatic cancer, Merkel cell carcinoma colorectal cancer, acute myeloid leukemia, acute lymphoblastic leukemia, chronic lymphocytic leukemia, non-Hodgkin lymphoma, multiple myeloma, ovarian cancer, cervical cancer, and any tumor types selected by a diagnostic test, such as microsatellite instability, tumor mutational burden, PD-L1 expression level, or the immunoscore assay (as developed by the Society for Immunotherapy of Cancer).

The subject may be any subject that has or is at risk of developing cancer. In one embodiment, the subject is a mammal, including but not limited to humans, dogs, cats, horses, cattle, etc.

In a further aspect, the present disclosure provides methods for modulating an immune response in a subject by administering to a subject a polypeptide, recombinant nucleic acid, expression vector, recombinant host cell, or the pharmaceutical composition of the present disclosure.

As used herein, an "immune response" being modulated refers to a response by a cell of the immune system, such as a B cell, T cell (CD4 or CD8), regulatory T cell, antigen-presenting cell, dendritic cell, monocyte, macrophage, NKT cell, NK cell, basophil, eosinophil, or neutrophil, to a stimulus. In some embodiments, the response is specific for a particular antigen (an "antigen-specific response"), and refers to a response by a CD4 T cell, CD8 T cell, or B cell via their antigen-specific receptor. In some embodiments, an immune response is a T cell response, such as a CD4+ response or a CD8+ response. Such responses by these cells can include, for example, cytotoxicity, proliferation, cytokine or chemokine production, trafficking, or phagocytosis, and can be dependent on the nature of the immune cell undergoing the response. In some embodiments of the compositions and methods described herein, an immune response being modulated is T-cell mediated.

In some aspects, the immune response is an anti-cancer immune response. In some such aspects, an IL-2 mimetic described herein is administered to a subject having cancer to modulate an anti-cancer immune response in the subject.

In some aspects, the immune response is a tissue reparative immune response. In some such aspects, an IL-4 mimetic described here is administered to a subject in need thereof to modulate a tissue reparative immune response in the subject.

In some aspects, the immune response is a wound healing immune response. In some such aspects, an IL-4 mimetic described here is administered to a subject in need thereof to modulate a wound healing immune response in the subject.

In some aspects, methods are provided for modulating an immune response to a second therapeutic agent in a subject. In some such aspects, the method comprises administering a polypeptide of the present disclosure in combination with an effective amount of the second therapeutic agent to the subject. The second therapeutic agent can be, for example, a chemotherapeutic agent or an antigen-specific immunotherapeutic agent. In some aspects, the antigen-specific immunotherapeutic agent comprises chimeric antigen receptor T cells (CAR-T cells). In some aspects, the polypeptide of the present disclosure enhances the immune response of the subject to the therapeutic agent. The immune response can be enhanced, for example, by improving the T cell response (including CAR-T cell response), augmenting the innate T cell immune response, decreasing inflammation, inhibiting T regulatory cell activity, or combinations thereof.

In some aspects, a cytokine mimetic of the present invention, e.g., an IL-4 mimetic as described herein, will be impregnated to or otherwise associated with a biomaterial and the biomaterial will be introduced to a subject. In some aspects, the biomaterial will be a component of an implantable medical device and the device will be, for example, coated with the biomaterial. Such medical devices include, for example, vascular and arterial grafts. IL-4 and/or IL-4 associated biomaterials can be used, for example, to promote wound healing and/or tissue repair and regeneration.

As used herein, a "therapeutically effective amount" refers to an amount of the polypeptide, nucleic acids, expression vectors, and/or host cells that is effective for treating and/or limiting cancer. The polypeptides, nucleic acids, expression vectors, and/or host cells are typically formulated as a pharmaceutical composition, such as those disclosed above, and can be administered via any suitable route, including but not limited to orally, by inhalation spray, ocularly, intravenously, subcutaneously, intraperitoneally, and intravesicularly in dosage unit formulations containing conventional pharmaceutically acceptable carriers, adjuvants, and vehicles. In one particular embodiment, the polypeptides, nucleic acids, expression vectors, and/or host cells are administered mucosally, including but not limited to intraocular, inhaled, or intranasal administration. In another particular embodiment, the polypeptides, nucleic acids, expression vectors, and/or host cells are administered orally. Such particular embodiments can be administered via droplets, nebulizers, sprays, or other suitable formulations.

Any suitable dosage range may be used as determined by attending medical personnel. Dosage regimens can be adjusted to provide the optimum desired response (e.g., a therapeutic or prophylactic response). A suitable dosage range for the polypeptides may, for instance, be 0.1 ug/kg-100 mg/kg body weight; alternatively, it may be 0.5 ug/kg to 50 mg/kg; 1 ug/kg to 25 mg/kg, or 5 ug/kg to 10 mg/kg body weight. In some embodiments, the recommended dose could be lower than 0.1 mcg/kg, especially if administered locally. In other embodiments, the recommended dose could be based on weight/$m^2$ (i.e. body surface area), and/or it could be administered at a fixed dose (e.g., 0.05-100 mg). The polypeptides, nucleic acids, expression vectors, and/or host cells can be delivered in a single bolus, or may be administered more than once (e.g., 2, 3, 4, 5, or more times) as determined by an attending physician.

The polypeptides, nucleic acids, expression vectors, and/or host cells made be administered as the sole prophylactic or therapeutic agent, or may be administered together with (i.e.: combined or separately) one or more other prophylactic or therapeutic agents, including but not limited to tumor resection, chemotherapy, radiation therapy, immunotherapy, etc.

Example Computing Environment

FIG. 22 is a block diagram of an example computing network. Some or all of the above-mentioned techniques disclosed herein, such as but not limited to techniques disclosed as part of and/or being performed by software, the Rosetta software suite, RosettaScripts, PyRosetta, Rosetta applications, and/or other herein-described computer software and computer hardware, can be part of and/or performed by a computing device. For example, FIG. X1 shows protein design system 102 configured to communicate, via network 106, with client devices 104*a*, 104*b*, and 104*c* and protein database 108. In some embodiments, protein design system 102 and/or protein database 108 can be a computing device configured to perform some or all of the herein described methods and techniques, such as but not limited to, method 300 and functionality described as being part of or related to Rosetta. Protein database 108 can, in some embodiments, store information related to and/or used by Rosetta.

Network 106 may correspond to a LAN, a wide area network (WAN), a corporate intranet, the public Internet, or any other type of network configured to provide a communications path between networked computing devices. Network 106 may also correspond to a combination of one or more LANs, WANs, corporate intranets, and/or the public Internet.

Although FIG. 22 only shows three client devices 104*a*, 104*b*, 104*c*, distributed application architectures may serve tens, hundreds, or thousands of client devices. Moreover, client devices 104*a*, 104*b*, 104*c* (or any additional client devices) may be any sort of computing device, such as an ordinary laptop computer, desktop computer, network terminal, wireless communication device (e.g., a cell phone or smart phone), and so on. In some embodiments, client devices 104*a*, 104*b*, 104*c* can be dedicated to problem solving/using the Rosetta software suite. In other embodiments, client devices 104*a*, 104*b*, 104*c* can be used as general purpose computers that are configured to perform a number of tasks and need not be dedicated to problem solving/using the Rosetta software suite. In still other embodiments, part or all of the functionality of protein design system 102 and/or protein database 108 can be incorporated in a client device, such as client device 104*a*, 104*b*, and/or 104*c*.

Computing Environment Architecture

FIG. 23A is a block diagram of an example computing device (e.g., system) In particular, computing device 200 shown in FIG. 23A can be configured to: include components of and/or perform one or more functions of some or all of the herein described methods and techniques, such as but not limited to, method 300 and functionality described as being part of or related to Rosetta. Computing device 200 may include a user interface module 201, a network-communication interface module 202, one or more processors 203, data storage 204, and protein synthesis device 220, all of which may be linked together via a system bus, network, or other connection mechanism 205.

User interface module 201 can be operable to send data to and/or receive data from external user input/output devices. For example, user interface module 201 can be configured to send and/or receive data to and/or from user input devices such as a keyboard, a keypad, a touch screen, a computer mouse, a track ball, a joystick, a camera, a voice recognition module, and/or other similar devices. User interface module 201 can also be configured to provide output to user display devices, such as one or more cathode ray tubes (CRT), liquid crystal displays (LCD), light emitting diodes (LEDs), displays using digital light processing (DLP) technology, printers, light bulbs, and/or other similar devices, either now known or later developed. User interface module 201 can also be configured to generate audible output(s), such as a speaker, speaker jack, audio output port, audio output device, earphones, and/or other similar devices.

Network-communications interface module 202 can include one or more wireless interfaces 207 and/or one or more wireline interfaces 208 that are configurable to communicate via a network, such as network 106 shown in FIG. 22. Wireless interfaces 207 can include one or more wireless transmitters, receivers, and/or transceivers, such as a Bluetooth transceiver, a Zigbee transceiver, a Wi-Fi transceiver, a WiMAX transceiver, and/or other similar type of wireless transceiver configurable to communicate via a wireless network. Wireline interfaces 208 can include one or more wireline transmitters, receivers, and/or transceivers, such as an Ethernet transceiver, a Universal Serial Bus (USB) transceiver, or similar transceiver configurable to communicate via a twisted pair, one or more wires, a coaxial cable, a fiber-optic link, or a similar physical connection to a wireline network.

In some embodiments, network communications interface module 202 can be configured to provide reliable, secured, and/or authenticated communications. For each communication described herein, information for ensuring reliable communications (i.e., guaranteed message delivery) can be provided, perhaps as part of a message header and/or footer (e.g., packet/message sequencing information, encapsulation header(s) and/or footer(s), size/time information, and transmission verification information such as CRC and/or parity check values). Communications can be made secure (e.g., be encoded or encrypted) and/or decrypted/decoded using one or more cryptographic protocols and/or algorithms, such as, but not limited to, DES, AES, RSA, Diffie-Hellman, and/or DSA. Other cryptographic protocols and/or algorithms can be used as well or in addition to those listed herein to secure (and then decrypt/decode) communications.

Processors 203 can include one or more general purpose processors and/or one or more special purpose processors (e.g., digital signal processors, application specific integrated circuits, etc.). Processors 203 can be configured to execute computer-readable program instructions 206 contained in data storage 204 and/or other instructions as described herein. Data storage 204 can include one or more computer-readable storage media that can be read and/or accessed by at least one of processors 203. The one or more computer-readable storage media can include volatile and/or non-volatile storage components, such as optical, magnetic, organic or other memory or disc storage, which can be integrated in whole or in part with at least one of processors 203. In some embodiments, data storage 204 can be implemented using a single physical device (e.g., one optical, magnetic, organic or other memory or disc storage unit), while in other embodiments, data storage 204 can be implemented using two or more physical devices.

Data storage 204 can include computer-readable program instructions 206 and perhaps additional data. For example, in some embodiments, data storage 204 can store part or all of data utilized by a protein design system and/or a protein database; e.g., protein designs system 102, protein database 108. In some embodiments, data storage 204 can additionally include storage required to perform at least part of the herein-described methods and techniques and/or at least part of the functionality of the herein-described devices and networks.

In some examples, computing device 200 includes protein synthesis device 220. Protein synthesis device can synthesize (or generate polypeptides based on input data provided to protein synthesis device 220 using commands and/or data provided by processors 203 and/or data storage 204. For example, part or all of the functionality of protein synthesis device 220 can be performed by a semi-automated or an automated peptide synthesizer.

FIG. 23B depicts a network 106 of computing clusters 209*a*, 209*b*, 209*c* arranged as a cloud-based server system in accordance with an example embodiment. Data and/or software for protein design system 102 can be stored on one or more cloud-based devices that store program logic and/or data of cloud-based applications and/or services. In some examples, protein design system 102 can be a single computing device residing in a single computing center. In other examples, protein design system 102 can include multiple computing devices in a single computing center, or even multiple computing devices located in multiple computing centers located in diverse geographic locations.

In some examples, data and/or software for protein design system 102 can be encoded as computer readable information stored in tangible computer readable media (or computer readable storage media) and accessible by client devices 104*a*, 104*b*, and 104*c*, and/or other computing devices. In some examples, data and/or software for protein design system 102 can be stored on a single disk drive or other tangible storage media, or can be implemented on multiple disk drives or other tangible storage media located at one or more diverse geographic locations.

FIG. 23B depicts a cloud-based server system in accordance with an example embodiment. In FIG. 23B, the functions of protein design system 102 can be distributed among three computing clusters 209*a*, 209*b*, and 209*c*. Computing cluster 209*a* can include one or more computing devices 200*a*, cluster storage arrays 210*a*, and cluster routers 211*a* connected by a local cluster network 212*a*. Similarly, computing cluster 209*b* can include one or more computing devices 200*b*, cluster storage arrays 210*b*, and cluster routers 211*b* connected by a local cluster network 212*b*. Likewise, computing cluster 209*c* can include one or more computing devices 200*c*, cluster storage arrays 210*c*, and cluster routers 211*c* connected by a local cluster network 212*c*.

In some examples, each of the computing clusters 209*a*, 209*b*, and 209*c* can have an equal number of computing devices, an equal number of cluster storage arrays, and an equal number of cluster routers. In other examples, however, each computing cluster can have different numbers of computing devices, different numbers of cluster storage arrays, and different numbers of cluster routers. The number of computing devices, cluster storage arrays, and cluster routers in each computing cluster can depend on the computing task or tasks assigned to each computing cluster.

In computing cluster 209*a*, for example, computing devices 200*a* can be configured to perform various computing tasks of protein design system 102. In one example, the various functionalities of protein design system 102 can be distributed among one or more of computing devices 200*a*, 200*b*, and 200*c*. Computing devices 200*b* and 200*c* in computing clusters 209*b* and 209*c* can be configured similarly to computing devices 200*a* in computing cluster 209*a*. On the other hand, in some examples, computing devices 200*a*, 200*b*, and 200*c* can be configured to perform different functions.

In some examples, computing tasks and stored data associated with protein design system 102 can be distributed across computing devices 200*a*, 200*b*, and 200*c* based at least in part on the processing requirements of protein design system 102, the processing capabilities of computing devices 200*a*, 200*b*, and 200*c*, the latency of the network links between the computing devices in each computing cluster and between the computing clusters themselves, and/or other factors that can contribute to the cost, speed, fault-tolerance, resiliency, efficiency, and/or other design goals of the overall system architecture.

The cluster storage arrays 210*a*, 210*b*, and 210*c* of the computing clusters 209*a*, 209*b*, and 209*c* can be data storage arrays that include disk array controllers configured to manage read and write access to groups of hard disk drives. The disk array controllers, alone or in conjunction with their respective computing devices, can also be configured to manage backup or redundant copies of the data stored in the cluster storage arrays to protect against disk drive or other cluster storage array failures and/or network failures that prevent one or more computing devices from accessing one or more cluster storage arrays.

Similar to the manner in which the functions of protein design system 102 can be distributed across computing devices 200*a*, 200*b*, and 200*c* of computing clusters 209*a*, 209*b*, and 209*c*, various active portions and/or backup portions of these components can be distributed across cluster storage arrays 210*a*, 210*b*, and 210*c*. For example, some cluster storage arrays can be configured to store one portion of the data and/or software of protein design system 102, while other cluster storage arrays can store a separate portion of the data and/or software of protein design system 102. Additionally, some cluster storage arrays can be configured to store backup versions of data stored in other cluster storage arrays.

The cluster routers 211*a*, 211*b*, and 211*c* in computing clusters 209*a*, 209*b*, and 209*c* can include networking equipment configured to provide internal and external communications for the computing clusters. For example, the cluster routers 211*a* in computing cluster 209*a* can include one or more internet switching and routing devices configured to provide (i) local area network communications between the computing devices 200*a* and the cluster storage arrays 201*a* via the local cluster network 212*a*, and (ii) wide area network communications between the computing cluster 209*a* and the computing clusters 209*b* and 209*c* via the wide area network connection 213*a* to network 106. Cluster routers 211*b* and 211*c* can include network equipment similar to the cluster routers 211*a*, and cluster routers 211*b* and 211*c* can perform similar networking functions for computing clusters 209*b* and 209*b* that cluster routers 211*a* perform for computing cluster 209*a*.

In some examples, the configuration of the cluster routers 211*a*, 211*b*, and 211*c* can be based at least in part on the data communication requirements of the computing devices and cluster storage arrays, the data communications capabilities of the network equipment in the cluster routers 211*a*, 211*b*, and 211*c*, the latency and throughput of local networks 212*a*, 212*b*, 212*c*, the latency, throughput, and cost of wide area network links 213*a*, 213*b*, and 213*c*, and/or other factors that can contribute to the cost, speed, fault-tolerance, resiliency, efficiency and/or other design goals of the moderation system architecture.

Example Methods of Operation

FIG. 24 is a flow chart of an example method 300. Method 300 can be carried out by a computing device, such as computing device 200 described in the context of at least FIG. 2A. At least the examples of method 300 mentioned below are discussed above.

Method 300 can begin at block 310, where the computing device can determine a structure for a plurality of residues of a protein using a computing device, where the structure of the plurality of residues provides a particular receptor binding interface. As will be understood by the skilled practitioner, the determining of a structure for a plurality of residues of a protein where the structure of the plurality of residues provides a particular receptor binding interface is typically the identification of the original residues of a native protein that bind to a particular receptor binding interface whereas the plurality of designed residues are identified residues that can bind to the same receptor binding interface.

At block 320, the computing device can determine a plurality of designed residues using a mimetic design protocol, where the plurality of designed residues provide the particular receptor binding interface, and where the plurality of designed residues differ from the plurality of residues.

In some examples, determining the plurality of designed residues using the mimetic design protocol can include determining an idealized residue using a database of idealized residues, where the idealized residue is related to a designed residue of the plurality of designed residues. In some of these examples, determining the idealized residue using the database of idealized residues can include: retrieving one or more idealized fragments related to the idealized residue from the database of idealized residues; and determining the idealized residue by reconstructing the related designed residue using the one or more idealized fragments. In some of these examples, reconstructing the related designed residue using the one or more idealized fragments can include: reconnecting pairs of the one or more idealized fragments by: use of combinatorial fragment assembly of the pairs of the one or more idealized fragments; and using Cartesian-constrained backbone minimization to determine whether the pairs of the one or more idealized fragments link two or more of the plurality of designed residues. In some of these examples, reconstructing the related designed residue using the one or more idealized fragments can include: verifying that overlapping fragments of the idealized residue are idealized fragments using the database of idealized residues; verifying whether the idealized residue does not clash with a target receptor associated with the particular receptor binding interface; and after verifying that the idealized residue does not clash with a target receptor associated with the particular receptor binding interface, determining a most probable amino acid at each position of the idealized residue using the database of idealized residues. In some of these examples, determining the first protein backbone for the protein by assembling the one or more connecting helix structures and the plurality of designed residues over the plurality of combinations can include: recombining the pairs of the one or more idealized fragments by combinatorially recombining the pairs of the one or more idealized fragments; and determining the first protein backbone for the protein using the recombined pairs of the one or more idealized fragments. In some of these examples, combinatorially recombining the pairs of the one or more idealized fragments can include ranking the pairs of the one or more idealized fragments based on an interconnection length between idealized fragments of the pairs of the one or more idealized fragments.

In other examples, determining the plurality of designed residues using the mimetic design protocol can include: determining an idealized residue using one or more parametric equations that represent a shape of a designed residue of the plurality of designed residues; and determining a single fragment that closes the idealized residue with at least one designed residue of the plurality of designed residues. In some of these examples, the designed residue can include a helical structure, and the one or more parametric equations can include an equation related to phi and psi angles of the helical structure. In some of these examples, the equation related to phi and psi angles of the helical structure can include one or more terms related to an angular pitch of the phi and psi angles of the helical structure.

At block 330, the computing device can determine one or more connecting helix structures that connect the plurality of designed residues.

At block 340, the computing device can determine a first protein backbone for the protein by assembling the one or more connecting helix structures and the plurality of designed residues over a plurality of combinations.

At block 350, the computing device can design a second protein backbone for the protein for flexibility and low energy structures based on the first protein backbone.

At block 360, the computing device can generate an output related to at least the second protein backbone. In some examples, generating the output related to the second protein backbone for the protein can include designing one or more molecules based on the second protein backbone for the protein.

In other examples, generating the output related to the second protein backbone for the protein can include: generating a synthetic gene for the protein that is based the second protein backbone for the protein; expressing a particular protein in vivo using the synthetic gene; and purifying the particular protein. In some of these examples, expressing the particular protein sequence in vivo using the synthetic gene can include expressing the particular protein sequence in one or more *Escherichia coli* that include the synthetic gene.

In other examples, generating the output related to the second protein backbone for the protein can include generating one or more images that include at least part of the second protein backbone for the protein.

In other examples, the computing device can include a protein synthesis device; then, generating the output related to at least the second protein backbone for the protein can include synthesizing at least the second protein backbone for the protein using the protein synthesis device.

In one embodiment, the methods are for designing a protein mimetic, as exemplified herein.

Also included are non-naturally occurring proteins prepared by the computational methods described herein. The non-naturally occurring proteins can be cytokines, for example, non-naturally occurring IL-2 or IL-4 mimetics.

The particulars shown herein are by way of example and for purposes of illustrative discussion of embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The above definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, $3^{rd}$ Edition or a dictionary known to those of skill in the art, such as the Oxford Dictionary of Biochemistry and Molecular Biology (Ed. Anthony Smith, Oxford University Press, Oxford, 2004).

The above description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure. The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize.

All of the references cited herein are incorporated by reference. Aspects of the disclosure can be modified, if necessary, to employ the systems, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The above detailed description describes various features and functions of the disclosed systems, devices, and methods with reference to the accompanying figures. In the figures, similar symbols typically identify similar components, unless context dictates otherwise. The illustrative embodiments described in the detailed description, figures, and claims are not meant to be limiting. Other embodiments can be utilized, and other changes can be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the ladder diagrams, scenarios, and flow charts in the figures and as discussed herein, each block and/or communication may represent a processing of information and/or a transmission of information in accordance with example embodiments. Alternative embodiments are included within the scope of these example embodiments. In these alternative embodiments, for example, functions described as blocks, transmissions, communications, requests, responses, and/or messages may be executed out of order from that shown or discussed, including substantially concurrent or in reverse order, depending on the functionality involved. Further, more or fewer blocks and/or functions may be used with any of the ladder diagrams, scenarios, and flow charts discussed herein, and these ladder diagrams, scenarios, and flow charts may be combined with one another, in part or in whole.

A block that represents a processing of information may correspond to circuitry that can be configured to perform the specific logical functions of a herein-described method or technique. Alternatively or additionally, a block that represents a processing of information may correspond to a module, a segment, or a portion of program code (including related data). The program code may include one or more instructions executable by a processor for implementing specific logical functions or actions in the method or technique. The program code and/or related data may be stored on any type of computer readable medium such as a storage device including a disk or hard drive or other storage medium.

The computer readable medium may also include non-transitory computer readable media such as computer-readable media that stores data for short periods of time like register memory, processor cache, and random access memory (RAM). The computer readable media may also include non-transitory computer readable media that stores program code and/or data for longer periods of time, such as secondary or persistent long term storage, like read only memory (ROM), optical or magnetic disks, compact-disc read only memory (CD-ROM), for example. The computer readable media may also be any other volatile or non-volatile storage systems. A computer readable medium may be considered a computer readable storage medium, for example, or a tangible storage device. Moreover, a block that represents one or more information transmissions may correspond to information transmissions between software and/or hardware modules in the same physical device. However, other information transmissions may be between software modules and/or hardware modules in different physical devices.

Numerous modifications and variations of the present disclosure are possible in light of the above teachings.

EXAMPLES

A computational approach for designing de novo cytokine mimetics is described that recapitulate the functional sites of the natural cytokines, but otherwise are unrelated in topology or amino acid sequence. This strategy was used to design de novo mimetics of IL-2 and interleukin-15 (IL-15)[15] that bind to the IL-2 receptor $\beta\gamma_c$ heterodimer (IL-2R$\beta\gamma_c$)[16,17], but have no binding site for IL-2R$\alpha$ or IL-15R$\alpha$. The designs are hyper-stable, bind to human and mouse IL-2R$\beta\gamma_c$ with higher affinity than the natural cytokines, and elicit downstream cell signaling independent of IL-2R$\alpha$ and IL-15R$\alpha$. Crystal structures of an experimentally optimized mimetic, neoleukin-2/15, are very close to the design model and provide the first structural information on the murine IL-2R$\beta\gamma_c$ complex. Neoleukin-2/15 has highly efficacious therapeutic activity compared to IL-2 in murine models of melanoma and colon cancer, with reduced toxicity and no signs of immunogenicity. This strategy for building hyper-stable de novo mimetics can be readily applied to a multitude of natural cytokines and other signaling proteins, enabling the creation of superior therapeutic candidates with enhanced clinical profiles.

Because of the potent biological activity of natural protein hormones and cytokines, there have been extensive efforts to improve their potential therapeutic efficacy through protein engineering. Such efforts have sought to simplify manufacturing, extend half-life, and modulate receptor interactions[18-20]. However, there are inherent challenges to the development of a new therapeutic when starting with a naturally occurring bioactive protein. First, most natural proteins are only marginally stable[21-25], hence amino acid substitutions aimed at increasing efficacy can decrease expression or cause aggregation, making manufacturing and storage difficult. More substantial changes, such as the deletion or fusion of functional or targeting domains, are often unworkable and can dramatically alter pharmacokinetic properties and tissue penetration[19]. Second, any immune response against the engineered variant may cross-react with the endogenous molecule[26-35] with potentially catastrophic consequences. A computational design approach was developed to generate analogues of natural proteins with improved therapeutic properties that circumvent these challenges, focusing effort on engineering de novo cytokine mimetics displaying specific subsets of the receptor binding interfaces optimal for treating disease.

Figure 1A:
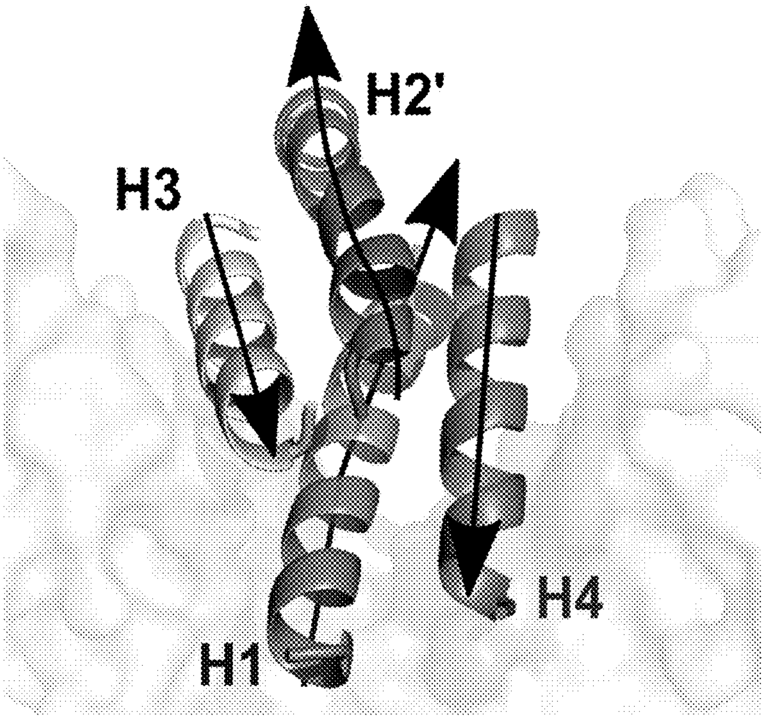
FIG. 1A-1D. Computational design of de novo cytokine mimetics.
Figure 1A:
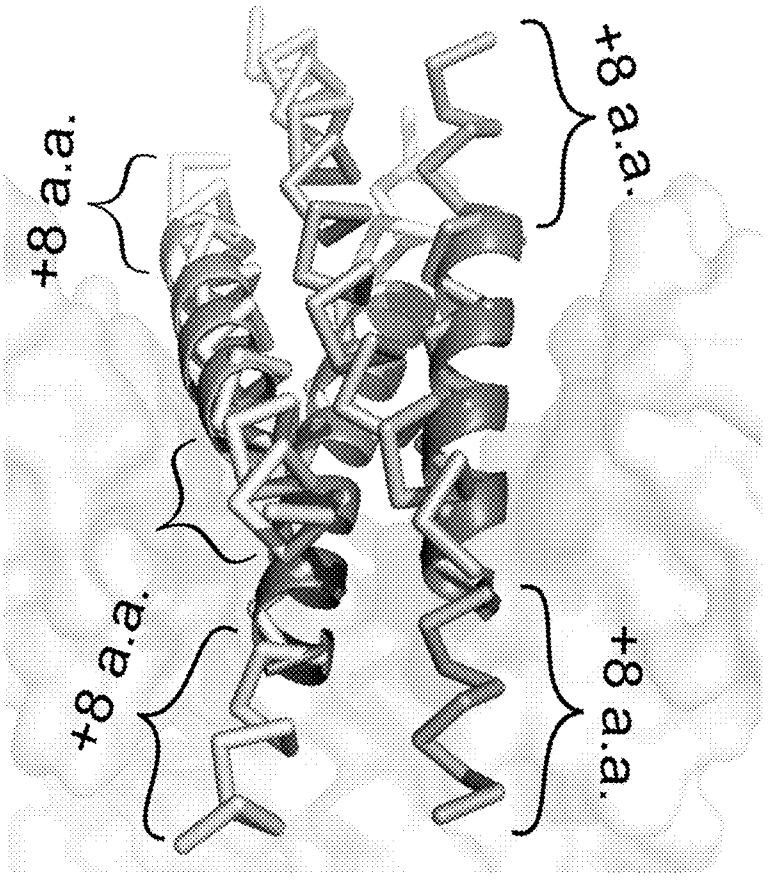
Figure 1B:
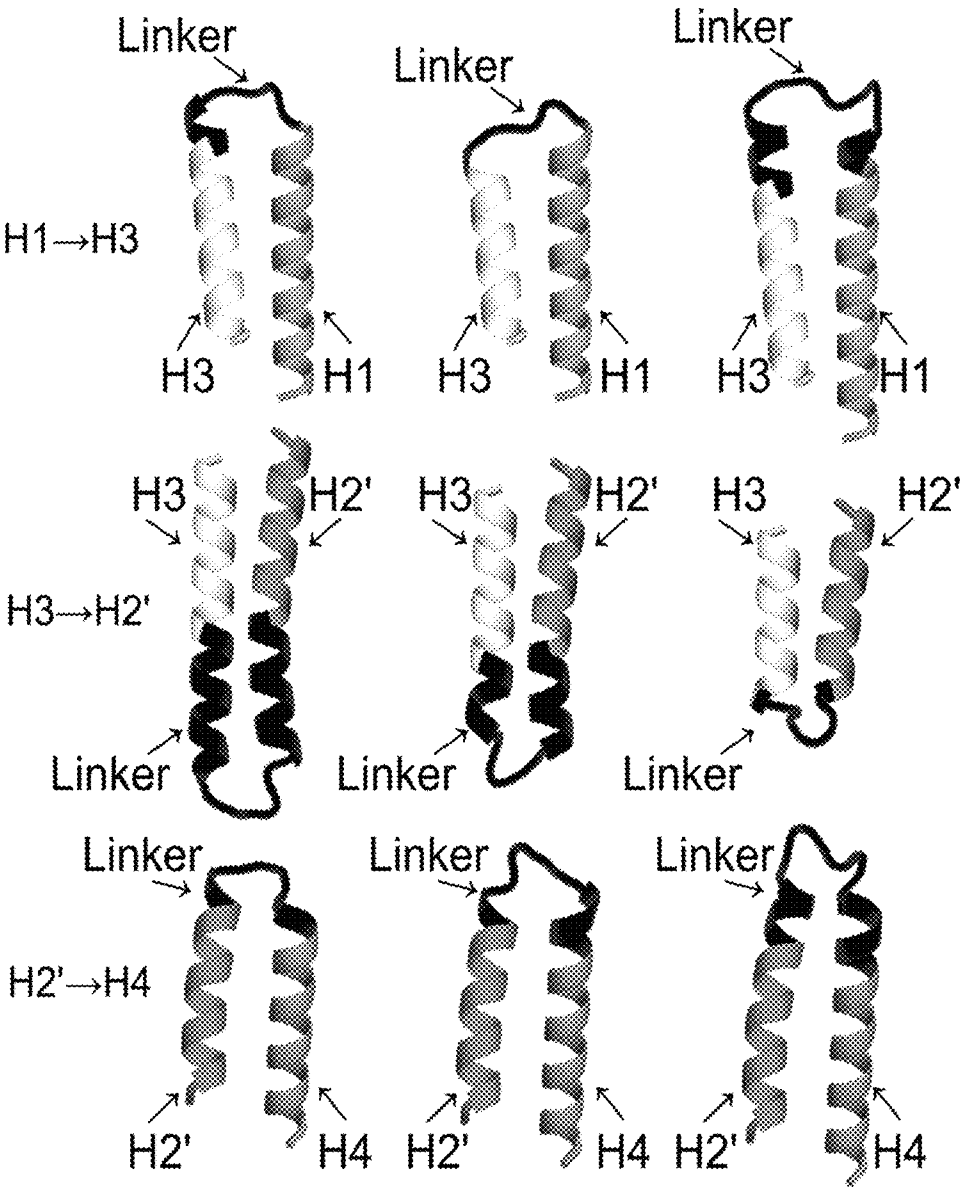

Many cytokines interact with multiple different receptor subunits[15,16,36-39], and like most naturally occurring proteins, contain non-ideal structural features that compromise stability but are important for function. A computational protocol was developed in which the structural elements interacting with the desired receptor subunit(s) are fixed in space, and an idealized globular protein structure is built to support these elements. Previous efforts were extended using combinatorial fragment assembly to support short linear epitopes with parametric construction of disembodied helices coupled with knowledge-based loop closure (FIG. 1*a-b*). The approach was tested by attempting to de novo design stable idealized proteins with interaction surfaces mimicking those of human IL-2 (hIL-2) and human IL-15 (hIL-15) for the human IL-2Rβ $\gamma_c$ (hIL-2Rβ $\gamma_c$), but entirely lacking the IL-2 receptor alpha (IL-2Rα) interaction surface. Previous efforts at removing the alpha interaction region in hIL-2, by either mutation[9,44,45] (e.g. F42A mutation of Super-2, also known as H9[9]) or PEGylation (e.g. NKTR-214[9,13]) have resulted in markedly reduced stability, binding and/or potency of the cytokine on the hIL-2Rβ $\gamma_c$ receptor while failing to completely eliminate the alpha interaction.

Figure 1C:
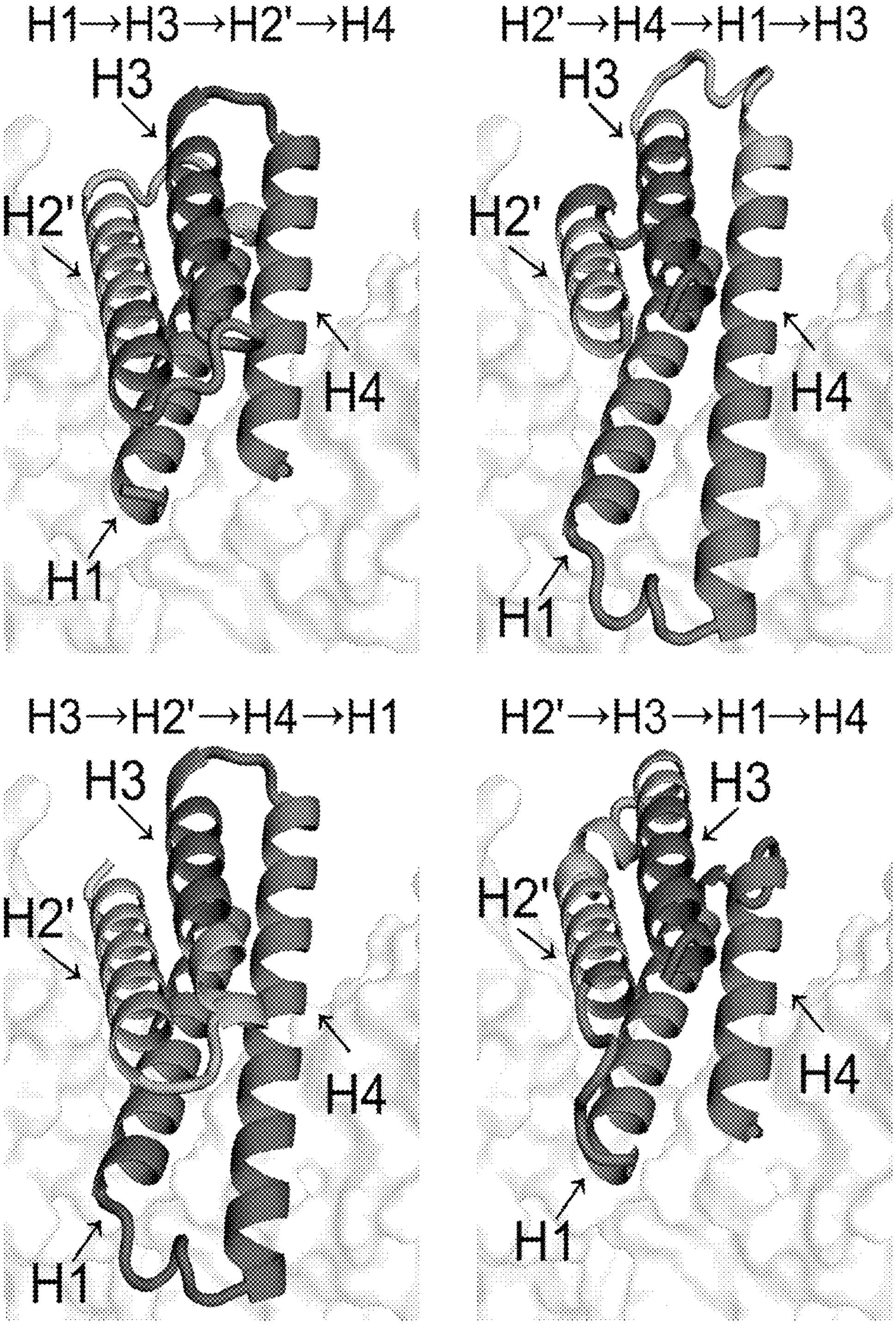
Figure 1D:
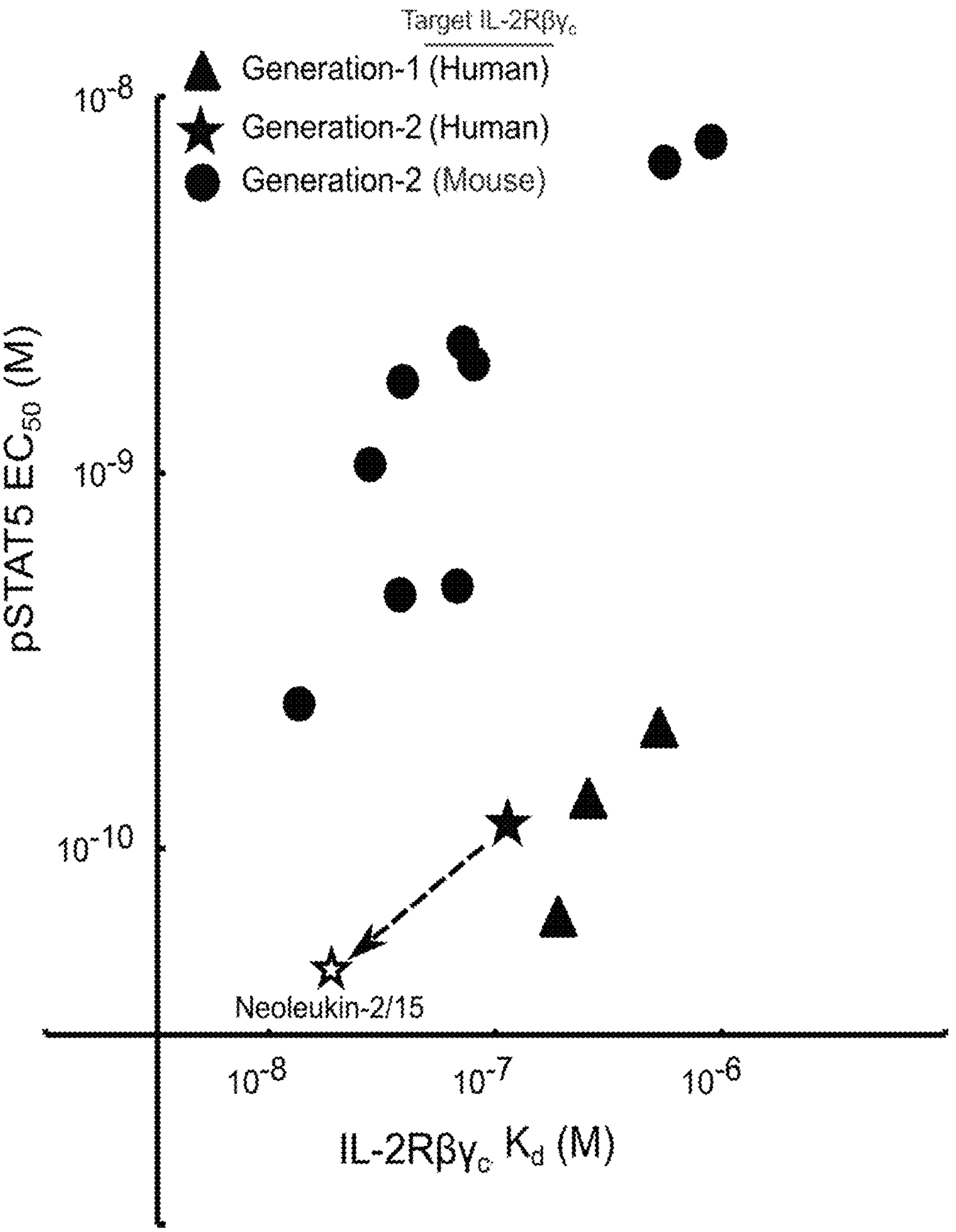

Computational Design of IL-2/IL-15 Mimetics that Bind and Activate IL-2Rβ $\gamma_c$:

Native hIL-2 comprises four helices connected by long irregular loops. The N-terminal helix (H1) interacts with both the beta and gamma subunits of the IL-2 receptor, the third helix (H3) interacts with the beta subunit, and the C-terminal helix (H4) with the gamma subunit; the alpha subunit interacting surface is formed by the irregular second helix (H2) and two long loops, one connecting H1 to H2 and the other connecting H3 and H4. An idealized protein was designed that recapitulates the interface formed by H1, H3 and H4 with beta and gamma and to replace H2 with a regular helix that offers better packing. The helices H1, H3 and H4 (see FIG. 1*a*) were used as a template for the binding site, while helix H2 was reconstructed (H2') using a database off highly-represented clustered-fragments (see Methods). Pairs of helices were connected with loops extracted from the same database (see FIG. 1*b*), the resulting helical hairpins combined into fully connected backbones (see FIG. 1*c*), and Rosetta[46-48] combinatorial flexible backbone sequence design calculations were carried out in the presence of hIL-2Rβ $\gamma_c$ (see Methods). The top four computational designs and eight single-disulfide stapled variations (see Table S1) were selected for experimental characterization by yeast display (see Methods). Eight designs were found to bind fluorescently-tagged beta-gamma chimeric IL-2 receptor at low-nanomolar concentrations. The best non-disulfide design (G1_neo2_40) was subjected to site saturation mutagenesis followed by selection and combination of affinity-increasing substitutions for the murine IL-2Rβ $\gamma_c$ (mIL-2Rβ $\gamma_c$, see FIG. 10). Optimized designs (were expressed recombinantly in *E. coli* and found to elicit pSTAT5 signaling in vitro on IL-2-responsive murine cells at low-nanomolar or even picomolar concentrations (see Table E1), but had relatively low thermal stability (Tm~<45° C., see FIGS. 14 and 15). To improve stability, the computational design protocol was repeated starting from the backbone of the highest affinity first round design (G1_neo2_40_1F, topology: H1→H4→H2'→H3), coupling the loop building process with parametric variation in helix length (+/−8 amino acids, see FIG. 1*a* bottom panel). This second approach improved the quality of the models by enabling the exploration of substantially more combinations of loops connecting each pair of helices. The fourteen best designs of the second generation, along with twenty-seven Rosetta sequence redesigns of G1_neo2_40_1F (see Table S3), were experimentally characterized and all but one were found to bind IL-2 receptor at low-nanomolar concentrations (FIG. 1*d*, Table E1, and FIG. 16). The three highest affinity and stability designs (one sequence redesign and two new mimetics) were subjected to site saturation mutagenesis for mIL-2Rβ $\gamma_c$ binding (FIGS. 11-13), followed by selection and combination of affinity-increasing substitutions for both human and mouse IL-2Rβ $\gamma_c$. The matured designs (see Table S4) showed enhanced binding while retaining hyperstability (see Table E1). The top design, neoleukin-2/15 (also referred to herein as Neo-2/15), is a 100 residue protein with a new topology and sequence quite different from human or murine IL-2 (29% sequence identity to hIL-2 over 89 residues, and 16% sequence identity to mIL-2 over 76 aligned residues, in structural topology-agnostic based alignment, see Table E1).

Figure 2A:
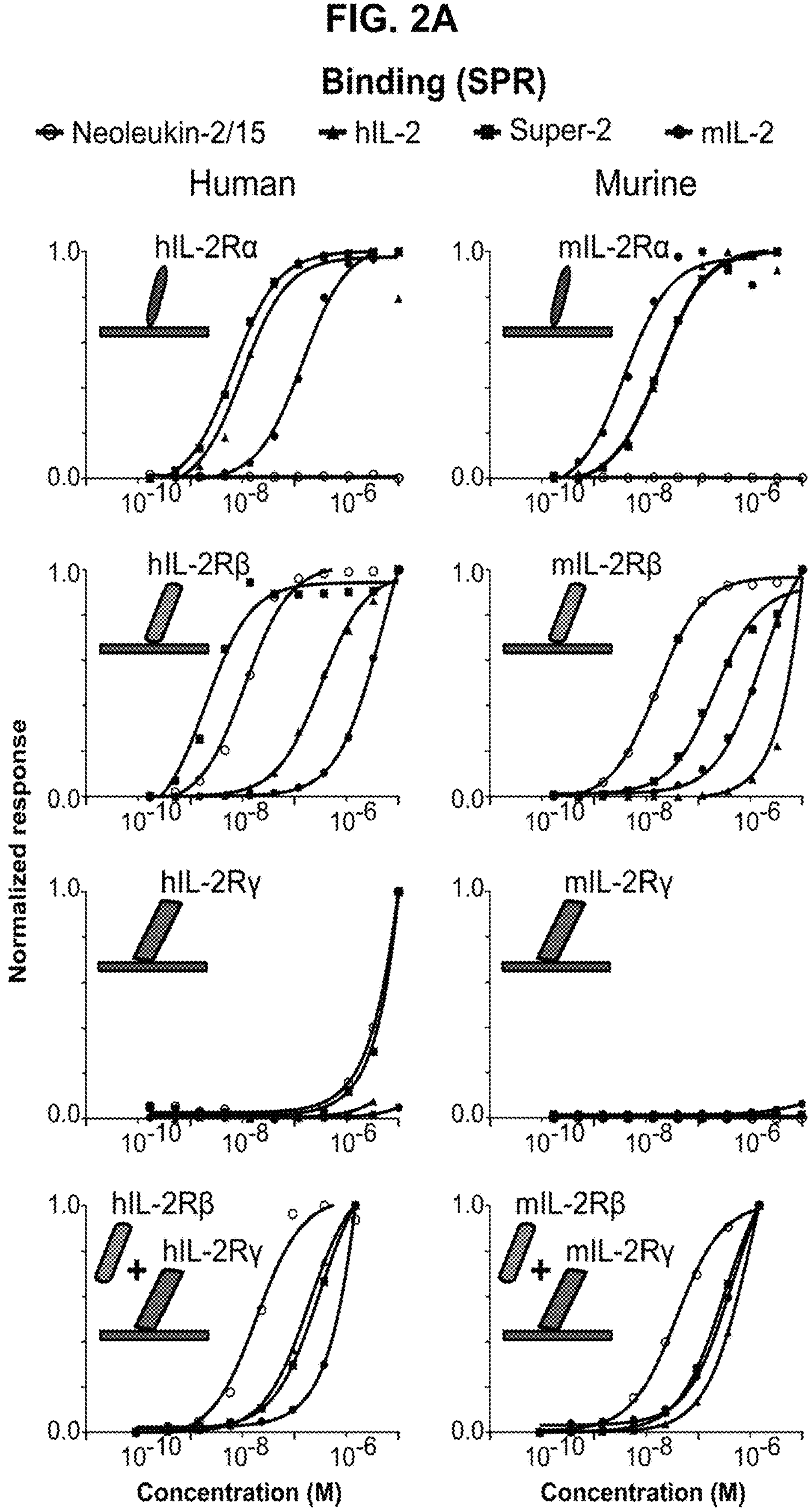
FIG. 2A-2C. Characterization of neoleukin-2/15.
Figure 2B:
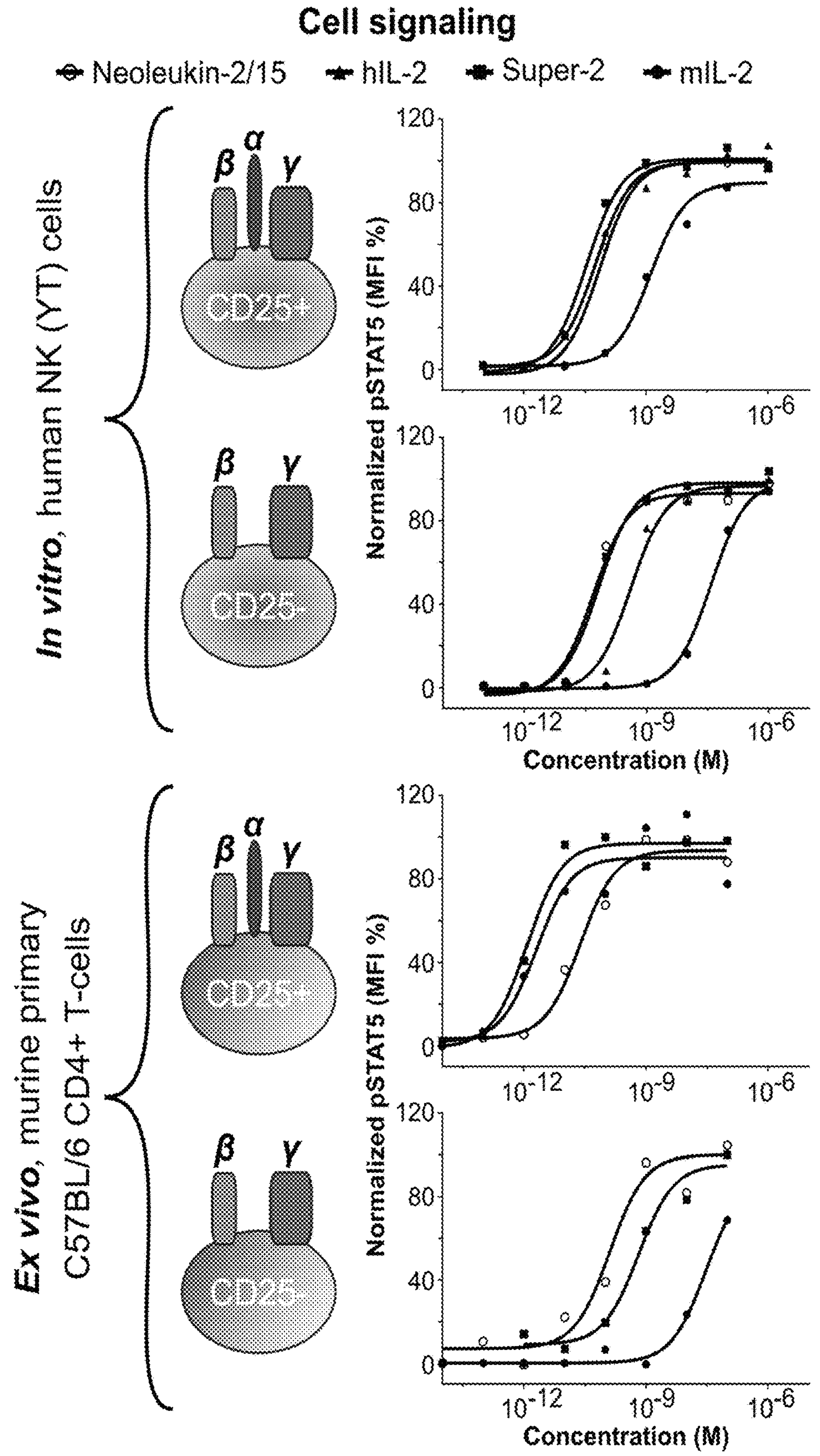
Figure 2C:
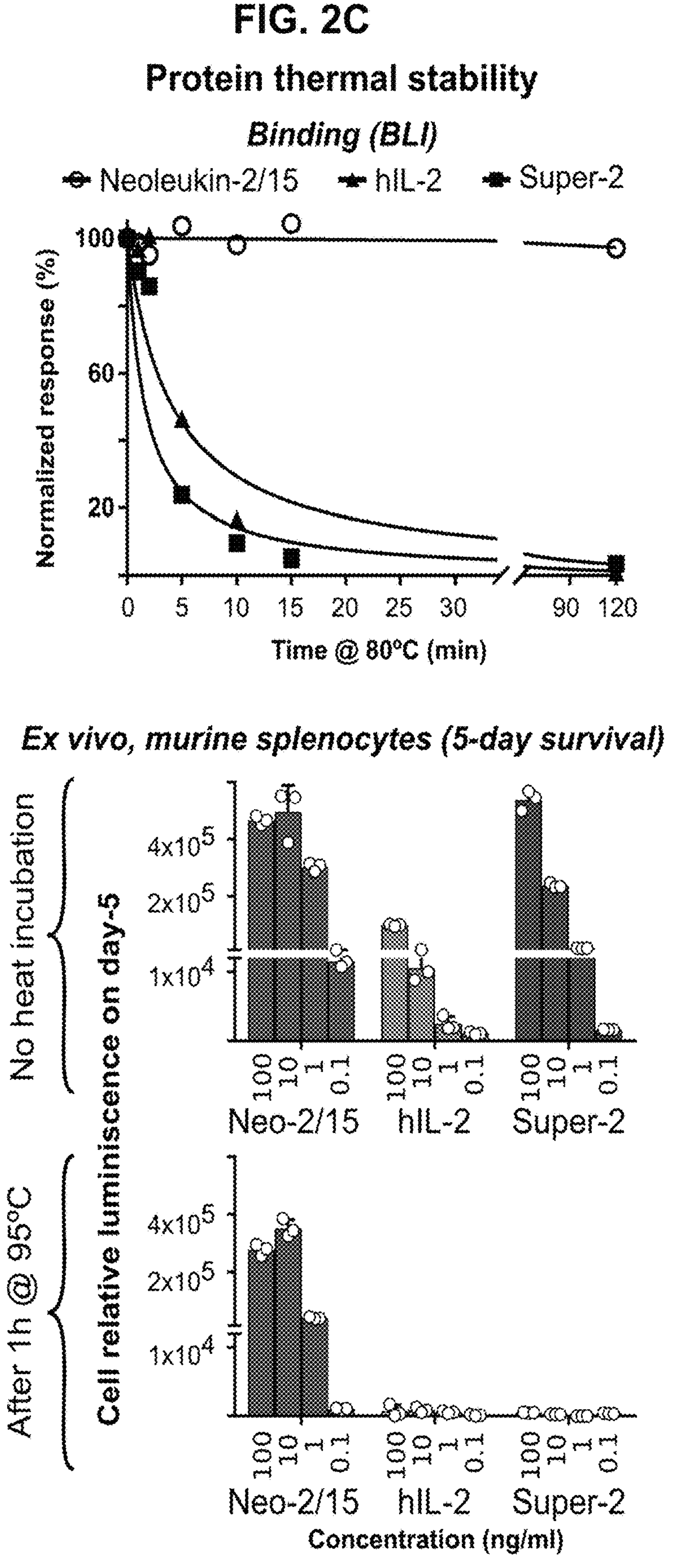

Functional Characterization of Neoleukin-2/15:

Neoleukin-2/15 binds with high affinity to human and mouse IL-2Rβ $\gamma_c$ (Kd~38 nM and ~19 nM, respectively), but does not interact with IL-2Rα (FIG. 2*a*). The affinities of Neoleukin-2/15 for the human and mouse IL-2 receptors (IL-2Rβ and IL-2Rβ $\gamma_c$) are significantly higher than those of the corresponding native IL-2 cytokines. In contrast with native IL-2, Neoleukin-2/15 elicits IL-2Rα-independent signaling in both human and murine IL-2-responsive cells (FIG. 2*b*, top), and in murine primary T cells (FIG. 2*b*, bottom). Neoleukin-2/15 activates IL-2Rα− cells more potently than native human or murine IL-2 in accordance with its higher binding affinity. In primary cells, neoleukin-2/15 is more active on IL-2Rα− cells and less active on IL-2Rα+ compared to Super-2, presumably due to its complete lack of IL-2Rα binding. Neoleukin-2/15 is hyperstable (see FIG. 17) and does not lose binding affinity for hIL-2Rβ $\gamma_c$ following incubation at 80° C. for 2 hours, while hIL-2 and Super-2 are completely inactivated after 10 minutes (half-inactivation time=~4.2 min and ~2.6 min, respectively, FIG. 2*c*). Similarly, in ex vivo primary cell cultures, neoleukin-2/15 drove T cell survival effectively after being boiled for 60 minutes at 95° C., while these conditions inactivated both IL-2 and Super-2 (FIG. 2*c*, bottom). Thermal denaturation studies were carried out on many other of the designed mimetics, demonstrating their thermal stability as well (see FIG. 14-16). This unprecedented stability for a cytokine-like molecule, beyond eliminating the requirement for cold chain storage, suggests a robustness to mutations (see FIGS. 13 and 18-19), genetic fusions and chemical modification greatly exceeding that of native IL-2, which could contribute to the development of improved or new therapeutic properties (see FIG. 7).

Figure 3A:
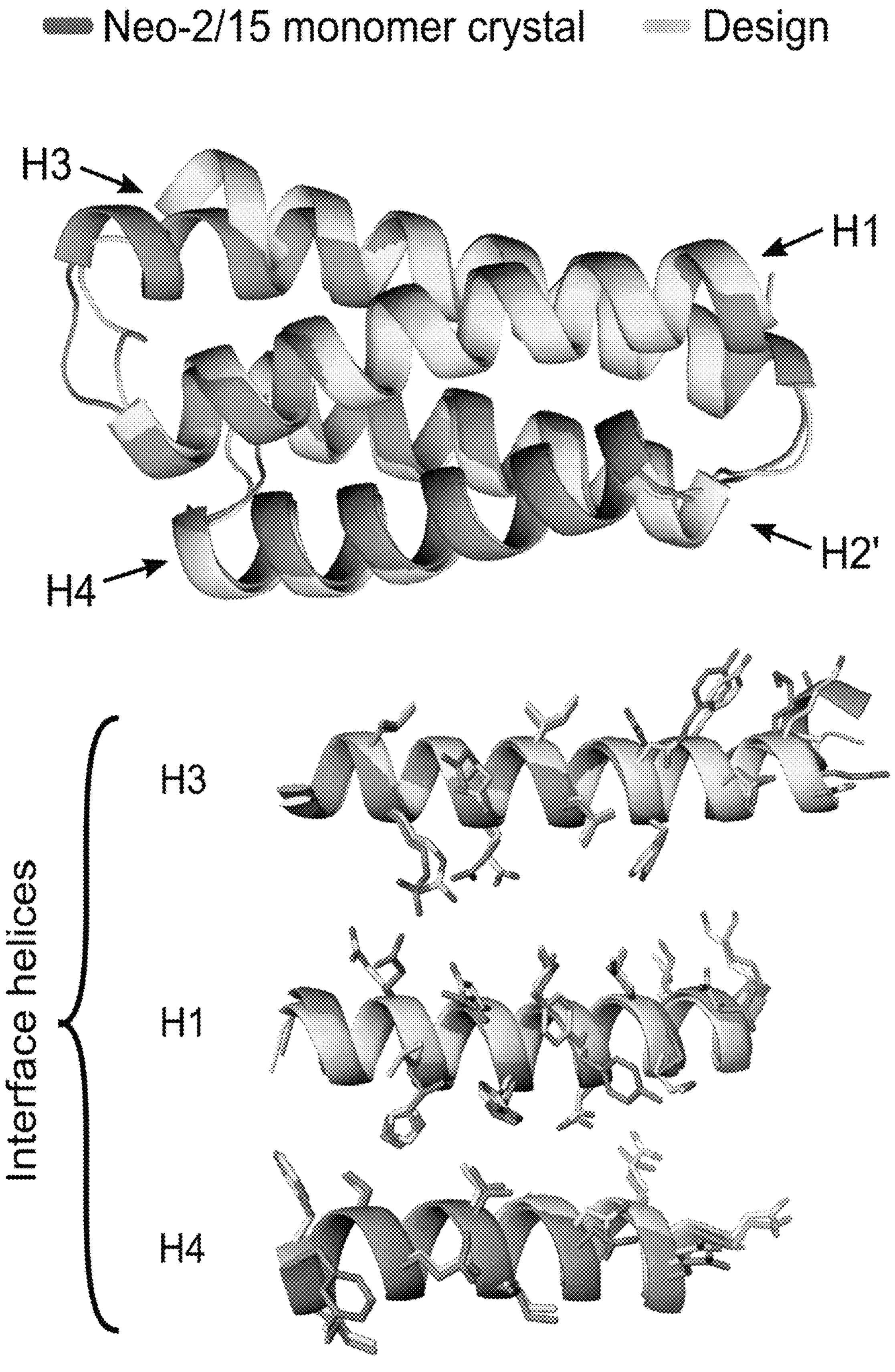
FIG. 3A-3E. Structure of neoleukin-2/15 (Neo-2/15) and its ternary complex with mIL-2R$\beta\gamma_e$.
Figure 3B:
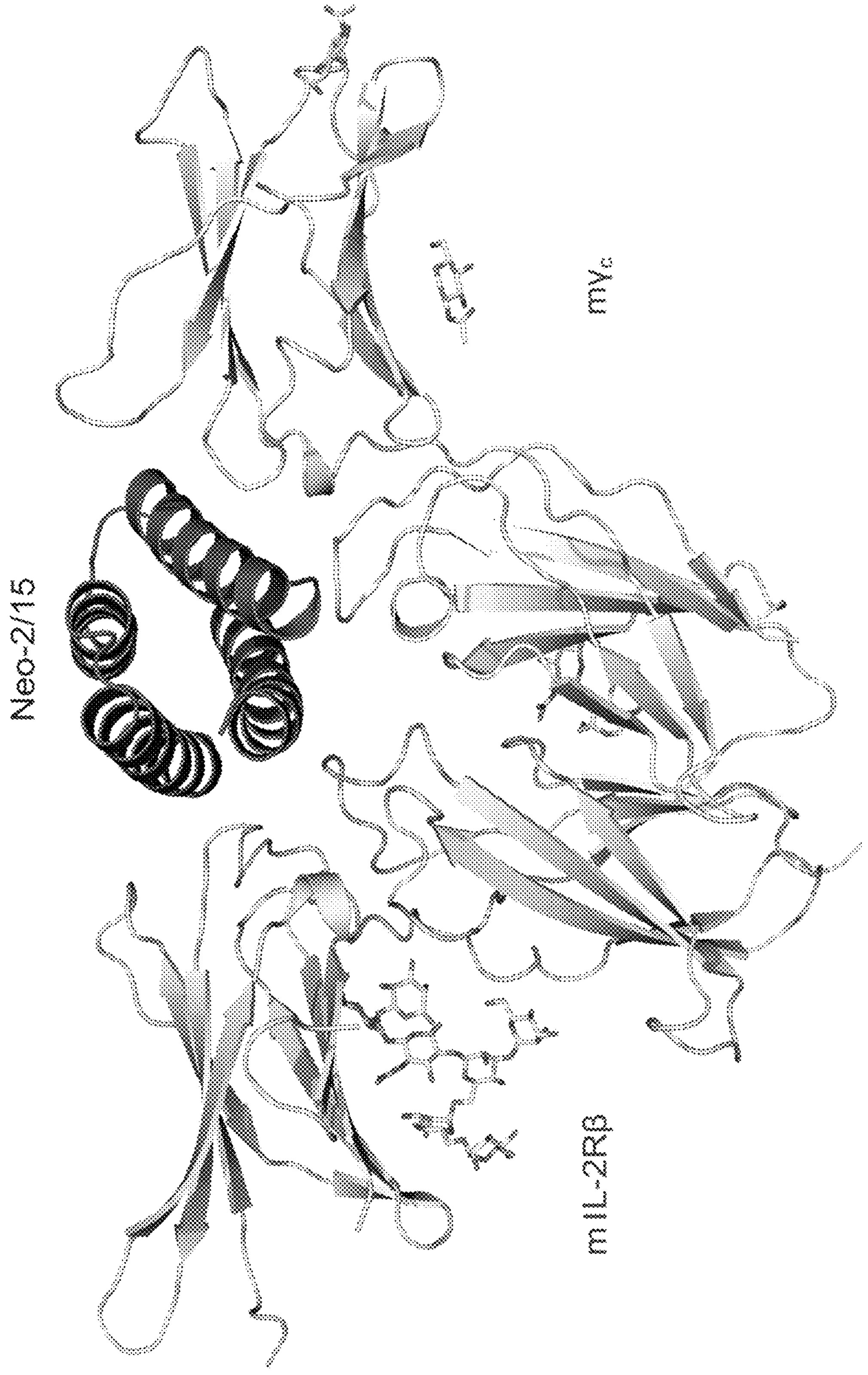
Figure 3C:
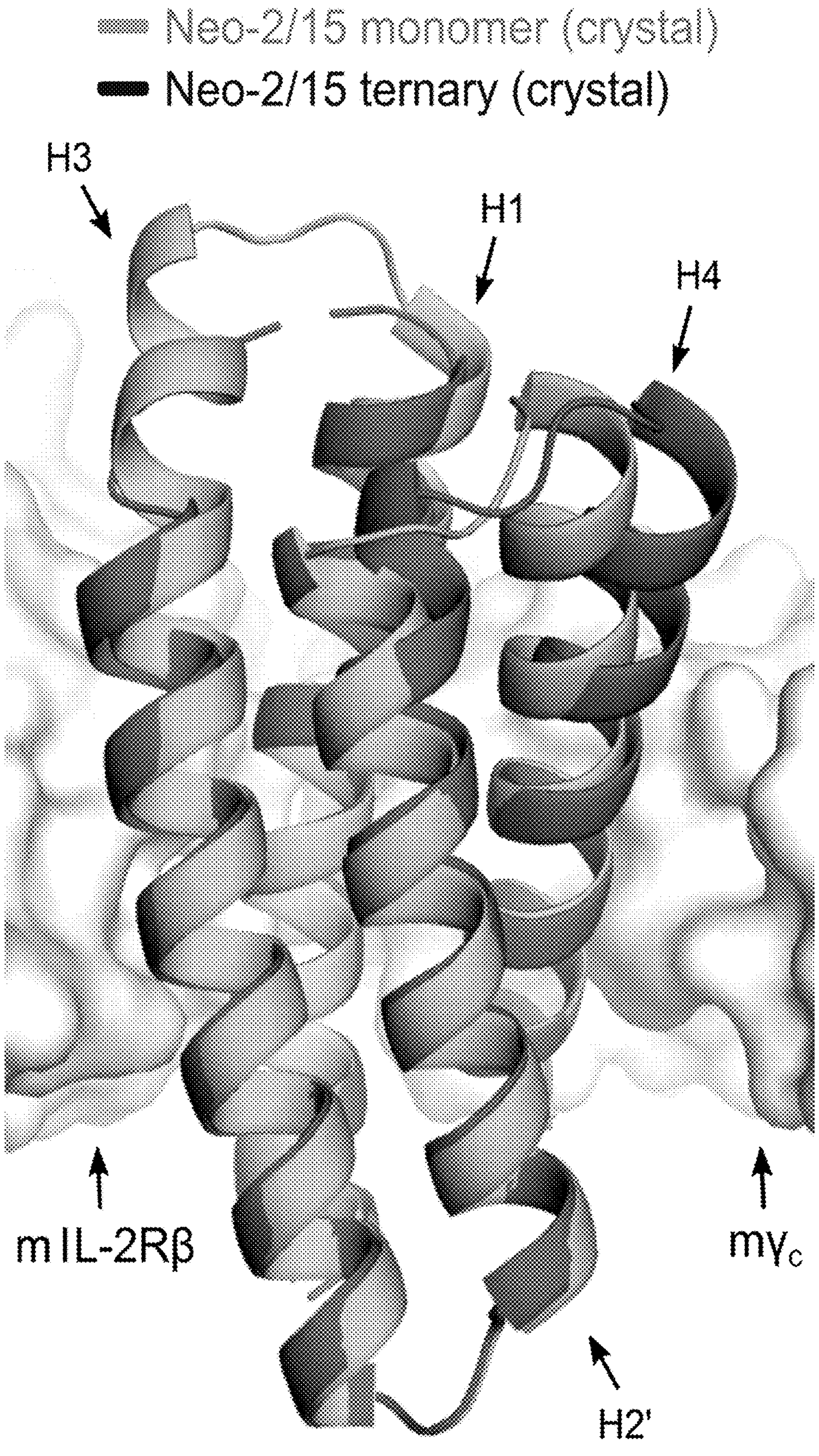
Figure 3D:
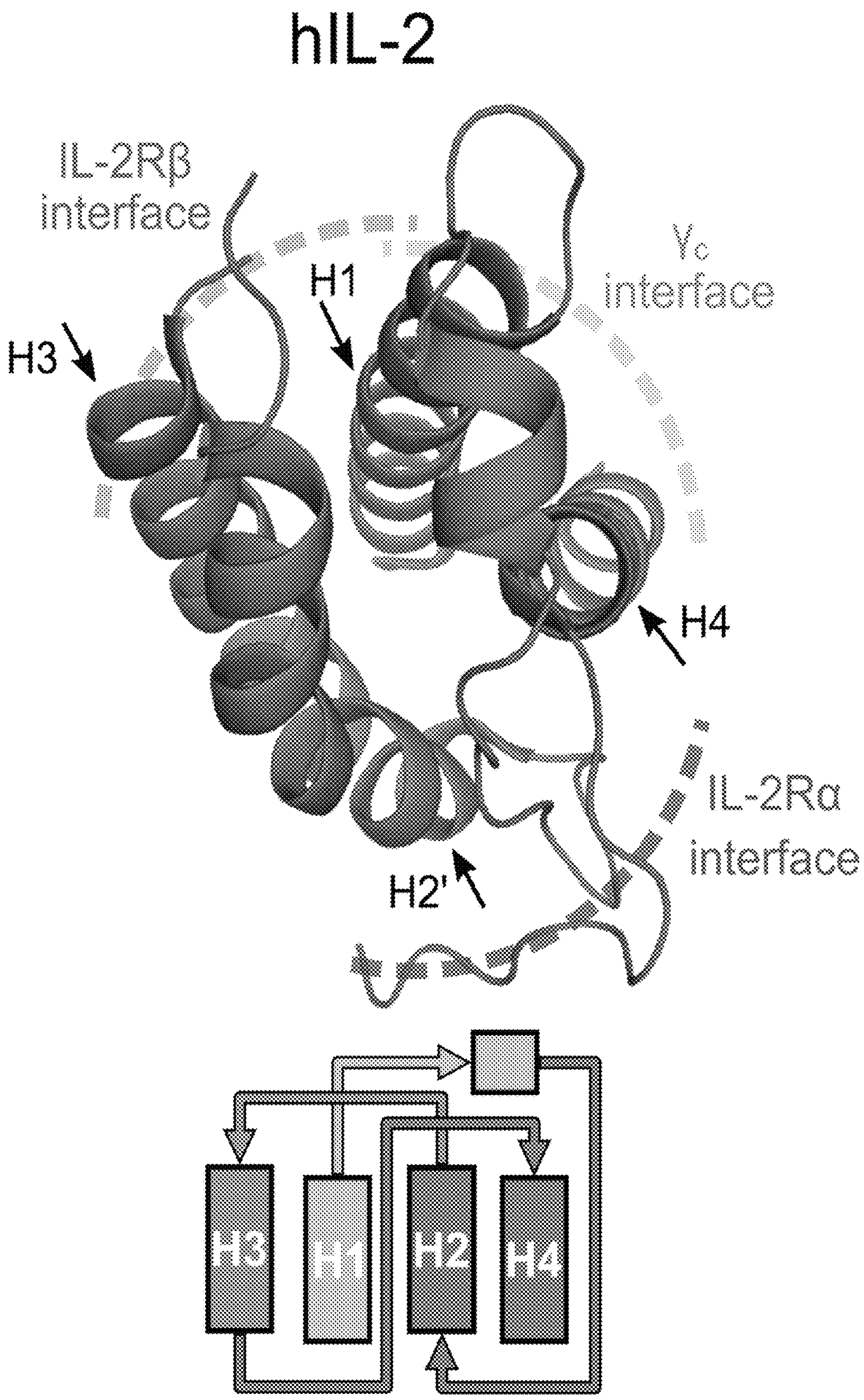
Figure 3E:
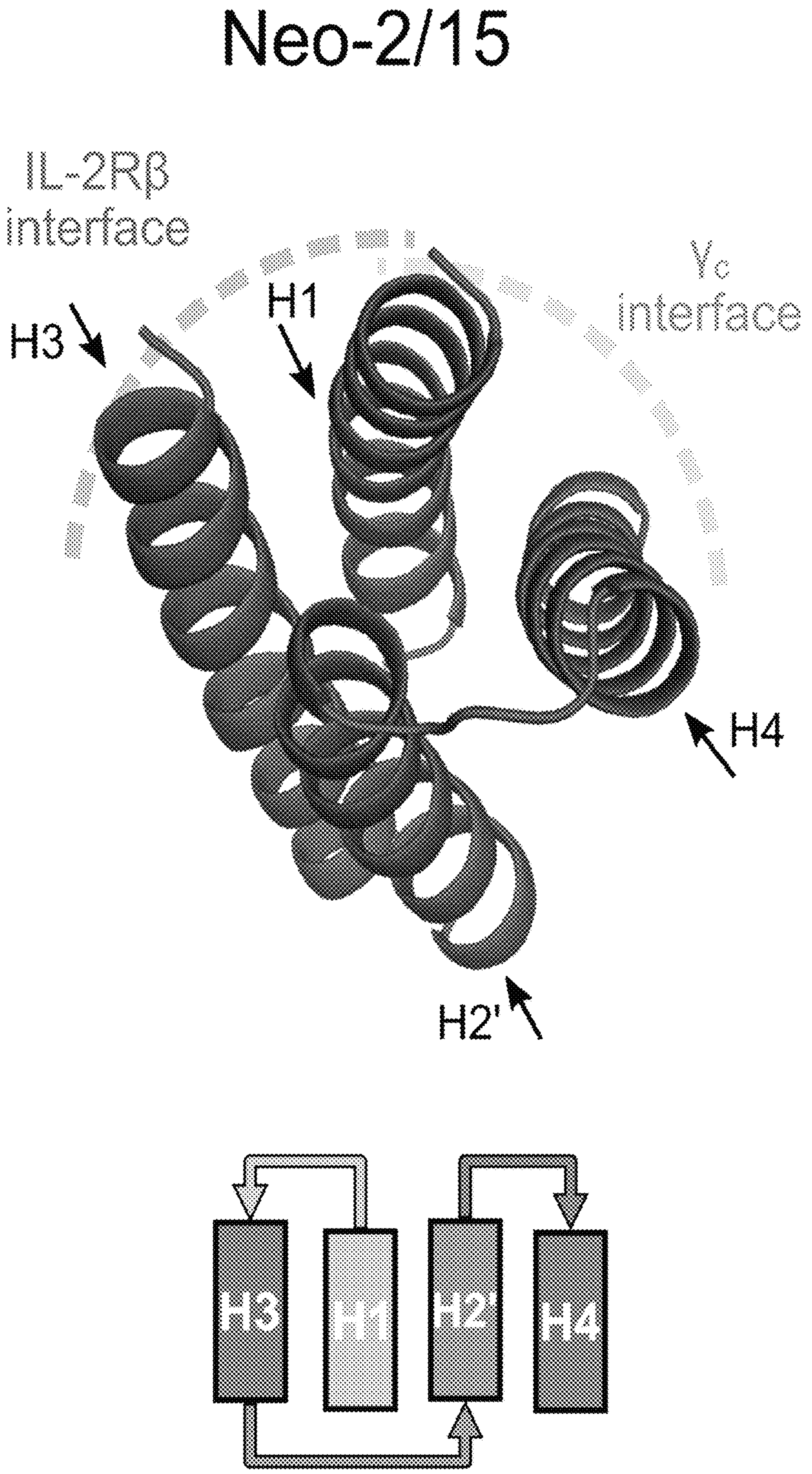

Structure of Monomeric Neoleukin-2/15 and Ternary Complex with mIL-2Rβ $\gamma_c$:

The X-ray crystal structure of neoleukin-2/15 was determined and found it to be very close to the computational design model (r. m.s.d.$_{C\alpha}$=1.1-1.3 Å for the 6 copies in the asymmetric unit, FIG. 3*a*). The crystal structure of neoleukin-2/15 in a ternary complex with murine IL-2Rβ $\gamma_c$ (FIG. 3*b*, Table E2) was solved; this may be the first example in which a de novo designed protein enabled the structural determination of a previously unsolved natural receptor complex. The neoleukin-2/15 design model and crystal structure align with the mouse ternary complex structure with r.m.s.d.$_{C\alpha}$ of 1.27 and 1.29 Å, respectively (FIG. 3*c*). The order of helices in Neoleukin-2/15 (in IL-2 numbering) is H1→H3→H2'→H4 (see FIGS. 1*a* and 3*a,d*). The H1-H3 loop is disordered in the ternary complex, but helix H3 is in close agreement with the predicted structure; there is also an outward movement of helix H4 and the H2'-H4 loop compared to the monomeric structure (FIG. 3*c*). Neoleukin-2/15 interacts with mIL-2Rβ via helices H1 and H3, and with $\gamma_c$ via the H1 and H4 helices (FIG. 3*c*), and these regions align closely with both the computational design model (FIG. 3*a*) and the monomeric crystal structure (FIG. 3*c*). Structural alignment to the previously reported crystal structure of the hIL-2 receptor complex[49] reveals a close agreement between the helical backbones of Neoleukin-2/15 and hIL-2 in the binding site, despite the different topology of the two proteins (FIG. 3*d-e*). Some side chain interactions between neoleukin-2/15 and mIL-2Rβ $\gamma_c$ are present in the hIL-2—hIL-2Rβ γ complex, while others such as L19Y, arose during the computational design process.

Therapeutic Applications of Neoleukin-2/15:

The clinical use of IL-2 has been mainly limited by toxicity[50-52] Although the interactions responsible for IL-2 toxicity in humans are incompletely understood, in murine models toxicity is T cell independent and ameliorated in animals deficient in the IL-2Rα chain (CD25+). Thus, many efforts have been directed to reengineer IL-2 to weaken interactions with IL-2Rα, but mutations in the CD25 binding site can be highly destabilizing[6]. The inherent low stability of IL-2 and its tightly evolved dependence on CD25 have been barriers to the translation of reengineered IL-2 compounds. Other efforts have focused on IL-15[53,54], since it elicits similar signaling to IL-2 by dimerizing the IL-2Rβ $\gamma_c$ but has no affinity for CD25. However, IL-15 is dependent on trans presentation by the IL-15α (CD215) receptor that is displayed primarily on antigen-presenting cells and natural killer cells. The low stability of native IL-15 and its dependence on trans presentation have also been substantial barriers to reengineering efforts[53-55].

Figure 4A:
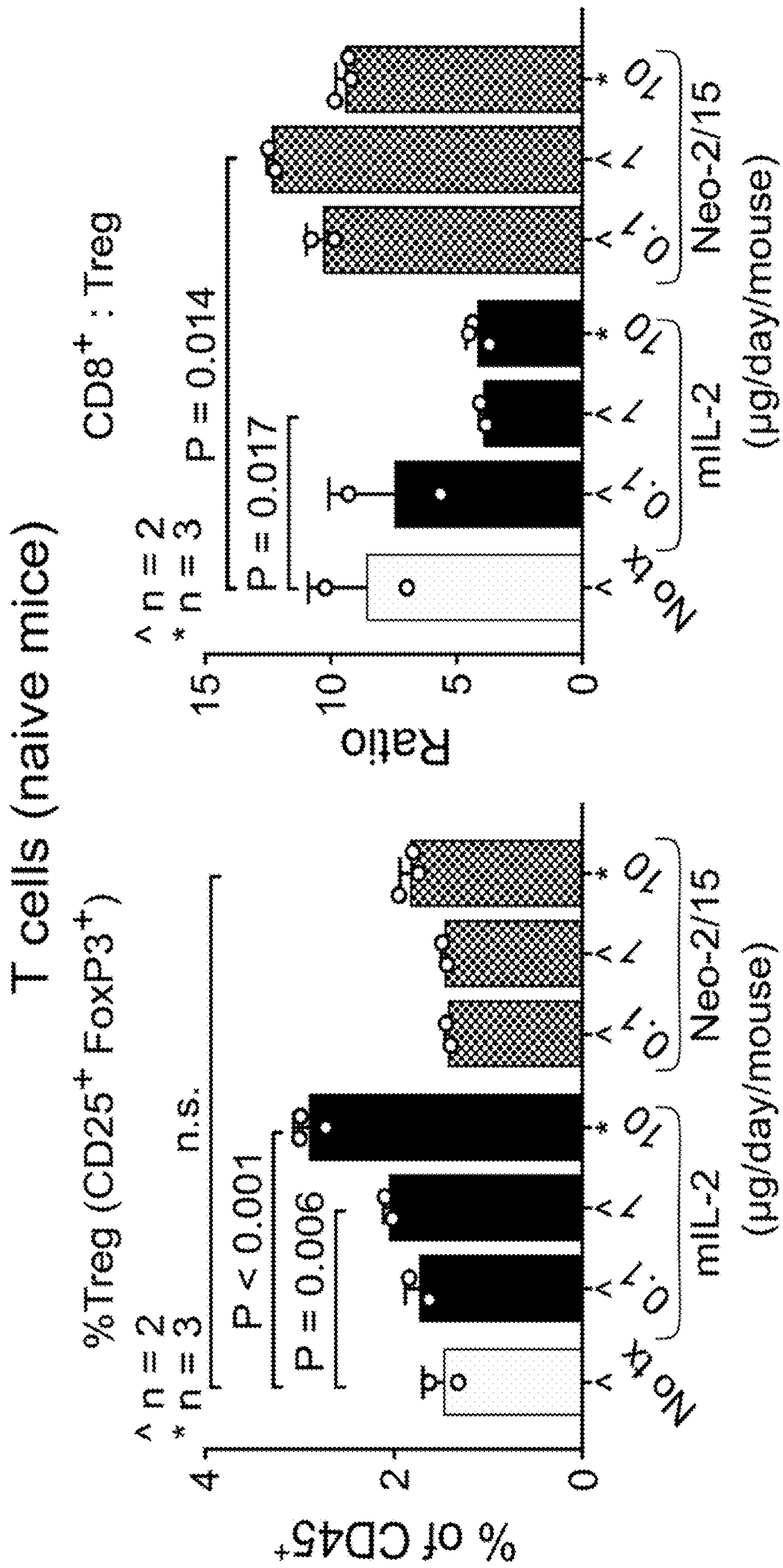
FIG. 4A-4G. Immunogenicity, immunostimulatory and therapeutic activity of neoleukin-2/15.
Figure 4B:
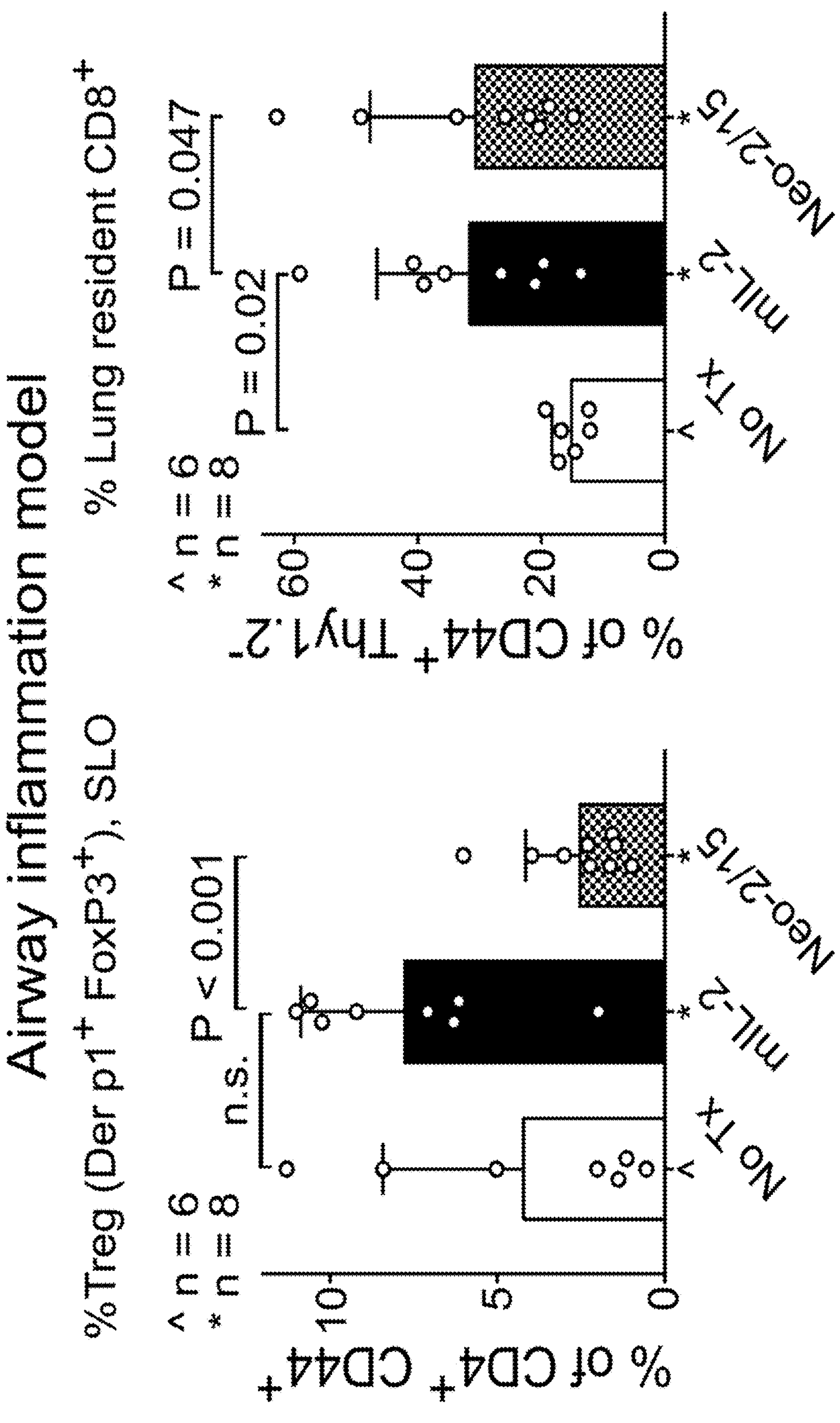

Dose escalation studies on naive mice show that mIL-2 preferentially expands regulatory T cells, consistent with preferential binding to CD25+ cells[41,56,57], while neoleukin-2/15 primarily drives expansion of $CD8^+$ T cells (FIG. 4*a*) and does not induce or minimally induces expansion of regulatory T cells only at the highest dose tested. Similarly, in a murine model of airway inflammation, which normally induces a small percentage of tissue resident CD8+ T cells, neoleukin-2/15 produces an increase in Thy $1.2^-$ $CD44^+$ $CD8^+$ T cells without increasing $CD4^+$ $Foxp3^+$ antigen-specific Tregs in the lymphoid organs (FIG. 4*b*).

Figure 4C:
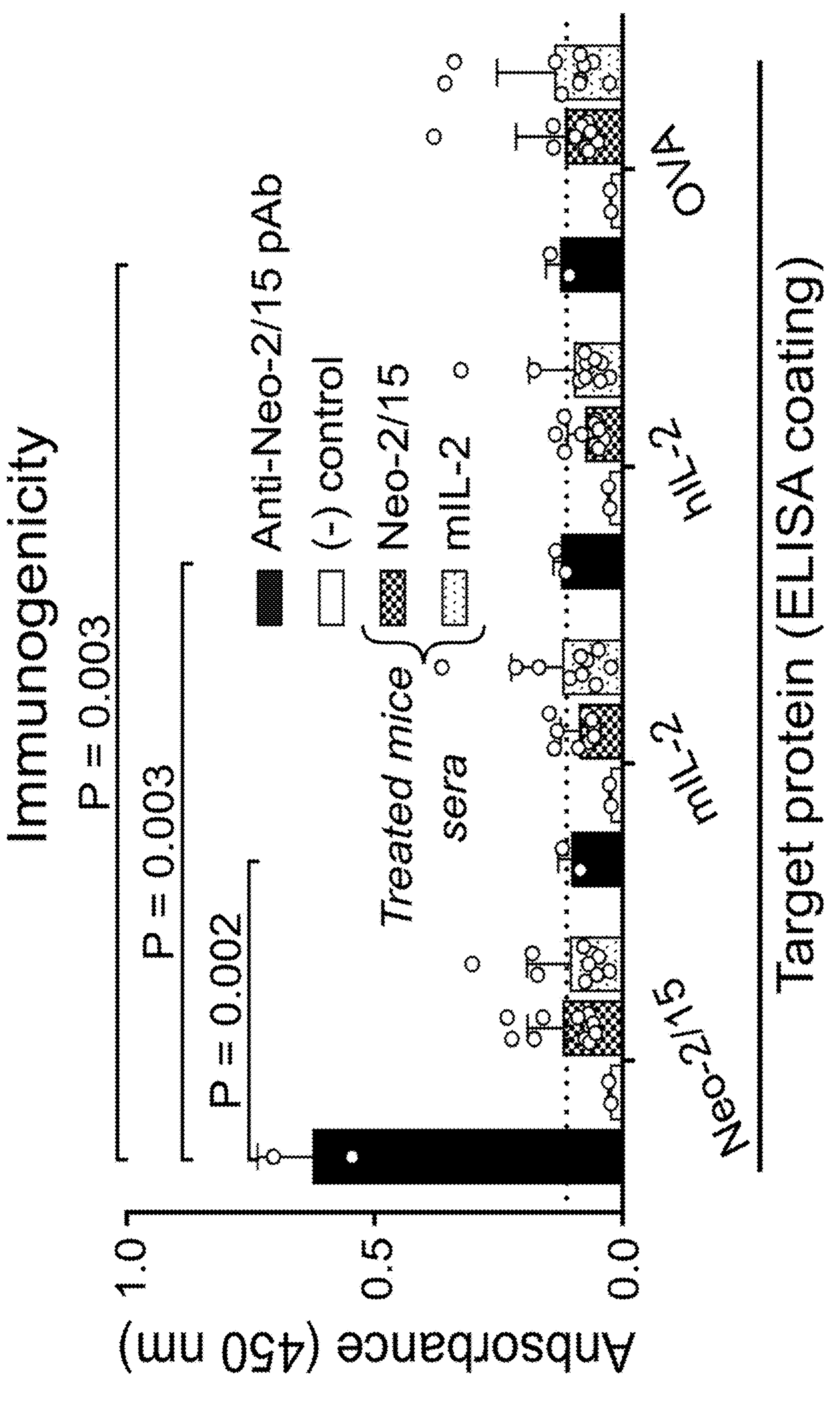

De novo protein design allows the circumvention of the structural limitations of native cytokines, but there is a possibility of eliciting anti-drug antibodies. To test whether neoleukin-2/15 elicits an anti-drug response, tumor-bearing mice were treated daily with neoleukin-2/15 over a period of 2 weeks, and no evidence of anti-drug antibodies was observed in any of the treated animals (FIG. 4*c*, left panel; a similar lack of immune response was observed for other de novo design therapeutic candidates[41]). Polyclonal antibodies against neoleukin-2/15 were produced by vaccinating mice with an inactive neoleukin-2/15 mutant (K.O. neoleukin) in complete Freund's adjuvant. These polyclonal anti-neoleukin-2/15 antibodies did not cross react with human or mouse IL-2 (FIG. 4*c*). The absence of binding to native IL-2 suggests that even if there is an immune response to neoleukin-2/15, this response is unlikely to cross-react with endogenous IL-2. Furthermore, since the sequence identity between neoleukin-2/15 and hIL-2 is low (<30%, see Table E1), an autoimmune response against host IL-2 is much more likely with previous engineered hIL-2 variants (e.g. Super-2, see Table E1) which differ from endogenous IL-2 by only a few mutations.

Figure 4D:
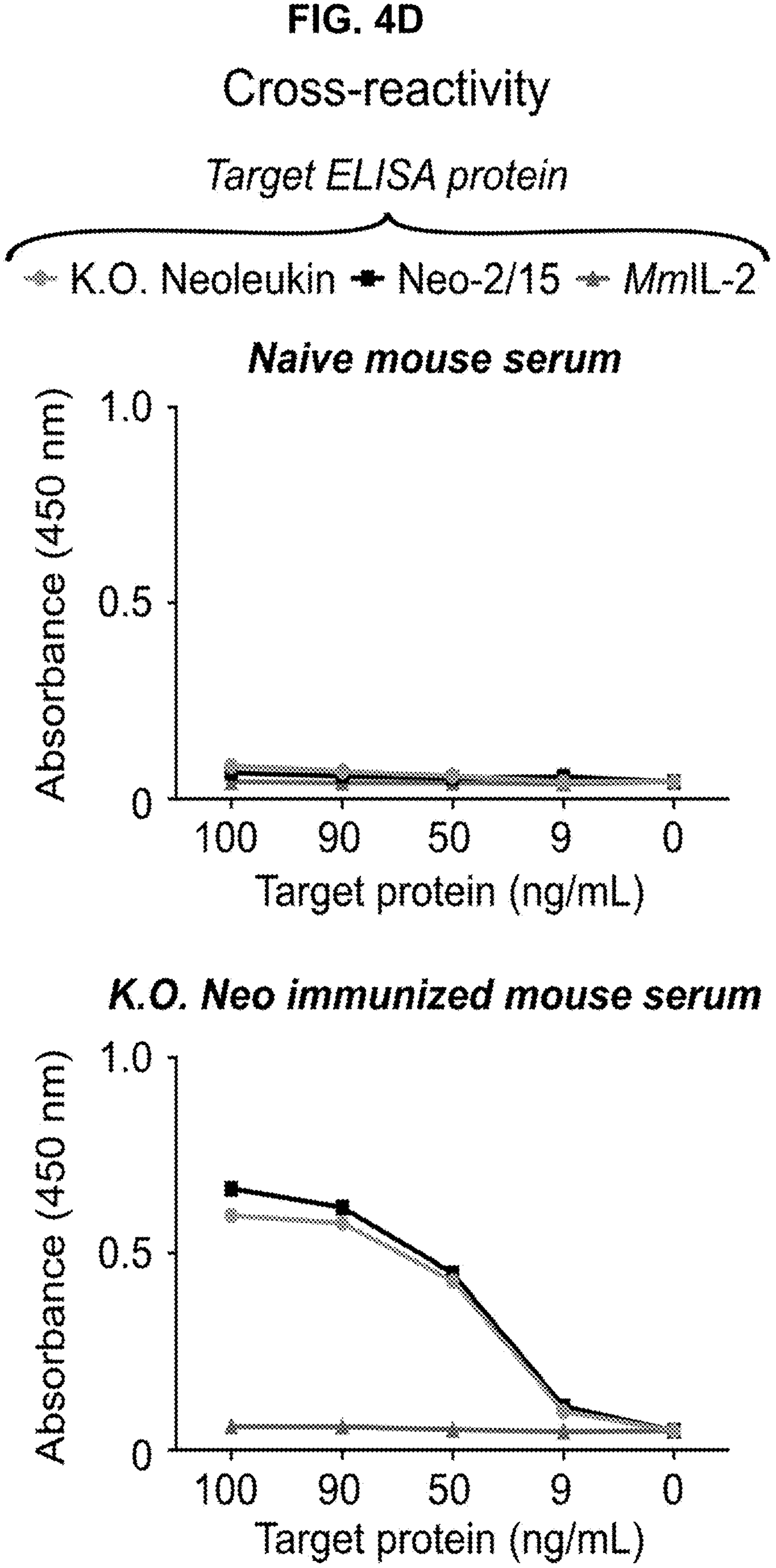
Figure 4E:
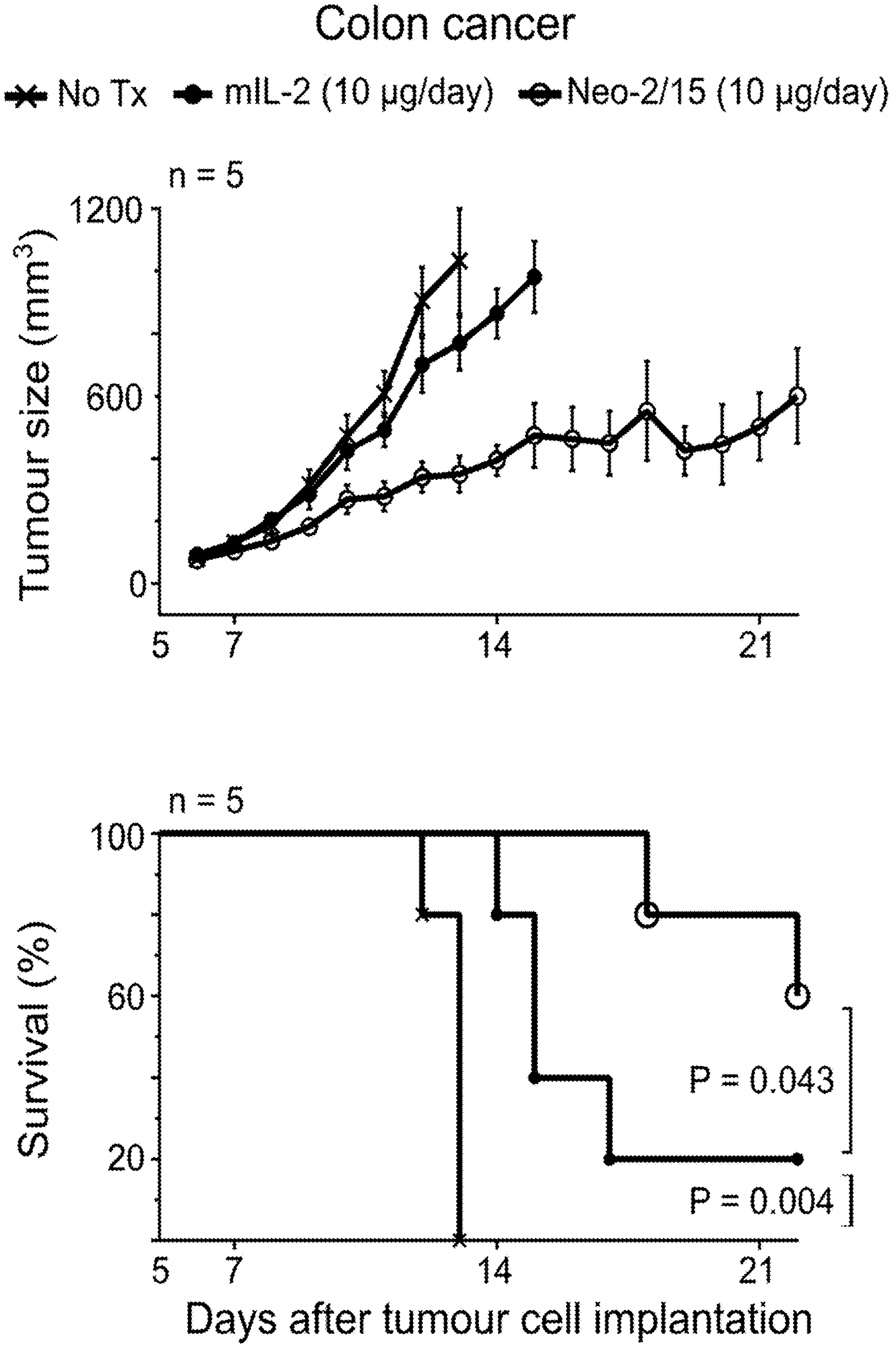
Figure 4F:
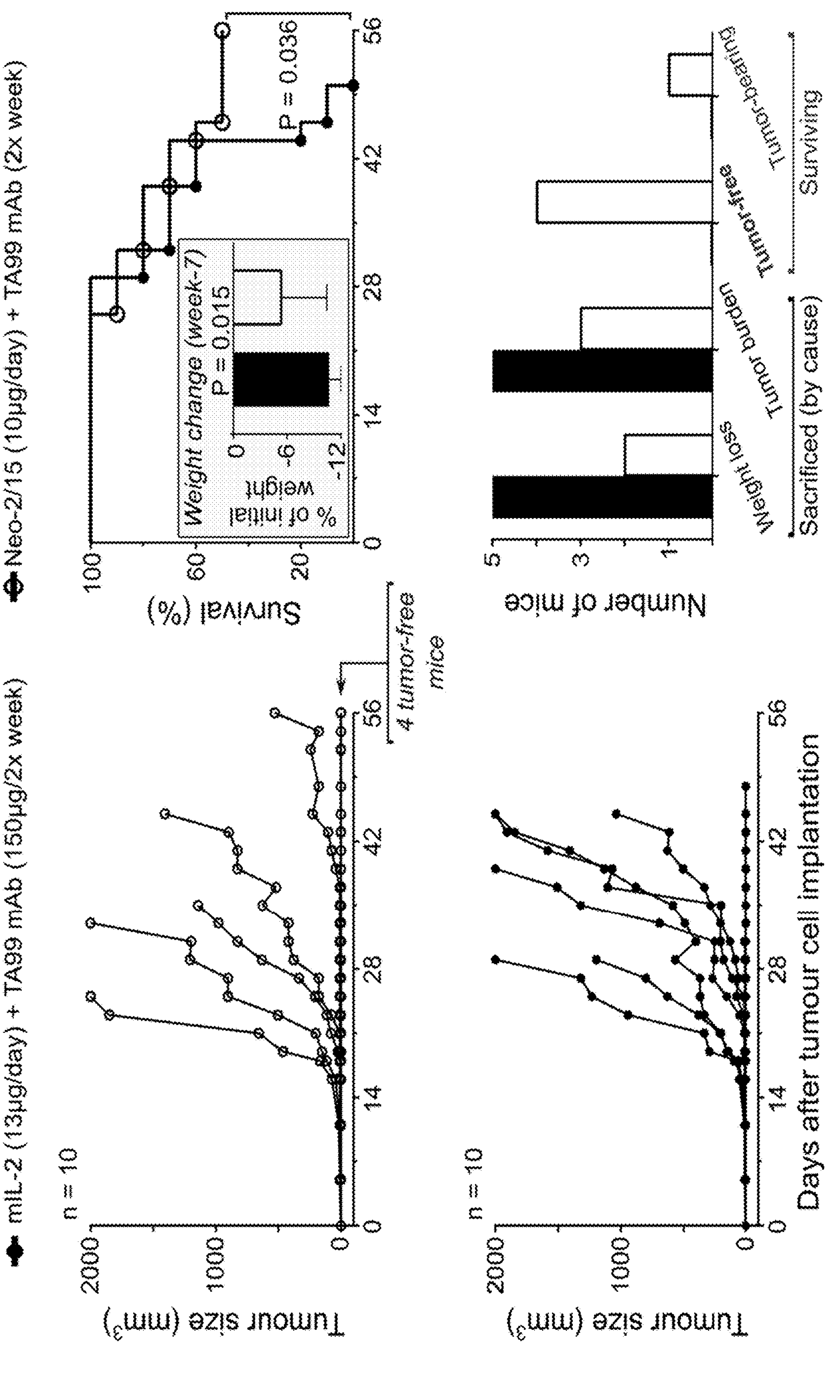
Figure 4G:
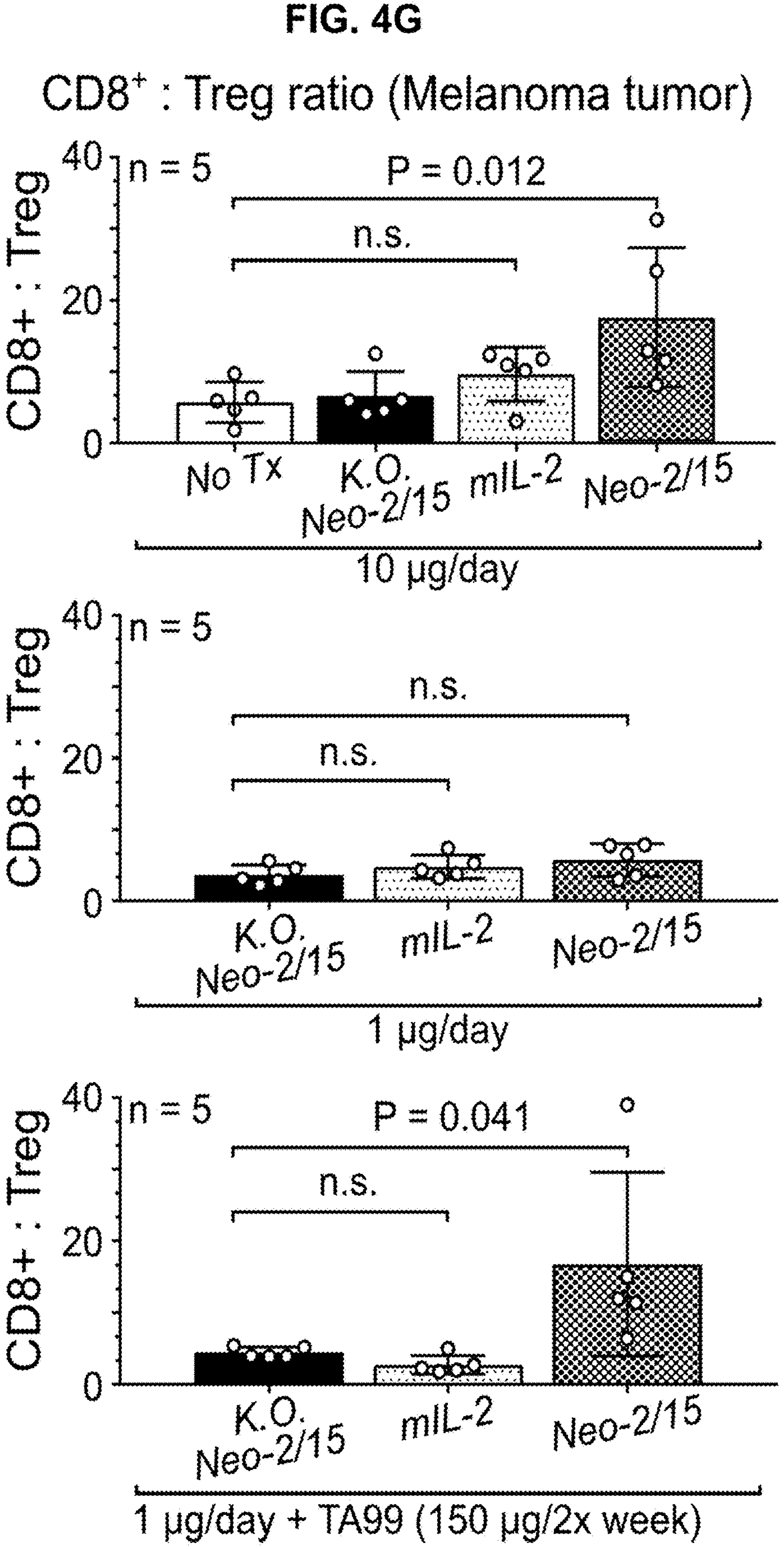
Figure 5A:
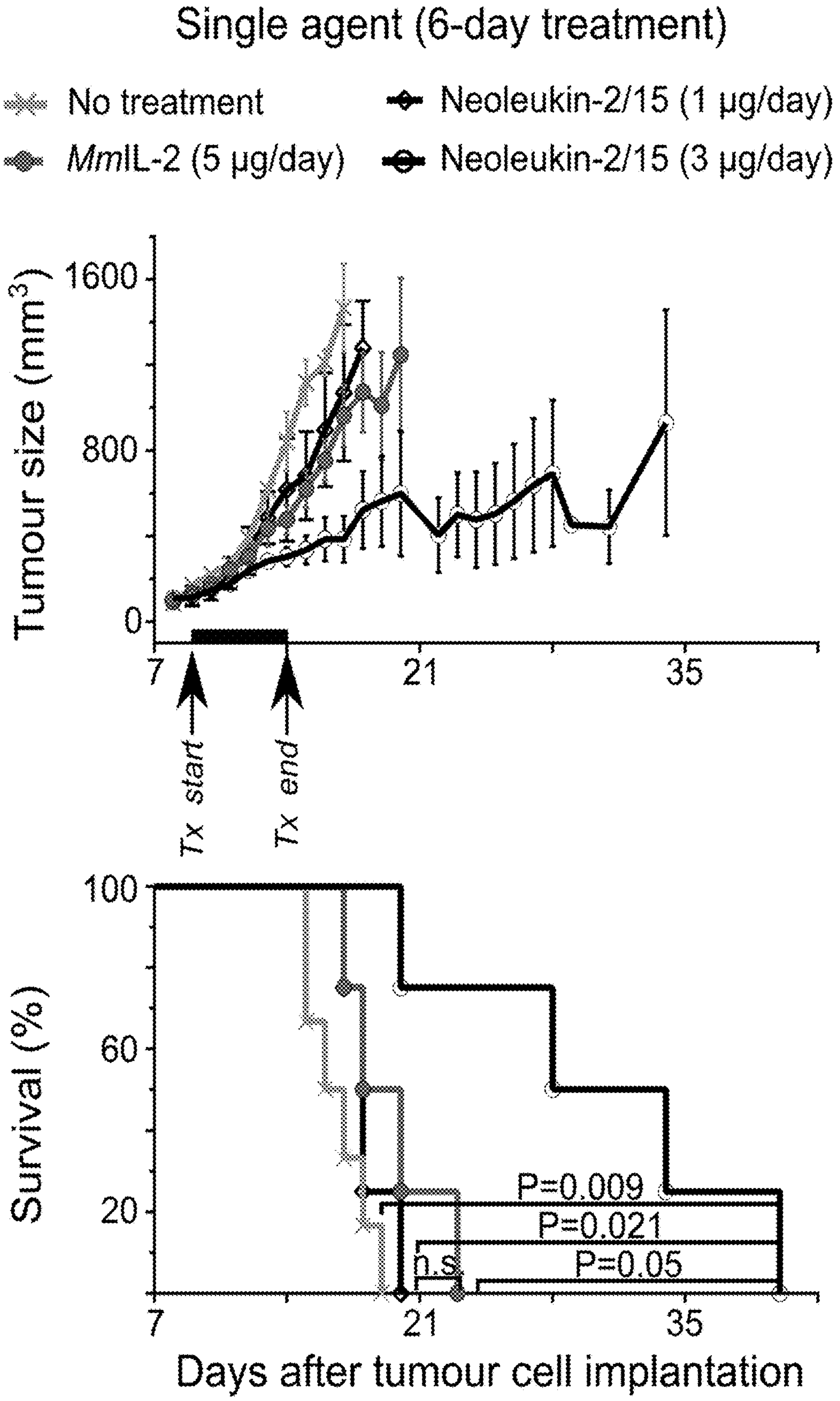
FIG. 5A-5D. Therapeutic effect of neoleukin-2/15 on colon cancer.
Figure 5B:
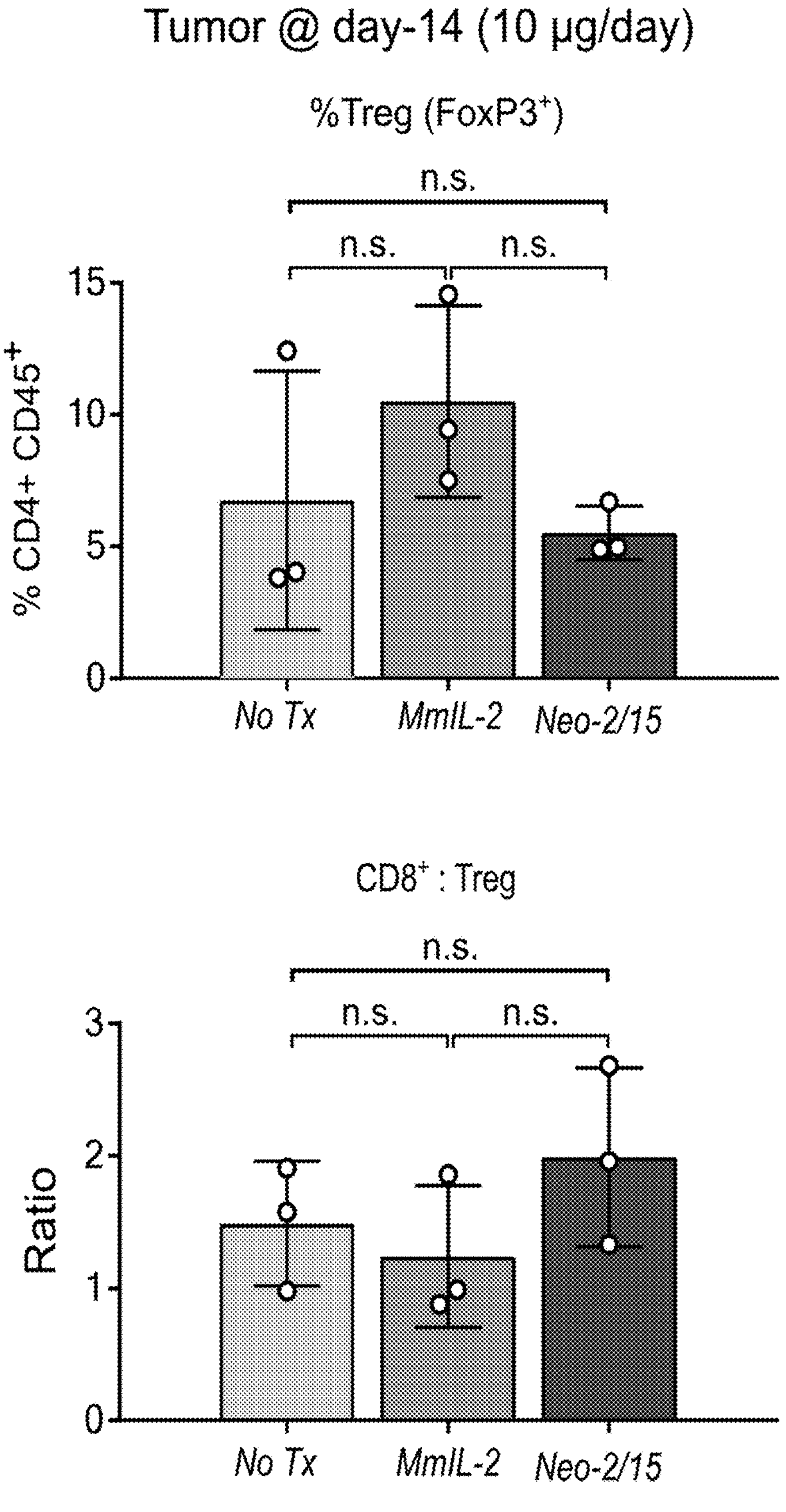
Figure 5C:
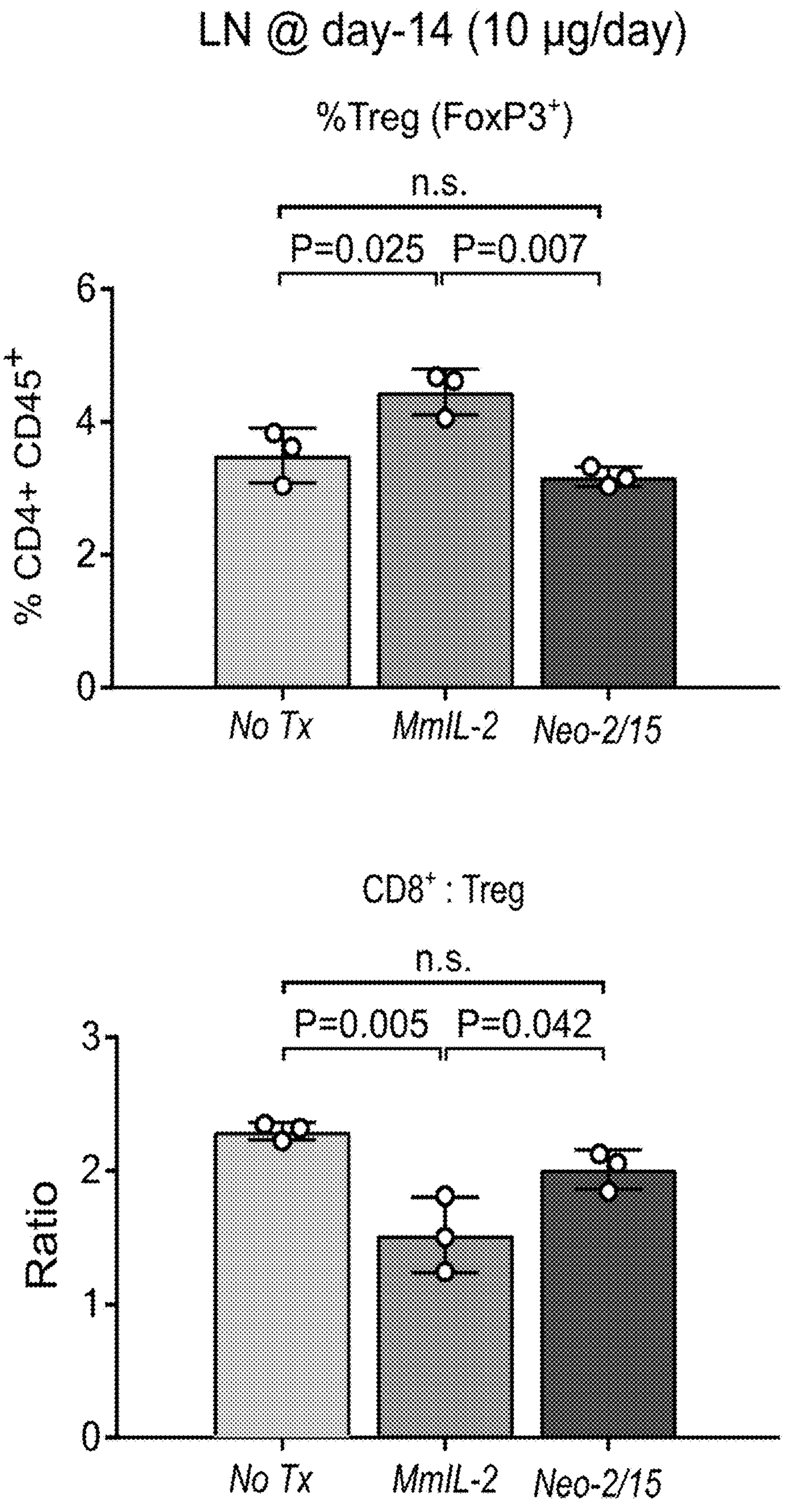
Figure 5D:
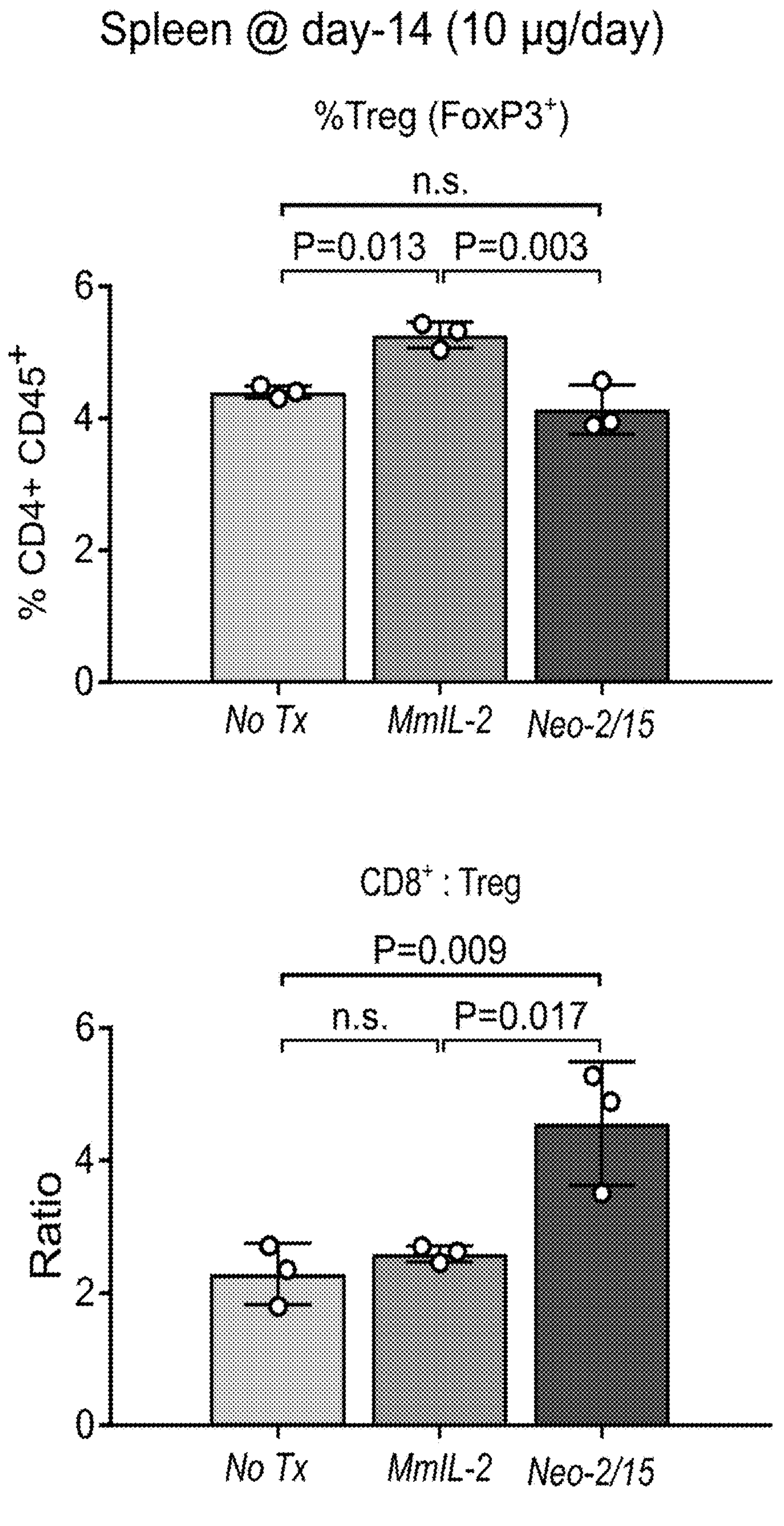
Figure 6A:
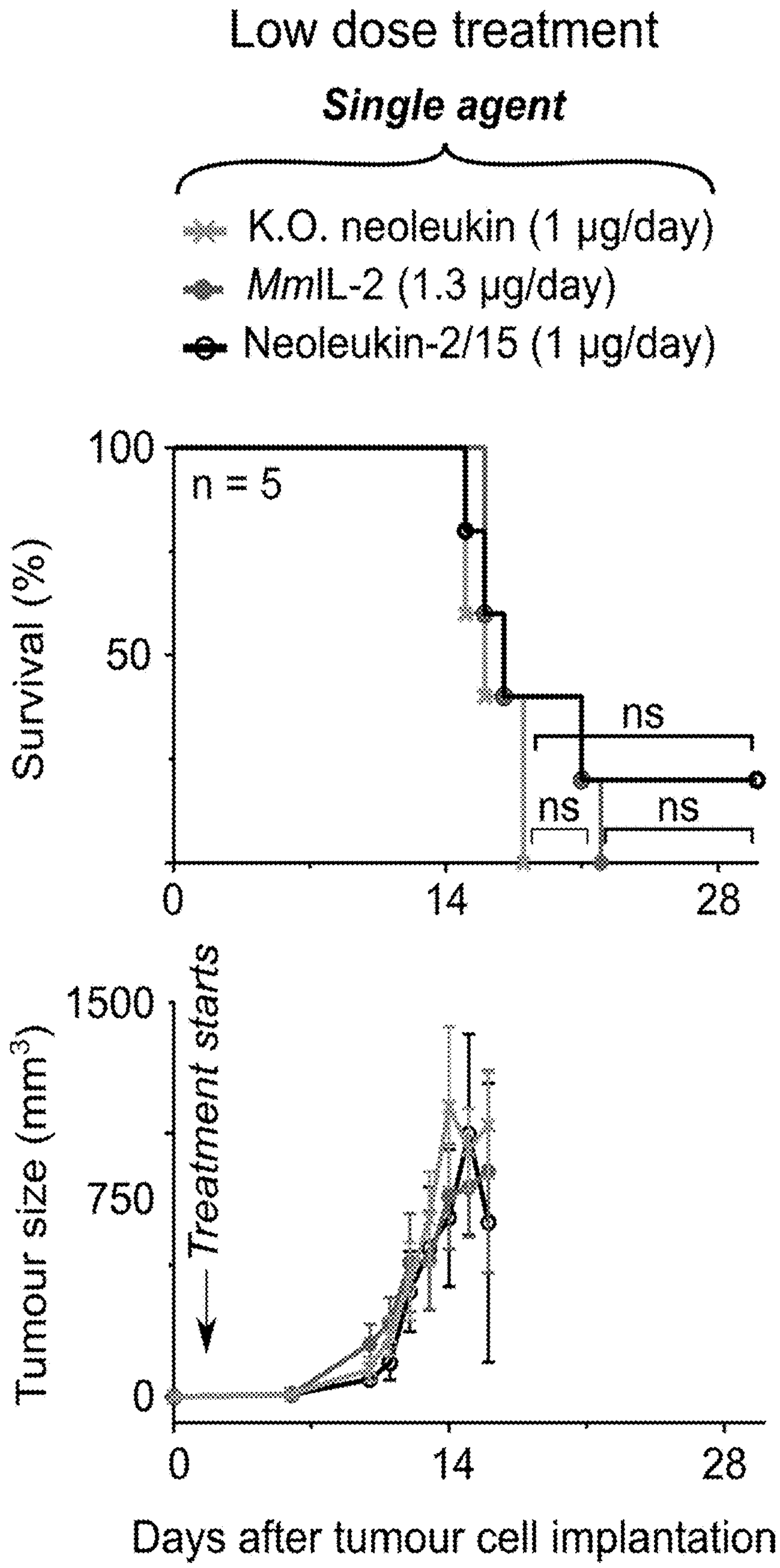
FIG. 6A-6D. Therapeutic effect of neoleukin-2/15 on melanoma.
Figure 6B:
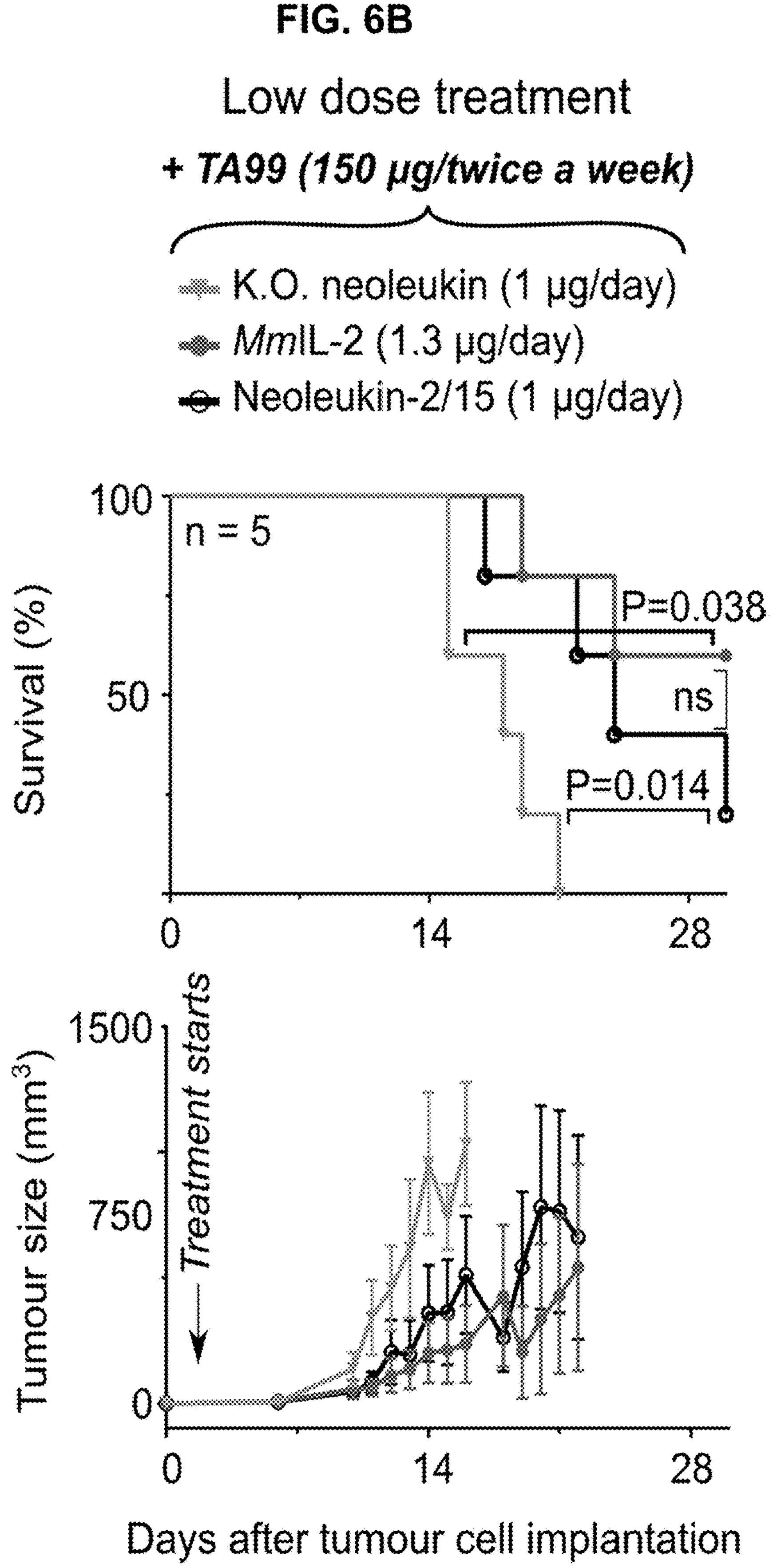
Figure 6C:
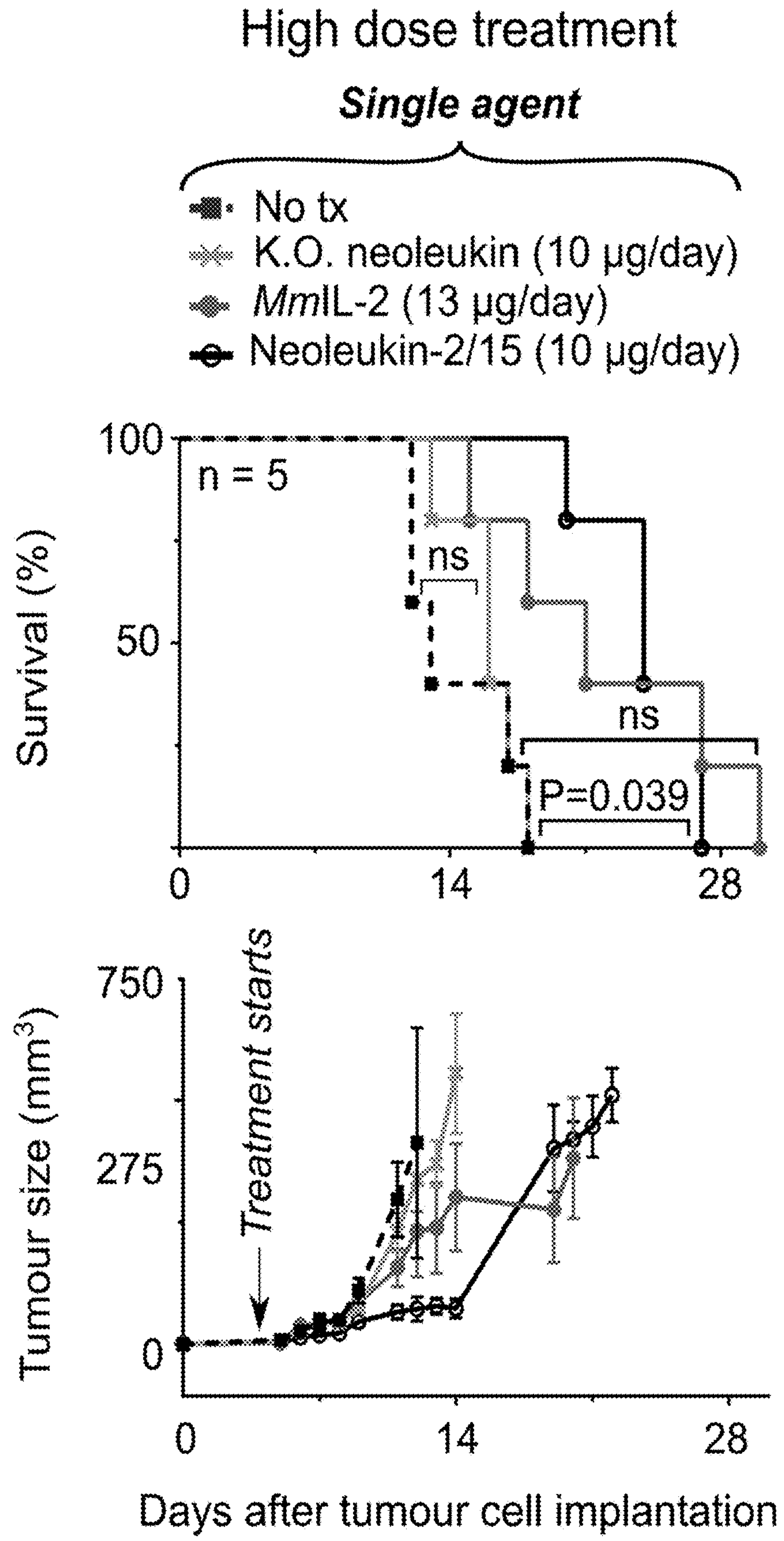
Figure 6D:
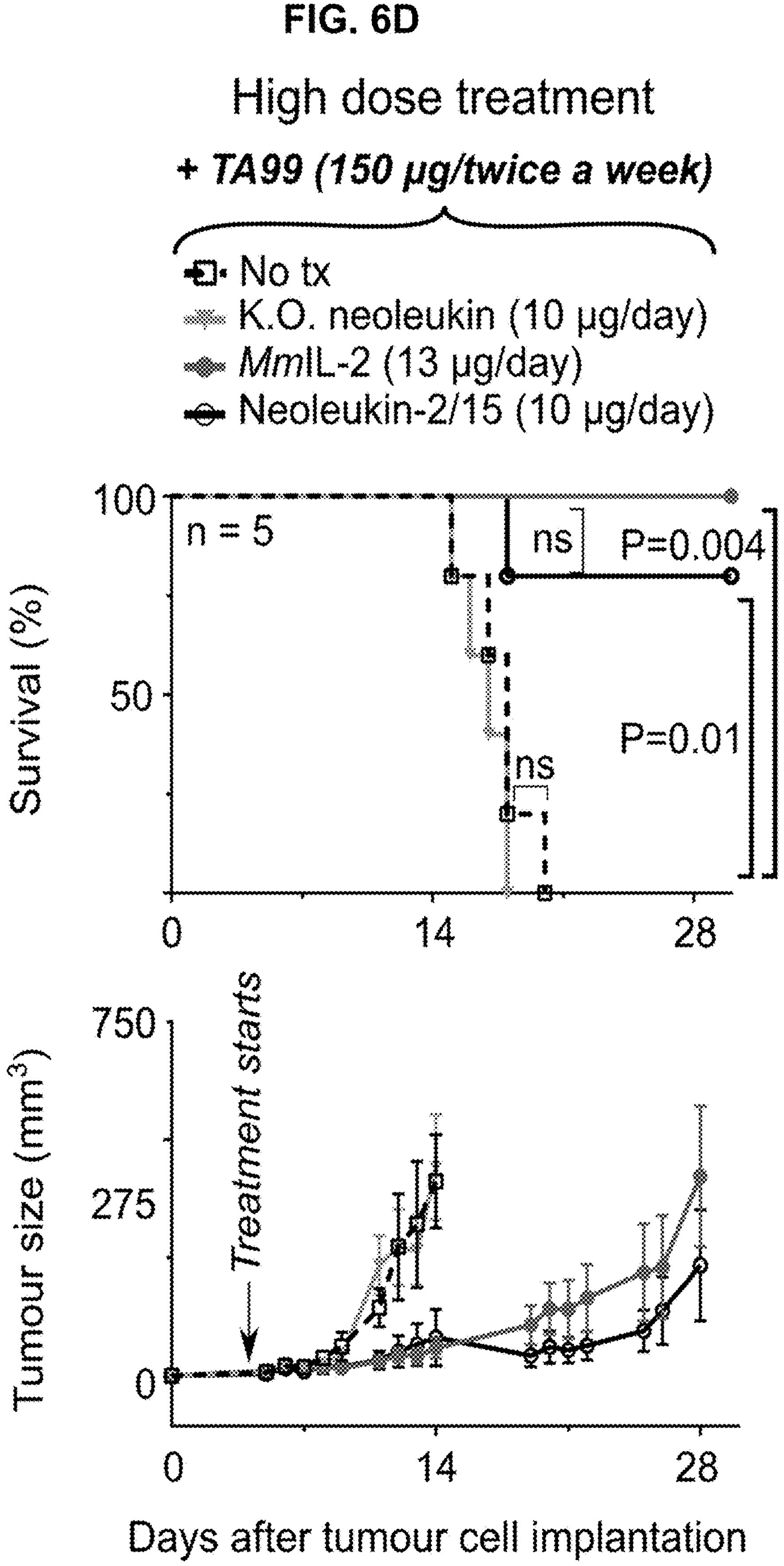
Figure 8A:
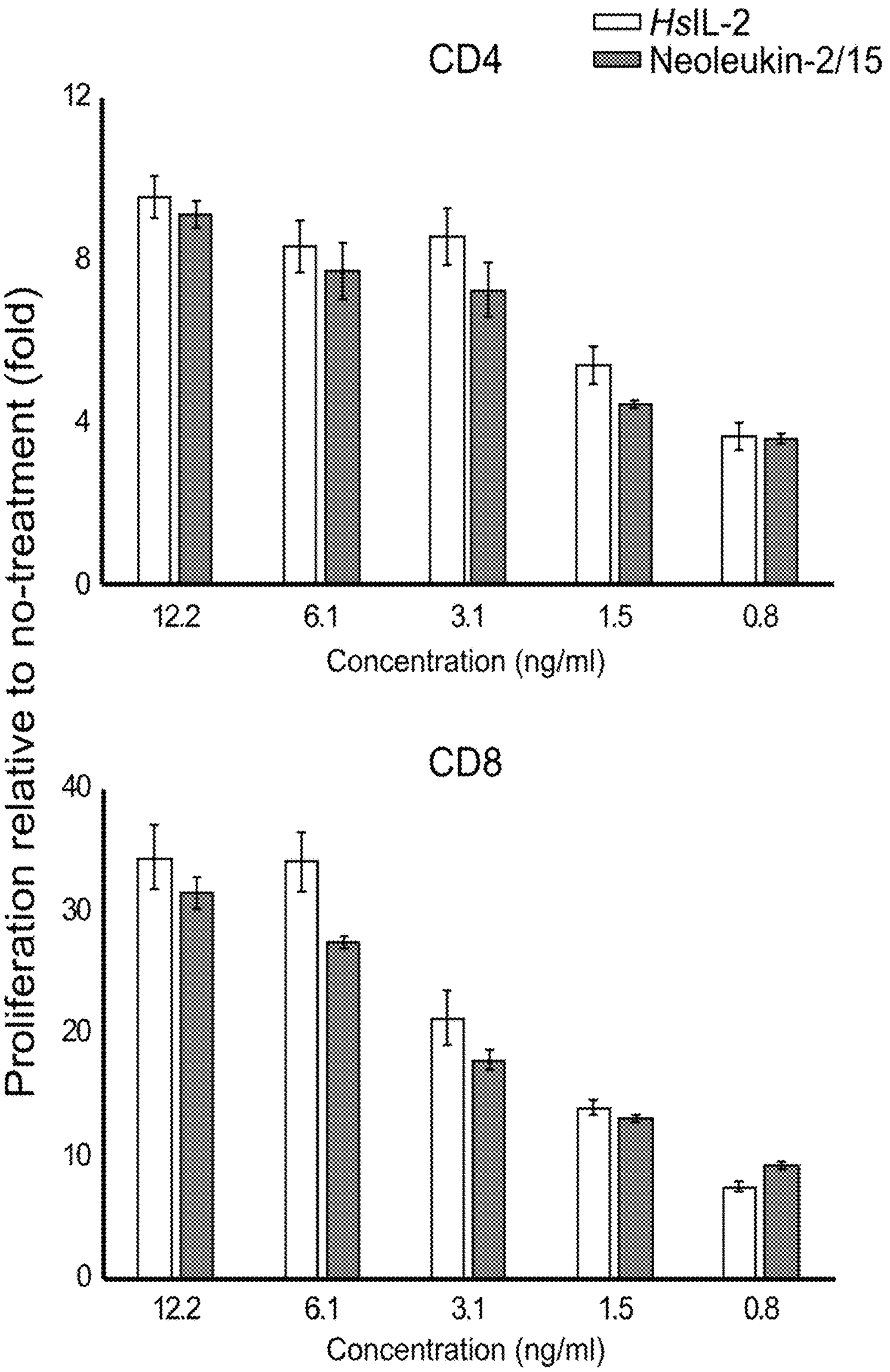
FIG. 8A-8B. Stimulatory effect of Neoleukin-2/15 on human CAR-T cells.
Figure 8B:
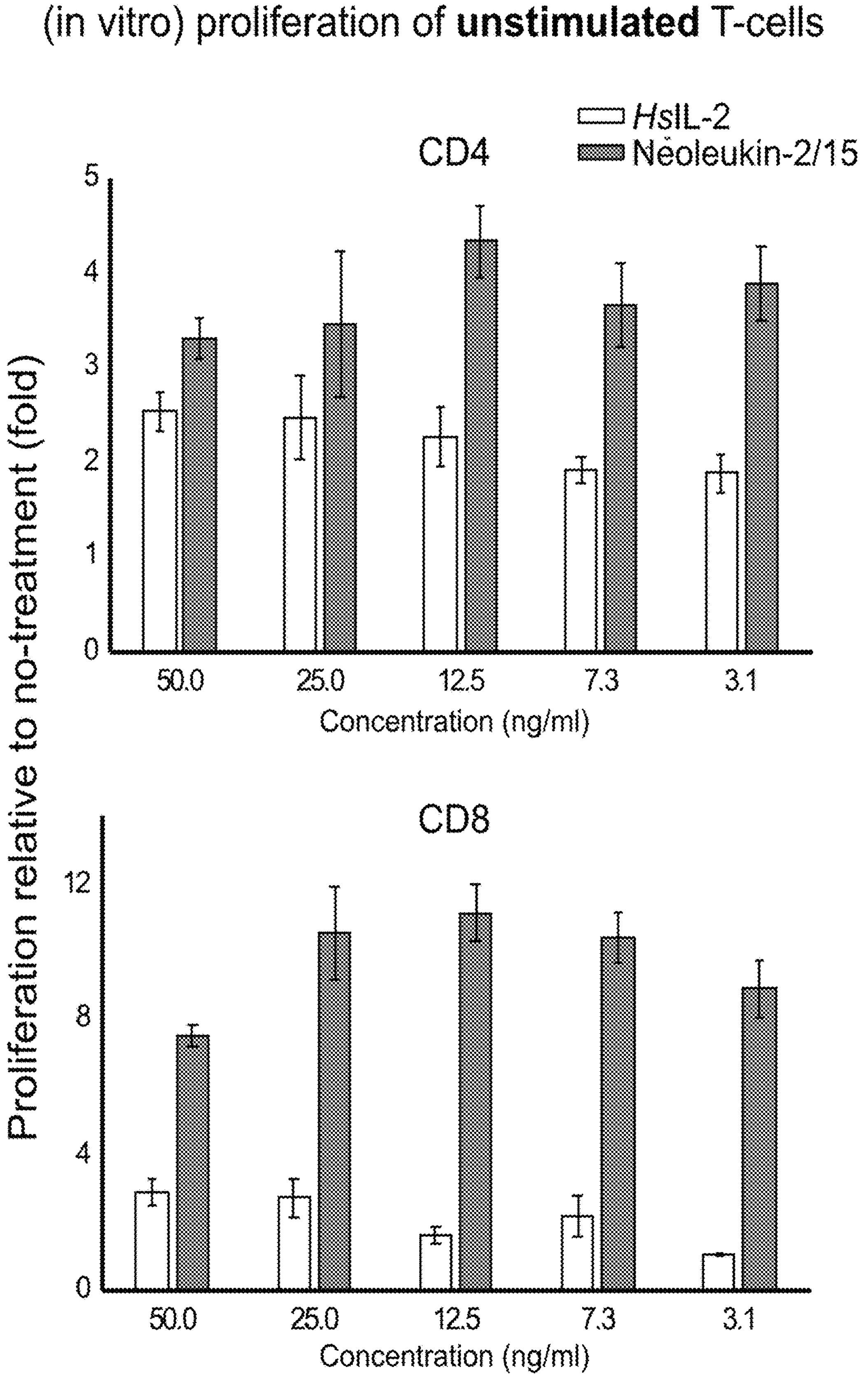
Figure 9A:
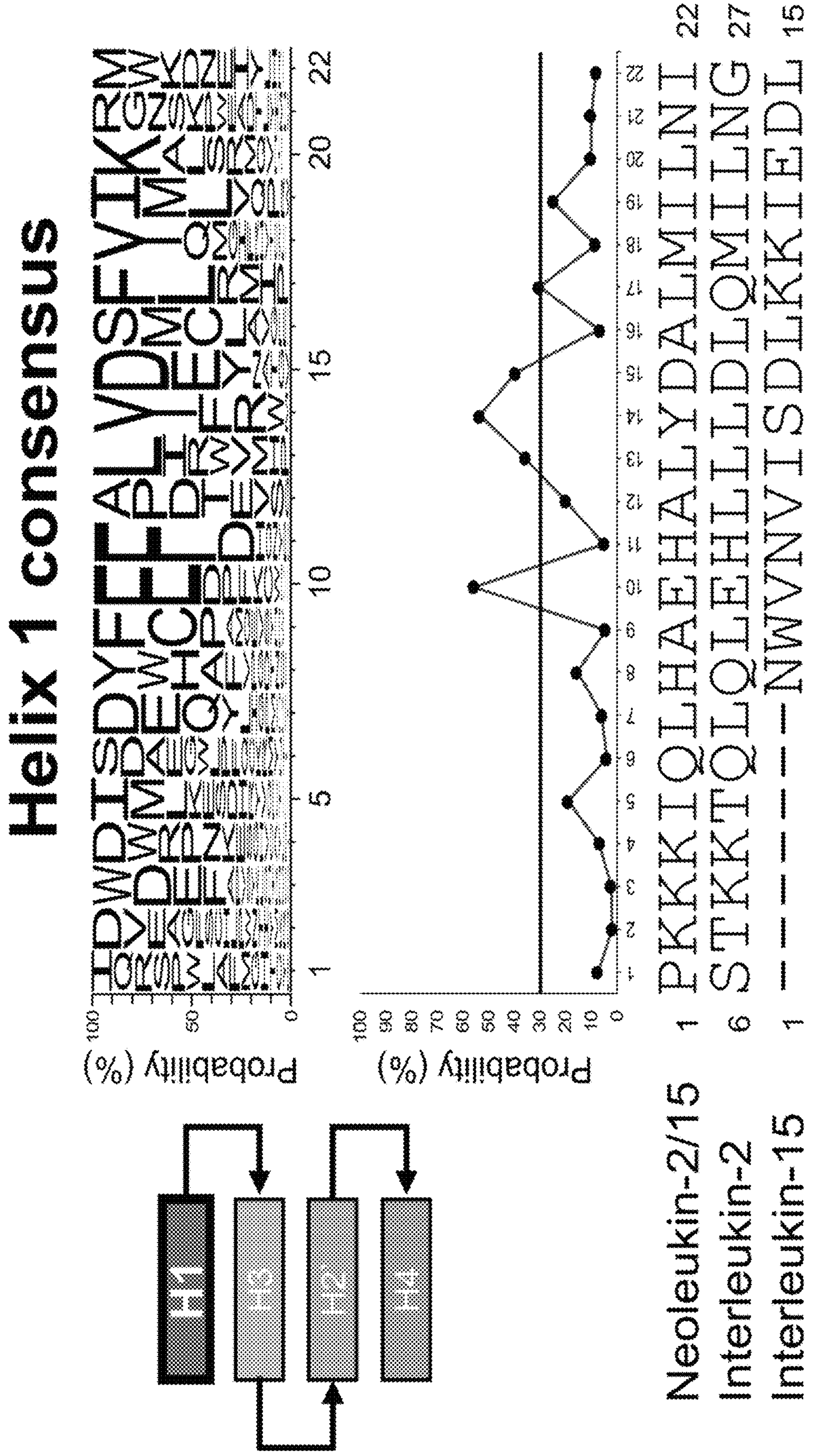
FIG. 9A-9D. Overall sequence conservation in binding residues for each of the four common helices, combining information from three different de novo-designed IL-2 mimics. Sequence logos were generated using combined data from binding experiments (using the heterodimeric mouse IL-2Rβ$\gamma$c) from three independent SSM mutagenesis libraries for G2_neo2_40_1F_seg27, G2_neo2_40_1F_seg29 and G2_neo2_40_1F_seg36 (FIGS. 11-13). All of these proteins are functional high-affinity de novo mimetics of mouse and human IL-2, some having topologies that differ from that of Neo-2/15, but all containing the four Helices H1 (FIG. 9A; Neo-2/15 1-22 is SEQ ID NO:248, IL-2 6-27 is SEQ ID NO:249, IL-15 1-15 is SEQ ID NO:250), H3 (FIG. 9B; Neo-2/15 34-55 is SEQ ID NO:251, IL-2 82-103 is SEQ ID NO:252, IL-15 59-80 is SEQ ID NO:253), H2' (FIG. 9C; Neo-2/15 58-76 is SEQ ID NO:254, IL-2 50-68 is SEQ ID NO:255, IL-15 34-52 is SEQ ID NO:256) and H4 (FIG. 9D; Neo-2/15 80-100 is SEQ ID NO:257, IL-2 111-131 is SEQ ID NO:258, IL-15 93-113 is SEQ ID NO:259). The logos show the combined information for each helix independently. Below each logo, a line graph shows the probability score (higher means more conserved) for each amino acid in the Neo-2/15 sequence.
Figure 9B:
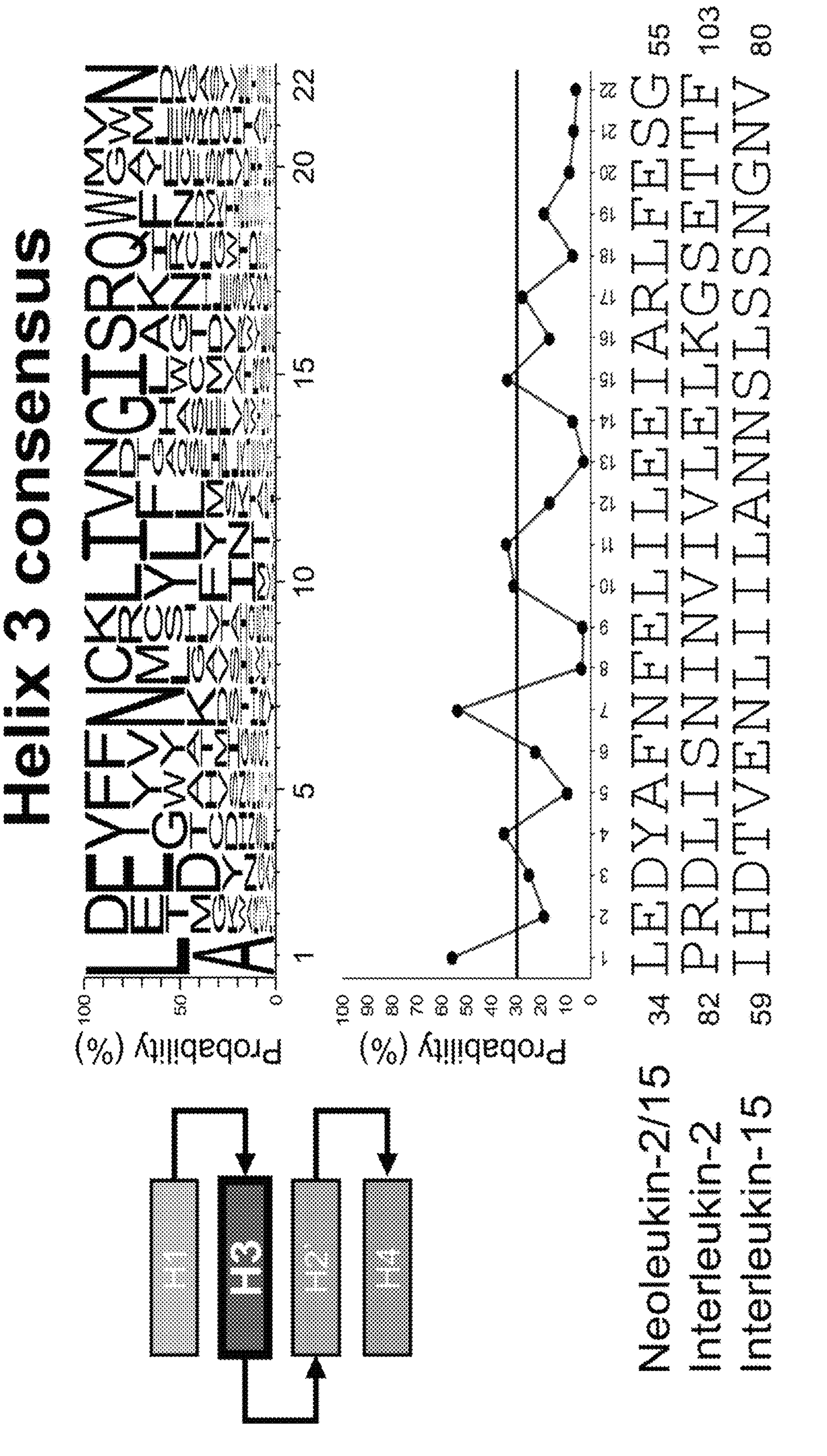
Figure 9C:
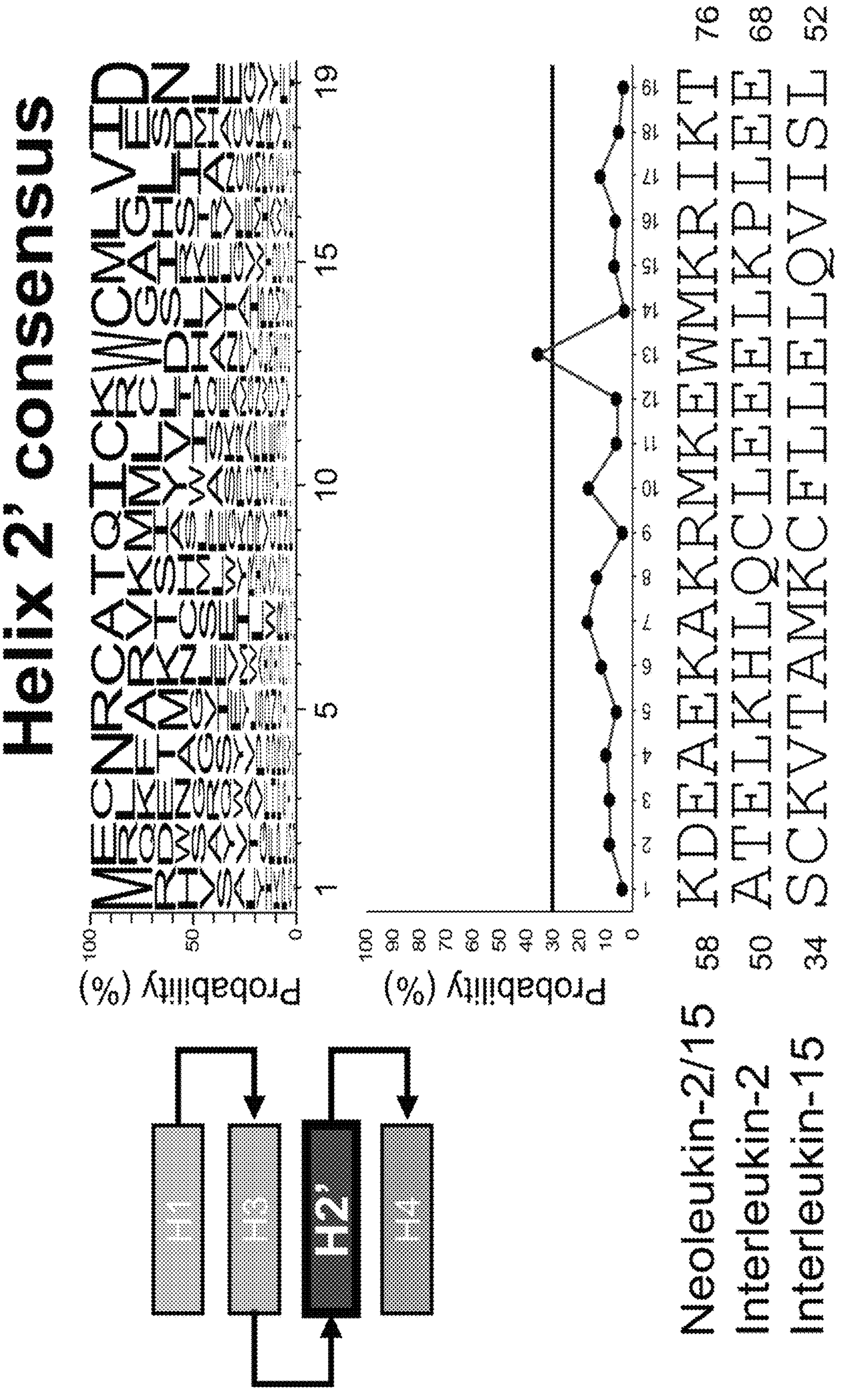
Figure 9D:
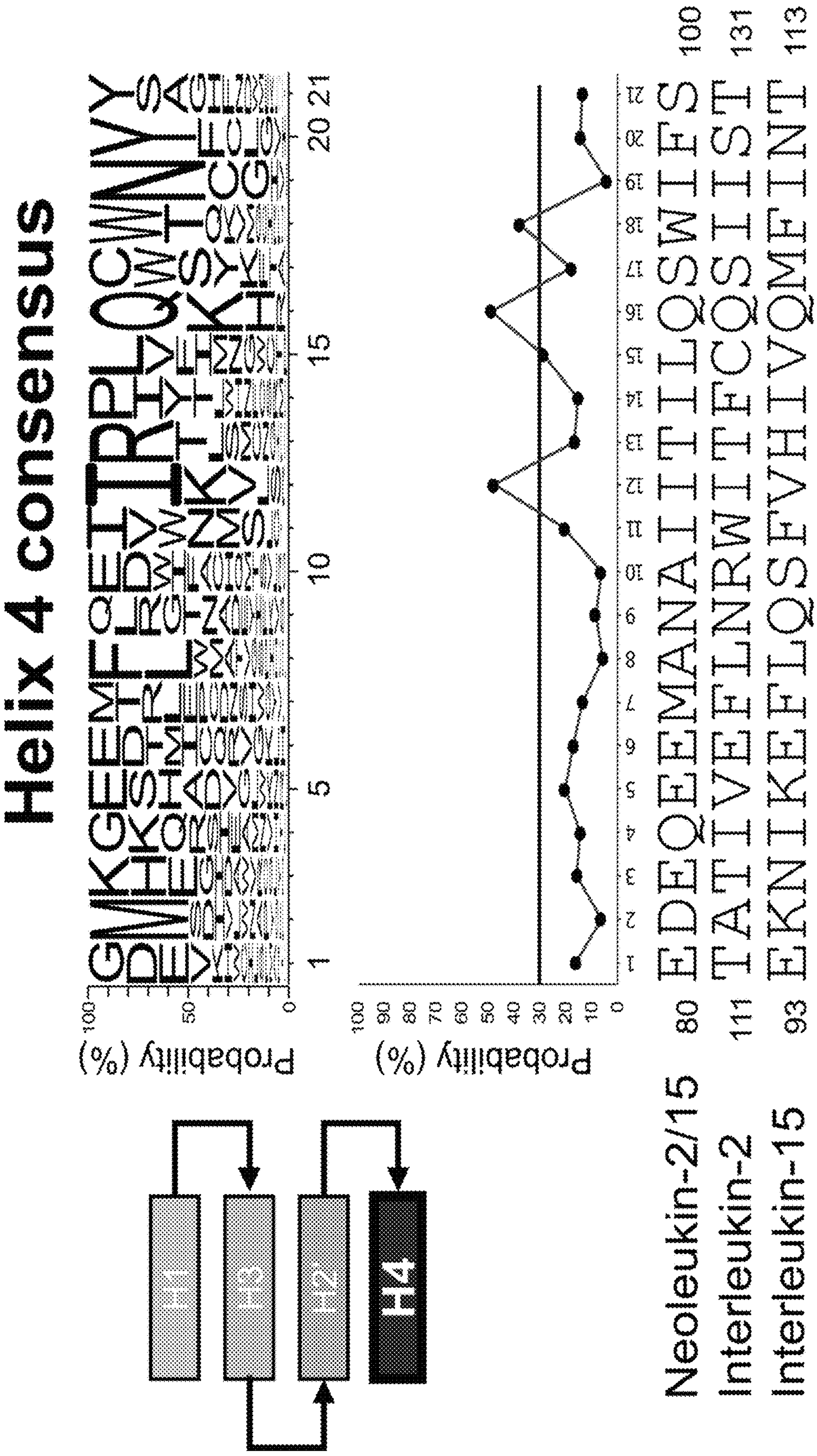

The therapeutic efficacy of neoleukin-2/15 was tested in the poorly immunogenic B16F10 melanoma and the more immunogenic CT26 colon cancer mouse models. Single agent treatment with neoleukin-2/15 led to dose-dependent delays in tumour growth in both cancer models. In CT26 colon cancer, single agent treatment showed improved efficacy to that observed for recombinant mIL-2 (FIG. 4*d* and FIG. 5). In B16F10 melanoma, co-treatment with the anti-melanoma antibody TA99 (anti-TRP1) led to significant tumour growth delays, while TA99 treatment alone had little effect (FIG. 4*e* and FIG. 6). In long term survival experiments (8 weeks), neoleukin-2/15 in combination with TA99 showed substantially reduced toxicity and an overall superior therapeutic effect compared to mIL-2 (FIG. 4*e*). Mice treated with the combination mIL-2 and TA99 steadily lost weight and their overall health declined to the point of requiring euthanasia, whereas little decline was observed with the combination of neoleukin-2/15 and TA99 (FIG. 4*e*). Consistent with a therapeutic benefit, neoleukin-2/15 treatment led to a significant increase in intratumoral CD8:$T_{reg}$ ratios (see FIG. 4*f* and FIG. 5), which has been previously correlated with effective antitumor immune responses[58]. The increases of CD8:$T_{reg}$ ratios by neoleukin-2/15 are dose and antigen dependent (FIG. 40; optimum therapeutic effects were obtained at higher doses and in combination with other immunotherapies (see FIG. 6). Altogether, these data show that neoleukin-2/15 exhibits the predicted homeostatic benefit derived from its IL-2 like immunopotentiator activity, but without the adverse effects associated with $CD25^+$ preferential binding. These enhanced properties and low-toxicity may allow the routine use of neoleukin-2/15 for other immunotherapies where recombinant IL-2 is not broadly used. As an example of such a use, the potential application of neoleukin-2/15 to enhance CAR-T cell therapy (see FIG. 8) was investigated. NSG mice inoculated with $0.5\times10^6$ RAJI tumor cells were left untreated, were treated with $0.8\times10^6$ anti-CD19 CAR-T cells (infused 7 days after inoculation of tumor cells), or were similarly treated with anti-CD19 CAR-T cells plus 20 μg/day of either human IL-2 or neoleukin-2/15 on days 8-14 after tumor inoculation. As expected, Neoleukin-2/15 significantly enhanced the anti-tumor effect of CAR-T cell therapy in this model, slowing growth of the tumor and extending the survival of the mouse (data not shown).

Figure 7A:
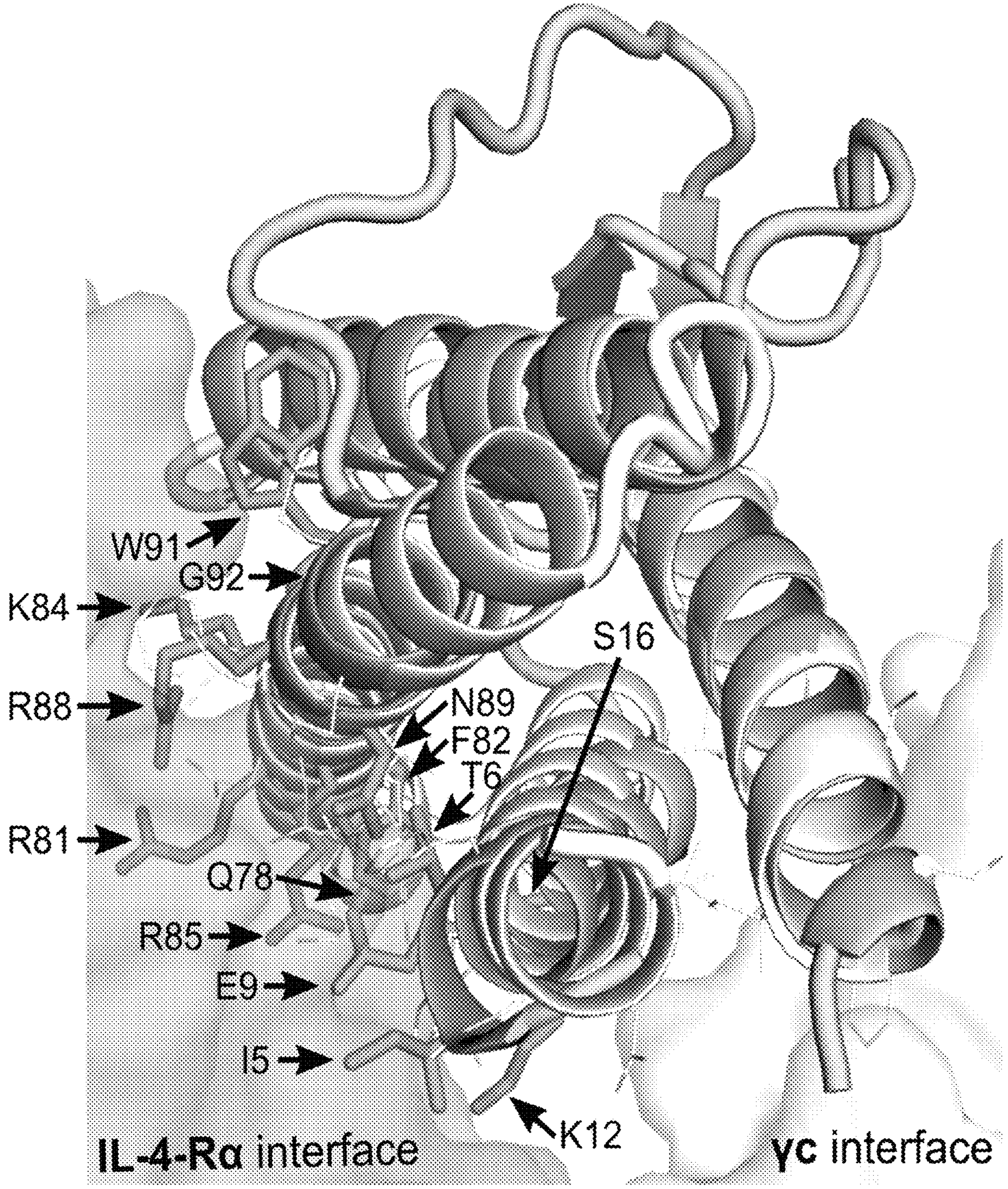
FIG. 7A-7C. Reengineering of neoleukin-2/15 into a human interleukin-4 (hIL-4) mimetic (neoleukin-4).
Figure 7B:
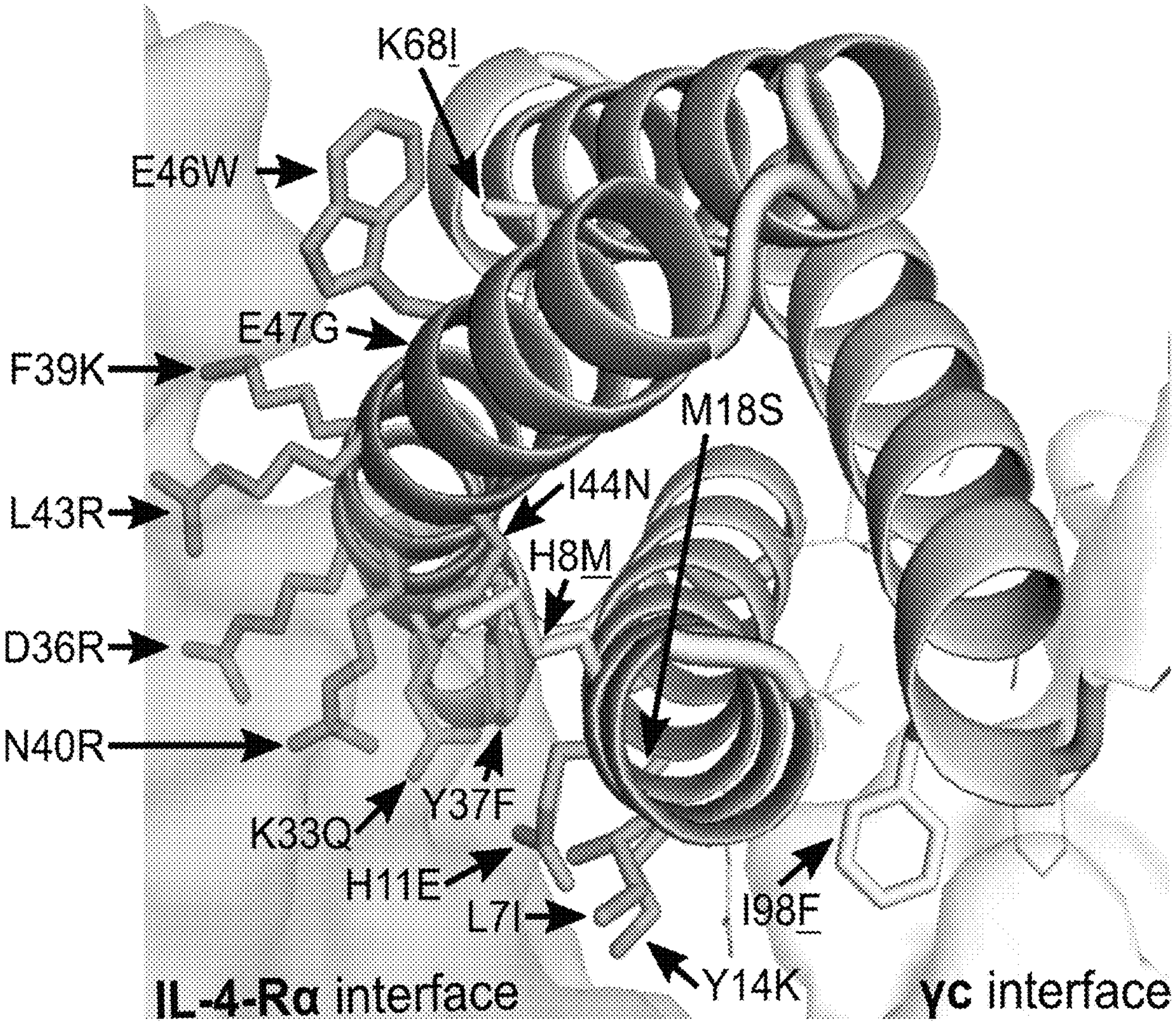
Figure 7C:
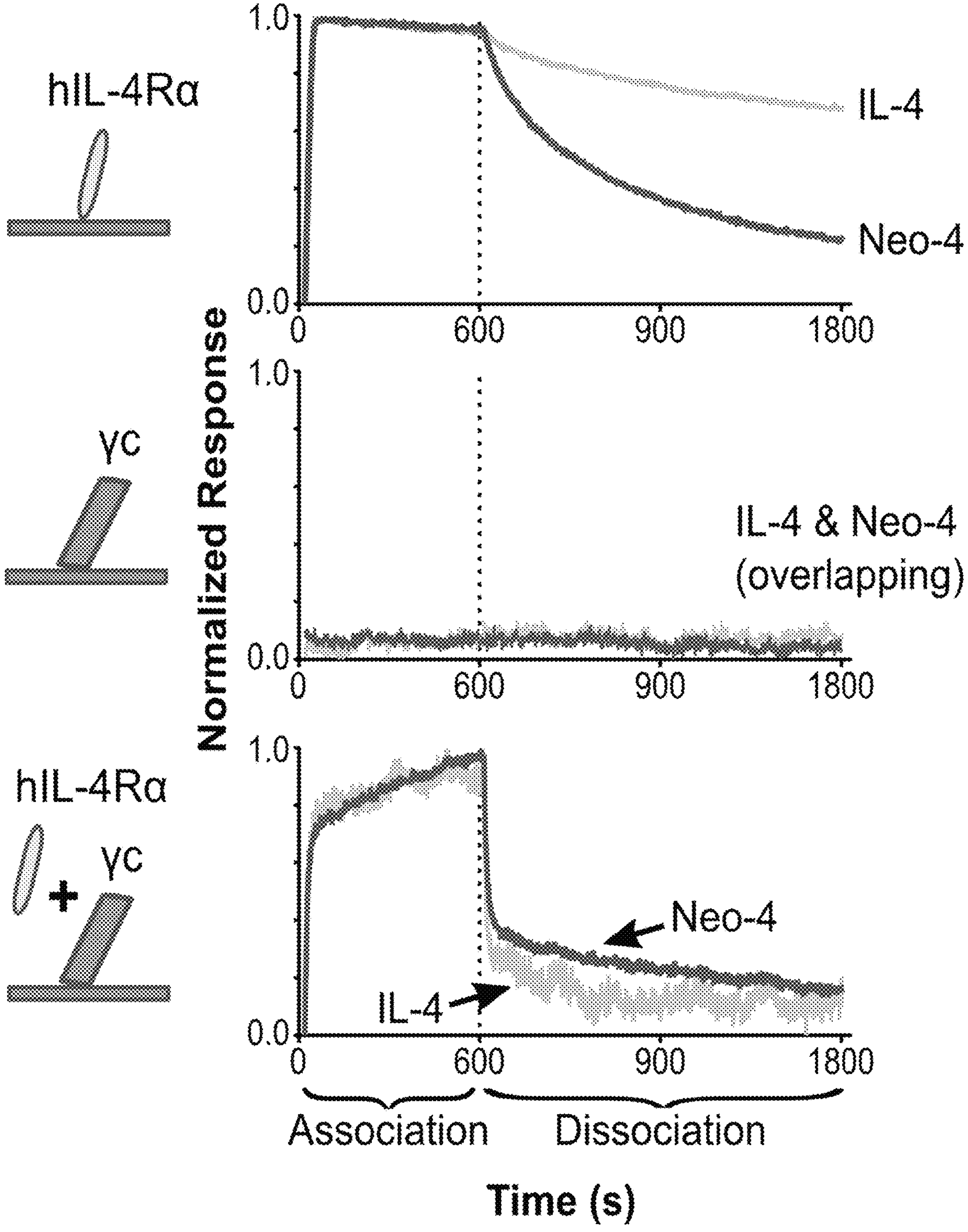

De novo design of protein mimetics has the potential to transform the field of protein-based therapeutics, enabling the development of biosuperior molecules with enhanced therapeutic properties and reduced side-effects, not only for cytokines, but for virtually any biologically active molecule with known or accurately predictable structure. Because of the incremental nature of current traditional engineering approaches (e.g. 1-3 amino acid substitutions, chemical modification at a single site), most of the shortcomings of the parent molecule are inevitably passed on to the resulting engineered variants, often in an exacerbated form. By building mimetics de novo, these shortcomings can be completely avoided: unlike recombinant IL-2 and engineered variants of hIL-2, neoleukin-2/15 can be solubly expressed in *E. coli* (see FIG. 17), retains activity at high temperature, does not interact with IL-2Rα and is robust to substantial sequence changes that allow the engineering of new functions (FIG. 7). Likely because of the small size and high stability of de novo designed proteins, immunogenicity appears to be low, and in contrast to incremental variants of hIL-2, any antibody response to the mimetic is unlikely to cross react with the natural parent cytokine. Because of their high stability and robustness, and their tailored interaction surfaces, designed mimetics are likely to be particularly powerful in next generation therapeutics which combine different protein functionalities, for example targeted versions of neoleukin-2/15.

Robust Modularity of Neoleukin-2/15. Disulfide-Stapling and Reengineering into an IL-4 Mimetic:

Neoleukin-2/15 is highly modular, allowing to easily tune its properties, such as increasing its stability or modify its binding preference. This modularity and robustness was taken advantage of by introducing, by computational design, stability enhancing single-disulfide staples that preserve the function of neoleukin-2/15[59]. For this, two orthogonal strategies were used. First, a disulfide bridge was introduced by searching pairs of positions with favorable geometrical arrangements followed by flexible backbone minimization. The final design introduced a single disulfide between residues 38 and 75, which stabilizes helices H3 and H2. In the second approach, the N- and C-terminus of neoleukin-2/15 was remodeled to allow the introduction of a single-disulfide staple that encompasses the entire protein (added sequences CNSN (SEQ ID NO:260) and NFQC (SEQ ID NO:261), for N- and C-termini, respectively after removing terminal P and S residues, see FIG. 18). Both disulfide stapling strategies increased the stability of neoleukin-2/15 (Tm>95° C.), while retaining its sequence and function mostly unaffected (see FIG. 18). The modularity properties of neoleukin-2/15 were used to modify its binding preference. All cytokines in the interleukin-2 family interact with the $\gamma_c$ and share a common architecture. Therefore, it was hypothesized that neoleukin-2/15 could be transformed into another cytokine mimetic of the IL-2 family by changing only amino acids in the half of the binding-site that interacts with IL-2Rβ (helices H1 and H3). As proof of a concept, human interleukin-4 (hIL-4) was chosen as target, since it shares extensive structural homology with IL-2 and has potential applications in regenerative medicine[60,61]. Neo-2/15 was modified to bind to the human IL-4 receptor (comprising IL-4Rα and $\gamma_c$) and not to the human IL-2 receptor (comprising IL-2Rβ and $\gamma_c$) by aligning the Neo-2/15 model into the structure of human IL-4 bound to its IL-4 receptor, and mutating 14 residues in Neo-2/15 to match the amino-acids of IL-4 at those structural positions that mediate interactions between IL-4 and IL4r (FIG. 7). Binding was further optimized by directed evolution using random mutagenesis and screening for high binding affinity variants, which introduced two additional amino acid substitutions and modified one of the fourteen original residues grafted from the IL-4 protein, thereby creating a new protein Neoleukin-4 with a total of sixteen mutations from Neoleukin-2/15. The resulting optimized design, neoleukin-4 (see Table S5), was recombinantly expressed and purified from *E. coli* and tested for binding. Neoleukin-4 binds with high affinity to IL-4Rα receptor, binds cooperatively to IL-4Rα$\gamma_c$ (see FIG. 7), and does not bind with any affinity to the IL-2 receptor (data not shown) Neoleukin-4 retains the superior thermostable properties of neoleukin-2/15 (see FIG. 20*b,c*), and binds to the IL-13 receptor as expected given the natural cross-reactivity of IL-4 to IL-13 receptor (data not shown). Altogether, this shows that neoleukin-2/15 is robust enough to act as a modular scaffold where significant rational sequence changes can be introduced to modify its function or physical properties in a highly predictable way Methods Computational Design of De Novo Cytokine Mimetics:

The design of de novo cytokine mimetics began by defining a the structure of hIL-2 in the quaternary complex with the IL-2Rβ$\gamma_c$ receptor as template for the design. After inspection, the residues composing the binding-site were defined as hotspots using Rosetta's metadata (PDBInfoLabels). The structure was feed into the new mimetic design protocol that is programmed in PyRosetta, and which can automatically detect the core-secondary structure elements that compose the target-template and produce the resulting de novo mimetic backbones with full RosettaScripts compatible information for design. Briefly, the mimetic building algorithm works as follows. For the first generation of designs, each of the core-elements was idealized by reconstruction using loops from a clustered database of highly-ideal fragments (fragment-size 4 amino acids). After idealization, the mimetic building protocol aims to reconnect the idealized elements by pairs in all possible combinations. To do this it uses combinatorial fragment assembly of sequence-agnostic fragments from the database, followed by cartesian-constrained backbone minimization for potential solutions (i.e. where the N- and C-ends of the built fragment are close enough to link the two secondary structures). After minimization, the solutions are verified to contain highly ideal fragments (i.e. that every overlapping fragment that composes the two connected elements is also contained within the database) and no backbone clashes with the target (context) receptor. Passing backbone solutions were then profiled using the same database of fragments in order to determine the most probable amino acids at each position (this information was encoded in metadata on the design). Next, solutions for pairs of connected secondary structures were combinatorially recombined to produce fully connected backbones by using graph theory connected components. Since the number of solutions grows exponentially with each pair of elements, at each fragment combination step we ranked the designs to favor those with shorter interconnections between pairs of core elements, and kept only the top solutions to proceed to the next step. Fully connected solutions were then profiled by layer (interface, core, non-core-surface, surface), in order to restrict the identities of the possible amino acids to be layer-compatible. Finally, all the information on hotspots, compatible built-fragment amino acids and layers were combined (hotspot has precedence to amino acid probability, and amino acid probability took precedence to layer). These fully profiled backbones were then passed to RosettaScripts for flexible backbone design and filtering (see rosetta-script in Appendix A). For the second generation of designs, two approaches were followed. In the first approach, sequence redesigns of the best first generation optimized design were executed (G1_neo2_40_1F, see Appendix B). In the second approach new mimetics were engineered using G1_neo2_40_1F as the target template. The mimetic design protocol in this second generation was similar to the one described for the first generation, but with two key differences. Firstly, the core-fragments were no longer built from fragments, but instead by discovering parametric equations of repetitive phi and psi angles (omega fixed to 180°) that result in repetitive secondary structures that recapitulated each of the target helices as close as possible, a "pitch" on the phi and psi angles was allowed every X-amino acids in order to allow the helices the possibility to have curvature (final parameters: H1:, H2:, H3, H4), the sue of these parametric equations allowed to change the size of each of the core-elements in the target structure at will (either increase or decrease the size), which was coupled (max/min 8.a.a.) with the loop building process, and reductions in the size of the core elements were not allowed to remove hotspots from the binding site. The second difference in the second generation designs, is that instead of reconnecting the secondary structure core-elements we used a fragment-size of 7 amino acids, and no combinatorial assembly of more than one fragment was allowed (i.e. a single fragment has to be able to close a pair of secondary structures). The rest of the design algorithm was in essence similar to the one followed in the generation one (see Appendix C). The Rosetta energy functions used were "talaris2013" and "talaris2014", for the first and second generation of designs, respectively.

The databases of highly ideal fragments used for the design of the backbones for the de novo mimetics were constructed with the new Rosetta application "kcenters_clustering_of_fragments" using an extensive database of non-redundant publicly available protein structures from the RCSB protein data bank, which was comprised of 16767 PDBs for the 4-mer database used for the first generation designs, and 7062 PDBs for the 7-mer database used for the second generation designs.

Yeast display: Yeast were transformed with genes encoding the proteins to be displayed together with linearized pETcon3 vector. The vector was linearized by 100 fold overdigestion by NdeI and XhoI (New England Biolabs) and then purified by gel extraction (Qiagen). The genes included 50 bases of overlap with the vector on both the 5' and 3' ends such that homologous recombination would place the genes in frame between the AGA2 gene and the myc tag on the vector. Yeast were grown in C-Trp-Ura media prior to induction in SGCAA media as previously described. 12-18 hours after induction, cells were washed in chilled display buffer (50 mM NaPO$_4$ pH 8, 20 mM NaCl, 0.5% BSA) and incubated with varying concentrations of biotinylated receptor (either human or murine IL-2Rα, IL-2Rβ, IL-2Rγ, or human IL-4Rα) while being agitated at 4° C. After approximately 30 minutes, cells were washed again in chilled buffer, and then incubated on ice for 5 minutes with FITC-conjugated anti-c-Myc antibody (1 uL per 3×10$^6$ cells) and streptavidin-phycoerythrin (1 uL per 100 uL volume of yeast). Yeast were then washed and counted by flow cytometry (Accuri C6) or sorted by FACS (Sony SH800). For experiments in which the initial receptor incubation was conducted with a combination of biotinylated IL-2Rγ and non-biotinylated IL-4Rα, the non-biotinylated receptor was provided in molar excess.

Mutagenesis and Affinity Maturation:

For error-prone PCR based mutagenesis, the design to be mutated was cloned into pETcon3 vector and amplified using the MutaGene II mutagenesis kit (Invitrogen) per manufacturer's instructions to yield a mutation frequency of approximately 1% per nucleotide. 1 μg of this mutated gene was electroporated into EBY100 yeast together with 1 μg of linearized pETcon3 vector, with a transformation efficiency on the order of 10$^8$. The yeast were induced and sorted multiple times in succession with progressively decreasing concentrations of receptor until convergence of the population. The yeast were regrown in C-Trp-Ura media between each sort.

Site-saturation mutagenesis (SSM) libraries were constructed from synthetic DNA from Genscript. For each amino acid on each design template, forward primers and reverse primers were designed such that PCR amplification would result in a 5' PCR product with a degenerate NNK codon and a 3' PCR product, respectively. Amplification of "left" and "right" products by COF and COR primers yielded a series of template products each consisting of a degenerate NNK codon at a different residue position. For each design, these products were pooled to yield the SSM library. SSM libraries were transformed by electroporation into conditioned *Saccharomyces cerevisiae* strain EBY100 cells, along with linearized pETCON3 vector, using the protocol previously described by Benatuil et al.

Combinatorial libraries were constructed from synthetic DNA from Genscript containing ambiguous nucleotides and similarly transformed into linearized pETCON3 vector.

Protein Expression:

Genes encoding the designed protein sequences were synthesized and cloned into pET-28b(+) *E. coli* plasmid expression vectors (GenScript, N-terminal 6×His tag and thrombin cleavage site). Plasmids were then transformed into chemically competent *E. coli* Lemo21 cells (NEB). Protein expression was performed using Terrific Broth and M salts, cultures were grown at 37° C. until OD$^{600}$ reached approximately 0.8, then expression was induced with 1 mM of isopropyl β-D-thiogalactopyranoside (IPTG), and temperature was lowered to 18° C. After expression for approximately 18 hours, cells were harvested and lysed with a Microfluidics M110P microfluidizer at 18,000 psi, then the soluble fraction was clarified by centrifugation at 24,000 g for 20 minutes. The soluble fraction was purified by Immobilized Metal Affinity Chromatograpy (Qiagen) followed by FPLC size-exclusion chromatography (Superdex 75 10/300 GL, GE Healthcare). The purified neoleukin-2/15 was characterized by Mass Spectrum (MS) verification of the molecular weight of the species in solution (Thermo Scientific), Size Exclusion—MultiAngle Laser Light Scattering (SEC-MALLS) in order to verify monomeric state and molecular weight (Agilent, Wyatt), SDS-PAGE, and endotoxin levels (Charles River).

Human and mouse IL-2 complex components including hIL-2 (a.a. 1-133), hIL-2Rα (a.a. 1-217), hIL-2Rβ (a.a. 1-214) hIL-2Rγ (a.a. 1-232), mIL-2 (a.a. 1-149), mIL-2Rα ectodomain (a.a. 1-213), mIL-2Rβ ectodomain (a.a. 1-215), and mγ$_c$ ectodomain (a.a. 1-233) were secreted and purified using a baculovirus expression system, as previously described[17,49] All proteins were purified to >98% homogeneity with a Superdex 200 sizing column (GE Healthcare) equilibrated in HBS. Purity was verified by SDS-PAGE analysis. For expression of biotinylated human IL-2 and mouse IL-2 receptor subunits, proteins containing a C-terminal biotin acceptor peptide (BAP)-LNDIFEAQKIEWHE (SEQ ID NO:262) were expressed and purified as described via Ni-NTA affinity chromatography and then biotinylated with the soluble BirA ligase enzyme in 0.5 mM Bicine pH 8.3, 100 mM ATP, 100 mM magnesium acetate, and 500 mM biotin (Sigma). Excess biotin was removed by size exclusion chromatography on a Superdex 200 column equilibrated in HBS.

Neoleukin-2 Crystal and Co-Crystal Structures:

C-terminally 6×His-tagged endoglycosidase H (endoH) and murine IL-2Rβ and IL-2Rγ were expressed separately in Hi-five cells using a baculovirus system as previously described. IL-2Rγ was grown in the presence of 5 μM kifunensin. After approximately 72 hours, the secreted proteins were purified from the media by passing over a Ni-NTA agarose column and eluted with 200 mM imidazole in HBS buffer (150 mM NaCl, 10 mM HEPES pH 7.3). EndoH was exchanged into HBS buffer by diafiltration. mIL-2Rγ was deglycosylated by overnight incubation with 1:75 (w/w) endoH. mIL-2Rβ and mIL-2Rγ were further purified and buffer exchanged by FPLC using an 5200 column (GE Life Sciences).

Monomeric neoleukin-2/15 was concentrated to 12 mg/ml and crystallized by vapor diffusion from 2.4 M sodium malonate pH 7.0, and crystals were harvested and flash frozen without further cryoprotection. Crystals diffracted to 2.0 Å resolution at Stanford Synchrotron Radiation Laboratory beamline 12-2 and were indexed and integrated using XDS (Kabsch, 2010). The space group was assigned with Pointless (Evans, 2006), and scaling was performed with Aimless (Evans and Murshudov, 2013) from the CCP4 suite (Winn et al., 2013). Our predicted model was used as a search ensemble to solve the structure by molecular replacement in Phaser (McCoy et al., 2007), with six protomers located in the asymmetric unit. After initial rebuilding with Autobuild (Terwilliger et al., 2008), iterative cycles of manual rebuilding and refinement were performed using Coot (Emsley et al., 2010) and Phenix (Adams et al., 2010).

To crystallize the ternary neoleukin:mIL-2Rβ:mIL-2Rγ complex, the three proteins were combined in equimolar ratios, digested overnight with 1:100 (w/w) carboxypeptidases A and B to remove purification tags, and purified by FPLC using an 5200 column; fractions containing all three proteins were pooled and concentrated to 20 mg/ml. Initial needlelike microcrystals were formed by vapor diffusion from 0.1 M imidazole pH 8.0, 1 M sodium citrate and used to prepare a microseed stock for subsequent use in microseed matrix screening (MMS, (D'Arcy et al., 2014)). After a single iteration of MMS, crystals grown in the same precipitant were cryoprotected with 30% ethylene glycol, harvested and diffracted anisotropically to 3.4 Å×3.8 Å×4.1 Å resolution at Advanced Photon Source beamline 231D-B. The structure was solved by molecular replacement in Phaser using the human IL-2Rβ and IL-2Rγ structures (pdb ID 2B5I) as search ensembles. This produced an electron density map into which two poly-alanine alpha helices could be manually built. Following rigid body refinement in Phenix, electron density for the two unmodeled alpha helices, along with the BC loop and some aromatic side chains, became visible, allowing docking of the monomeric neoleukin. Two further iterations of MMS and use of an additive screen (Hampton Research) produced crystals grown by vapor diffusion using 150 nl of protein, 125 nl of well solution containing 0.1 M Tris pH 7.5, 5% dextran sulfate, 2.1 M ammonium sulfate and 25 nl of microseed stock containing 1.3 M ammonium sulfate, 50 mM Tris pH 7.5, 50 mM imidazole pH 8.0, 300 mM sodium citrate. Crystals cryoprotected with 3 M sodium malonate were flash frozen and diffracted anisotropically to 2.5 Å×3.7 Å×3.8 Å at Advanced Light Source beamline 5.0.1. After processing the data with XDS, an elliptical resolution limit was applied using the STARANISO server (Bruhn et al., 2017). Rapid convergence of the model was obtained by refinement against these reflections using TLS and target restraints to the higher resolution human receptor (PDB id 2B5I) and neoleukin-2/15 structures in Buster (Smart et al., 2012; Bricogne et al., 2016), with manual rebuilding in Coot, followed by a final round of refinement in Phenix with no target restraints. Structure figures were prepared with PyMol (Schrodinger, LLC. 2010. The PyMOL Molecular Graphics System, Version 2.1.0). Software used in this project was installed and configured by SBGrid (Morin et al., 2013).

Cell Lines:

Unmodified YT-1[64] and IL-2Rα$^+$ YT-1 human natural killer cells[65] were cultured in RPMI complete medium (RPMI 1640 medium supplemented with 10% fetal bovine serum, 2 mM L-glutamine, minimum non-essential amino acids, sodium pyruvate, 25 mM HEPES, and penicillin-streptomycin [Gibco]). CTLL-2 cells purchased from ATCC were cultured in RPMI complete with 10% T-STIM culture supplement with ConA (Corning). All cells were maintained at 37° C. in a humidified atmosphere with 5% $CO_2$. The subpopulation of YT-1 cells expressing IL-2Rα was purified via magnetic selection as described previously[17]. Enrichment and persistence of IL-2Rα expression was monitored by analysis of PE-conjugated anti-human IL-2Rα (Biolegend) antibody binding on an Accuri C6 flow cytometer (BD Biosciences).

Circular Dichroism (CD):

Far-ultraviolet CD measurements were carried out with an AVIV spectrometer model 420 in PBS buffer (pH 7.4) in a 1 mm path-length cuvette with protein concentration of ~0.20 mg/ml (unless otherwise mentioned in the text). Temperature melts where from 25 to 95° C. and monitored absorption signal at 222 nm (steps of 2° C./min, 30 s of equilibration by step). Wavelength scans (195-260 nm) were collected at 25° C. and 95° C., and again at 25° C. after fast refolding (~5 min).

Binding Studies:

Surface plasmon resonance (SPR): For IL-2 receptor affinity titration studies, biotinylated human or mouse IL-2Rα, IL-2Rβ, and IL-2Rγ receptors were immobilized to streptavidin-coated chips for analysis on a Biacore T100 instrument (GE Healthcare). An irrelevant biotinylated protein was immobilized in the reference channel to subtract non-specific binding. Less than 100 response units (RU) of each ligand was immobilized to minimize mass transfer effects. Three-fold serial dilutions of hIL-2, mIL-2, Super-2, or engineered IL-2 mimetics were flowed over the immobilized ligands for 60 s and dissociation was measured for 240 s. For IL-2Rβ $\gamma_c$ binding studies, saturating concentrations of hIL-2Rβ (3 uM) or mIL-2Rβ? (5 uM) were added to the indicated concentrations of hIL-2 or mIL-2, respectively. Surface regeneration for all interactions was conducted using 15 s exposure to 1 M MgCl2 in 10 mM sodium acetate pH 5.5. SPR experiments were carried out in HBS-P+ buffer (GE Healthcare) supplemented with 0.2% bovine serum albumin (BSA) at 25° C. and all binding studies were performed at a flow rate of 50 L/min to prevent analyte rebinding. Data was visualized and processed using the Biacore T100 evaluation software version 2.0 (GE Healthcare). Equilibrium titration curve fitting and equilibrium binding dissociation (KD) value determination was implemented using GraphPad Prism assuming all binding interactions to be first order. Biolayer interferometry: binding data were collected in a Octet RED96 (ForteBio, Menlo Park, Calif.) and processed using the instrument's integrated software using a 1:1 binding model. Biotinylated target receptors, either human or murine IL-2Rα, IL-2Rβ, IL-2Rγ, or human IL-4Rα, were functionalized to streptavidin coated biosensors (SA ForteBio) at 1 μg/ml in binding buffer (10 mM HEPES [pH 7.4], 150 mM NaCl, 3 mM EDTA, 0.05% surfactant P20, 0.5% non-fat dry milk) for 300 seconds. Analyte proteins were diluted from concentrated stocks into binding buffer. After baseline measurement in binding buffer alone, the binding kinetics were monitored by dipping the biosensors in wells containing 100 nM of the designed protein (association) and then dipping the sensors back into baseline wells (dissociation). For binding experiments in which either IL-2Rβ or IL-4Rα were supplemented in solution while IL-2Rγ was bound to the sensor, the supplemental proteins were provided in 2.5 fold molar excess STAT5 Phosphorylation Studies:

In vitro studies: Approximately $2\times10^5$ YT-1, IL-2Rα$^+$ YT-1, or CTLL-2 cells were plated in each well of a 96-well plate and re-suspended in RPMI complete medium containing serial dilutions of hIL-2, mIL-2, Super-2, or engineered IL-2 mimetics. Cells were stimulated for 15 min at 37° C. and immediately fixed by addition of formaldehyde to 1.5% and 10 min incubation at room temperature. Permeabilization of cells was achieved by resuspension in ice-cold 100% methanol for 30 min at 4° C. Fixed and permeabilized cells were washed twice with FACS buffer (phosphate-buffered saline [PBS] pH 7.2 containing 0.1% bovine serum albumin) and incubated with Alexa Fluor® 647-conjugated anti-STAT5 pY694 (BD Biosciences) diluted in FACS buffer for 2 hours at room temperature. Cells were then washed twice in FACS buffer and MFI was determined on a CytoFLEX flow cytometer (Beckman-Coulter). Dose-response curves were fitted to a logistic model and half-maximal effective concentration ($EC_{50}$ values) were calculated using GraphPad Prism data analysis software after subtraction of the mean fluorescence intensity (MFI) of unstimulated cells and normalization to the maximum signal intensity. Experiments were conducted in triplicate and performed three times with similar results. Ex vivo studies: Spleens and lymph nodes were harvested from wild-type C57BL/6J or B6; 129S4-$Il2ra^{Tm1Dw}$ (CD25KO) mice purchased from The Jackson Laboratory and made into a single cell suspension in sort buffer (2% Fetal Calf Serum in pH 7.2 phosphate-buffered saline). CD4+ cells were enriched through negative selection by staining the cell suspension with biotin-conjugated anti-B220, CD, NK1.1, CD11b, CD11c, Ter119, and CD19 antibodies at 1:100 for 30 min on ice, Following a wash with sort buffer, anti-biotin MicroBeads (Miltenyi Biotec) were added to the cell suspension at 20 μL per $10^7$total cells and incubated on ice for 20 minutes. Cells were washed, resuspended and negative selection was then performed using Easy Sep Magnets (STEMCELL Technologies). Approximately $1\times10^5$enriched cells were added to each well of a 96-well plate in RPMI complete medium with 5% FCS with 10-fold serial dilutions of mIL-2. Super-2, or Neoleukin-2/15. Cells were stimulated for 20 minutes at 37° C. in 5% $CO_2$, fixed with 4% PFA and incubated for 30 minutes at 4° C. Following fixation, cells were harvested and washed twice with sort buffer and again fixed in 500 μL 90% ice-cold methanol in $dH_2O$ for 30 minutes on ice for permeabilization. Cells were washed twice with Perm/Wash Buffer (BD Biosciences) and stained with anti-CD4-PerCP in Perm/Wash buffer (1:300). anti-CD44-Alexa Fluor 700 (1:200), anti-CD25-PE-Cy7 (1:200), and 5 μL per sample of anti-pSTAT5-PE pY694 for 45 min at room temperature in the dark. Cells were washed with Perm/Wash and re-suspended in sort buffer for analysis on a BD LSR II flow cytometer (BD Biosciences).

In Vivo Murine Airway Inflammation Experiments:

C5791/6J were purchased from The Jackson Laboratory. Mice were inoculated intranasally with 20 μL of whole house dust mite antigen (Greer) resuspended in PBS to a total of 23 μg Derp1 per mouse. From Days 1-7, mice were given a daily intraperitoneal injection of 20 μg mIL-2 in sterile PBS (pH 7.2), a molar equivalent of Neoleukin-2/15 in sterile PBS, or no injection. On Day 8, circulating cells were intravascularly labeled and tetramer positive cells were enriched from lymph nodes and spleen or lung as previously described (Hondowicz, Immunity, 2016), Both the column flow-through and bound fractions were saved for flow cytometry analysis. Cells were surface stained with antibodies and analyzed on a BD LSR II flow cytometer (BD Biosciences) Animal models: C57BL/6 mice were purchased from The Jackson Laboratory or bred in house and. BALB/c mice were purchased from Charles River. Animals were maintained according to protocols approved by Dana-Farber Cancer Institute (DFCI) Institutional Animal Care and Use Committee, Direção Geral de Veterinária and iNIM Lisboa ethical committee.

Colorectal carcinoma in vivo mice experiments: CT26 cells were sourced from Jocelyne Demengeot's research group at IGC (Institut® Gulbenkian de Ciência), Portugal. On day 0, 5×10^5 cells were injected subcutaneously (s.c.) into the flanks of BALB/c mice with 50 μL of a 1:1 mixture of Dulbecco's modified Eagle medium (Gibco) with Matrigel (Corning). Starting on day 6, when tumour volume reached around 100 mm3, neoleukin-2/15 and mIL-2 (Peprotech) were administered daily by intraperitoneal (i.p.) injection in 50 μL of PBS (Gibco). Treatment with anti-PD-1 antibody (Bio X Cell) was performed twice a week by i.p. injection of 200 μg per mouse in PBS. Mice were sacrificed when tumour volume reached 1,300 mm3.

Melanoma In Vivo Experiments:

816F10 cells were purchased from ATCC. On day 0, $5\times10^5$ cells were inoculated by s.c. injection in 500 μL of Hank's Balanced Salt Solution (Gibco). Starting on day 1, neoleukin-2/15 and mIL-2 (Peprotech) were administered daily by intraperitoneal (i.p.) injection in 200 μL of LPS-free PBS (Teknova). Treatment with TA99 (a. gift from Noor Momin and Dane Wittrup, Massachusetts institute of Technology) at 150 μg/mouse was added several days later as indicated. Mice were sacrificed when tumor volume reached 2,000 mm3.

Flow Cytometry:

Excised tumors were minced, enzymatically digested (Miltenyi. Biotec), and passed through a 40-μm filter. Cells from spleens and tumor-draining lymph nodes were dispersed into PBS through a 40-μm cell strainer using the back of a 1-mL syringe plunger. All cell suspensions were washed once with PBS, and the cell pellet was resuspended in 2% inactivated fetal calf serum containing fluorophore-conjugated antibodies. Cells were incubated for 15 minutes at 4° C. then fixed, permeabilized, and stained using a BioLegend FoxP3 staining kit. Samples were analyzed on a BD Fortessa flow cytometer. Antibodies (BioLegend) used in melanoma experiments were: CD45-BV711 (clone 30-F11), CD8-BV650 (53-6.7), CD4-BV421 (GK1.5), TCRβ-BV510 (H57-597), CD25-AF488 (PC61), FoxP3-PE (MF-14). Antibodies (eBioscience) used in colon carcinoma experiments were: CD45-BV510 (30-F11), CD3-BV711 (17A2), CD49b-FITC (DX5), CD4-BV605 (GK1.5), CD8-PECy7 (53-6.7), Foxp3-APC (FJK-16s). Fixable Viability Dye of eFluor 780 (eBioscience) was used to exclude dead cells.

Generation of Anti-Neoleukin-2/15 Polygonal Antibody:

Mice were injected i.p. with 500 μg of K.O. neoleukin in 200 μL of a 1:1 emulsion of PBS and Complete Freund's Adjuvant. Mice were boosted on days 7 and 15 with 500 μg of K.O. neoleukin in 200 μL of a 1:1 emulsion of PBS and incomplete Freund's Adjuvant. On day 20, serum was collected and recognition of neoleukin-2/15 was confirmed by ELISA.

Enzyme-Linked Immunosorbant Assay (ELISA):

High-binding 96-well plates (Corning) were coated overnight at 4° C. with 100 ng/mL of neoleukin-2/15, mIL-2 (Peprotech), hIL-2 (Peprotech), or ovalbumin (Sigma-Aldrich) in carbonate buffer. Antibody binding to target proteins was detected using HRP-conjugated sheep anti-mouse IgG (GE Healthcare) at 75 ng/mL. Plates were developed with tetramethylbenzidine and HCL Absorbance was measured at 450 nm with an EnVision M4 Multimode Plate Reader (PerkinElmer).

T Cell Proliferation Assay:

Cells were isolated from a mouse spleen using an Easy Sep T Cell Isolation Kit (Sterncell Technologies), They were plated in RPMI in 96-well culture plates at a density of 10,000 cells/well. Media were supplemented with regular or heat-treated neoleukin-2/15, rmIL-2, or Super-2. After 5 days of incubation at 37° C. cell survival and proliferation were measured by CellTiter-Glo Luminescent Cell Viability Assay (Promega).

Statistical and Power Analyses:

In vivo murine airway inflammation experiments: MIKEL. In vivo murine Colon cancer experiments: CARLOS. In vivo murine Melanoma experiments: Comparisons of the survival of tumor-hearing mice were performed using the log-rank (Mantel-Cox) test. Comparisons of weight loss in tumor-bearing mice were performed using a two-tailed t test. A P value less than 0.05 was considered to be significant. The minimum group size was determined using G*Power for an expected large effect size (Cohen's d=1.75).

Biolayer Interferometry analysis of a Mouse Serum Albumin (MSA) fusion to Neoleukin-2/15. Genetic fusion of Neoleukin-2/15 to MSA for extended half-life and preserves intact binding affinity of the cytokine mimetic to murine IL-2RBeta and IL-2RGamma (33.5±0.2 nM) (data not shown). The construct utilized in this study was as follows:

Optional: (HisTag TEV cleavage site in parentheses)

Mouse Serum Albumin (Italicized)

Linker

Neo2/15 (Bold Font)

(SEQ ID NO: 244)

(GSDGGSHHHHHHGSGSENLYFQGSG) *EAHKSEIAHRYNDLGEQHFKGLVL*

*IAFSQYLQKCSYDEHAKLVQEVTDFAKTCVADESAANCDKSLHTLFGDKLC*

*AIPNIRENYGELADCCTKQEPERNECFLQHKDDNPSLPPFERPEAEAMCTS*

*FKENPTTFMGHYLHEVARRHPYFYAPELLYYAEQYNEILTQCCAEADKESC*

*LTPKLDGVKEKALVSSVRQRMKCSSMQKFGERAFKAWAVARLSQTFPNADF*

*AEITKLATDLTKVNKECCHGDLLECADDRAELAKYMCENQATISSKLQTCC*

*DKPLLKKAHCLSEVEHDTMPADLPAIAADFVEDQEVCKNYAEAKDVFLGTF*

*LYEYSRRHPDYSVSLLLRLAKKYEATLEKCCAEANPPACYGTVLAEFQPLV*

*EEPKNLVKTNCDLYEKLGEYGFQNAILVRYTOKAPQVSTPTLVEAARNLGR*

*VGTKCCTLPEDQRLPCVEDYLSAILNRVCLLHEKTPVSEHVTKCCSGSLVE*

*RRPCFSALTVDETYVPKEFKAETFTFHSDICTLPEKEKQIKKQTALAELVK*

*HKPKATAEQLKTVMDDFAQFLDTCCKAADKDTCFSTEGPNLVTRCKDALA*G

GGSGGSGGGSGGSGSGPKKKIQLHAEHALYDALMILNIVKTNSPPAEEKLE

DYAFNFELILEEIARLFESGDQKDEAEKAKRMKEWMKRIKTTASEDEQEEM

ANAIITILQSWIFS

Biotin-mIL2Gamma was immobilized on a Streptavidin biosensor, MSA-Neo2 concentration was titrated from 729 to 1 nM in presence of saturating concentrations of mIL2Beta. Biolayer interferometry was carried out as above: binding data were collected in a Octet RED96 (ForteBio, Menlo Park, Calif.) and processed using the instrument's integrated software using a 1:1 binding model. Biotinylated target receptors, either human or murine IL-2Rα, IL-2Rβ, IL-2Rγ, or human IL-4Rα, were functionalized to streptavidin coated biosensors (SA ForteBio) at 1 μg/ml in binding buffer (10 mM HEPES [pH 7.4], 150 mM NaCl, 3 mM EDTA, 0.05% surfactant P20, 0.5% non-fat dry milk) for 300 seconds. Analyte proteins were diluted from concentrated stocks into binding buffer. After baseline measurement in binding buffer alone, the binding kinetics were monitored by dipping the biosensors in wells containing 100 nM of the designed protein (association) and then dipping the sensors back into baseline wells (dissociation).

CAR-T cell in vivo experiments: In vitro T cell proliferation assay. Primary human T cells were obtained from healthy donors. Peripheral blood mononuclear cells (PBMC) were isolated by centrifugation over Ficoll-Hypaque (Sigma). T cells were isolated using EasySep CD8 or CD4 negative isolation kits (STEMCELL Technologies). To stimulate T cells, T cells were thawed and incubated with anti-CD3/CD28 Dynabeads (Gibco) at 1:1 ratio in media supplemented with 50 IU/ml (3.1 ng/ml) of IL2. Beads were removed after four days of incubation. Stimulated or freshly thawed unstimulated T cells were plated at 30000 or 50000 cells/well, respectively, in 96 well format and cultured in indicated concentrations of IL2 or neoleukin-2/15 in triplicate. Three days later, proliferation was measured using CellTiter-Glo 2.0. (Promega).

In vivo RAJI experiment: Six- to eight-week old NSG mice were obtained from the Jackson Laboratory. 0.5*10^6 RAJI tumor cells transduced with ffluc/eGFP were tail vein injected into the NSG mice. Seven days post tumor inject, lentiviral transduced anti-CD19 CART cells (0.4*10^CD4, 0.4*10^CD8) prepared as described in (Liu et al, 2016) were infused i.v. into mice. hIL2 or neoleukin-2/15 at 20 μg/mouse were given i.p. from day 8 to 16 post tumor injection.

Preparation of PEGylated Polypeptides:

Neo-2/15 stocks with either single or dual cysteine mutations were dialyzed into phosphate buffer, pH7.0 and adjusted to 1.0-2.0 mg/ml. TCEP was added at a molar ratio of 10:1 to protein and incubated for 10 minutes at RT to reduce disulfides. Maleimide-modified PEG40k (PEG40k-MA) or PEG30k (PEG30k-MA) powder was added directly to the reduced protein solution at a molar ratio of 10:1 PEG:cysteine and incubated for 2 hours with stirring. Aliquots for SDS-PAGE were taken directly from the reaction mixture. These data demonstrate the rapid, spontaneous, and near-quantitative formation of covalent linkages between PEG40k-MA or PEG30k-MA and Neo-2/15 cysteine mutants in the expected stoichiometry.

Treatment with Neo-2/15 and PEGylated Neo-2/15-E62C (Neo-2/15-PEG) Demonstrated Changes in the Levels of Multiple Inflammatory Markers:

Two non-human primates (NHP), one male and one female per group, were assigned to treatment with either vehicle (group 1), Neo-2/15 (w/o PEG) (groups 2-4) or Neo-2/15 PEG (groups 5-7; single cysteine mutation of E62C and PEG40K). Animals treated with vehicle or Neo-2/15 (w/o PEG) were dosed by intravenous (IV) bolus on study days 1, 2, 3, 4, 5, 6 and 7 (once daily for one week) at dose levels of either 0 (vehicle) or dose adjusted values of 0.07, 0.21 or 0.14 mg/kg/day Neo 2/15 (w/o PEG) (groups 2, 3 and 4, respectively). Animals treated with Neo-2/15 PEG were dosed by IV bolus on study days 1 and 7 at dose levels of 0.05, 0.15 or 0.10 mg/kg/day Neo-2/15PEG (groups 5, 6 and 7, respectively). Cytokine samples were taken on day 1 and 7 at timepoints of 0, 4, 8 and 24 hours post dose. Cytokine serum samples were prepared and frozen at ≤70° C. and shipped for analysis where samples were analyzed through a Luminex multiplex immunoassays system. Several cytokines, including IL-15 and IL-10 demonstrated marked differences in the time-course of cytokine production, consistent with a more sustained pharmacodynamic effect for the PEGylated molecule.

Targeted Neo-2/15 Fusions Retained their IL-2R Binding Affinity and Demonstrated Anti-Tumor Effects.

Select targeting domains were fused to the N- or C-termini of Neo-2/15 via peptide linkers and were tested in vitro to characterize their binding affinity to human and mouse IL-2R by Biolayer Interferometry. The results confirmed that fusions to Neo-2/15 at either the N or C termini did not hinder its ability to bind IL-2R. Subsequent in vitro Flow Cytometry studies confirmed that the fusion proteins were capable of binding a target receptor on the surface of a cell. The efficacy of the targeted constructs was evaluated in in vivo mouse experiments, in which it was demonstrated that a targeted Neo-2/15 moiety to tumor cells or immune cells has a beneficial anti-tumor effect over a non-targeted control (data not shown).

Fusions that were tested include but are not limited to: (i) a fusion of an anti-CD47 nanobody to the C terminus of Neo 2/15 via the linker of SEQ ID NO:100; (b) a fusion of an anti-CD47 nanobody to the N terminus of Neo 2/15 via the linker of SEQ ID NO:100; (c) a fusion of an anti-CTLA4 nanobody to the C terminus of Neo 2/15 via the linker of SEQ ID NO:100; (d) a fusion of anti-CTLA4 nanobody to the N terminus of Neo 2/15 via the linker of SEQ ID NO:100; (e) a fusion of an anti-PDL-1 nanobody to the C terminus of Neo 2/15 via the linker of SEQ ID NO:100; and (f) a fusion of an anti-PDL-1 nanobody to the N terminus of Neo 2/15 via the linker of SEQ ID NO:100.

Fusions of Albumin to Neo-2/15 Maintained IL-2R Binding Affinity.

Mouse serum albumin (MSA) was fused to the N-terminus of Neo 2/15 via a peptide linker and was tested in vitro to characterize its binding affinity to mouse IL-2R by Biolayer Interferometry. Biotin-mIL2Gamma was immobilized on a Streptavidin biosensor, MSA-Neo2 concentration was titrated from 729 to 1 nM in presence of saturating concentrations of mIL2Beta. The fusions maintained IL-2R binding capacity (data not shown).

PEGylated and Non-PEGylated Neo-2/15 does not Elicit a Meaningful Anti-Drug Antibody (ADA) Response in Non-Human Primates (NHPs).

The potential of PEGylated and non-PEGylated Neo-2/15 (for PEGylated Neo-2/15: single cysteine mutation of E62C and PEG40K) to elicit ADAs was tested in non-human primates. Animals were administered intravenously with either compound for 1 week: PEGylated Neo-2/15on days 1 and 7; wild-type Neo-2/15 on days 1-7. Blood was drawn at various times thereafter and analyzed for the presence of antibodies specific for the administered compound. Each dose group consisted of 1 male and 1 female macaque. Non-PEGylated Neo-2/15 was administered via daily iv bolus injection for 7 consecutive days at 0.1m/kg, 0.2 mg/kg, or 0.3 mg/kg. PEGylated Neo-2/15 was administered via iv bolus injection at 0.015 mg/kg, 0.050 mg/kg, and 0.10 mg/kg on days 1 and 7. An equivalent volume of saline was administered daily to a vehicle control group for 7 consecutive days. Approximately 750 ul of blood was collected from each animal for ADA analysis on study Days 1 (pre-dose), 22, 29, and 43 via the cephalic or saphenous vein. Serum was extracted from blood using a serum separator tube on wet ice and subsequently stored at −80C until analysis. All cynomolgus macaques receiving either vehicle or PEGylated Neo-2/15 tested negative for ADAs on days 22, 29, and 43 demonstrating that PEGylated Neo-2/15 did not elicit a detectable immune response, even after repeat dosing, despite being a computationally-designed protein that is entirely foreign to the macaque immune system. Both (1 male; 1 female) macaques receiving vehicle control tested negative for ADAs against wild-type Neo-2/15 on days 1, 15, 22, and 28. All animals (3 males; 2 females) in the groups receiving non-PEGylated Neo-2/15 tested negative for ADAs on day 1 (pre-dose). Of these, 3 out of 5 (60%) remained negative for ADAs on days 22, 29, and 43. The remaining two animals subsequently tested positive for ADAs on days 22, 29, or 43. One subject tested positive on days 22 and 29, but returned negative by day 43. For that subject, the ADA response was low and transient, suggesting minimal clinical significance. Another subject tested positive on days 22, 29, and 43. For that subject, the measured ADA concentrations were well below 100 ng/ml and thus of unclear clinical relevance.

Data Tables

Table E1. Characterization of Several De Novo Designed Mimetics of IL-2/IL-15.

The table shows the Kd of de novo IL-2/IL-15 mimetics and reference cytokines for: mIL-2Rβ, mIL-2Rγc, $EC_{50}$, the sequence similarity by structural alignment (MICAN[63]) against hIL-2 (PDB: 2B5I) and mIL-2 (PDB:), the parent of each molecule, its amino acid length, and the sequences for the de novo IL-2 mimetics. "N/S" stands for non-significant and "N/A" for non-available.

TABLE E1

Binding affinity (Kd) to HsIL-2Rβɣc, and cell signaling in human NK (YT, CD25−) cells

| Name | Kd HsIL-2Rβc (nM) | Kd HsIL-2Rβ (nM) | EC50 (CD25−) pSTAT5p (nM)/ (exp i.d.) | Seq identity to HsIL-2 (%/(num a.a. algn)) | Seq identity to MmIL-2 (%/(num a.a. algn)) | Exp. opti-mized | Parent molecule | a.a. length |
|---|---|---|---|---|---|---|---|---|
| HsIL-2 | 193.6 | 326.9 | 0.41/(a) | 100.0/(120) | 54.5/(112) | — | — | 133 |
| MmIL-2 | 8034.0 | 4950.0 | 39.05/(a) | 54.5/(112) | 100/(122) | — | — | 130 |
| Super-2/ Superkine (PDB: 3QAZ) | 300.9 | 2.0 | 0.07/(a) | 94.9/(117) | 50.9/(114) | Y | HsIL-2 | 133 |
| G1_neo2_40 | 260.0 | 1457.0 | 0.14/(b) | 47.7/(86) | 30.4/(79) | N | — | 87 |
| G1_neo2_41 | 187.0 | 720.6 | 0.07/(b) | 47.7/(86) | 30.4/(79) | N | — | 87 |
| G1_neo2_43 | 533.4 | 2861.0 | 0.21/(b) | 50.0/(86) | 32.9/(79) | N | — | 87 |
| G1_neo2_40_1F | 2.3 | 2.6 | 0.09/(c) | 44.2/(86) | 26.6/(79) | Y | G1_neo2_40 | 87 |
| G2_neo2_40_1F_dsn36 | 113.9 | 27.6 | 0.12/(a) | 33.7/(89) | 17.6/(85) | N | De novo mimetic design inspired on template: G1_neo2_40_1F | 100 |

TABLE E1-continued

| | | | | | | | | |
|---|---|---|---|---|---|---|---|---|
| Neoleukin-2/15 (G2_neo2_40_1F_dsn36_opt) | 18.8 | 11.2 | 0.05/(a) | 29.2/(89) | 15.7/(83) | Y | G2_neo2_40_1F_dsn36 | 100 |

Binding affinity (Kd) to MmIL-2Rβγc, and cell signaling (EC50) in murine T (CTLL-2, CD25+) cells

| Name | Kd MmIL-2Rβc (nM) | Kd MmIL-2Rβ (nM) | EC50 (CD25+) pSTAT5 (nM)/ (exp i.d.) | Seq identity to HsIL-2 (%/(num a.a. algn)) | Seq identity to MmIL-2 (%/(num a.a. algn)) | Exp. opti-mized | Parent molecule | a.a. length |
|---|---|---|---|---|---|---|---|---|
| HsIL-2 | 492.2 | 8106.0 | 0.002/(d) | | | *see top table | | |
| MmIL-2 | 126.2 | 1496.0 | 0.003/(e) | | | *see top table | | |
| Super-2/ Superkine (PDB: 3QAZ) | 312.2 | 214.0 | N/A | | | *see top table | | |
| G1_neo2_40_1F | 7.9 | 485.5 | 0.2/(e) | | | *see top table | | |
| G1_neo2_40_1F_H1 | 2654.0 | 6799.0 | 37.38/(d) | 39.5/(86) | 25.0/(80) | Y | G1_neo2_40_1F | 87 |
| G1_neo2_40_1F_H2 | 963.7 | 68300.0 | 9.38/(d) | 40.7/(86) | 26.2/(80) | Y | G1_neo2_40_1F | 87 |
| G1_neo2_40_1F_H3 | 3828.0 | N/S | 35.2/(d) | 39.5/(86) | 25.0/(80) | Y | G1_neo2_40_1F | 87 |
| G1_neo2_40_1F_H4 | 391.8 | 10070.0 | 0.93/(d) | 41.9/(86) | 26.2/(80) | Y | G1_neo2_40_1F | 87 |
| G1_neo2_40_1F_H5 | 5123.0 | 45300.0 | 84.69/(d) | 39.5/(86) | 23.8/(80) | Y | G1_neo2_40_1F | 87 |
| G1_neo2_40_1F_M1 | 4.3 | 213.9 | 0.007/(d) | 36.0/(86) | 25.0/(80) | Y | G1_neo2_40_1F | 87 |
| G1_neo2_40_1F_M2 | 886.3 | 2599.0 | 3.11/(d) | 37.2/(86) | 25.0/(80) | Y | G1_neo2_40_1F | 87 |
| G1_neo2_40_1F_M3 | 64.8 | 402.3 | 0.08/(d) | 34.9/(86) | 25.3/(79) | Y | G1_neo2_40_1F | 87 |
| G2_neo2_40_1F_seq04 | 80.0 | N/A | 1.95/(f) | 38.4/(86) | 23.8/(80) | N | Sequence redesign of G1_neo2_40_1F | 87 |
| G2_neo2_40_1F_seq12 | 39.1 | N/A | 1.74/(f) | 38.4/(86) | 25.3/(79) | N | Sequence redesign of G1_neo2_40_1F | 87 |
| G2_neo2_40_1F_seq16 | 71.5 | N/A | 2.20/(f) | 34.9/(86) | 22.5/(80) | N | Sequence redesign of G1_neo2_40_1F | 87 |
| G2_neo2_40_1F_seq26 | 27.8 | N/A | 1.06/(f) | 39.5/(86) | 25.3/(79) | N | Sequence redesign of G1_neo2_40_1F | 87 |
| G2_neo2_40_1F_seq27 | 13.6 | N/A | 0.24/(f) | 36.0/(86) | 25.0/(80) | N | Sequence redesign of G1_neo2_40_1F | 87 |
| G2_neo2_40_1F_dsn29 | 38.2 | N/A | 0.48/(f) | 36.6/(82) | 8.9/(90) | N | De novo mimetic design using template: G1_neo2_40_1F | 107 |
| G2_neo2_40_1F_dsn30 | 925.0 | N/A | 7.61/(f) | 33.0/(97) | 23.4/(94) | N | De novo mimetic design using template: G1_neo2_40_1F | 107 |
| G2_neo2_40_1F_dsn36 | 568.5 | 2432.0 | 1.36/(e) | | | *see top table | | |
| G2_neo2_40_1F_dsn40 | 69.2 | N/A | 0.50/(f) | 33.7/(89) | 17.9/(84) | N | De novo mimetic design inspired on template: G1_neo2_40_1F | 100 |
| Neoleukin-2/15 (G2_neo2_40_1F_dsn36_opt) | 38.4 | 16.1 | 0.07/(e) | | | *see top table | | |

TABLE E2

Crystallographic data table for neoleukin-2/15 and neoleukin-2/15 quaternary complex with mIL-2R$\beta\gamma_c$.

| | Neolukin-2/15 (6DG6) | Neoleukin-2/15 ternary complex with IL-2R (6DG5) |
|---|---|---|
| Wavelength | | |
| Resolution range | 39.28-1.999 (2.07-1.999) | 47.005-2.516 (2.828-2.516) |
| | — | 3.687 (0.065 a* + 0.998 c*) |
| Ellipsoidal resolution limit (Å) (direction) | — | 3.756 (0.884 a* + 0.468 c*) |
| | — | 2.516 (0.132 a* + 0.859 b* + 0.495 c*) |
| Space group | P 21 21 21 | P 21 2 21 |
| Unit cell (Å, °) | 73.73, 86.8, 92.31, 90, 90, 90 | 65.125, 67.914, 172.084, 90, 90, 90 |
| Total reflections | 351741 (32344) | 132356 (7834) |
| Unique reflections | 40650 (3977) | 13961 (698) |
| Multiplicity | 8.7 (8.1) | 9.5 (11.2) |
| Completeness (spherical) (%) | 92.58 (77.83) | 52.3 (9.0) |
| Completeness (ellipsoidal) (%) | | 93.2 (77.2) |
| Mean I/sigma(I) | 12.19 (1.25) | 68 (1.3) |

TABLE E2-continued

Crystallographic data table for neoleukin-2/15 and neoleukin-2/15 quaternary complex with mIL-2Rβ$\gamma_c$.

| | Neolukin-2/15 (6DG6) | Neoleukin-2/15 ternary complex with IL-2R (6DG5) |
|---|---|---|
| Wilson B-factor | 34.54 | 39.86 |
| R-merge | 0.1027 (1.709) | 0.359 (2.516) |
| R-meas | 0.1094 (1.824) | 0.380 (2.636) |
| R-pim | 0.0369 (0.8252) | 0.122 (0.780) |
| CC1/2 | 0.999 (0.557) | 0.987 (0.445) |
| CC* | 1 (0.846) | 0.993 (0.328) |
| Resolution range used in refinement | 39.28-1.999 (2.07-1.999) | 43.82-2.516 (2.606-2.516) |
| Reflections used in refinement | 37747 (3125) | 13923 (136) |
| Reflections used for R-free | 1840 (143) | 1366 (14) |
| R-work | 0.2037 (0.3137) | 0.2211 (0.3271) |
| R-free | 0.2260 (0.3377) | 0.2658 (0.4429) |
| Number of non-hydrogen atoms | 4791 | 4100 |
| macromolecules | 4735 | 3949 |
| ligands | — | 138 |
| solvent | 56 | 13 |
| Protein residues | 597 | 492 |
| RMS(bonds) | 0.005 | 0.004 |
| RMS(angles) | 0.86 | 0.94 |
| Ramachandran favored (%) | 97.41 | 97.1 |
| Ramachandran allowed (%) | 2.59 | 2.9 |
| Ramachandran outliers (%) | 0 | 0 |
| Rotamer outliers (%) | 1.26 | 4.6 |
| Clashscore | 2.14 | 4.55 |
| Average B-factor | 52.56 | 47.05 |
| macromolecules | 52.54 | 46.39 |
| ligands | — | 67.79 |
| solvent | 54.21 | 27.31 |
| Number of TLS groups | 20 | 3 |

*Statistics for the highest-resolution shell are shown in parentheses.

TABLE S1

Amino acid sequences for the best twelve first-round designs. Ten of the designs were (G1_neo2_35-44) were experimentally characterized by yeast display and all but two (G1_neo2_35 and G1_neo2_44) were found to bind fluorescently labeled chimeric ILRβ$\gamma_c$ at low nanomolar concentrations via flow cytometry screening of designed first-round protein binders. Designs indicated were expressed on yeast and incubated with 2 nM hIL-2Rβ$\gamma_c$ or 0 nM IL-2Rβ$\gamma_c$ (data not shown).

| Design | Sequence |
|---|---|
| G1_neo2_33 | STKKWQLQAEHALLDWQMALNKSPEPNENLNRAITAAQSWISTGKIDLDKAEDIRRNSDQ ARREAEKRGIDVRDLISNAQVILLEAR (SEQ ID NO: 103) |
| G1_neo2_34 | STKKWQLQAEHALLDWQMALNKSPEPNENLNRAITAAQSCISTGKCDLDKAEDIRRNSDQ ARREAEKRGIDVRDLISNAQVILLEAR (SEQ ID NO: 104) |
| G1_neo2_35 | STKKWQLQAEHALLDWQMALNKSPEPNENLNRAITAAQSWISTGKIDCDKAEDIRRNSDQ ARREAEKRGIDVRDLISNAQVILLEAC (SEQ ID NO: 105) |
| G1_neo2_36 | STKKLQLQAEHFLLDVQMILNESPEPNEELNRAITDAQSWISTGKIDLDRAEELARNLEK VRDEALKRGIDVRDLVSNAKVIALELK (SEQ ID NO: 106) |
| G1_neo2_37 | STKKLQLQAEHFLLDVQMILNESPEPNEELNRCITDAQSWISTGKIDLDRAEECARNLEK VRDEALKRGIDVRDLVSNAKVIALELK (SEQ ID NO: 107) |
| G1_neo2_38 | STKKLQLQAEHFLLDVQMILNESPEPNEELNRAITDAQSCISTGKCDLDRAEELARNLEK VRDEALKRGIDVRDLVSNAKVIALELK (SEQ ID NO: 108) |
| G1_neo2_39 | STKKLQLQAEHFLLDVQMILNESPEPNEELNRAITDAQSWISTGKIDLDRAEELCRNLEK VRDEALKRGIDVRDLVSNACVIALELK (SEQ ID NO: 109) |
| G1_neo2_40 | STKKLQLQAEHALLDAQMMLNRSPEPNEKLNRIITTMQSWISTGKIDLDGAKELAKEVEE LRQEAEKRGIDVRDLASNLKVILLELA (SEQ ID NO: 110) |
| G1_neo2_41 | STKKLQLQAEHALLDAQMMLNRSPEPNEKLNRIITTMQSCISTGKCDLDGAKELAKEVEE LRQEAEKRGIDVRDLASNLKVILLELA (SEQ ID NO: 111) |
| G1_neo2_42 | STKKIQLQLEHALLDVQMALNRSPEPNESLNRMITWLQSWISTGKIDLDNAQEMAKEAEK IRKEMEKRGIDVRDLISNIIVILLELS (SEQ ID NO: 112) |

TABLE S1-continued

Amino acid sequences for the best twelve first-round designs. Ten of the designs were (G1_neo2_35-44) were experimentally characterized by yeast display and all but two (G1_neo2_35 and G1_neo2_44) were found to bind fluorescently labeled chimeric ILR$\beta\gamma_c$ at low nanomolar concentrations via flow cytometry screening of designed first-round protein binders. Designs indicated were expressed on yeast and incubated with 2 nM hIL-2R$\beta\gamma_c$ or 0 nM IL-2R$\beta\gamma_c$ (data not shown).

| Design | Sequence |
|---|---|
| G1_neo2_43 | STKKIQLQLEHALLDVQMALNRSPEPNESLNRMITWLQSCISTGKCDLDNAQEMAKEAEK IRKEMEKRGIDVRDLISNIIVILLELS (SEQ ID NO: 113) |
| G1_neo2_44 | STKKIQLQLEHALLDVQMALNRSPEPNESLNRMITWLQSWISTGKIDLDNAQEMCKEAEK IRKEMEKRGIDVRDLISNICVILLELS (SEQ ID NO: 114) |

TABLE S2

Amino acid sequences for the experimentally optimized first-round designs.

| Design | Sequence |
|---|---|
| G1_neo2_40_1A | STKKTQLLAEHALLDAFMMLNVVPEPNEKLNRIITTMQSWIYTGKIDADGAKELAKEVEELE QEYEKRGIDVEDDASNLKVILLELA (SEQ ID NO: 115) |
| G1_neo2_40_1B | STKKTQLLAEHALLDAHMMLNMLPEPNEKLNRIITTMQSWIHTGKIDGDGAQELAKEVEELE QEYEKRGIDVEDEASNLKVILLELA (SEQ ID NO: 116) |
| G1_neo2_40_1C | STKKTQLLAEHALLDAFMMLNMVPEPNEKLNRIITTMQSWIFTGKIDGDGAKELAKEVEELE QEFEKRGIDVEDEASNLKVILLELA (SEQ ID NO: 117) |
| G1_neo2_40_1D | STKKTQLLAEHALLDALMMLNMVPEPNEKLNRIITTMQSWIFTGKIDGDGAQELAKEVEELE QELEKRGIDVEDYASNLKVILLELA (SEQ ID NO: 118) |
| G1_neo2_40_1E | STKKTQLLAEHALLDAHMMLNVVPEPNEKLNRIITTMQSWIYTGKIDRDGAQELAKEVEELE QELEKRGIDVDDDASNLKVILLELA (SEQ ID NO: 119) |
| G1_neo2_40_1F | STKKTQLLAEHALLDALMMLNLLPEPNEKLNRIITTMQSWIFTGKIDGDGAQELAKEVEELE QEHEKRGIDVEDYASNLKVILLELA (SEQ ID NO: 120) |
| G1_neo2_40_1G | STKKTQLLAEHALLDAYMMLNMVPEPNEKLNRIITTMQSWILTGKIDSDGAQELAKEVEELE QELEKRGIDVDDDASNLKVILLELA (SEQ ID NO: 121) |
| G1_neo2_40_1H | STKKTHLLAEHALLDAYMMLNVMPEPNEKLNRIITTMQSWIFTGKIDGDGAKELAKEVEELE QEFEKRGIDVDDDASNLKVILLELA (SEQ ID NO: 122) |
| G1_neo2_40_1I | STKKTQLLAEHALLDAYMMLNLVPEPNEKLNRIITTMQSWIFTGKIDADGAQELAIEVEELE QEYEKRGIDVDDYASNLKVILLELA (SEQ ID NO: 123) |
| G1_neo2_40_1J | STKKTQLMAEHALLDAFMMLNVLPEPNEKLNRIITTMQSWIFTGKIDGDDAQELAKEVEELE QELEKRGIDVDDDASNLKVILLELA (SEQ ID NO: 124) |
| G1_neo2_40_1F_H1 | STKKTQLLIEHALLDALDMSRNLPEPNEKLSRIITTMQSWIFTGKIDGDGAQQLAKEVEELE QEHEKRGEDVEDEASNLKVILLELA (SEQ ID NO: 125) |
| G1_neo2_40_1F_H2 | STKKTQLLLEHALLDALHMRRNLPEPNEKLSRIITTMQSWIFTGKIDGDGAQELAKEVEELE QEHEKRGRDVEDDASNLKVILLELA (SEQ ID NO: 126) |
| G1_neo2_40_1F_H3 | STKKTQLLIEHALLDALNMRKKLPEPNEKLSRIITDMQSWIFTGKIDGDGAQQLAKEVEELE QEHEKRGGDVEDYASNLKVILLELA (SEQ ID NO: 127) |
| G1_neo2_40_1F_H4 | STKKTQLLLEHALLDALHMSRELPEPNEKLNRIITDMQSWIFTGKIDGDGAQDLAKEVEELE QEHEKRGGDVEDYASNLKVILLELA (SEQ ID NO: 128) |
| G1_neo2_40_1F_H5 | STKKTQLLIEHALLDALHMSRKLPEPNEKLSRIITTMQSWIFTGKIDGDGAQHLAKEVEELE QEHEKRGGEVEDEASNLKVILLELA (SEQ ID NO: 129) |
| G1_neo2_40_1F_H6 | STKKTQLLIEHALLDALHMKRKLPEPNEKLNRIITNMQSWIFTEKIDGDGAQDLAKEVEELE QEHEKRGQDVEDYASNLKVILLELA (SEQ ID NO: 130) |
| G1_neo2_40_1F_M1 | STEKTQLAAEHALRDALMLKHLLNEPNEKLARIITTMQSWQFTGKIDGDGAQELAKEVEELQ QEHEVRGIDVEDYASNLKVILLHLA (SEQ ID NO: 131) |
| G1_neo2_40_1F_M2 | STKNTQLAAEDALLDALMLRNLLNEPNEKLARIITTMQSWQFTEKIDGDGAQELAKEVEELQ QEHEERGIDVEDYASNLKVILLQLA (SEQ ID NO: 132) |

TABLE S2-continued

Amino acid sequences for the experimentally optimized first-round designs.

| Design | Sequence |
|---|---|
| G1_neo2_40_1F_M3 | STEKTQHAAEDALRDALMLRNLLNEPNEKLARIITTMQSWQFTEKIDGDGAQELAKEVEELQ QEHEVRGIDVEDYASNLKVILLQLA (SEQ ID NO: 133) |

TABLE S3

Amino acid sequences for second-round designs.
G2_neo2_40_1F_seq02 to G2_neo2_40_1F_seq28 correspond to the 27 Rosetta
sequence redesigns of G1_neo2_40_1F; G2_neo2_40_1F_seq29 to
G2_neo2_40_1F_seq42 represent the 14 new de novo mimetic designs.

| Design | Sequence |
|---|---|
| G2_neo2_40_1F_seq02 | TQKKQQLLAEHALLDALMILNMLKTSSEAVNRMITIAQSWIFTGTSNPEEAKEMIKMA EQAEEEARREGVDTEDYVSNLKVILKEIA (SEQ ID NO: 134) |
| G2_neo2_40_1F_seq03 | TTKKYQLLEHALLDALMMLNLSSESNEKMNRIITTMQSWIFTGTFDPQAEELAKLV EELREEFKRKRGIDTEDYASNLKVILKELS (SEQ ID NO: 135) |
| G2_neo2_40_1F_seq04 | TTKKIQLLVEHALLDALMILNLSSESNEKLNRIITTLQSWIFRGEIDPDRARELAKLL EEIREEMRKRGIDTEDYVSNMIVIIRELA (SEQ ID NO: 136) |
| G2_neo2_40_1F_seq05 | TKKKIQLLAEHVLLDLLMMLNLSSESNEKMNRLITIVQSWIFTGTIDPDQAEEMAKMV EELREEFKRGIDTEDYASNVKVILKELS (SEQ ID NO: 137) |
| G2_neo2_40_1F_seq06 | TKKKYQLLIEHLLDALMVLNMSSESNEKLNRIITILQSWIFTGTWDPDLAEEMEKLM QEIEEELRRRGIDTEDYMSNMRVIIKELS (SEQ ID NO: 138) |
| G2_neo2_40_1F_seq07 | TKKKLQLLVEHLLLDMLMILNMSSESNEKLNRLITELQSWIFRGEIDPDKAEEMWKIM EEIEKELRERGIDTEDYMSNAKVIIKELS (SEQ ID NO: 139) |
| G2_neo2_40_1F_seq08 | TSKKQQLLAEHALLDALMILNISSESSEAVNRAITWLQSWIFKGTVNPDQAEEMRKLA EQIREEMRKRGIDTEDYVSNLEVIAKELS (SEQ ID NO: 140) |
| G2_neo2_40_1F_seq09 | TKKKYQLLIEHLLLDLLMVLNMSSESNEKINRLITWLQSWIFTGTYDPDLAEEMYKIL EELREEMRERGIDTEDYMSNMRVIVKELS (SEQ ID NO: 141) |
| G2_neo2_40_1F_seq10 | TKKKWQLLIEHLLLDLLMILNLSSESNEKLNRLITWLQSWIFTGTYDPDLAEEMKKMM DEIEDELRERGIDTEDYMSNAKVIIKELS (SEQ ID NO: 142) |
| G2_neo2_40_1F_seq11 | TKKIQLLVEHLALLDLLMILNLSSESNEKLNRLITWLQSWIFTGTIDPDQAEELSKLV EEIREEMRKRGIDTEDYVSNLKVILDELS (SEQ ID NO: 143) |
| G2_neo2_40_1F_seq12 | TEKKLQLLVEHALLDALMILNLWSESNEKLNRIITTMQSWIFTGRIDPDKAEELAKLV EELREEARERGIDTEDYVSNLKVILKELS (SEQ ID NO: 144) |
| G2_neo2_40_1F_seq13 | TKKKYQLLMEHLLLDLLMVLNMSSESNEKLNRLITIIQSWIFTGTWDPDKAEEMAKML KEIEDELRERGIDTEDYMSNMIVIMKELS (SEQ ID NO: 145) |
| G2_neo2_40_1F_seq14 | TTKKIQLLVEHALLDALMLLNLSSESNEKMNRIITTMQSWIFEGRIDPDQAQELAKLV EELREEFRKRGIDTEDYVSNLKVILEELS (SEQ ID NO: 146) |
| G2_neo2_40_1F_seq15 | TKKKIQLLVEHALLDALMMLNLSSESNEKLNRIITTMQSWIFTGTIDPDQAEELAKLV RELREEFRKRGIDTEDYASNLEVILRELS (SEQ ID NO: 147) |
| G2_neo2_40_1F_seq16 | TKKKIQLLVEHALLDALMILNLSSKSNEKLNRIITTMQSWIFNGTIDPDRARELAKLV EEIRDEMEKNGIDTEDYVSNLKVILEELA (SEQ ID NO: 148) |
| G2_neo2_40_1F_seq17 | TKKKYQLLIEHVLLDLLMLLNLSSESNEKMNRLITILQSWIFTGTYDPDKAEEMAKLL KELREEFRERGIDTEDYISNAIVILKELS (SEQ ID NO: 149) |
| G2_neo2_40_1F_seq18 | TKKKIQLLVEHALLDALMMLNLSSESNEKLNRIITTMQSWIFTGTIDPDRAEELAKLV EELREEFRKRGIDTEDYASNLKVILKELS (SEQ ID NO: 150) |
| G2_neo2_40_1F_seq19 | TKKKIQLLVEHALLDALMMLNLSSESNEKLNRIITTMQSWIFNGTIDPDQARELAKLV EELREEFRKRGIDTEDYASNLKVILEELA (SEQ ID NO: 151) |
| G2_neo2_40_1F_seq20 | TKKKLQLLVEHALLDALMLLNLSSESNEKLNRIITTMQSWIFTGTVDPDQAEELAKLV EEIREELRKRGIDTEDYVSNLKVILKELS (SEQ ID NO: 152) |
| G2_neo2_40_1F_seq21 | TTKKYQLLVEHALLDALMILNLSSESNEKLNRIITTMQSWIFTGTFDPDQAEELAKLV REIREEMRKRGIDTEDYVSNLEVILRESL (SEQ ID NO: 153) |

TABLE S3-continued

Amino acid sequences for second-round designs. G2_neo2_40_1F_seq02 to G2_neo2_40_1F_seq28 correspond to the 27 Rosetta sequence redesigns of G1_neo2_40_1F; G2_neo2_40_1F_seq29 to G2_neo2_40_1F_seq42 represent the 14 new de novo mimetic designs.

| Design | Sequence |
| --- | --- |
| G2_neo2_40_1F_seq22 | TKKKIQLLVEHALLDALMILNLSSESNEKLNRIITTMQSWIFTGTIDPDRAEELAKLV REIREEMRKRGIDTEDYVSNLEVILRELS (SEQ ID NO: 154) |
| G2_neo2_40_1F_seq23 | TKKKYQLLIEHLLLDLLMILNLSSESNEKLNRLITWLQSWIFRGEWDPDKAEEWAKIL KEIREELRERGIDTEDYMSNAIVIMKELS (SEQ ID NO: 155) |
| G2_neo2_40_1F_seq24 | TDKKLQLLVEHLLLDLLMMLNLSSKSNEKMNRLITIAQSWIFTGKVDPDLAREMIKLL EETEDENRKNGIDTEDYVSNARVIAKELE (SEQ ID NO: 156) |
| G2_neo2_40_1F_seq25 | TKKKIQLLVEHALLDALMLLNLSSESNEKMNRIITTMQSWIFTGTIDPDQAEELAKLV EELKEEFKKRIGDTEDYVSNLKVILKELS (SEQ ID NO: 157) |
| G2_neo2_40_1F_seq26 | TKKKYQLLIEHALLDALMILNLWSESNEKLNRIITTMQSWIFTGTYDPDKAEELEKLA KEIEDEARERGIDTEDYMSNLRVILKELS (SEQ ID NO: 158) |
| G2_neo2_40_1F_seq27 | TKKKAQLLAEHALLDALMLLNLSSESNERLNRIITWLQSIIFTGTYDPDMVKEAVKLA DEIEDEMRKRGIDTEDYVSNLRVILQELA (SEQ ID NO: 159) |
| G2_neo2_40_1F_seq28 | TQKKNQLLAEHLLLDALMVLNQSSESSEVANRIITWAQSWIFEGRVDPNKAEEAKKLA KKLEEEMRKRGIDMEDYISNMKVIAEEMS (SEQ ID NO: 160) |
| G2_neo2_40_1F_seq29 | EDYYSNLKVILEELAREMERNGLSDKAEEWRQWKKIVERIRQIRSNNSDLNEKAELLN RLITYIQSQIFEISERIRETDQEKKEESWKKWQLLLEHALLDVLMLLND (SEQ ID NO: 161) |
| G2_neo2_40_1F_seq30 | PEKKRQLLLEHILLDALMLLNLLETNPQNTESKFEDYISNAEVIAEELAKLMESLGLS DEQEKFKKIKQWLREVWRIWSSTNWSTLEDKARELLNRIITTIQSQIFY (SEQ ID NO: 162) |
| G2_neo2_40_1F_seq31 | PEKKRQLLLEHILLDLLMILNMIETNRENTESEMEDYWSNVRVILRELARLMEELNKY ELSELMERMRKIVEKIRQIVTNNSSLDTAREWLNRLITWIQSLIFR (SEQ ID NO: 163) |
| G2_neo2_40_1F_seq32 | PEKKRQLLAEHALLDALMLLNIIETNSKNTESKMEDYVSNLEVILTEFKKLAEKLNFS EEAERAERMKRWARKAYQMMTLDLSLDKAKEMLNRIITILQSIIFN (SEQ ID NO: 164) |
| G2_neo2_40_1F_seq33 | PEKKRQLLAEHLLLDVLMMLNGNASLKDYASNAQVIAEDFRELARELGLTDEAKKAEK IIEALERAREWLLNNKDKEKAKEALNRAITIAQSWIFN (SEQ ID NO: 165) |
| G2_neo2_40_1F_seq34 | PEKKRQLLLEHLLLDLLMILNMLRTNPKNIESDWEDYMSNIEVIIEELRKIMESLGRS EKAKEWKRMKQWVRRILEIVKNNSDLEEAKEWLNRLITIVQSEIFE (SEQ ID NO: 166) |
| G2_neo2_40_1F_seq35 | WEKKRQLLLEHLLLDLLMILNMWRTNPQNTESLMEDYMSNAKVIVEELARMMRSQGLE DKAREWEEMKKRIEEIRQIIQNNSSKERAKEELNRLITYVQSEIFR (SEQ ID NO: 167) |
| G2_neo2_40_1F_seq36 | PKKKIQLLAEHALLDALMILNIVKTNSQNAEEKLEDYASNVEVILEEIARLMESGDQK DEAEKAKRMKEWMKRIKTTASEDEQEEMANRIITLLQSWIFS (SEQ ID NO: 168) |
| G2_neo2_40_1F_seq37 | PEKKRQLLAEHALLDALMILNILQTNPQNAEEKLEDYMSNVEVIMEEFARMMRNGDRS EEAENAERIKKWVRKASSTASSEEQREMMNRAITLMQSWIFE (SEQ ID NO: 169) |
| G2_neo2_40_1F_seq38 | PEKKRQLLAEHLLLDALMVLNMLTTNSKNTEEKLEDYISNMKVIIKEMIELMRSLGRL EEAEKWKEALKAVEKIGSRMDSETARELANRIITLAQSAIFY (SEQ ID NO: 170) |
| G2_neo2_40_1F_seq39 | PEKKRQLLAEHALLDALMFLNLVETNPDQAEEKIEDYASNLRVIAEELARLFENLGRL DEAQKAKDIKELAERARSRVSSEKRKEAMNRAITILQSMIFR (SEQ ID NO: 171) |

TABLE S3-continued

Amino acid sequences for second-round designs. G2_neo2_40_1F_seq02 to G2_neo2_40_1F_seq28 correspond to the 27 Rosetta sequence redesigns of G1_neo2_40_1F; G2_neo2_40_1F_seq29 to G2_neo2_40_1F_seq42 represent the 14 new de novo mimetic designs.

| Design | Sequence |
|---|---|
| G2_neo2_40_1F_seq40 | PEKKRQLLAEHALLDALMILNIIRTNSDNTESKLEDYISNLKVILEEIARLMESLGLS DEAEKAKEAMRLADKAGSTASEEEKKEAMNRVITWAQSWIFN (SEQ ID NO: 172) |
| G2_neo2_40_1F_seq41 | PEKKRQLLAEHALLDALMMLNILRTNPDNAEEKLEDYWSNLIVILREIAKLMESLGLT DEAEKAKEAARWAEEARTTASKDQRRELANRIITLLQSWIFS (SEQ ID NO: 173) |
| G2_neo2_40_1F_seq42 | PEKKRQLLAEHLLLDALMILNIIETNEQNAESKLEDYISNAKVILDEFREMARDLGLL DEAKKAEKMKRWLEKMRSNASSDERREWANRMITTAQSWIFN (SEQ ID NO: 174) |

TABLE S4

Amino acid sequences for the experimentally optimized second-round designs.

| Design | Sequence |
|---|---|
| G2_neo2_40_1F_seq27_S18 | TNKEAQLHAEFALYDALMLLNLSSESNERLNRIITWLQSIIFYETYDPDMVKEAV KLADEIEDEMRKRKIDTEDYVVNLRLILQELA (SEQ ID NO: 175) |
| G2_neo2_40_1F_seq27_S22 | TKKDAELLAEFALYDALMLLNLSSESNERLNEIITWLQSIIFYGTYDPDMVKEAV KLADEIEDEMRKRGIDTEDYVSNLRLILQELA (SEQ ID NO: 176) |
| G2_neo2_40_1F_seq27_S24 | TNKKAQLHAEFALYDALMLLNLSSESNERLNDIITWLQSIIFTGTYDPDMVKEAV KLADEIEDEMRKRKIDTEDYVVNLRYILQELA (SEQ ID NO: 177) |
| G2_neo2_40_1F_seq29_S6 | EDYYSNLKLILEELAREMERNGLSDKAEEWRQWKKIVERIRQIRSNNSDLNEAKE LLNRLITYIQSQIFEVLHGVGETDQEKKEESWKKWDLLLEHALLDVLMLLND (SEQ ID NO: 178) |
| G2_neo2_40_1F_seq29_S7 | EDYYSNLKVILEELAREMERNGLSDKAEEWRQWKKIVERIRQIRSNNSDLNEAKE LLNELITYIQSQIFEVIEREGETDQEKKEESWKKWELHLEHALLDVLMLLND (SEQ ID NO: 179) |
| G2_neo2_40_1F_seq29_S8 | EDYYSNLKLILEELAREMERNGLSDKAEEWRQWKKIVERIRQIRSNNSDLNEAKE LLNRLITYIQSQIFEVLEGVGETDQEKKEESWKKWELHLEHALLDVLMLLND (SEQ ID NO: 180) |
| Neolukin-2/15 (i.e. G2_neo2_40_1F_seq36_S11) | PKKKIQLHAEHALYDALMILNIVKTNSPPAEEKLEDYAFNFELILEEIARLFESG DQKDEAEKAKRMKEWMKRIKTTASEDEQEEMANAIITILQSWIFS (SEQ ID NO: 181) |
| G2_neo2_40_1F_seq36_S12 | PKKKIQLLAEHALFDLLMILNIVKTNSQNAEEKLEDYAYNAGVILEEIARLFESG DQKDEAEKAKRMKEWMKRIKDTASEDEQEEMANEIITILQSWNFS (SEQ ID NO: 182) |

Neoleukin-2/15-H8Y-K33E: H1->H3->H2'->H4

PKKKIQLYAEHALYDALMILNIVKTNSPPAEEELEDYAFNFELILEEIARLFESGDQKDEAEKAKRMKEWMKRIKT TASEDEQEEMANAIITILQSWIFS (SEQ ID NO: 94)

Binding of Neoleukin-2/15-H8Y-K33E to the IL2 receptor was measured by biolayer interferometry, and it was found to have higher binding affinity than Neoleukin-2 for IL2-Rbeta, both when tested against IL2Rbeta alone and when tested against the IL2Rbeta-gamma complex. This increased affinity was attributable mostly to an improved off-rate from IL2-Rbeta.

TABLE S5

Amino acid sequences for the interleukin-4 mimetic designs based on reengineering of neolukin-2/15.

| Design | Sequence |
|---|---|
| IL4_G2_neo2_40_1F_seq36_S11 | PKKKIQITAEEALKDALSILNIVKTNSPPAEEQLERFAKRFERNLWGIARLF ESGDQKDEAEKAKRMKEWMKRIKTTASEDEQEEMANAIITILQSWIFS (SEQ ID NO: 183) |

TABLE S5-continued

| Amino acid sequences for the interleukin-4 mimetic designs based on reengineering of neolukin-2/15. | |
|---|---|
| Design | Sequence |
| Neoleukin-4 (i.e. IL4_G2_neo2_40_1F_seq36_S11_MIF) | PKKKIQIMAEEALKDALSILNIVKTNSPPAEEQLERFAKRFERNLWGIARLF ESGDQKDEAEKAKRMIEWMKRIKTTASEDEQEEMANAIITILQSWFFS (SEQ ID NO: 184) |

APPENDIX A

RosettaScripts XML protocol for sequence design of mimetics generation-1.

```
<ROSETTASCRIPTS>
    <SCOREFXNS>
        <SFXN6 weights=talaris2013.wts />
        <SFXN6dA weights=talaris2013_downAla.wts />
    </SCOREFXNS>
        <FILTERS>
            <SSPrediction name="sspred"
cmd="/work/dadriano/PROGRAMS/psipred/runpsipred_single"
use_probability="0" use_svm="0" threshold=0.80
confidence="1"/>
            <ScoreType name="rama" scorefxn="SFXN6"
score_type="rama" threshold=0.0 confidence="0" />
            <PackStat name=pack threshold=0.63 confidence=1/>
            <Holes name=holes threshold=1.2 confidence=0/>
            <ScoreType name="score" scorefxn="SFXN6"
score_type="total_score" threshold=0.0 confidence="0" />
            <ResidueCount name="nres" confidence="0" />
            <CalculatorFilter name="score_res"
equation="SCORE/NRES" threshold="-1.7" confidence="1">
                <SCORE name="SCORE" filter_name="score" />
                <NRES name="NRES" filter_name="nres" />
            </CalculatorFilter>
            <CompoundStatement name=filt >
                <AND filter_name=sspred />
                <AND filter_name=rama />
                <AND filter_name=score_res />
                <AND filter_name=pack />
            </CompoundStatement>
    </FILTERS>
    <TASKOPERATIONS>
            <InitializeFromCommandline name="init"/>
            <IncludeCurrent name="inclcur"/>
            <LimitAromaChi2 name=limitchi2 />
            DisallowIfNonnative name="not_aa_H" disallow aas="H"/>
            <ReadResfile name="resfile" filename="./input.resfile"
/>
```

APPENDIX A-continued

RosettaScripts XML protocol for sequence design of mimetics generation-1.

```
    </TASKOPERATIONS>
    <MOVERS>
        <Dssp name=dssp/>
        <FastDesign name="fdesign"
task_operations="init,resfile,limitchi2" scorefxn="SFXN6dA"
allow_design="1" only_design_worst_region="0"
design_by_psipred="0" design_by_frag_qual="0" repeats="2"
clear_designable_residues="0" max_redesigns="2000" />
        <FastRelax name=relax />
        <ParsedProtocol name="complexDesign" >
            <Add mover_name="fdesign" />
            <Add mover_name="relax" />
            <Add mover_name="dssp" />
        </ParsedProtocol>
        <LoopOver name="fastDesignProtein"
mover_name="complexDesign" filter_name=filt drift=0
iterations="10" ms_whenfail=FAIL_DO_NOT_RETRY/>
    </MOVERS>
    <APPLY_TO_POSE>
    </APPLY_TO_POSE>
    <PROTOCOLS>
        <Add mover_name=fastDesignProtein />
        <Add filter_name=sspred />
        <Add filter_name=pack />
        <Add filter_name=score />
        <Add filter_name=score_res />
        <Add filter_name=holes />
        <Add filter_name=rama />
    </PROTOCOLS>
</ROSETTASCRIPTS>
```

We claim:

1. A nucleic acid encoding a non-naturally occurring polypeptide comprising domains X1, X2, X3, and X4, wherein:

(a) X1 is a peptide comprising the amino acid sequence EHALYDAL (SEQ ID NO:1);

(b) X2 is a helical-peptide of at least 8 amino acids in length;

(c) X3 is a peptide comprising the amino acid sequence YAFNFELI (SEQ ID NO:2);

(d) X4 is a peptide comprising the amino acid sequence ITILQSWIF (SEQ ID NO:3);

wherein X1, X2, X3, and X4 may be in any order in the polypeptide;

wherein amino acid linkers may be present between any of the domains; and wherein the polypeptide binds to IL-2 receptor $\beta\gamma_c$ heterodimer (IL-2R$\beta\gamma_c$).

2. The nucleic acid of claim 1, wherein:

X1 is a peptide comprising an amino acid sequence at least 60% identical to the peptide PKKKIQLHAEHALYDALMILNI (SEQ ID NO: 4) provided that the amino acids at positions 10-17 relative to SEQ ID NO:4 are identical to SEQ ID NO:1;

X3 is a peptide comprising an amino acid sequence at least 60% identical to the peptide LEDYAFNFELILEEIARLFESG (SEQ ID NO:5) provided that the amino acids at positions 4-11 relative to SEQ ID NO:5 are identical to SEQ ID NO:2; and X4 is a peptide comprising an amino acid sequence at least 60% identical to the peptide EDEQEEMANAIITILQSWIFS (SEQ ID NO:6) provided that the amino acids at positions 12-20 relative to SEQ ID NO:6 are identical to SEQ ID NO:3.

3. The nucleic acid of claim 2, wherein X2 is a peptide comprising an amino acid sequence at least 50% identical to the peptide KDEAEKAKRMKEWMKRIKT (SEQ ID NO:7).

4. The nucleic acid of claim 1, wherein:

X1 is a peptide comprising an amino acid sequence at least 80% identical to the peptide PKKKIQLHAEHALYDALMILNI (SEQ ID NO: 4) provided that the amino acids at positions 10-17 relative to SEQ ID NO:4 are identical to SEQ ID NO:1;

X3 is a peptide comprising an amino acid sequence at least 80% identical to the peptide LEDYAFNFELILEEIARLFESG (SEQ ID NO:5) provided that the amino acids at positions 4-11 relative to SEQ ID NO:5 are identical to SEQ ID NO:2; and X4 is a peptide comprising an amino acid sequence at least 80% identical to the peptide EDEQEEMANAIITILQSWIFS (SEQ ID NO:6) provided that the amino acids at positions 12-20 relative to SEQ ID NO:6 are identical to SEQ ID NO:3.

5. The nucleic acid of claim 4, wherein X2 is a peptide comprising an amino acid sequence at least 80% identical to the peptide KDEAEKAKRMKEWMKRIKT (SEQ ID NO:7).

6. The nucleic acid of claim 4 wherein the domains are arranged N-terminal to C-terminal in an arrangement selected from X1-X3-X2-X4.

7. The nucleic acid of claim 1, wherein:

X1 is a peptide comprising the amino acid sequence PKKKIQLHAEHALYDALMILNI (SEQ ID NO: 4);

X3 is a peptide comprising the amino acid sequence LEDYAFNFELILEEIARLFESG (SEQ ID NO:5); and X4 is a peptide comprising the amino acid sequence EDEQEEMANAIITILQSWIFS (SEQ ID NO:6).

8. The nucleic acid of claim 7, wherein X2 is a peptide comprising an amino acid sequence at least 90% identical to the peptide KDEAEKAKRMKEWMKRIKT (SEQ ID NO:7).

9. The nucleic acid of claim 8 wherein the domains are arranged N-terminal to C-terminal in an arrangement selected from X1-X3-X2-X4.

10. The nucleic acid of claim 1 wherein the domains are arranged N-terminal to C-terminal in an arrangement selected from X1-X3-X2-X4.

11. A nucleic acid encoding a non-naturally occurring polypeptide comprising domains X1, X2, X3, and X4, wherein:

X1 is a peptide comprising an amino acid sequence at least 80% identical to the peptide PKKKIQLHAEHALYDALMILNI (SEQ ID NO: 4);

X2 is a helical-peptide of at least 8 amino acids in length;

X3 is a peptide comprising an amino acid sequence at least 80% identical to the peptide LEDYAFNFELILEEIARLFESG (SEQ ID NO:5); and X4 is a peptide comprising an amino acid sequence at least 80% identical to the peptide EDEQEEMANAIITILQSWIFS (SEQ ID NO:6);

wherein X1, X2, X3, and X4 may be in any order in the polypeptide;

wherein amino acid linkers may be present between any of the domains; and wherein the polypeptide binds to IL-2 receptor $\beta\gamma_c$ heterodimer (IL-2R$\beta\gamma_c$).

12. The nucleic acid of claim 11, wherein:

X1 is a peptide comprising an amino acid sequence at least 80% identical to the peptide PKKKIQLHAEHALYDALMILNI (SEQ ID NO: 4), wherein the amino acid at position 1 is P or if substituted is A, F, I, L, M, Q, R, S, or W;

the amino acid at position 2 is K or if substituted is A, D, E, G, or V;

the amino acid at position 3 is K or if substituted is D, E, F, or W;

the amino acid at position 4 is K or if substituted is D, E, N, P, R, or W;

the amino acid at position 5 is I or if substituted is D, E, H, K, L, M, or S;

the amino acid at position 6 is Q or if substituted is A, D, E, G, L, P, S, or W;

the amino acid at position 7 is L or if substituted is D, E, Q, Y, or I;

the amino acid at position 8 is H or if substituted is A, F, W, Y, M, or T;

the amino acid at position 9 is A or if substituted is C, F, or P;

the amino acid at position 10 is E or if substituted is C, D, F, K, or P;

the amino acid at position 11 is H or if substituted is D, F, or E;

the amino acid at position 12 is A or if substituted is D, E, P, S, T, or V;

the amino acid at position 13 is L or if substituted is H, I, M, P, R, V, or W;

the amino acid at position 14 is Y or if substituted is F, R, W, or K;

the amino acid at position 15 is D or if substituted is E, N, or Y;

the amino acid at position 16 is A or if substituted is C, L, M, or S;

the amino acid at position 17 is L or if substituted is F, I, M, P, or R;

the amino acid at position 18 is M or if substituted is G, Q, Y, or S;

the amino acid at position 19 is I or if substituted is L, M, P, Q, or V;

the amino acid at position 20 is L or if substituted is A, K, M, Q, R, or S;

the amino acid at position 21 is N or if substituted is G, K, P, R, S, or W;

the amino acid at position 22 is I or if substituted is D, E, K, M, N, W, or Y, wherein the position numbering is relative to SEQ ID NO: 4;

X3 is a peptide comprising an amino acid sequence at least 80% identical to the peptide LEDYAFNFELILEEIARLFESG (SEQ ID NO:5); wherein the amino acid at position 1 is L or if substituted is A;

the amino acid at position 2 is E or if substituted is D, G, K, M, or T;

the amino acid at position 3 is D or if substituted is E, N, Y, or R;

the amino acid at position 4 is Y or if substituted is C, D, G, T, or F;

the amino acid at position 5 is A or if substituted is F, H, S, V, W, or Y;

the amino acid at position 6 is F or if substituted is A, I, M, T, V, Y, or K;

the amino acid at position 7 is N or if substituted is D, K, S, T, or R;

the amino acid at position 8 is F or if substituted is A, C, G, L, M, S, or V;

the amino acid at position 9 is E or if substituted is C, H, K, L, R, S, T, or V;

the amino acid at position 10 is L or if substituted is F, I, M, Y, or R;

the amino acid at position 11 is I or if substituted is L, N, T, or Y;

the amino acid at position 12 is L or if substituted is F, K, M, S, or V;

the amino acid at position 13 is E or if substituted is A, D, F, G, I, N, P,Q, S, T, or W;

the amino acid at position 14 is E or if substituted is A, F, G, H, S, or V;

the amino acid at position 15 is I or if substituted is C, L, M, V, or W;

the amino acid at position 16 is A or if substituted is D, G, S, T, or V;

the amino acid at position 17 is R or if substituted is H, K, L, or N;

the amino acid at position 18 is L or if substituted is C, D, G, I, Q, R, T, or W;

the amino acid at position 19 is F or if substituted is D, M, N, or W;

the amino acid at position 20 is E or if substituted is A, C, F, G, M, S, or Y;

the amino acid at position 21 is S or if substituted is D, E, G, H, L, M, R, T, V, or W;

the amino acid at position 22 is G or if substituted is A, D, K, N, S, or Y, wherein the position numbering is relative to SEQ ID NO: 5; and X4 is a peptide comprising an amino acid sequence at least 80% identical to the peptide EDEQEEMANAIITILQSWIFS (SEQ ID NO:6); wherein the amino acid at position 1 is E or if substituted is D, G, K, or V;

the amino acid at position 2 is D or if substituted is I, M, or S;

the amino acid at position 3 is E or if substituted is G, H, or K;
the amino acid at position 4 is Q or if substituted is E, G, I, K, R, or S;
the amino acid at position 5 is E or if substituted is A, D, G, H, S, or V;
the amino acid at position 6 is E or if substituted is C, D, G, I, M, Q, R, T, or V;
the amino acid at position 7 is M or if substituted is C, E, L, P, R, or T;
the amino acid at position 8 is A or if substituted is F, L, M, or W;
the amino acid at position 9 is N or if substituted is A, G, L, Q, R, or T;
the amino acid at position 10 is A or if substituted is C, D, E, F, H, I, or W;
the amino acid at position 11 is I or if substituted is M, N, S, V, or W;
the amino acid at position 12 is I or if substituted is K, L, S, or V;
the amino acid at position 13 is T or if substituted is C, L, M, R, or S;
the amino acid at position 14 is I or if substituted is L, P, T, or Y;
the amino acid at position 15 is L or if substituted is F, G, I, M, N, or V;
the amino acid at position 16 is Q or if substituted is H, K, or R;
the amino acid at position 17 is S or if substituted is C, F, K, W, or Y;
the amino acid at position 18 is W or if substituted is K, Q, or T;
the amino acid at position 19 is I or if substituted is C, G, or N;
the amino acid at position 20 is F or if substituted is C, G, L, or Y; and
the amino acid at position 21 is S or if substituted is A, F, G, H, or Y, wherein the position numbering is relative to SEQ ID NO: 6.

13. The nucleic acid of claim 11, wherein X2 is a peptide comprising an amino acid sequence at least 50% identical to the peptide KDEAEKAKRMKEWMKRIKT (SEQ ID NO:7).

14. The nucleic acid of claim 11, wherein X2 is a peptide comprising an amino acid sequence at least 80% identical to the peptide KDEAEKAKRMKEWMKRIKT (SEQ ID NO:7).

15. The nucleic acid of claim 11 wherein the domains are arranged N-terminal to C-terminal in an arrangement selected from X1-X3-X2-X4.

16. A nucleic acid encoding a non-naturally occurring polypeptide wherein the polypeptide comprises an amino acid sequence at least 80% identical to the amino acid sequence set forth in SEQ ID NO: 181, wherein the polypeptide binds to IL-2 receptor $\beta\gamma_c$ heterodimer (IL-2R$\beta\gamma_c$).

17. The nucleic acid of claim 16 wherein the polypeptide comprises an amino acid sequence at least 85% identical to the amino acid sequence set forth in SEQ ID NO: 181.

18. The nucleic acid of claim 16 wherein the polypeptide comprises an amino acid sequence at least 90% identical to the amino acid sequence set forth in SEQ ID NO: 181.

19. The nucleic acid of claim 18, wherein the amino acids at positions 10-17 relative to SEQ ID NO: 181 are identical to SEQ ID NO:1; the amino acids at positions 37-44 relative to SEQ ID NO: 181 are identical to SEQ ID NO:2; and the amino acids at positions 91-99 relative to SEQ ID NO: 181 are identical to SEQ ID NO:3.

20. The nucleic acid of claim 16 wherein the polypeptide comprises an amino acid sequence at least 95% identical to the amino acid sequence set forth in SEQ ID NO: 181.

21. The nucleic acid of claim 16 wherein the polypeptide comprises an amino acid sequence at least 97% identical to the amino acid sequence set forth in SEQ ID NO: 181.

22. The nucleic acid of claim 21, wherein the amino acids at positions 10-17 relative to SEQ ID NO: 181 are identical to SEQ ID NO:1; the amino acids at positions 37-44 relative to SEQ ID NO: 181 are identical to SEQ ID NO:2; and the amino acids at positions 91-99 relative to SEQ ID NO: 181 are identical to SEQ ID NO:3.

23. The nucleic acid of claim 16 wherein the polypeptide comprises an amino acid sequence at least 98% identical to the amino acid sequence set forth in SEQ ID NO: 181.

24. The nucleic acid of claim 23, wherein the amino acids at positions 10-17 relative to SEQ ID NO: 181 are identical to SEQ ID NO:1; the amino acids at positions 37-44 relative to SEQ ID NO: 181 are identical to SEQ ID NO:2; and the amino acids at positions 91-99 relative to SEQ ID NO: 181 are identical to SEQ ID NO:3.

25. The nucleic acid of claim 23 wherein the polypeptide comprises an amino acid sequence that is 98% identical to the amino acid sequence set forth in SEQ ID NO:181 and comprises a tyrosine at position 8 and a glutamic acid at position 33.

26. The nucleic acid of claim 23 wherein the polypeptide comprises an amino acid sequence that is 99% identical to the amino acid sequence set forth in SEQ ID NO:181 and comprises a cysteine at position 62.

27. The nucleic acid of claim 16, wherein the amino acids at positions 10-17 relative to SEQ ID NO: 181 are identical to SEQ ID NO:1; the amino acids at positions 37-44 relative to SEQ ID NO: 181 are identical to SEQ ID NO:2; and the amino acids at positions 91-99 relative to SEQ ID NO: 181 are identical to SEQ ID NO:3.

28. The nucleic acid of claim 16 wherein the polypeptide comprises the amino acid sequence set forth in SEQ ID NO: 181.

* * * * *